(12) United States Patent
Wang et al.

(10) Patent No.: US 11,091,372 B2
(45) Date of Patent: *Aug. 17, 2021

(54) MOLECULAR SIEVE, ITS PREPARATION AND APPLICATION THEREOF

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Yongrui Wang, Beijing (CN); Jincheng Zhu, Beijing (CN); Mingyi Sun, Beijing (CN); Xuhong Mu, Beijing (CN); Xingtian Shu, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/946,927

(22) Filed: Jul. 11, 2020

(65) Prior Publication Data

US 2020/0339433 A1    Oct. 29, 2020

Related U.S. Application Data

(63) Continuation of application No. 16/095,208, filed as application No. PCT/CN2017/000327 on Apr. 26, 2017, now Pat. No. 10,737,945.

(30) Foreign Application Priority Data

Apr. 27, 2016  (CN) .......................... 201610267141.9
Apr. 27, 2016  (CN) .......................... 201610267143.8
Dec. 23, 2016  (CN) .......................... 201611204950.1

(51) Int. Cl.
    *C01B 39/48* (2006.01)
    *B01J 29/70* (2006.01)
    (Continued)

(52) U.S. Cl.
    CPC ............ *C01B 39/48* (2013.01); *B01J 29/047* (2013.01); *B01J 29/70* (2013.01); *C01B 37/00* (2013.01);
    (Continued)

(58) Field of Classification Search
    CPC ..... C01B 37/00; C01B 39/48; C01P 2002/60; C01P 2002/72; C01P 2004/40;
    (Continued)

(56) References Cited

U.S. PATENT DOCUMENTS 3,140,249 A    7/1964  Plank et al.
3,140,253 A    7/1964  Plank et al.
(Continued)

FOREIGN PATENT DOCUMENTS

CN    101024499 A    8/2007
CN    104370296 A    2/2015
(Continued)

OTHER PUBLICATIONS

Burton and Zones, Chapter 5, Organic Molecules in Zeolite Synthesis: Their Preparation and Structure-Directing Effects p. 140, Elsevier 2007 (Year: 2007).*
(Continued)

*Primary Examiner* — David M Brunsman
(74) *Attorney, Agent, or Firm* — Novick, Kim & Lee, PLLC; Allen Xue

(57) ABSTRACT

The present invention relates to a molecular sieve, particularly to an ultra-macroporous molecular sieve. The present
(Continued)

invention also relates to a process for the preparation of the molecular sieve and to its application as an adsorbent, a catalyst, or the like. The molecular sieve has a unique X-ray diffraction pattern and a unique crystal particle morphology. The molecular sieve can be produced by using a compound represented by the following formula (I),

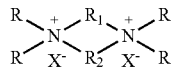
(I)

wherein the definition of each group and value is the same as that provided in the specification, as an organic template. The molecular sieve is capable of adsorbing more/larger molecules, thereby exhibiting excellent adsorptive/catalytic properties.

20 Claims, 42 Drawing Sheets

(51) Int. Cl.
| | | |
|---|---|---|
| $C07C\ 2/12$ | (2006.01) | |
| $C07C\ 4/06$ | (2006.01) | |
| $C07C\ 5/22$ | (2006.01) | |
| $C01B\ 37/02$ | (2006.01) | |
| $C01B\ 39/04$ | (2006.01) | |
| $C01B\ 37/00$ | (2006.01) | |
| $C07C\ 2/54$ | (2006.01) | |
| $C07C\ 2/02$ | (2006.01) | |
| $B01J\ 29/04$ | (2006.01) | |
| $C01B\ 39/02$ | (2006.01) | |

(52) U.S. Cl.
CPC ............ *C01B 37/02* (2013.01); *C01B 39/026* (2013.01); *C01B 39/04* (2013.01); *C07C 2/02* (2013.01); *C07C 2/12* (2013.01); *C07C 2/54* (2013.01); *C07C 4/06* (2013.01); *C07C 5/222* (2013.01); *C01P 2002/60* (2013.01); *C01P 2002/72* (2013.01); *C01P 2002/90* (2013.01); *C01P 2004/40* (2013.01); *C01P 2004/54* (2013.01); *C01P 2004/61* (2013.01); *C01P 2004/62* (2013.01); *C01P 2006/12* (2013.01); *C01P 2006/14* (2013.01); *C01P 2006/16* (2013.01); *C01P 2006/17* (2013.01); *C07C 2529/70* (2013.01)

(58) Field of Classification Search
CPC .............. C01P 2004/54; C01P 2004/61; C01P 2006/12; C01P 2006/14; C01P 2006/16; C01P 2006/17; B01J 29/047; B01J 29/70; C07C 2/02; C07C 2/12; C07C 2/54; C07C 4/06; C07C 5/222; C07C 2529/70
See application file for complete search history.

(56) References Cited

U.S. PATENT DOCUMENTS

| | | | |
|---|---|---|---|
| 5,271,922 A * | 12/1993 | Nakagawa | ............... C01B 37/02 423/328.2 |
| 5,362,695 A | 11/1994 | Beck et al. | |
| 5,538,711 A | 7/1996 | Emerson et al. | |
| 5,593,655 A | 1/1997 | Jongkind et al. | |
| 5,689,024 A | 11/1997 | Schmitt | |
| 5,800,800 A | 9/1998 | Pinnavaia et al. | |
| 6,136,290 A | 10/2000 | Benazzi et al. | |
| 6,342,200 B1 | 1/2002 | Rouleau et al. | |
| 9,205,416 B2 | 12/2015 | Burton et al. | |
| 2002/0051745 A1 | 5/2002 | Pinnavaia et al. | |
| 2002/0127164 A1 | 9/2002 | Liu et al. | |
| 2015/0360964 A1 | 12/2015 | Rimer et al. | |

FOREIGN PATENT DOCUMENTS

| | | | | |
|---|---|---|---|---|
| CN | 105129816 A | 12/2015 | | |
| CN | 106542539 A | 3/2017 | | |
| CN | 106608636 A | 5/2017 | | |
| CN | 107445178 A | 12/2017 | | |
| CN | 106608857 B | 11/2018 | | |
| CN | 107285330 B | 4/2019 | | |
| KR | 101147007 B1 * | 5/2012 | .......... | B01J 29/7007 |
| WO | 9209527 A1 | 6/1992 | | |
| WO | 2010087633 A2 | 8/2010 | | |
| WO | 2015001004 A1 | 1/2015 | | |
| WO | 2015198268 A1 | 12/2015 | | |
| WO | 2017151845 A1 | 9/2017 | | |

OTHER PUBLICATIONS

Russian federal institute of industrial property, Office Action of RU 2018141094, dated Apr. 21, 2020.
Russian federal institute of industrial property, Search Report of RU 2018141094, dated Apr. 21, 2020.
European Patent Office, Supplementary Partial European Search Report and Office Action for EP 177884833, dated Aug. 19, 2019.
Kyungsu Na et al.; "Cyclic diquaternary ammoniums for nanocrystalline BEA, MTW and MFI zeolites with intercrystalline mesoporosity", Journal of Materials Chemistry, vol. 19, No. 37, Aug. 4, 2009, p. 6713, XP055635577.
Song, Ho Lee et al.; Synthesis, characterization, and catalytic properties of zeolites IM-5 and NU-88; Journal of Catalysis, Academic Press, Duluth, MN, US vol. 215, No. 1,Apr. 1, 2003, pp. 151-170, XP002741995.
European Patent Office, the supplementary European search report and the European search opinion for EP 17788483, dated Nov. 11, 2019.
Chen et al., "AN Extra-Large-Pore Zeolite with Intersecting 18-, 12- and 10- Membered Ring Channels", Angew. Chem, Int. Ed. (2014), vol. 53, Issue 36, Sep. 1, 2014, pp. 9592-9596.
Giuseppe Bellussi, et al., New trends in the synthesis of crystalline microporous materials, Catalysis Science & Technology 3 (2013) 833-857.
German Sastre, et al., Computational and experimental approach to the role of structure-directing agents in the synthesis of zeolites: the case of cyclohexyl alkyl pyrrolidinium salts in the synthesis of β, EU-1, ZSM-11, and ZSM-12 zeolites, J. Phys. Chem. B 107 (2003) 5432-5440.
Yoshihiro Kubota, et al., Properties of organic cations that lead to the structure-direction of high-silica molecular sieves, Microporous Mater. 6 (1996) 213-229.
Tom. Willhammar, et al., EMM-23: a stable high-silica multidimensional zeolite with extra-large trilobe-shaped channels, J. Am. Chem. Soc. 136 (2014) 13570-13573.
Mark.E. Davis, et al., Zeolite and molecular sieve synthesis, Chem. Mater. 4 (1992) 756-768.
Devi W.Lewis, et al., De novo design of structure-directing agents for the synthesis of microporous solids, Nature 382 (1996) 604-606.

\* cited by examiner $2\theta/(°)$ 2 theta

MOLECULAR SIEVE, ITS PREPARATION AND APPLICATION THEREOF

CROSS-REFERENCE TO RELATED APPLICATIONS

This application is a continuation application of U.S. application Ser. No. 16/095,208 filed Oct. 19, 2018, now U.S. Pat. No. 10,737,945, which is the national stage of international application no. PCT/CN2017/000327 filed Apr. 26, 2017, which claims the benefit of priority to Chinese patent application no. 201611204950.1 (filed Dec. 23, 2016), Chinese patent application no. 201610267141.9 (filed Apr. 27, 2016), and Chinese patent application no. 201610267143.8 (filed Apr. 27, 2016), the content of which is incorporated herein by reference in its entirety.

TECHNICAL FIELD

The present invention relates to molecular sieves, particularly to an ultra-macroporous molecular sieve. The present invention also relates to a process for the preparation of the molecular sieve and to its use as an adsorbent or a catalyst, and the like.

BACKGROUND ART

Molecular sieves can be widely used in various applications, and different applications often impose different requirements on the pore structure in the framework of the molecular sieve. There are four types of pore structures in the framework of molecular sieves: microporous, mesoporous, macroporous and ultra-macroporous: microporous molecular sieves have a pore diameter ranging from 3 Å to 5 Å, such as CHA, LEV, SOD, LTA, EM, KFI; mesoporous molecular sieves have a pore diameter ranging from 5 Å to 7 Å, such as MFI, MEL, EUO, MWW, TON, MTT, MFS, AEL, AFO, HEU, FER; macroporous molecular sieves have a pore diameter of 7 Å, such as FAU, BEA, MOR, LTL, VFI, MAZ; and ultra-macroporous molecular sieves have a pore diameter greater than 7 Å. In these molecular sieves with different pore structures in framework, ultra-macroporous molecular sieves have broken the limits on the pore of molecular sieves, and have shown many advantages in improving the reactivity of macromoleculars, prolonging the life of molecular sieves and improving product selectivity, and are expected to be well applicable in the processing of heavy oils and the production of organic chemical raw materials.

Among the current 232 kinds of molecular sieves with a pore structure in framework, there are only 10 kinds of ultra-macroporous molecular sieves, mainly including three types: aluminum-phosphorus/gallium molecular sieves, such as AlPO-8 (AET, 14-ring, 7.9×8.7 Å), VPI-5 (VFI, 18-ring, 12.1 Å), Cloverite (-CLO, 20-ring, 13.2 Å), JDF-20 (20-ring) and ND-1 (24-ring, 10.5 Å); silicon-germanium/ Gallium molecular sieves, such as OSB-1 (OSO, 14-ring, Si/Be=2, 7.3×5.4 Å), ECR-34 (ETR, 18-ring, 10.5 Å, Si/Ga=3), ITQ-37 (30-ring), ITQ-43 (28-ring), ITQ-33 (18-ring), ITQ-44 (18-ring), ITQ-40 (16-ring) SSZ-53 (14-ring) and SSZ-59 (14-ring); and silica-alumina molecular sieves such as UTD-1 (DON, 14-ring, $Si/Al_2$=∞, 10×7.5 Å) and CIT-5 (CFI, 14-ring, 7.5×7.2 Å, $Si/Al_2$=190).

In view of its good performance and application prospects, there is still a need in the art to develop more types of ultra-macroporous molecular sieves.

SUMMARY OF THE INVENTION

On the basis of the prior art, the inventors have developed a novel ultra-macroporous molecular sieve, and a novel method for the preparation of molecular sieves through hard research, thereby satisfying the aforementioned need in the art.

In particular, the present invention is directed to the following aspects:

First Embodiment

1. A molecular sieve, having a schematic chemical composition represented by the formula "first oxide·second oxide" or the formula "first oxide·second oxide·organic template·water", wherein the molar ratio of the first oxide to the second oxide is in a range from 5 to ∞, preferably from 25 to 95, more preferably from 30 to 70; the first oxide is at least one selected from the group consisting of silica, germanium dioxide, tin dioxide, titania and zirconium dioxide, preferably silica or a combination of silica and germanium dioxide; the second oxide is at least one selected from the group consisting of alumina, a boron oxide, an iron oxide, a gallium oxide, a rare earth oxide, an indium oxide and a vanadium oxide, preferably alumina; the molar ratio of water to said first oxide is in a range from 5 to 50, preferably from 5 to 15; the molar ratio of said organic template to said first oxide is in a range from 0.02 to 0.5, preferably from 0.05 to 0.5, from 0.15 to 0.5 or from 0.3 to 0.5, and said molecular sieve has an X-ray diffraction pattern substantially as shown in the following table.

| 2θ (°) | d-distance (Å) | Relative intensity ($I/I_0$ × 100) |
|---|---|---|
| 5.2048 ± 0.05 | 16.96501 ± 0.05 | VS |
| 8.4762 ± 0.27 | 10.42335 ± 0.34 | W |
| 9.0095 ± 0.06 | 9.80755 ± 0.07 | M |
| 10.3943 ± 0.05 | 8.50381 ± 0.05 | W |
| 16.1228 ± 0.50 | 5.49296 ± 0.50 | W |
| 23.7405 ± 0.22 | 3.74484 ± 0.03 | W |

2. The molecular sieve according to any one of the preceding aspects, wherein the X-ray diffraction pattern further comprises an X-ray diffraction peak substantially as shown in the following table.

| 2θ (°) | d-distance (Å) | Relative intensity ($I/I_0$ × 100) |
|---|---|---|
| 14.3448 ± 0.66 | 6.16955 ± 0.27 | W |
| 15.2971 ± 0.50 | 5.78752 ± 0.50 | W |
| 16.1979 ± 0.50 | 5.46765 ± 0.50 | W |
| 20.8653 ± 0.11 | 4.25393 ± 0.02 | W |
| 23.9532 ± 0.14 | 3.71207 ± 0.02 | W |

3. The molecular sieve according to any one of the preceding aspects, wherein the X-ray diffraction pattern further comprises an X-ray diffraction peak substantially as shown in the following table.

| 2θ (°) | d-distance (Å) | Relative intensity ($I/I_0$ × 100) |
|---|---|---|
| 14.4217 ± 0.56 | 6.13681 ± 0.43 | W |
| 15.1988 ± 0.50 | 5.82474 ± 0.50 | W |

-continued

| 2θ (°) | d-distance (Å) | Relative intensity (I/I₀ × 100) |
|---|---|---|
| 15.5903 ± 0.50 | 5.67936 ± 0.50 | W |
| 20.6353 ± 0.50 | 4.30082 ± 0.10 | W |
| 22.7406 ± 0.08 | 3.90718 ± 0.02 | W |
| 24.4468 ± 0.26 | 3.63823 ± 0.04 | W |

4. The molecular sieve according to any one of the preceding aspects, having a columnar (preferably prismatic, more preferably hexagonal) crystal particle morphology.

5. The molecular sieve according to any one of the preceding aspects, wherein the crystal particle morphology has a size defined by an effective diameter ranging from 100 nm to 1000 nm, preferably from 300 nm to 700 nm, a height ranging from 100 nm to 1000 nm, preferably from 150 nm to 700 nm, and an aspect ratio from 1/3 to 8, preferably from 1.5 to 5 or from 2 to 5.

6. The molecular sieve according to any one of the preceding aspects, wherein the molecular sieve has a total specific surface area ranging from 400 m²·g⁻¹ to 600 m²·g⁻¹, preferably from 450 m²·g⁻¹ to 580 m²·g⁻¹, and a pore volume ranging from 0.3 ml/g to 0.5 ml/g, preferably from 0.30 ml/g to 0.40 ml/g.

7. A method for the preparation of a molecular sieve, comprising a step of contacting a first oxide source, a second oxide source, an optional alkali source, an organic template, and water under crystallization conditions to produce a molecular sieve, and optionally a step of calcining the resultant molecular sieve, wherein the organic template comprises a compound represented by the following formula (I),

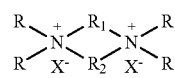

(I)

wherein the groups R₁ and R₂ are identical or different from each other, each independently selected from the group consisting of C₃₋₁₂ linear or branched alkylene groups and C₃₋₁₂ linear or branched oxaalkylene groups, preferably each independently selected from the group consisting of C₃₋₁₂ linear alkylene groups and C₃₋₁₂ linear oxaalkylene groups, or preferably one of them is selected from the group consisting of C₃₋₁₂ linear or branched alkylene groups, and the other is selected from the group consisting of C₃₋₁₂ linear or branched alkylene groups and C₃₋₁₂ linear or branched oxaalkylene groups, more preferably one of them is selected from the group consisting of C₃₋₁₂ linear alkylene groups and the other is selected from the group consisting of C₃₋₁₂ linear alkylene groups and C₃₋₁₂ linear oxaalkylene groups, particularly preferably one of them is selected from the group consisting of C₃₋₁₂ linear alkylene groups and the other is selected from the group consisting of C₄₋₆ linear alkylene groups and C₄₋₆ linear oxaalkylene groups (preferably C₄₋₆ linear monooxaalkylene groups, more preferably —(CH₂)ₘ—O—(CH₂)ₘ—, wherein each value m, being identical or different from each other, independently represents 2 or 3); the plural groups R are identical or different from each other, each independently selected from the group consisting of C₁₋₄ linear or branched alkyl groups, preferably each independently selected from the group consisting of methyl and ethyl, more preferably all methyl; and X is OH.

8. The method according to any one of the preceding aspects, wherein the first oxide source is at least one selected from the group consisting of a silica source, a germanium dioxide source, a tin dioxide source, a titania source, and a zirconium dioxide source, preferably a silica source or a combination of a silica source and a germanium dioxide source, and the second oxide source is at least one selected from the group consisting of an alumina source, a boron oxide source, an iron oxide source, a gallium oxide source, a rare earth oxide source, an indium oxide source and a vanadium oxide source, preferably an alumina source.

9. The method according to any one of the preceding aspects, wherein the crystallization conditions include: a crystallization temperature ranging from 80° C. to 120° C., preferably from 120° C. to 170° C. or from 120° C. to 200° C., a crystallization period of at least 1 day, preferably at least 2 days, preferably from 3 days to 8 days, from 5 days to 8 days or from 4 days to 6 days, and the calcination conditions include: a calcination temperature ranging from 300° C. to 750° C., preferably from 400° C. to 600° C., a calcination period ranging from 1 hour to 10 hours, preferably from 3 hours to 6 hours.

10. The method according to any one of the preceding aspects, wherein the molar ratio of the first oxide source (calculated on the basis of the first oxide) to the second oxide source (calculated on the basis of the second oxide) is in a range from 5 to ∞, preferably from 25 to 95, more preferably from 30 to 70; the molar ratio of water to the first oxide source (calculated on the basis of the first oxide) is in a range from 5 to 50, preferably from 5 to 15; the molar ratio of the organic template to the first oxide source (calculated on the basis of the first oxide) is in a range from 0.02 to 0.5, preferably from 0.05 to 0.5, from 0.15 to 0.5 or from 0.3 to 0.5; the molar ratio of the alkali source (calculated on the basis of OH⁻) to the first oxide source (calculated on the basis of the first oxide) is in a range from 0 to 1, preferably from 0.04 to 1, from 0.1 to 1, from 0.2 to 1, from 0.3 to 0.7 or from 0.45 to 0.7.

Second Embodiment

1. A molecular sieve having a (native) sponge structure and having an X-ray diffraction pattern substantially as shown in the following table.

| 2θ (°) | d-distance (Å) | Relative intensity (I/I₀ × 100) |
|---|---|---|
| 5.2048 ± 0.05 | 16.96501 ± 0.05 | VS |
| 8.4762 ± 0.27 | 10.42335 ± 0.34 | W |
| 9.0095 ± 0.06 | 9.80755 ± 0.07 | M |
| 10.3943 ± 0.05 | 8.50381 ± 0.05 | W |
| 16.1228 ± 0.50 | 5.49296 ± 0.50 | W |
| 23.7405 ± 0.22 | 3.74484 ± 0.03 | W |

2. The molecular sieve according to any one of the preceding aspects, wherein the X-ray diffraction pattern further comprises an X-ray diffraction peak substantially as shown in the following table.

| 2θ (°) | d-distance (Å) | Relative intensity (I/I₀ × 100) |
|---|---|---|
| 14.3448 ± 0.66 | 6.16955 ± 0.27 | W |
| 15.2971 ± 0.50 | 5.78752 ± 0.50 | W |
| 16.1979 ± 0.50 | 5.46765 ± 0.50 | W |

-continued

| 2θ (°) | d-distance (Å) | Relative intensity (I/I₀ × 100) |
|---|---|---|
| 20.8653 ± 0.11 | 4.25393 ± 0.02 | W |
| 23.9532 ± 0.14 | 3.71207 ± 0.02 | W |

3. The molecular sieve according to any one of the preceding aspects, wherein the X-ray diffraction pattern further comprises an X-ray diffraction peak substantially as shown in the following table.

| 2θ (°) | d-distance (Å) | Relative intensity (I/I₀ × 100) |
|---|---|---|
| 14.4217 ± 0.56 | 6.13681 ± 0.43 | W |
| 15.1988 ± 0.50 | 5.82474 ± 0.50 | W |
| 15.5903 ± 0.50 | 5.67936 ± 0.50 | W |
| 20.6353 ± 0.50 | 4.30082 ± 0.10 | W |
| 22.7406 ± 0.08 | 3.90718 ± 0.02 | W |
| 24.4468 ± 0.26 | 3.63823 ± 0.04 | W |

4. The molecular sieve according to any one of the preceding aspects, wherein the sponge structure comprises coarse pores and/or mesopores, preferably the coarse pores and/or the mesopores are opened at an end face and/or a side face of the sponge structure.

5. The molecular sieve according to any one of the preceding aspects, wherein the coarse pores have a diameter ranging from 80 nm to 2 μm, preferably from 80 nm to 1.5 μm, and the mesopores have a diameter ranging from 2 nm to 30 nm, preferably from 2 nm to 4 nm and/or from 7 nm to 15 nm (preferably from 8 nm to 9 nm).

6. The molecular sieve according to any one of the preceding aspects, wherein the mesopores have a total specific surface area ranging from 50 m²·g⁻¹ to 250 m²·g⁻¹, preferably from 100 m²·g⁻¹ to 150 m²·g⁻¹, and a pore volume ranging from 0.05 ml/g to 0.40 ml/g, preferably from 0.15 ml/g to 0.30 ml/g, and the coarse pores have a total specific surface area ranging from 10 m²·g⁻¹ to 100 m²·g⁻¹, preferably from 50 m²·g⁻¹ to 100 m²·g⁻¹, and a pore volume ranging from 0.5 ml/g to 3.0 ml/g, preferably from 1.0 ml/g to 2.0 ml/g.

7. The molecular sieve according to any one of the preceding aspects, wherein the sponge structure comprises micropores, wherein the micropores have a diameter ranging from 0.5 nm to less than 2 nm, preferably from 0.5 nm to 0.8 nm and/or from 1.1 nm to 1.8 nm, a total specific surface area ranging from 100 m²·g⁻¹ to 300 m²·g⁻¹, preferably from 150 m²·g⁻¹ to 250 m²·g⁻¹, and a pore volume ranging from 0.03 ml/g to 0.20 ml/g, preferably from 0.05 ml/g to 0.15 ml/g.

8. The molecular sieve according to any one of the preceding aspects, having a columnar (preferably prismatic, more preferably hexagonal) crystal particle morphology, preferably having a hollow columnar crystal particle morphology.

9. The molecular sieve according to any one of the preceding aspects, wherein the crystal particle morphology has a size defined by an effective diameter ranging from 100 nm to 5000 nm, preferably from 1000 nm to 3000 nm, a height ranging from 500 nm to 3000 nm, preferably from 1000 nm to 3000 nm, an aspect ratio ranging from 1/3 to 5, preferably from 1/3 to 3.

10. The molecular sieve according to any one of the preceding aspects, having a schematic chemical composition represented by the formula "first oxide·second oxide" or the formula "first oxide·second oxide·organic template·water", wherein the molar ratio of the first oxide to the second oxide is in a range from 30 to 100, preferably from 55 to 100; the first oxide is at least one selected from the group consisting of silica, germanium dioxide, tin dioxide, titania and zirconium dioxide, preferably silica or a combination of silica and germanium dioxide; the second oxide is at least one selected from the group consisting of alumina, a boron oxide, an iron oxide, a gallium oxide, a rare earth oxide, an indium oxide and a vanadium oxide, preferably alumina; the molar ratio of water to the first oxide is in a range from 5 to 50, preferably from 5 to 15; the molar ratio of the organic template to the first oxide is in a range from 0.02 to 0.5, preferably from 0.05 to 0.5, from 0.15 to 0.5 or from 0.3 to 0.5.

11. A method for the preparation of a molecular sieve, comprising a step of contacting a first oxide source, a second oxide source, an optional alkali source, an organic template, and water under crystallization conditions to produce a molecular sieve, and optionally a step of calcining the resultant molecular sieve, wherein the organic template comprises a compound represented by the following formula (I)

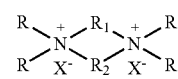

(I)

wherein the groups R₁ and R₂ are different from each other, one of which is selected from the group consisting of C₃₋₁₂ linear or branched alkylene groups, and the other is selected from the group consisting of C₃₋₁₂ linear or branched oxaalkylene groups, preferably one of which is selected from the group consisting of C₃₋₁₂ linear alkylene groups, the other is selected from the group consisting of C₃₋₁₂ linear oxaalkylene groups (preferably C₄₋₆ linear oxaalkylene groups, more preferably C₄₋₆ linear monooxaalkylene groups, more preferably —(CH₂)$_m$—O—(CH₂)$_m$—, wherein each value m, being identical or different from each other, independently represents 2 or 3); the plural groups R are identical or different from each other, each independently selected from the group consisting of C₁₋₄ linear or branched alkyl groups, preferably each independently selected from the group consisting of methyl and ethyl, more preferably all methyl; and X is OH.

12. The method according to any one of the preceding aspects, wherein the first oxide source is at least one selected from the group consisting of a silica source, a germanium dioxide source, a tin dioxide source, a titania source, and a zirconium dioxide source, preferably a silica source or a combination of a silica source and a germanium dioxide source, and the second oxide source is at least one selected from the group consisting of an alumina source, a boron oxide source, an iron oxide source, a gallium oxide source, a rare earth oxide source, an indium oxide source and a vanadium oxide source, preferably an alumina source.

13. The method according to any one of the preceding aspects, wherein the crystallization conditions include: a crystallization temperature ranging from 80° C. to 120° C., preferably from 120° C. to 170° C. or from 120° C. to 200° C., a crystallization period of at least 1 day, preferably at least 2 days, preferably from 3 days to 8 days, from 5 days to 8 days or from 4 days to 6 days, and the calcination conditions include: a calcination temperature ranging from 300° C. to 750° C., preferably from 400° C. to 600° C., and a calcination period ranging from 1 hour to 10 hours, preferably from 3 hours to 6 hours.

14. The method according to any one of the preceding aspects, wherein the molar ratio of the first oxide source (calculated on the basis of the first oxide) to the second oxide source (calculated on the basis of the second oxide) is in a range from 30 to 100, preferably from 55 to 100; the molar ratio of water to the first oxide source (calculated on the basis of the first oxide) is in a range from 5 to 50, preferably from 5 to 15; the molar ratio of the organic template to the first oxide source (calculated on the basis of the first oxide) is in a range from 0.02 to 0.5, preferably from 0.05 to 0.5, from 0.15 to 0.5, or from 0.3 to 0.5, the molar ratio of the alkali source (calculated on the basis of $OH^-$) to the first oxide source (calculated on the basis of the first oxide) is in a range from 0 to 1, preferably from 0.04 to 1, from 0.1 to 1, from 0.2 to 1, from 0.3 to 0.7 or from 0.45 to 0.7.

Third Embodiment

1. A molecular sieve having a (native) crystal particle morphology of from a flat prismatic shape to a flat cylindrical shape, preferably one or two of the contours of its end face in the longitudinal section have a convex shape, and having an X-ray diffraction pattern substantially as shown in the following table.

| 2θ (°) | d-distance (Å) | Relative intensity ($I/I_0 \times 100$) |
|---|---|---|
| 5.2048 ± 0.05 | 16.96501 ± 0.05 | VS |
| 8.4762 ± 0.27 | 10.42335 ± 0.34 | W |
| 9.0095 ± 0.06 | 9.80755 ± 0.07 | M |
| 10.3943 ± 0.05 | 8.50381 ± 0.05 | W |
| 16.1228 ± 0.50 | 5.49296 ± 0.50 | W |
| 23.7405 ± 0.22 | 3.74484 ± 0.03 | W |

2. The molecular sieve according to any one of the preceding aspects, wherein the X-ray diffraction pattern further comprises an X-ray diffraction peak substantially as shown in the following table.

| 2θ (°) | d-distance (Å) | Relative intensity ($I/I_0 \times 100$) |
|---|---|---|
| 14.3448 ± 0.66 | 6.16955 ± 0.27 | W |
| 15.2971 ± 0.50 | 5.78752 ± 0.50 | W |
| 16.1979 ± 0.50 | 5.46765 ± 0.50 | W |
| 20.8653 ± 0.11 | 4.25393 ± 0.02 | W |
| 23.9532 ± 0.14 | 3.71207 ± 0.02 | W |

3. The molecular sieve according to any one of the preceding aspects, wherein the X-ray diffraction pattern further comprises an X-ray diffraction peak substantially as shown in the following table.

| 2θ (°) | d-distance (Å) | Relative intensity ($I/I_0 \times 100$) |
|---|---|---|
| 14.4217 ± 0.56 | 6.13681 ± 0.43 | W |
| 15.1988 ± 0.50 | 5.82474 ± 0.50 | W |
| 15.5903 ± 0.50 | 5.67936 ± 0.50 | W |
| 20.6353 ± 0.50 | 4.30082 ± 0.10 | W |
| 22.7406 ± 0.08 | 3.90718 ± 0.02 | W |
| 24.4468 ± 0.26 | 3.63823 ± 0.04 | W |

4. The molecular sieve according to any one of the preceding aspects, wherein the crystal particle morphology has a size defined by an effective diameter ranging from 100 nm to 1000 nm, preferably from 100 nm to 500 nm, a height ranging from 100 nm to 1000 nm, preferably from 150 nm to 300 nm, an aspect ratio ranging from 0.1 to 0.9, preferably from 0.4 to 0.7.

5. The molecular sieve according to any one of the preceding aspects, wherein the molecular sieve has a total specific surface area ranging from 400 $m^2 \cdot g^{-1}$ to 600 $m^2 \cdot g^{-1}$, preferably from 450 $m^2 \cdot g^{-1}$ to 580 $m^2 \cdot g^{-1}$, and a pore volume ranging from 0.3 ml/g to 0.5 ml/g, preferably from 0.30 ml/g to 0.40 ml/g.

6. The molecular sieve according to any one of the preceding aspects, having a schematic chemical composition represented by the formula "first oxide·second oxide" or the formula "first oxide·second oxide·organic template·water", wherein the molar ratio of the first oxide to the second oxide is in a range from 40 to 200, preferably from 40 to 150; the first oxide is at least one selected from the group consisting of silica, germanium dioxide, tin dioxide, titania and zirconium dioxide, preferably silica or a combination of silica and germanium dioxide, the second oxide is at least one selected from the group consisting of alumina, a boron oxide, an iron oxide, a gallium oxide, a rare earth oxide, an indium oxide and a vanadium oxide, preferably alumina; the molar ratio of water to the first oxide is in a range from 5 to 50, preferably from 5 to 15; the molar ratio of the organic template to the first oxide is in a range from 0.02 to 0.5, preferably from 0.05 to 0.5, from 0.08 to 0.5 or from 0.3 to 0.5.

7. A method for the preparation of a molecular sieve, comprising a step of contacting a first oxide source, a second oxide source, an optional alkali source, an organic template, and water under crystallization conditions to produce a molecular sieve, and optionally a step of calcining the resultant molecular sieve, wherein the organic template comprises a compound represented by the following formula (I),

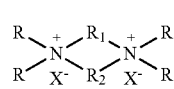

(I)

wherein the groups $R_1$ and $R_2$ are identical or different from each other, each independently selected from the group consisting of $C_{3-12}$ linear or branched alkylene groups, preferably each independently selected from the group consisting of $C_{3-12}$ linear alkylene groups, particularly preferably one of them is selected from the group consisting of $C_{3-12}$ linear alkylene groups, and the other is selected from the group consisting of $C_{4-6}$ linear alkylene groups; the plural groups R are identical or different from each other, each independently selected from the group consisting of $C_{1-4}$ linear or branched alkyl groups, preferably each independently selected from the group consisting of methyl and ethyl, more preferably all methyl; and X is OH.

8. The method according to any one of the preceding aspects, wherein the first oxide source is at least one selected from the group consisting of a silica source, a germanium dioxide source, a tin dioxide source, a titania source, and a zirconium dioxide source, preferably a silica source or a combination of a silica source and a germanium dioxide source, and the second oxide source is at least one selected from the group consisting of an alumina source, a boron oxide source, an iron oxide source, a gallium oxide source, a rare earth oxide source, an indium oxide source and a vanadium oxide source, preferably an alumina source.

9. The method according to any one of the preceding aspects, wherein the crystallization conditions include: a crystallization temperature ranging from 80° C. to 120° C., preferably from 120° C. to 170° C. or from 120° C. to 200° C., a crystallization period of at least 1 day, preferably at least 2 days, preferably from 3 days to 8 days, from 5 days to 8 days or from 4 days to 6 days, and the calcination conditions include: a calcination temperature ranging from 300° C. to 750° C., preferably from 400° C. to 600° C., and a calcination period ranging from 1 hour to 10 hours, preferably from 3 hours to 6 hours.

10. The method according to any one of the preceding aspects, wherein the molar ratio of the first oxide source (calculated on the basis of the first oxide) to the second oxide source (calculated on the basis of the second oxide) is in a range from 40 to 200, preferably from 40 to 150; the molar ratio of water to the first oxide source (calculated on the basis of the first oxide) is in a range from 5 to 50, preferably from 5 to 15; the molar ratio of the organic template to the first oxide source (calculated on the basis of the first oxide) is in a range from 0.02 to 0.5, preferably from 0.05 to 0.5, from 0.08 to 0.5, or from 0.3 to 0.5, the molar ratio of the alkali source (calculated on the basis of OH⁻) to the first oxide source (calculated on the basis of the first oxide) is in a range from 0 to 1, preferably from 0.04 to 1, from 0.1 to 1, from 0.2 to 1, from 0.3 to 0.7 or from 0.45 to 0.7.

Fourth Embodiment and Fifth Embodiment

1. A method for the preparation of a molecular sieve, comprising a step of contacting a first oxide source, a second oxide source, an optional alkali source, an organic template, and water under crystallization conditions to produce a molecular sieve, and optionally a step of calcining the resultant molecular sieve, wherein the organic template comprises a compound represented by the following formula (I),

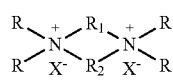

(I)

wherein the groups $R_1$ and $R_2$ are identical or different from each other, each independently selected from the group consisting of $C_{3-12}$ linear or branched alkylene groups and $C_{3-12}$ linear or branched oxaalkylene groups, preferably each independently selected from the group consisting of $C_{3-12}$ linear alkylene groups and $C_{3-12}$ linear oxaalkylene groups, or preferably one of them is selected from the group consisting of $C_{3-12}$ linear or branched alkylene groups, and the other is selected from the group consisting of $C_{3-12}$ linear or branched alkylene groups and $C_{3-12}$ linear or branched oxaalkylene groups, more preferably one of them is selected from the group consisting of $C_{3-12}$ linear alkylene groups and the other is selected from the group consisting of $C_{3-12}$ linear alkylene groups and $C_{3-12}$ linear oxaalkylene groups, particularly preferably one of them is selected from the group consisting of $C_{3-12}$ linear alkylene groups and the other is selected from the group consisting of $C_{4-6}$ linear alkylene groups and $C_{4-6}$ linear oxaalkylene groups (preferably $C_{4-6}$ linear monooxaalkylene groups, more preferably —$(CH_2)_m$—O—$(CH_2)_m$—, wherein each value m, being identical or different from each other, independently represents 2 or 3); the plural groups R are identical or different from each other, each independently selected from the group consisting of $C_{1-4}$ linear or branched alkyl groups, preferably each independently selected from the group consisting of methyl and ethyl, more preferably all methyl; and X is OH.

2. The method according to any one of the preceding aspects, wherein the groups $R_1$ and $R_2$ are identical or different from each other, each independently selected from the group consisting of $C_{3-12}$ linear or branched alkylene groups, preferably each independently selected from the group consisting of $C_{3-12}$ linear alkylene groups, particularly preferably one of them is selected from the group consisting of $C_{3-12}$ linear alkylene groups and the other is selected from the group consisting of $C_{4-6}$ linear alkylene groups; the plural groups R are identical or different from each other, each independently selected from the group consisting of $C_{1-4}$ linear or branched alkyl groups, preferably each independently selected from the group consisting of methyl and ethyl, more preferably all methyl; and X is OH.

3. The method according to any one of the preceding aspects, wherein the groups $R_1$ and $R_2$ are different from each other, one of which is selected from the group consisting of $C_{3-12}$ linear or branched alkylene groups, and the other is selected from the group consisting of $C_{3-12}$ linear or branched oxaalkylene groups, preferably one is selected from the group consisting of $C_{3-12}$ linear alkylene groups and the other is selected from the group consisting of $C_{3-12}$ linear oxaalkylene groups (preferably $C_{4-6}$ linear oxaalkylene groups, more preferably $C_{4-6}$ linear monooxaalkylene groups, more preferably —$(CH_2)_m$—O—$(CH_2)_m$—, wherein each value m, being identical or different from each other, independently represents 2 or 3); the plural groups R are identical or different from each other, each independently selected from the group consisting of $C_{1-4}$ linear or branched alkyl groups, preferably each independently selected from the group consisting of methyl and ethyl, more preferably all methyl; and X is OH.

4. The method according to any one of the preceding aspects, wherein the first oxide source is at least one selected from the group consisting of a silica source, a germanium dioxide source, a tin dioxide source, a titania source, and a zirconium dioxide source, preferably a silica source or a combination of a silica source and a germanium dioxide source, and the second oxide source is at least one selected from the group consisting of an alumina source, a boron oxide source, an iron oxide source, a gallium oxide source, a rare earth oxide source, an indium oxide source and a vanadium oxide source, preferably an alumina source.

5. The method according to any one of the preceding aspects, wherein the crystallization conditions include: a crystallization temperature ranging from 80° C. to 120° C., preferably from 120° C. to 170° C. or from 120° C. to 200° C., a crystallization period of at least 1 day, preferably at least 2 days, preferably from 3 days to 8 days, from 5 days to 8 days or from 4 days to 6 days, and the calcination conditions include: a calcination temperature ranging from 300° C. to 750° C., preferably from 400° C. to 600° C., and a calcination period ranging from 1 hour to 10 hours, preferably from 3 hours to 6 hours.

6. The method according to any one of the preceding aspects, wherein the molar ratio of the first oxide source (calculated on the basis of the first oxide) to the second oxide source (calculated on the basis of the second oxide) is in a range from 5 to ∞, particularly from 5 to less than 40 (e.g. from 20 to less than 40), from 40 to 200 (e.g. from 40 to 150), from greater than 200 to ∞ (e.g. from greater than 200 to 700); the molar ratio of water to the first oxide source (calculated on the basis of the first oxide) is in a range from 5 to 50, preferably from 5 to 15; the molar ratio of the organic template to the first oxide source (calculated on the basis of the first oxide) is in a range from 0.02 to 0.5, preferably from 0.05 to 0.5, from 0.08 to 0.5 or from 0.3 to 0.5; the molar ratio of the alkali source (calculated on the basis of OH⁻) to the first oxide source (calculated on the basis of the first oxide) is in a range from 0 to 1, preferably from 0.04 to 1, from 0.1 to 1, from 0.2 to 1, from 0.3 to 0.7, or from 0.45 to 0.7.

7. The method according to any one of the preceding aspects, wherein the molar ratio of the first oxide source (calculated on the basis of the first oxide) to the second oxide source (calculated on the basis of the second oxide) is in a range from 5 to ∞, especially from 5 to less than 30 (e.g. from 10 to less than 30), from 30 to 100 (e.g. from 55 to 100), and from greater than 100 to ∞ (e.g. from 200 to ∞, or from 200 to 700); the molar ratio of water to the first oxide source (calculated on the basis of the first oxide) is in a range from 5 to 50, preferably from 5 to 15; the molar ratio of the organic template to the first oxide source (calculated on the basis of the first oxide) is in a range from 0.02 to 0.5, preferably from 0.05 to 0.5, from 0.15 to 0.5 or from 0.3 to 0.5; the molar ratio of the alkali source (calculated on the basis of OH⁻) to the first oxide source (calculated on the basis of the first oxide) is in a range from 0 to 1, preferably from 0.04 to 1, from 0.1 to 1, from 0.2 to 1, from 0.3 to 0.7 or from 0.45 to 0.7.

8. A molecular sieve obtained by the method according to any one of the preceding aspects.

9. The molecular sieve of any one of the preceding aspects, having an X-ray diffraction pattern substantially as shown in the following table.

| 2θ (°) | d-distance (Å) | Relative intensity (I/I₀ × 100) |
|---|---|---|
| 5.2048 ± 0.05 | 16.96501 ± 0.05 | VS |
| 8.4762 ± 0.27 | 10.42335 ± 0.34 | W |
| 9.0095 ± 0.06 | 9.80755 ± 0.07 | M |
| 10.3943 ± 0.05 | 8.50381 ± 0.05 | W |
| 16.1228 ± 0.50 | 5.49296 ± 0.50 | W |
| 23.7405 ± 0.22 | 3.74484 ± 0.03 | W |

Sixth Embodiment

1. A molecular sieve composition, comprising a molecular sieve according to any one of the preceding aspects, or a molecular sieve obtained by the method according to any one of the preceding aspects, and a binder.

2. A process for the conversion of a hydrocarbon, comprising a step of subjecting the hydrocarbon to a conversion reaction in the presence of a catalyst, wherein the catalyst comprises or is produced from a molecular sieve according to any one of the preceding aspects, a molecular sieve obtained by the method according to any one of the preceding aspects, or a molecular sieve composition according to any one of the preceding aspects.

3. The process according to any one of the preceding aspects, wherein the conversion reaction is selected from the group consisting of catalytic cracking, hydrocracking, disproportionation, alkylation, oligomerization, and isomerization reactions.

Advantageous Effects

The molecular sieve according to the present invention has an ultra-macroporous pore structure in the framework, which can be reflected at least by the higher value of its pore volume.

The molecular sieve according to the present invention has good thermal/hydrothermal stability and a greater pore volume. Thus, the molecular sieve according to the present invention is capable of adsorbing more/larger molecules, thereby exhibiting excellent adsorptive/catalytic properties.

The molecular sieve according to the present invention, in an embodiment, has a unique X-ray diffraction spectrum (XRD) and a unique Si/Al₂ ratio. This molecular sieve has not been produced in the prior art.

The molecular sieve according to the present invention, in an embodiment, has a unique X-ray diffraction pattern (XRD) and a unique native crystal particle morphology, such as a crystal particle morphology from a flat prismatic shape to a flat cylindrical shape. This molecular sieve has not been produced in the prior art.

The molecular sieve according to the present invention, in an embodiment, has a unique X-ray diffraction pattern (XRD) and a unique native crystal particle morphology, such as a crystal particle morphology of sponge structure. This molecular sieve has not been produced in the prior art. As a result, in addition to the characteristics of microporous materials (i.e., the inherent characteristics of conventional molecular sieves), the molecular sieve according to the present invention further exhibits the characteristics of mesoporous materials and/or macroporous materials, and is capable of adsorbing more/larger molecules, thereby showing excellent adsorptive/catalytic properties.

The molecular sieve according to the present invention, in an embodiment, has a relatively strong acidity, particularly a relatively greater number of L acid sites. This molecular sieve has not been produced in the prior art. As a result, the molecular sieve according to the present invention shows better performance particularly in an acid-catalyzed reaction.

According to the method for the preparation of the molecular sieve of the present invention, an organic template having a specific chemical structure is used. Thus, the method has the characteristics that the process conditions are simple and the molecular sieve product can be easily synthesized.

DETAILED DESCRIPTION OF THE INVENTION

Figure 1:
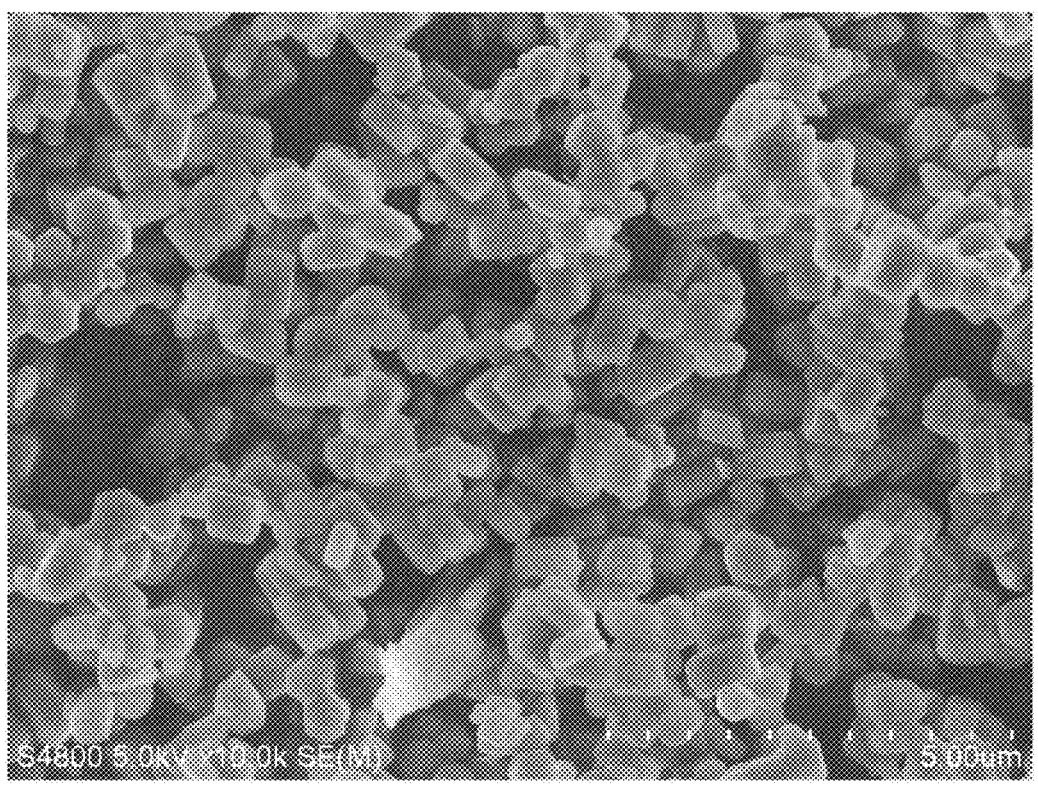
FIG. 1 is a scanning electron micrograph of the molecular sieve produced in Example I-3.

Specific embodiments of the present invention will be described in detail hereinbelow, but it should be noted that the scope of the present invention is not limited by those specific embodiments, but is defined by the appended claims.

All publications, patent applications, patents, and other references mentioned in the present specification are hereby incorporated by reference. Unless otherwise defined, all technical and scientific terms used in the specification have the meaning commonly understood by those skilled in the art. In case of conflict, the definition of the present specification shall prevail.

In the present specification, when a material, a substance, a method, a step, a device, or a component, etc., is modified by the wording "known to those skilled in the art", "prior art" or the like, it should be interpreted as encompassing not only those conventionally used in the field of the present application at the time of filing, but also those that are not commonly used at present, but will be recognized in the art to be useful for similar purposes.

In the context of the present specification, the symbol "I" is generally understood to mean "and/or", for example the expression "more/larger" means "more and/or larger", unless such understanding does not conform to the general knowledge of those skilled in the art.

In the context of the present specification, the term "organic template" is sometimes referred to in the art as structure directing agent or organic directing agent.

In the context of the present specification, as examples of $C_{1-4}$ linear or branched alkyl groups, methyl group, ethyl group or propyl group can be mentioned, among others.

In the context of the present invention, the term "linear or branched oxaalkylene group" refers to a divalent group in which the carbon chain structure of a linear or branched alkylene group is interrupted by one or more (for example 1 to 3, 1 to 2, or 1) hetero group —O—. From the viewpoint of structural stability, it is preferable that, when there are a plurality of hetero groups, any two of the groups are not directly bonded. It is apparent that the term "interrupted" means that the hetero group is not present at either end of the linear or branched alkylene group or the linear or branched oxaalkylene group. As an example, a $C_4$ linear alkylene group (—$CH_2$—$CH_2$—$CH_2$—$CH_2$—) can be interrupted by one hetero group —O— to produce a $C_4$ linear monooxaalkylene group, such as —$CH_2$—O—$CH_2$—$CH_2$—$CH_2$— or —$CH_2$—$CH_2$—O—$CH_2$—$CH_2$— and the like, can be interrupted by two hetero groups —O— to produce a $C_4$ linear dioxaalkylene group, such as —$CH_2$—O—$CH_2$—O—$CH_2$—$CH_2$— or —$CH_2$—O—$CH_2$—O—$CH_2$—$CH_2$— and the like, and can be interrupted by three hetero groups —O— to produce a $C_4$ linear trioxaalkylene group, such as —$CH_2$—O—$CH_2$—O—$CH_2$—O—$CH_2$— and the like. Alternatively, as another example, a $C_4$ branched alkylene group (—$CH_2(CH_3)$—$CH_2$—$CH_2$—) can be interrupted by one hetero group —O— to produce a $C_4$ branched monooxaalkylene group, such as —$CH_2(CH_3)$—O—$CH_2$—$CH_2$—, —$CH_2(CH_3)$—$CH_2$—O—$CH_2$— or —$CH_2(-O-CH_3)$—$CH_2$—$CH_2$— and the like, can be interrupted by two hetero groups —O— to produce a $C_4$ branched dioxaalkylene group, such as —$CH_2(CH_3)$—O—$CH_2$—O—$CH_2$—, —$CH_2(-O-CH_3)$—O—$CH_2$—$CH_2$— or —$CH_2(-O-CH_3)$—$CH_2$—O—$CH_2$—, and the like, and can be interrupted by three hetero groups —O— to produce a $C_4$ branched trioxaalkylene group, such as —$CH_2(-O-CH_3)$—O—$CH_2$—O—$CH_2$— and the like.

In the context of the present specification, the term "total specific surface area" refers to the total area per unit mass of a molecular sieve, including internal surface area and external surface area. Non-porous materials, such as Portland cement, some clay mineral particles, etc., have only an external surface area, while porous materials, such as asbestos fibers, diatomaceous earth, and molecular sieves, have both an external surface area and an internal surface area.

In the context of the present specification, the term "pore volume", also known as porosity volume, refers to the volume of pores per unit mass of a molecular sieve. Further, the term "micropore volume" refers to the volume of all micropores (that is, pores having a pore diameter of less than 2 nm) per unit mass of a molecular sieve.

In the context of the present specification, as well known to those skilled in the art, w, m, s, vs are used in the XRD data of the molecular sieve to describe the intensity of the diffraction peak, in which w means weak, m means medium, s means strong, and vs means very strong. In general, w means less than 20; m means 20-40; s means 40-70; vs means greater than 70.

All percentages, parts, ratios, etc. referred to in the present specification are by weight unless otherwise indicated, or it is not appropriate to be on the basis of weight according to the ordinary knowledge of those skilled in the art.

In the context of the present specification, any two or more aspects of the present invention can be arbitrarily combined, and the technical solution thus obtained forms a part of the original disclosure of the present specification, and also falls within the scope of the present invention.

According to the present invention, at least the following first to sixth embodiments are provided.

First Embodiment

According to an aspect of the present invention, there is provided a molecular sieve, wherein the molecular sieve has a schematic chemical composition represented by the formula "first oxide·second oxide". It is known that molecular sieves sometimes may contain a certain amount of moisture (especially just after its synthesis), but it is considered not necessary in the present application to specify the amount of moisture because the presence or absence of the moisture has no substantial impact on the XRD spectrum of the molecular sieve. In view of this, the schematic chemical composition actually represents a water-free chemical composition of the molecular sieve. Moreover, it is apparent that the schematic chemical composition represents the chemical composition of the framework of the molecular sieve.

According to an aspect of the present invention, the molecular sieve may typically further comprise, in its composition, an organic template and water, etc., such as those filled in its pores, just after its synthesis. Thus, the molecular sieve may sometimes have a schematic chemical composition represented by the formula "first oxide·second oxide·organic template·water". Here, the molecular sieve having the schematic chemical composition represented by the formula "first oxide·second oxide·organic template·water" can be calcined to remove any organic template and water present in the pores thereof, so that the molecular sieve having the schematic chemical composition represented by the formula "first oxide·second oxide" can be obtained. Further, the calcination can be carried out in any conventional manner known in the art, for example at a calcination temperature generally ranging from 300° C. to 750° C., preferably from 400° C. to 600° C., and for a calcination period generally ranging from 1 hour to 10 hours, preferably from 3 hours to 6 hours. In addition, the calcination is generally carried out under an oxygen-containing atmosphere, such as under an air or oxygen atmosphere.

According to an aspect of the present invention, in the aforementioned schematic chemical composition, the first oxide is generally a tetravalent oxide, and can be, for example, at least one selected from the group consisting of silica, germanium dioxide, tin dioxide, titania, and zirconium dioxide, preferably silica ($SiO_2$) or a combination of silica and germanium dioxide. Said first oxides can be used alone or in a combination of two or more thereof in any ratio. When two or more are used in combination, the molar ratio between any two of the first oxides can be, for example, from 20:200 to 35:100. As an example of the combination, silica and germanium dioxide can be used in combination, in which case the molar ratio between the silica and the germanium dioxide can be, for example, from 20:200 to 35:100.

According to an aspect of the present invention, in the aforementioned schematic chemical composition, the second oxide is generally a trivalent oxide, and can be, for example, at least one selected from the group consisting of alumina, a boron oxide, an iron oxide, a gallium oxide, a rare earth oxide, an indium oxide and a vanadium oxide, preferably alumina ($Al_2O_3$). Said second oxides can be used alone or in a combination of two or more thereof in any ratio. When two or more are used in combination, the molar ratio between any two of the second oxides can be, for example, from 30:200 to 60:150.

According to an aspect of the present invention, in the aforementioned schematic chemical composition, as an example of the organic template, any organic template useful in the preparation of molecular sieves can be mentioned, and especially, the organic template used in the preparation of the molecular sieve according to the present embodiment can be mentioned (see detailed description below). Said organic templates can be used alone or in a combination of two or more thereof in any ratio. In particular, examples of the organic template include compounds represented by the following formula (I).

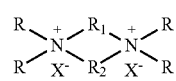

(I)

According to an aspect of the present invention, in the formula (I), the groups $R_1$ and $R_2$ are identical or different from each other, each independently selected from the group consisting of $C_{3-12}$ linear or branched alkylene groups and $C_{3-12}$ linear or branched oxaalkylene groups, the plural groups R are identical or different from each other, each independently selected from the group consisting of $C_{1-4}$ linear or branched alkyl groups, and X is OH.

According to an aspect of the present invention, in the aforementioned schematic chemical composition, the molar ratio of the first oxide to the second oxide (such as the molar ratio of $SiO_2$ to $Al_2O_3$) is generally in a range from 5 to ∞, preferably from 25 to 95, more preferably from 30 to 70. Here, when the molar ratio is ∞, it means that the second oxide is absent or the content of the second oxide in the schematic chemical composition is negligible. The inventors of the present invention have found through careful investigation that the molecular sieve has the molar ratio (such as the molar ratio of $SiO_2$ to $Al_2O_3$), particularly, from 25 to 95 (more particularly from 30 to 70) has not been produced in the prior art.

According to an aspect of the present invention, in the aforementioned schematic chemical composition, the molar ratio of water to the first oxide is generally in a range from 5 to 50, preferably from 5 to 15.

According to an aspect of the present invention, in the aforementioned schematic chemical composition, the molar ratio of the organic template to the first oxide is generally in a range from 0.02 to 0.5, preferably from 0.05 to 0.5, from 0.15 to 0.5 or from 0.3 to 0.5.

According to an aspect of the present invention, depending on the starting materials used in the preparation method, the molecular sieve may sometimes further comprise a metal cation such as an alkali metal and/or alkaline earth metal cation as a component in its composition (generally filled in its pores). In this case, the content of the metal cation, for example, the mass ratio of the metal cation to the first oxide is generally in a range from 0 to 0.02, preferably from 0.0002 to 0.006, but is not limited thereto.

According to an aspect of the present invention, the molecular sieve has an X-ray diffraction pattern substantially as shown in the following table.

| 2θ (°) | d-distance (Å) | Relative intensity ($I/I_0 \times 100$) |
|---|---|---|
| 5.2048 ± 0.05 | 16.96501 ± 0.05 | VS |
| 8.4762 ± 0.27 | 10.42335 ± 0.34 | W |
| 9.0095 ± 0.06 | 9.80755 ± 0.07 | M |
| 10.3943 ± 0.05 | 8.50381 ± 0.05 | W |
| 16.1228 ± 0.50 | 5.49296 ± 0.50 | W |
| 23.7405 ± 0.22 | 3.74484 ± 0.03 | W |

According to an aspect of the present invention, it is preferable that the X-ray diffraction pattern of the molecular sieve further includes an X-ray diffraction peak substantially as shown in the following table.

| 2θ (°) | d-distance (Å) | Relative intensity ($I/I_0 \times 100$) |
|---|---|---|
| 14.3448 ± 0.66 | 6.16955 ± 0.27 | W |
| 15.2971 ± 0.50 | 5.78752 ± 0.50 | W |
| 16.1979 ± 0.50 | 5.46765 ± 0.50 | W |
| 20.8653 ± 0.11 | 4.25393 ± 0.02 | W |
| 23.9532 ± 0.14 | 3.71207 ± 0.02 | W |

According to an aspect of the present invention, it is preferable that the X-ray diffraction pattern of the molecular sieve further includes an X-ray diffraction peak substantially as shown in the following table.

| 2θ (°) | d-distance (Å) | Relative intensity ($I/I_0 \times 100$) |
|---|---|---|
| 14.4217 ± 0.56 | 6.13681 ± 0.43 | W |
| 15.1988 ± 0.50 | 5.82474 ± 0.50 | W |
| 15.5903 ± 0.50 | 5.67936 ± 0.50 | W |
| 20.6353 ± 0.50 | 4.30082 ± 0.10 | W |
| 22.7406 ± 0.08 | 3.90718 ± 0.02 | W |
| 24.4468 ± 0.26 | 3.63823 ± 0.04 | W |

According to an aspect of the present invention, the molecular sieve generally has a columnar crystal particle morphology when observed using a scanning electron microscope (SEM). Here, the term "crystal particle morphology" refers to the (overall) outer shape exhibited by a single crystal particle of the molecular sieve in the observation field of the scanning electron microscope. Further, as the columnar shape, a prismatic shape, particularly a hexagonal prismatic shape, is preferred. Here, the prism refers to a convex prism and generally refers to a right prism and a regular polygonal prism (such as a regular hexagonal prism). It should be specially pointed out that since the growth process of the crystal of the molecular sieve may be disturbed by various factors, there may be a certain degree of deviation when its real crystal particle morphology is compared with a (truely) right prism or a (truely) regular polygonal prism in geometrical sense, such as a deviation of 30%, 20%, or 5%, resulting in the production of a beveled prism, or an irregular polygonal (or even a curved polygonal) prism, but the present invention is not intended to specify the degree of deviation. Moreover, any greater or smaller deviations do not depart from the scope of the present invention.

According to an aspect of the present invention, the molecular sieve (a single crystal particle) has an effective diameter generally ranging from 100 nm to 1000 nm, preferably from 300 nm to 700 nm, when observed using a scanning electron microscope (SEM). Here, the term "effective diameter" means that two points are arbitrarily selected at the cross section of the molecular sieve (a single crystal particle) along the contour (edge) of the cross section, and the linear distance between the two points is measured, where the greatest linear distance is taken as the effective diameter. If the profile of the cross section of the molecular sieve is presented as a polygon such as a hexagon, the effective diameter generally refers to the linear distance between two vertices of the polygon that are farthest from each other, i.e. the diagonal distance. Briefly, the effective diameter substantially corresponds to the diameter of the circumcircle of the polygon representing the contour of the cross section.

According to an aspect of the present invention, the height of the molecular sieve (a single crystal particle) is generally in a range from 100 nm to 1000 nm, preferably from 150 nm to 700 nm, when observed using a scanning electron microscope (SEM). Here, the term "height" refers to a linear distance between the centers of the two end faces of a single crystal particle (columnar crystal) of the molecular sieve. In the usual case, the two end faces of the column of the molecular sieve are substantially parallel to each other, and the linear distance is the vertical distance between the two end faces, but the present invention is not limited thereto.

According to an aspect of the present invention, the aspect ratio of the molecular sieve (a single crystal particle) is generally in a range from 1/3 to 8, preferably from 1.5 to 5 or from 2 to 5, when observed using a scanning electron microscope (SEM). Here, the term "aspect ratio" refers to the ratio of the height to the effective diameter.

According to an aspect of the present invention, the molecular sieve has a total specific surface area generally ranging from 400 $m^2 \cdot g^{-1}$ to 600 $m^2 \cdot g^{-1}$, preferably from 450 $m^2 \cdot g^{-1}$ to 580 $m^2 \cdot g^{-1}$. Here, the total specific surface area is obtained using the liquid nitrogen adsorption method, calculated with the BET model.

According to an aspect of the present invention, the molecular sieve has a pore volume (micropore volume) generally ranging from 0.3 ml/g to 0.5 ml/g, preferably from 0.30 ml/g to 0.40 ml/g. The molecular sieve according to the present invention has a very high micropore volume, which indicates that it belongs to an ultra-macroporous molecular sieve. Here, the pore volume is obtained using the liquid nitrogen adsorption method, calculated with the Horvath-Kawazoe model.

According to an aspect of the present invention, the molecular sieve can be prepared by the following method. Here, the preparation method comprises a step of contacting a first oxide source, a second oxide source, an optional alkali source, an organic template, and water under crystallization conditions to produce a molecular sieve (hereinafter referred to as the contacting step).

According to an aspect of the present invention, in the method for the preparation of the molecular sieve, the contacting step can be carried out in any conventional manner known in the art, for example by using a method comprising mixing the first oxide source, the second oxide source, the optional alkali source, the organic template, and water, and subjecting the mixture to crystallization under the crystallization conditions.

According to an aspect of the present invention, in the contacting step, the organic template comprises at least a compound represented by the following formula (I). Here, the compound represented by the formula (I) can be used alone or in a combination of two or more thereof in any ratio.

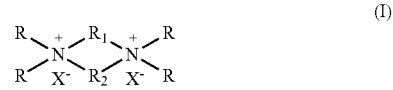
(I)

According to an aspect of the present invention, in the formula (I), the groups $R_1$ and $R_2$ are identical or different from each other, each independently selected from the group consisting of $C_{3-12}$ linear or branched alkylene groups and $C_{3-12}$ linear or branched oxaalkylene groups.

According to a variant embodiment of the present invention, in the formula (I), the groups $R_1$ and $R_2$ are identical or different from each other, one of which is selected from the group consisting of $C_{3-12}$ linear or branched alkylene groups, and the other is selected from the group consisting of $C_{3-12}$ linear or branched alkylene groups and $C_{3-12}$ linear or branched oxaalkylene groups.

According to a variant embodiment of the present invention, in the formula (I), the groups $R_1$ and $R_2$ are identical or different from each other, one of which is selected from the group consisting of $C_{3-12}$ linear alkylene groups and the other is selected from the group consisting of $C_{4-6}$ linear alkylene groups and $C_{4-6}$ linear oxaalkylene groups.

According to a variant embodiment of the present invention, in the formula (I), the groups $R_1$ and $R_2$ are identical or different from each other, each independently selected from the group consisting of $C_{3-12}$ linear or branched alkylene groups.

According to a variant embodiment of the present invention, in the formula (I), the groups $R_1$ and $R_2$ are identical or different from each other, one of which is selected from the group consisting of $C_{3-12}$ linear alkylene groups and the other is selected from the group consisting of $C_{4-6}$ linear alkylene groups.

According to a variant embodiment of the present invention, in the formula (I), the groups $R_1$ and $R_2$ are different from each other, one of which is selected from the group consisting of $C_{3-12}$ linear or branched alkylene groups and the other is selected from the group consisting of $C_{3-12}$ linear or branched oxaalkylene groups.

According to an aspect of the present invention, as an example of the $C_{3-12}$ linear or branched alkylene groups, a $C_{3-12}$ linear alkylene group can be mentioned, and specific examples thereof include n-propylene, isopropylidene, n-butylene, isobutylene, tert-butylene, n-pentylene, isopentylene, neopentylene, n-hexylene, isohexylene, n-octylene, isooctylene, neooctylene, nonylene (or an isomer thereof), decylene (or an isomer thereof), undecylene (or an isomer thereof) or dodecylene (or an isomer thereof), preferably n-propylene, n-butylene, n-pentylene, n-hexylene, n-heptylene, n-octylene, n-nonylene, n-decylene, n-undecylene or n-dodecylene. Further, as an example of the $C_{3-12}$ linear alkylene groups, a $C_{4-6}$ linear alkylene group can be mentioned, and particularly, n-butylene, n-pentylene or n-hexylene can be mentioned.

According to an aspect of the present invention, as the $C_{3-12}$ linear or branched oxaalkylene groups, for example, a $C_{3-12}$ linear oxaalkylene group can be mentioned, and specific examples thereof include —$(CH_2)_2$—O—$(CH_2)$—, —$(CH_2)_2$—O—$(CH_2)_2$—, —$(CH_2)$—O—$(CH_2)_3$—, —$(CH_2)_2$—O—$(CH_2)_3$—, —$(CH_2)$—O-propylene-, —$(CH_2)$—O—$(CH_2)_4$—, —$(CH_2)$—O—$(CH_2)_2$—O—$(CH_2)$—, —$(CH_2)$—O—$(CH_2)_2$—O—$(CH_2)_2$—, —$(CH_2)$—O-tertbutylene-, —$(CH_2)_2$—O—$(CH_2)_4$—, —$(CH_2)_3$—O—$(CH_2)_3$—, —$(CH_2)$—O-neopentylene-, —$(CH_2)_2$—O—$(CH_2)_6$—, —$(CH_2)_2$—O—$(CH_2)_7$—, —$(CH_2)$—O—$(CH_2)_8$—, —$(CH_2)$—O-isooctylene-, —$(CH_2)$—O—$(CH_2)_{10}$—, —$(CH_2)_2$—O-decylene or an isomer thereof-, —$(CH_2)$—O—$(CH_2)_6$—, —$(CH_2)$—O—$(CH_2)_7$—, —$(CH_2)$—O—$(CH_2)_8$—, —$(CH_2)$—O—$(CH_2)$1-, —$(CH_2)$—O—$(CH_2)_2$—O—$(CH_2)$—, —$(CH_2)_2$—O—$(CH_2)_2$—O—$(CH_2)_2$—, —$(CH_2)_2$—O—$(CH_2)_4$—O—$(CH_2)_2$—, —$(CH_2)_2$—O—$(CH_2)_6$—O—$(CH_2)_2$— or —$(CH_2)_2$—O—$(CH_2)_8$—O—$(CH_2)_2$—. Further, as the $C_{3-12}$ linear oxaalkylene groups, for example, a $C_{4-6}$ linear oxaalkylene group can be mentioned, particularly a $C_{4-6}$ linear monooxaalkylene group can be mentioned, and especially an monooxaalkylene group represented by the formula —$(CH_2)_m$—O—$(CH_2)_m$— (where each value m, being identical or different from each other, independently represents 2 or 3, such as 2) can be mentioned. More particularly, —$(CH_2)_2$—O—$(CH_2)_2$—, —$(CH_2)_2$—O—$(CH_2)_3$—, —$(CH_2)_3$—O—$(CH_2)_3$— or —$(CH_2)_2$—O—$(CH_2)_4$— can be mentioned.

According to an aspect of the present invention, in the formula (I), the plural groups R are identical or different from each other, each independently selected from the group consisting of $C_{1-4}$ linear or branched alkyl groups, preferably each independently selected from the group consisting of methyl and ethyl, more preferably all methyl.

According to an aspect of the present invention, in the formula (I), X is OH.

According to an aspect of the present invention, in the contacting step, the molar ratio of the organic template to the first oxide source (calculated on the basis of the first oxide) is generally in a range from 0.02 to 0.5, preferably from 0.05 to 0.5, from 0.15 to 0.5 or from 0.3 to 0.5.

According to an aspect of the present invention, in the contacting step, in addition to the compound represented by the formula (I), other organic templates conventionally used in the art for the preparation of molecular sieves may be further used as the organic template. Preferably, in the contacting step, only the compound represented by the formula (I) is used as the organic template. Here, the compound represented by the formula (I) can be used alone or in a combination of two or more thereof in any ratio.

According to an aspect of the present invention, in the contacting step, the first oxide source is generally a tetravalent oxide source, and for example, can be at least one selected from the group consisting of a silica source, a germanium dioxide source, a tin dioxide source, a titania source and a zirconium dioxide source, preferably a silica source ($SiO_2$) or a combination of a silica source and a germanium dioxide source. Said first oxide sources can be used alone or in a combination of two or more thereof in any ratio. When two or more are used in combination, the molar ratio between any two of the first oxide sources can be, for example, from 20:200 to 35:100. As an example of the combination, a combination of a silica source and a germanium dioxide source can be mentioned, in which case the molar ratio between the silica source and the germanium dioxide source can be, for example, from 20:200 to 35:100.

According to an aspect of the present invention, in the contacting step, as the first oxide source, any corresponding oxide source conventionally used for this purpose in the art can be used, including but not limited to, among others, oxides, hydroxides, alkoxides, metal oxyacid salts, acetates, oxalates, ammonium salts, sulfates, halogenated salts and nitrates of the corresponding metal in the first oxide. For example, when the first oxide is silica, examples of the first oxide source include silica sol, crude silica gel, tetraethyl orthosilicate, water glass, white carbon black, silicic acid, silica gel, potassium silicate, or the like. When the first oxide is germanium dioxide, examples of the first oxide source include germanium tetraalkoxide, germanium oxide, germanium nitrate, or the like. When the first oxide is tin dioxide, examples of the first oxide source include tin chloride, tin sulfate, tin nitrate, and the like. When the first oxide is titania, examples of the first oxide source include titanium tetraalkoxide, titanium dioxide, titanium nitrate, and the like. When the first oxide is zirconium dioxide, examples of the first oxide source include zirconium sulfate, zirconium chloride, zirconium nitrate, and the like. Said first oxide sources can be used alone or in a combination of two or more thereof in a desired ratio.

According to an aspect of the present invention, in the contacting step, the second oxide source is generally a trivalent oxide source, such as at least one selected from the group consisting of an alumina source, a boron oxide source, an iron oxide source, a gallium oxide source, a rare earth oxide source, an indium oxide source, and a vanadium oxide source, preferably an alumina ($Al_2O_3$) source. Said second oxide sources can be used alone or in a combination of two or more thereof in any ratio. When two or more are used in combination, the molar ratio between any two of the second oxide sources can be, for example, from 30:200 to 60:150.

According to an aspect of the present invention, in the contacting step, as the second oxide source, any corresponding oxide source conventionally used for this purpose in the art can be used, including but not limited to, among others, oxides, hydroxides, alkoxides, metal oxyacid salts, acetates, oxalates, ammonium salts, sulfates, halogenated salts and nitrates of the corresponding metal in the second oxide. For example, when the second oxide is alumina, examples of the second oxide source include aluminum chloride, aluminum sulfate, hydrated alumina, sodium metaaluminate, aluminum sol, aluminum hydroxide or the like. When the second oxide is boron oxide, examples of the second oxide source include boric acid, borate, borax, boron trioxide and the like. When the second oxide is iron oxide, examples of the second oxide source include iron nitrate, iron chloride, iron oxide, and the like. When the second oxide is gallium oxide, examples of the second oxide source include gallium nitrate, gallium sulfate, gallium oxide, and the like. When the second oxide is a rare earth oxide, examples of the second oxide source include lanthanum oxide, neodymium oxide, yttrium oxide, cerium oxide, lanthanum nitrate, neodymium nitrate, yttrium nitrate, ammonium cerium sulfate, and the like. When the second oxide is indium oxide, examples of the second oxide source include indium chloride, indium nitrate, indium oxide, and the like. When the second oxide is vanadium oxide, examples of the second oxide source include vanadium chloride, ammonium metavanadate, sodium vanadate, vanadium dioxide, vanadyl sulfate, and the like. Said second oxide sources can be used alone or in a combination of two or more thereof in a desired ratio.

According to an aspect of the present invention, in the contacting step, the molar ratio of the first oxide source (calculated on the basis of the first oxide, such as $SiO_2$) to the second oxide source (calculated on the basis of the second oxide, such as $Al_2O_3$) is generally in a range from 5 to ∞, preferably from 25 to 95, more preferably from 30 to 70. Here, when the molar ratio is ∞, it means that the second oxide source is not used or the second oxide source is not intentionally introduced in the contacting step.

According to an aspect of the present invention, in the contacting step, the molar ratio of water to the first oxide source (calculated on the basis of the first oxide) is generally in a range from 5 to 50, preferably from 5 to 15.

According to an aspect of the present invention, in the contacting step, an alkali source may or may not be used. When the alkali source is not intentionally used, the group X contained in the compound represented by the formula (I) can be used to provide the $OH^-$ required herein. Here, as the alkali source, any alkali source conventionally used for this purpose in the art can be used, including but not limited to inorganic bases comprising an alkali metal or alkaline earth metal as the cation, particularly sodium hydroxide and potassium hydroxide. Said alkali sources can be used alone or in a combination of two or more thereof in any ratio.

According to an aspect of the present invention, in the contacting step, the molar ratio of the alkali source (calculated on the basis of $OH^-$) to the first oxide source (calculated on the basis of the first oxide) is generally in a range from 0 to 1, preferably from 0.04 to 1, from 0.1 to 1, from 0.2 to 1, from 0.3 to 0.7 or from 0.45 to 0.7.

According to an aspect of the present invention, in the contacting step, as the crystallization condition, the crystallization temperature is generally in a range from 80° C. to 120° C., preferably from 120° C. to 170° C. or from 120° C. to 200° C.

According to an aspect of the present invention, in the contacting step, as the crystallization condition, the crystallization period is generally at least 1 day, preferably at least 2 days, preferably from 3 days to 8 days, from 5 days to 8 days or from 4 days to 6 days.

According to an aspect of the present invention, in the method for the preparation of the molecular sieve, after the contacting step is completed, the molecular sieve can be separated as a product from the resultant reaction mixture by any separation method commonly known. Here, the molecular sieve product comprises the molecular sieve according to the present invention. Further, as the separation method, for example, a method comprising filtering, washing, and drying the resultant reaction mixture can be mentioned.

According to an aspect of the present invention, in the method for the preparation of the molecular sieve, the filtration, washing and drying can be carried out in any conventional manner known in the art. By way of example, as the filtration, for example, the resultant reaction mixture can be simply subjected to suction filtration. As the washing, for example, washing with deionized water can be performed until the pH of the filtrate reaches 7-9, preferably 8-9. The drying temperature is, for example, 40 to 250° C., preferably 60 to 150° C., and the drying time is, for example, 8 to 30 hours, preferably 10 to 20 hours. The drying can be carried out under normal pressure or under reduced pressure.

According to an aspect of the present invention, the method for the preparation of the molecular sieve may further comprise a step of calcining the resultant molecular sieve (hereinafter referred to as the calcination step) as needed to remove the organic template and possible moisture, and the like, so that a calcined molecular sieve can be obtained. In the context of the present specification, the molecular sieves before and after calcination are collectively referred to as the molecular sieve of the present invention or the molecular sieve according to the present invention.

According to an aspect of the present invention, in the method for the preparation of the molecular sieve, the calcination can be carried out in any conventional manner known in the art, for example, at a calcination temperature generally ranging from 300° C. to 750° C., preferably from 400° C. to 600° C. for a calcination period generally ranging from 1 hour to 10 hours, preferably from 3 hours to 6 hours. In addition, the calcination is generally carried out under an oxygen-containing atmosphere, such as an air or oxygen atmosphere.

According to an aspect of the present invention, if desired, the molecular sieve according to the present invention or any molecular sieve produced by the method for the preparation of a molecular sieve according to the present invention (in the context of the present specification, both are collectively referred to as the molecular sieve of the present invention or the molecular sieve according to the present invention) can further be subjected to ion exchange by any conventional means known in the art, for example by using an ion exchange or solution impregnation process (see, for example, U.S. Pat. Nos. 3,140,249 and 3,140,253, etc.), so that the metal cation (such as Na ion or K ion, depending on the preparation method) contained therein can be replaced in whole or in part by other cation(s). Examples of said other cation include hydrogen ion, other alkali metal ions (including K ion, Rb ion, etc.), ammonium ions (including $NH_4$ ion, quaternary ammonium ions such as tetramethylammonium ion and tetraethylammonium ion, etc.), alkaline earth metal ions (including Mg ion, Ca ion), Mn ion, Zn ion, Cd ion, noble metal ions (including Pt ion, Pd ion, Rh ion, etc.), Ni ion, Co ion, Ti ion, Sn ion, Fe ion and/or rare earth metal ions, and the like.

The molecular sieve according to the present invention can be further treated with a dilute acid solution or the like as needed to increase the silica-alumina ratio, or treated with water vapor to improve the resistance of the molecular sieve crystal to acid attack.

The molecular sieve according to the present invention has good thermal/hydrothermal stability and has a larger pore volume. Thus, the molecular sieve according to the present invention is capable of adsorbing more/larger molecules, thereby exhibiting excellent adsorptive/catalytic properties.

The molecular sieve according to the present invention has a relatively strong acidity, particularly a large number of L acid sites. This molecular sieve has not been produced in the prior art. As a result, the molecular sieve according to the present invention has better performance particularly in an acid-catalyzed reaction.

The molecular sieve according to the present invention can be in any physical form, such as powders, granules or molded articles (e.g., strips, clovers, etc.). These physical forms can be obtained in any conventional manner known in the art, and are not particularly limited.

Second Embodiment

According to an aspect of the present invention, there is provided a molecular sieve having an X-ray diffraction pattern substantially as shown in the following table.

| 2θ (°) | d-distance (Å) | Relative intensity ($I/I_0 \times 100$) |
|---|---|---|
| 5.2048 ± 0.05 | 16.96501 ± 0.05 | VS |
| 8.4762 ± 0.27 | 10.42335 ± 0.34 | W |
| 9.0095 ± 0.06 | 9.80755 ± 0.07 | M |
| 10.3943 ± 0.05 | 8.50381 ± 0.05 | W |
| 16.1228 ± 0.50 | 5.49296 ± 0.50 | W |
| 23.7405 ± 0.22 | 3.74484 ± 0.03 | W |

According to an aspect of the present invention, it is preferable that the X-ray diffraction pattern of the molecular sieve further includes an X-ray diffraction peak substantially as shown in the following table.

| 2θ (°) | d-distance (Å) | Relative intensity ($I/I_0 \times 100$) |
|---|---|---|
| 14.3448 ± 0.66 | 6.16955 ± 0.27 | W |
| 15.2971 ± 0.50 | 5.78752 ± 0.50 | W |
| 16.1979 ± 0.50 | 5.46765 ± 0.50 | W |
| 20.8653 ± 0.11 | 4.25393 ± 0.02 | W |
| 23.9532 ± 0.14 | 3.71207 ± 0.02 | W |

According to an aspect of the present invention, it is preferable that the X-ray diffraction pattern of the molecular sieve further includes an X-ray diffraction peak substantially as shown in the following table.

| 2θ (°) | d-distance (Å) | Relative intensity ($I/I_0 \times 100$) |
|---|---|---|
| 14.4217 ± 0.56 | 6.13681 ± 0.43 | W |
| 15.1988 ± 0.50 | 5.82474 ± 0.50 | W |
| 15.5903 ± 0.50 | 5.67936 ± 0.50 | W |
| 20.6353 ± 0.50 | 4.30082 ± 0.10 | W |
| 22.7406 ± 0.08 | 3.90718 ± 0.02 | W |
| 24.4468 ± 0.26 | 3.63823 ± 0.04 | W |

According to an aspect of the present invention, the molecular sieve (referring to its single crystal particle) has a crystal particle morphology of sponge structure, particularly a native crystal particle morphology of sponge structure, when observed using a scanning electron microscope (SEM). Here, the term "crystal particle morphology" refers to the (overall) outer shape exhibited by a single crystal particle of the molecular sieve in the observation field of the scanning electron microscope. In addition, the term "native" refers to the structure of the molecular sieve objectively and directly presented after preparation, rather than the structure of the molecular sieve presented after being artificially processed after preparation.

The inventors of the present invention have found through careful investigation that the molecular sieve having both the aforementioned specific X-ray diffraction pattern and the aforementioned specific (native) crystal particle morphology has not been produced in the prior art.

According to an aspect of the present invention, the sponge structure generally comprises micropores (pores in framework). This is an inherent property of molecular sieves as microporous materials.

According to an aspect of the present invention, the diameter (average diameter) of the micropores is generally in a range from 0.5 nm to less than 2 nm. In a preferred case, the micropores have a diameter ranging from 0.5 nm to 0.8 nm, or from 1.1 nm to 1.8 nm. In a more preferred case, the diameter of the micropores exhibits a bimodal distribution, including both diameters ranging from 0.5 nm to 0.8 nm and from 1.1 nm to 1.8 nm. Here, the diameter is obtained using the liquid nitrogen adsorption method, calculated with the DFT density functional theory model. In view of the large diameter of micropores, the molecular sieve according to the present invention is considered to be an ultra-macroporous molecular sieve.

According to an aspect of the present invention, the total specific surface area of the micropores is generally in a range from 100 $m^2 \cdot g^{-1}$ to 300 $m^2 \cdot g^{-1}$, preferably from 150 $m^2 \cdot g^{-1}$ to 250 $m^2 \cdot g^{-1}$. Here, the total specific surface area is obtained using the liquid nitrogen adsorption method, calculated with the BET model.

According to an aspect of the present invention, the pore volume of the micropores is generally in a range from 0.03 ml/g to 0.20 ml/g, preferably from 0.05 ml/g to 0.15 ml/g. Here, the pore volume is measured by the Horvath-Kawazoe method. Further, without being bound by any theory, the inventors of the present invention believe that the pore volume of the micropores has such a low value because the original position of micropores has been occupied by coarse pores and/or mesopores as described below. Therefore, if these coarse pores and mesopores are replaced with micropores, the pore volume of micropores would have a very high value.

Figure 64A:
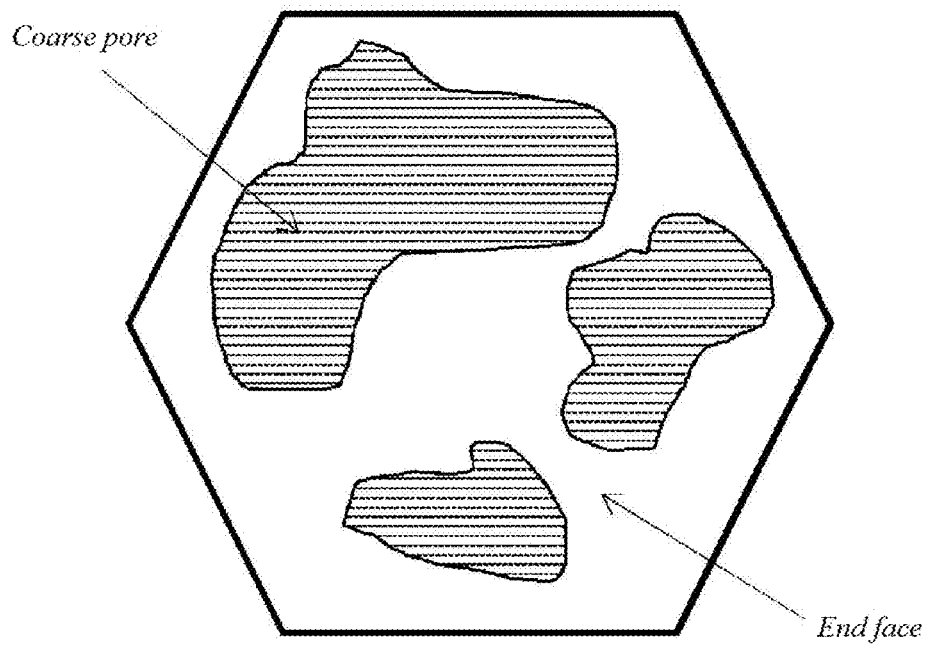
FIG. 64A is a schematic view of a sponge structure comprising coarse pores and/or mesopores.
Figure 64B:
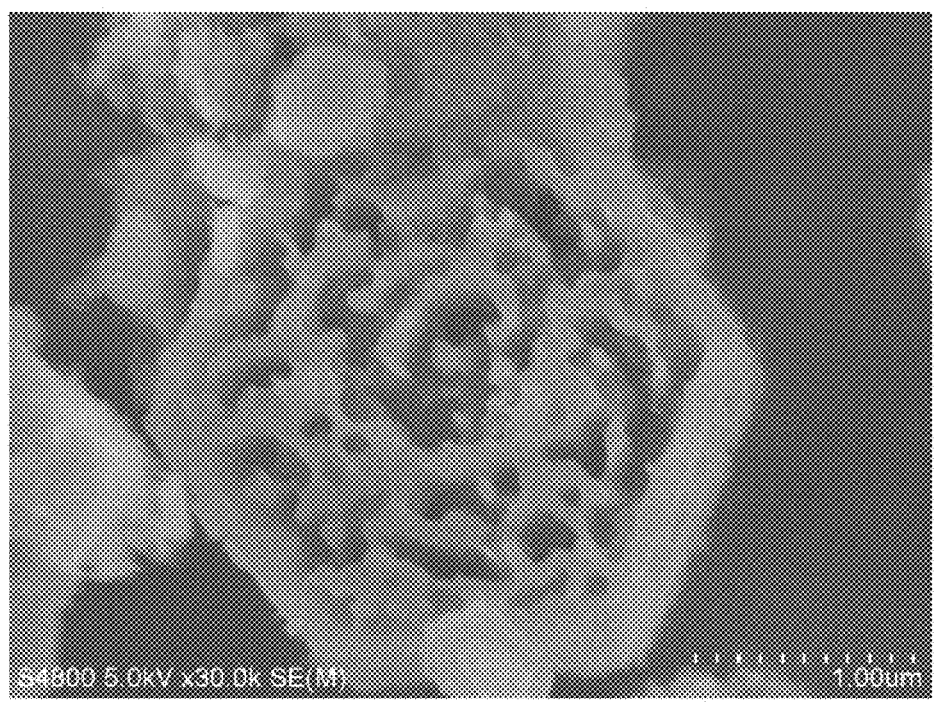
FIG. 64B is a scanning electron micrograph of a sponge structure comprising coarse pores and/or mesopores.

According to a variant embodiment of the present invention, the sponge structure may also comprise coarse pores when observed using a scanning electron microscope (SEM). This can be understood, for example, by referring to FIGS. 64A and 64B. Here, the FIGS. 64A and 64B are only provided for illustrating the present invention and are not intended to limit the present invention. In the sponge structure of the molecular sieve (a single crystal particle) of the present invention, the coarse pores and the micropores communicate with each other and intersect each other to form a pore structure with complicated network. This coarse-pored ultra-macroporous molecular sieve has not been produced in the prior art. As a result, the molecular sieve according to the present invention exhibits the characteristics of macroporous materials in addition to the characteristics of microporous materials.

According to a variant embodiment of the present invention, the sponge structure may also comprise mesopores when observed using a scanning electron microscope (SEM). In the sponge structure of the molecular sieve (a single crystal particle) of the present invention, the mesopores and the micropores communicate with each other and intersect each other to form a pore structure with complicated network. This mesoporous ultra-macroporous molecular sieve has not been produced in the prior art. As a result, the molecular sieve according to the present invention exhibits the characteristics of mesoporous materials in addition to the characteristics of microporous materials.

According to a variant embodiment of the present invention, the sponge structure may also comprise both coarse pores and mesopores when observed using a scanning electron microscope (SEM). This multiple-porous ultra-macroporous molecular sieve has not been produced in the prior art. As a result, the molecular sieve according to the present invention exhibits the characteristics of microporous materials, in combination with the characteristics of macroporous materials and mesoporous materials.

According to a variant embodiment of the present invention, the coarse pores are opened on one end face or both end faces of the sponge structure (in this case, the coarse pore becomes a full through hole or a half through hole), when observed using a scanning electron microscope (SEM). In this case, the sponge structure can exhibit, for example, a crystal particle morphology similar to honeycomb coal. Moreover, the sponge structure has an open or semi-open pore sponge structure. In addition, the coarse pores may also be opened on one or more side faces of the sponge structure, resulting in hollowed-out side face(s), thereby further increasing the permeability of the sponge structure.

According to a variant embodiment of the present invention, when observed using a scanning electron microscope (SEM), the mesopores are opened at one or both end faces of the sponge structure (in this case, the mesopore becomes a full through hole or a half through hole). In this case, the sponge structure can exhibit, for example, a crystal particle morphology similar to honeycomb coal. Moreover, the open pore sponge structure has an open pore or semi-open pore sponge structure. In addition, the mesopores may also be opened on one or more side faces of the sponge structure, resulting in hollowed-out side face(s), thereby further increasing the permeability of the sponge structure.

According to an aspect of the present invention, the diameter (average diameter) of the coarse pores is generally in a range from 80 nm to 2 μm, preferably from 80 nm to 1.5 μm. Here, the diameter is measured by the mercury intrusion method.

According to an aspect of the present invention, the total specific surface area of the coarse pores is generally in a range from 10 $m^2 \cdot g^{-1}$ to 100 $m^2 \cdot g^{-1}$, preferably from 50 $m^2 \cdot g^{-1}$ to 100 $m^2 \cdot g^{-1}$. Here, the total specific surface area is measured by the mercury intrusion method.

According to an aspect of the present invention, the pore volume of the coarse pores is generally in a range from 0.5 ml/g to 3.0 ml/g, preferably from 1.0 ml/g to 2.0 ml/g. Here, the pore volume is measured by the mercury intrusion method.

According to an aspect of the present invention, the diameter (average diameter) of the mesopores is generally in a range from 2 nm to 30 nm. In a preferred case, the mesopores have a diameter ranging from 2 nm to 4 nm, or from 7 nm to 15 nm, and the latter is more preferably from 8 nm to 9 nm. In a more preferred case, the diameter of the mesopores has a bimodal distribution, including both diameters ranging from 2 nm to 4 nm and from 7 nm to 15 nm. Here, the diameter is obtained using the liquid nitrogen adsorption method, calculated with the BET model.

According to an aspect of the present invention, the total specific surface area of the mesopores is generally in a range from 50 $m^2 \cdot g^{-1}$ to 250 $m^2 \cdot g^{-1}$, preferably from 100 $m^2 \cdot g^{-1}$ to 150 $m^2 \cdot g^{-1}$. Here, the total specific surface area is obtained using the liquid nitrogen adsorption method, calculated with the BET model.

According to an aspect of the present invention, the pore volume of the mesopores is generally in a range from 0.05 ml/g to 0.40 ml/g, preferably from 0.15 ml/g to 0.30 ml/g. Here, the pore volume is obtained using the liquid nitrogen adsorption method, calculated with the BET model.

According to a variant embodiment of the present invention, the sponge structure comprises the coarse pores, mesopores and micropores as previously described at the same time. In the sponge structure of the molecular sieve (a single crystal particle) of the present invention, the coarse pores, the mesopores and the micropores communicate with each other and intersect each other to form a pore structure with complicated network. This multiple-porous ultra-macroporous molecular sieve has not been produced in the prior art. As a result, the molecular sieve according to the present invention exhibits the characteristics of microporous materials, in combination with the characteristics of mesoporous materials and/or macroporous materials, so that it is capable of adsorbing more/larger molecules, thereby exhibiting excellent adsorptive/catalytic performance.

According to an aspect of the present invention, the molecular sieve generally also has a columnar crystal particle morphology when observed using a scanning electron microscope (SEM). Here, as the columnar shape, a prismatic shape, particularly a hexagonal prismatic shape, is preferred. In addition, the prism refers to a convex prism and generally refers to a right prism and a regular polygonal prism (such as a regular hexagonal prism). It should be specially pointed out that since the growth process of the crystal of the molecular sieve may be disturbed by various factors, there may be a certain degree of deviation when its real crystal particle morphology is compared with a (truely) right prism or a (truely) regular polygonal prism in geometrical sense, such as a deviation of 30%, 20%, or 5%, resulting in the production of a beveled prism, or an irregular polygonal (or even a curved polygonal) prism, but the present invention is not intended to specify the degree of deviation. Moreover, any greater or smaller deviations do not depart from the scope of the present invention.

According to an aspect of the present invention, the molecular sieve (a single crystal particle) has an effective diameter generally ranging from 100 nm to 5000 nm, preferably from 1000 nm to 3000 nm, when observed using a scanning electron microscope (SEM). Here, the term "effective diameter" means that two points are arbitrarily selected at the cross section of the molecular sieve (a single crystal particle) along the contour (edge) of the cross section, and the linear distance between the two points is measured, where the greatest linear distance is taken as the effective diameter. If the profile of the cross section of the molecular sieve is presented as a polygon such as a hexagon, the effective diameter generally refers to the linear distance between two vertices of the polygon that are farthest from each other, i.e. the diagonal distance. Briefly, the effective diameter substantially corresponds to the diameter of the circumcircle of the polygon representing the contour of the cross section.

Figure 65A:
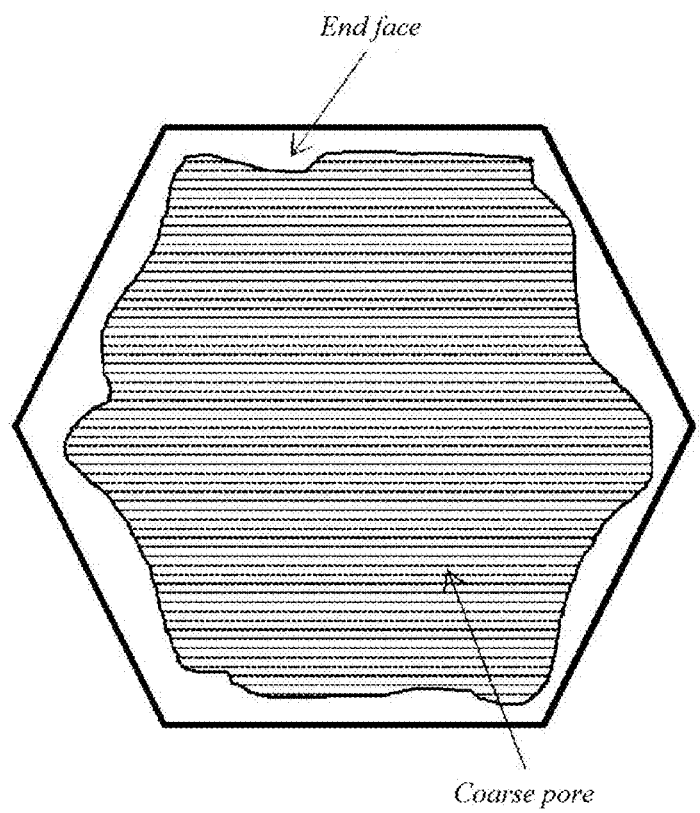
FIG. 65A is a schematic view of a molecular sieve having a hollow columnar crystal particle morphology.
Figure 65B:
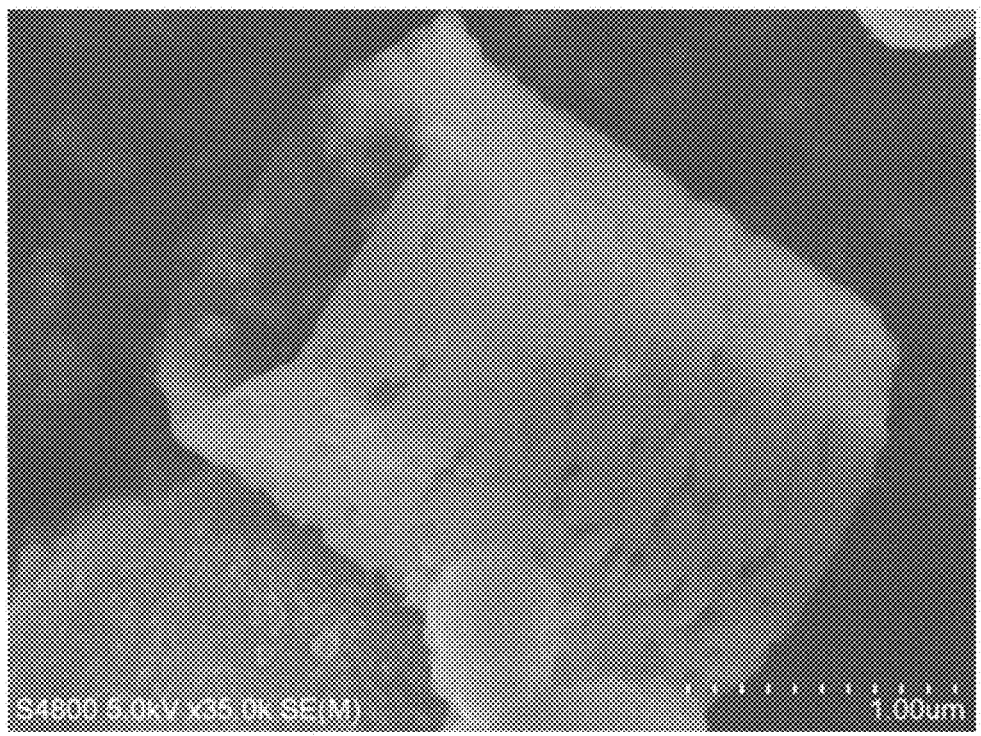
FIG. 65B is a scanning electron micrograph of a molecular sieve having a hollow columnar crystal particle morphology.
Figure 66:
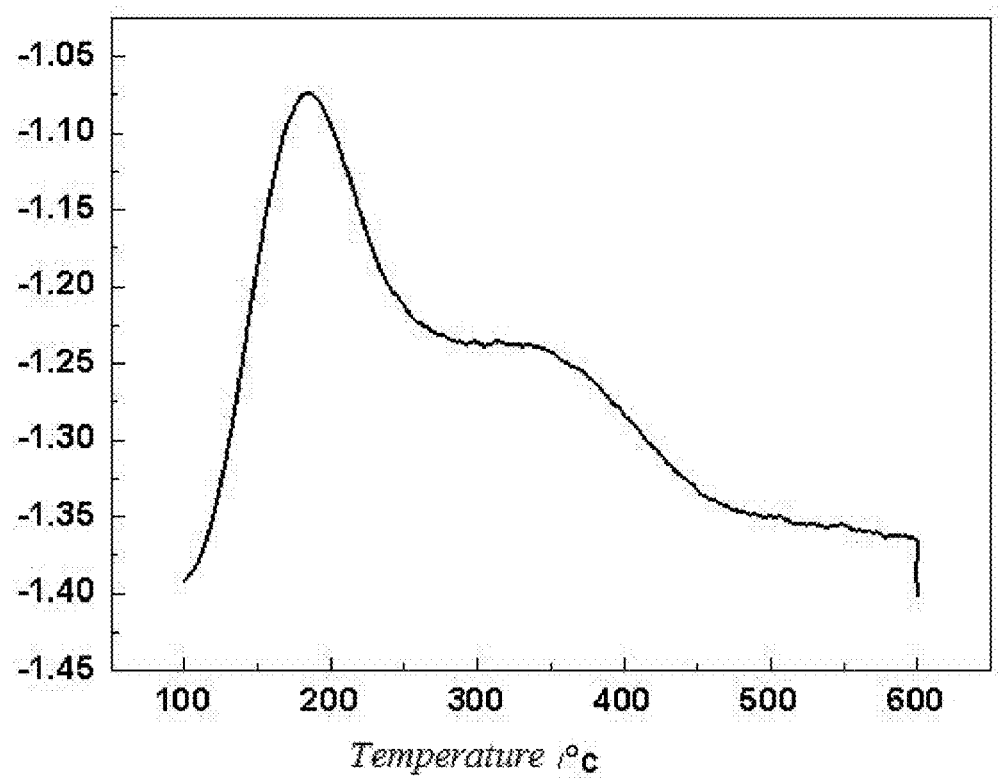
FIG. 66 is a NH3-TPD pattern of the molecular sieve produced in Example V-7.

According to an aspect of the present invention, the molecular sieve may exhibit a hollow columnar crystal particle morphology, where the diameter of the coarse pores is sufficiently large (e.g., close to the effective diameter of the molecular sieve). This can be understood, for example, by referring to FIGS. 65A and 65B. Here, the FIGS. 65A and 65B are only provided for illustrating the present invention, and are not intended to limit the present invention. Here, the term "hollow columnar" means a tubular structure. Here, the wall thickness of the tubular structure can be, for example, from 50 nm to 400 nm, but the present invention is not limited thereto, and it is not intended to specify the wall thickness.

According to an aspect of the present invention, the molecular sieve (a single crystal particle) has a height generally ranging from 500 nm to 3000 nm, preferably from 1000 nm to 3000 nm, when observed using a scanning electron microscope (SEM). Here, the term "height" refers to a linear distance between the centers of the two end faces of a single crystal particle (columnar crystal particle) of the molecular sieve. In the usual case, the two end faces of the column of the molecular sieve are substantially parallel to each other, and the linear distance is the vertical distance between the two end faces, but the present invention is not limited thereto.

According to an aspect of the present invention, the molecular sieve (a single crystal particle) has an aspect ratio generally ranging from 1/3 to 5, preferably from 1/3 to 3, when observed using a scanning electron microscope (SEM). Here, the term "aspect ratio" refers to the ratio of the height to the effective diameter.

According to an aspect of the present invention, the molecular sieve generally has a schematic chemical composition represented by the formula "first oxide·second oxide". It is known that molecular sieves may sometimes contain a certain amount of moisture (especially just after synthesis), but it is considered not necessary in the present application to specify the amount of moisture because the presence or absence of the moisture has no substantial compact on the XRD spectrum of the molecular sieve. In view of this, the schematic chemical composition actually represents a water-free chemical composition of the molecular sieve. Moreover, it is apparent that the schematic chemical composition represents the chemical composition of the framework of the molecular sieve.

According to an aspect of the present invention, the molecular sieve may typically further comprise, in its composition, an organic template and water, etc., such as those filled in its pores, just after its synthesis. Therefore, the molecular sieve may sometimes have a schematic chemical composition represented by the formula "first oxide·second oxide·organic template·water". Here, the molecular sieve having the schematic chemical composition represented by the formula "first oxide·second oxide·organic template·water" can be calcined to remove any organic template and water present in the pores thereof, so that the molecular sieve having the schematic chemical composition represented by the formula "first oxide·second oxide" can be obtained. Further, the calcination can be carried out in any conventional manner known in the art, for example at a calcination temperature generally ranging from 300° C. to 750° C., preferably from 400° C. to 600° C. for a calcination period generally ranging from 1 hour to 10 hours, preferably from 3 hours to 6 hours. In addition, the calcination is generally carried out under an oxygen-containing atmosphere, such as an air or oxygen atmosphere.

According to an aspect of the present invention, in the aforementioned schematic chemical composition, the first oxide is generally a tetravalent oxide, and can be, for example, at least one selected from the group consisting of silica, germanium dioxide, tin dioxide, titania, and zirconium dioxide, preferably silica ($SiO_2$) or a combination of silica and germanium dioxide. Said first oxides can be used alone or in a combination of two or more thereof in any ratio. When two or more are used in combination, the molar ratio between any two of the first oxides can be, for example, from 20:200 to 35:100. As an example of the combination, silica and germanium dioxide can be used in combination, in which case the molar ratio between the silica and the germanium dioxide can be, for example, from 20:200 to 35:100.

According to an aspect of the present invention, in the aforementioned schematic chemical composition, the second oxide is generally a trivalent oxide, and can be, for example, at least one selected from the group consisting of alumina, a boron oxide, an iron oxide, a gallium oxide, a rare earth oxide, an indium oxide and a vanadium oxide, preferably alumina ($Al_2O_3$). Said second oxides can be used alone or in a combination of two or more thereof in any ratio. When two or more are used in combination, the molar ratio between any two of the second oxides can be, for example, from 30:200 to 60:150.

According to an aspect of the present invention, in the aforementioned schematic chemical composition, as an example of the organic template, any organic template useful in the preparation of molecular sieves can be mentioned, and especially, the organic template used in the preparation of the molecular sieve according to the present embodiment can be mentioned (see detailed description below). Said organic templates can be used alone or in a combination of two or more thereof in any ratio. In particular, examples of the organic template include compounds represented by the following formula (I).

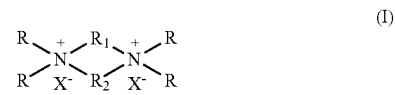

(I)

According to an aspect of the present invention, in the formula (I), the groups $R_1$ and $R_2$ are different from each other, one of which is selected from the group consisting of $C_{3-12}$ linear or branched alkylene groups and the other is selected from the group consisting of $C_{3-12}$ linear or branched oxaalkylene groups, the plural groups R are identical or different from each other, each independently selected from the group consisting of $C_{1-4}$ linear or branched alkyl groups, and X is OH.

According to an aspect of the present invention, in the aforementioned schematic chemical composition, the molar ratio of the first oxide to the second oxide (such as a molar ratio of $SiO_2$ to $Al_2O_3$) is generally in a range from 30 to 100, preferably from 55 to 100.

According to an aspect of the present invention, in the aforementioned schematic chemical composition, the molar ratio of water to the first oxide is generally in a range from 5 to 50, preferably from 5 to 15.

According to an aspect of the present invention, in the aforementioned schematic chemical composition, the molar ratio of the organic template to the first oxide is generally in a range from 0.02 to 0.5, preferably from 0.05 to 0.5, from 0.15 to 0.5 or from 0.3 to 0.5.

According to an aspect of the present invention, depending on the starting materials used in the preparation method, the molecular sieve may sometimes further comprise a metal cation such as an alkali metal and/or alkaline earth metal cation as a component in its composition (generally filled in its pores). In this case, the content of the metal cation, for example, the mass ratio of the metal cation to the first oxide is generally in a range from 0 to 0.02, preferably from 0.0002 to 0.006, but is not limited thereto.

According to an aspect of the present invention, the molecular sieve can be prepared by the following method. Here, the preparation method comprises a step of contacting a first oxide source, a second oxide source, an optional alkali source, an organic template, and water under crystallization conditions to produce a molecular sieve (hereinafter referred to as the contacting step).

According to an aspect of the present invention, in the method for the preparation of the molecular sieve, the contacting step can be carried out in any conventional manner known in the art, for example by using a method comprising mixing the first oxide source, the second oxide source, the optional alkali source, the organic template, and water, and subjecting the mixture to crystallization under the crystallization conditions.

According to an aspect of the present invention, in the contacting step, the organic template comprises at least a compound represented by the following formula (I). Here, the compound represented by the formula (I) can be used alone or in a combination of two or more thereof in any ratio.

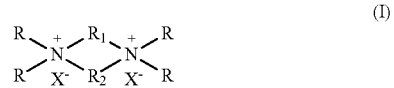

(I)

According to an aspect of the present invention, in the formula (I), the groups $R_1$ and $R_2$ are different from each other, one of which is selected from the group consisting of $C_{3-12}$ linear or branched alkylene groups, and the other is selected from the group consisting of $C_{3-12}$ linear or branched oxaalkylene groups.

According to an aspect of the present invention, as an example of the $C_{3-12}$ linear or branched alkylene groups, a $C_{3-12}$ linear alkylene group can be mentioned, and specific examples thereof include n-propylene, isopropylidene, n-butylene, isobutylene, tert-butylene, n-pentylene, isopentylene, neopentylene, n-hexylene, isohexylene, n-octylene, isooctylene, neooctylene, nonylene (or an isomer thereof), decylene (or an isomer thereof), undecylene (or an isomer thereof) or dodecylene (or an isomer thereof), preferably n-propylene, n-butylene, n-pentylene, n-hexylene, n-heptylene, n-octylene, n-nonylene, n-decylene, n-undecylene or n-dodecylene.

According to an aspect of the present invention, as the $C_{3-12}$ linear or branched oxaalkylene groups, for example, a $C_{3-12}$ linear oxaalkylene group can be mentioned, and specific examples thereof include —(CH$_2$)$_2$—O—(CH$_2$)—, —(CH$_2$)$_2$—O—(CH$_2$)$_2$—, —(CH$_2$)—O—(CH$_2$)$_3$—, —(CH$_2$)$_2$—O—(CH$_2$)$_3$—, —(CH$_2$)—O-propylene-, —(CH$_2$)—O—(CH$_2$)$_4$—, —(CH$_2$)—O—(CH$_2$)$_2$—O—(CH$_2$)—, —(CH$_2$)—O—(CH$_2$)$_2$—O—(CH$_2$)$_2$—, —(CH$_2$)—O-tertbutylene-, —(CH$_2$)$_2$—O—(CH$_2$)$_4$—, —(CH$_2$)$_3$—O—(CH$_2$)$_3$—, —(CH$_2$)—O-neopentylene-, —(CH$_2$)$_2$—O—(CH$_2$)$_6$—, —(CH$_2$)$_2$—O—(CH$_2$)$_7$—, —(CH$_2$)—O—(CH$_2$)$_8$—, —(CH$_2$)—O-isooctylene-, —(CH$_2$)—O—(CH$_2$)$_{10}$—, —(CH$_2$)$_2$—O-decylene or an isomer thereof-, —(CH$_2$)—O—(CH$_2$)$_6$—, —(CH$_2$)—O—(CH$_2$)$_7$—, —(CH$_2$)—O—(CH$_2$)$_8$—, —(CH$_2$)—O—(CH$_2$)—, —(CH$_2$)—O—(CH$_2$)$_2$—O—(CH$_2$)—, —(CH$_2$)$_2$—O—(CH$_2$)$_2$—O—(CH$_2$)$_2$—, —(CH$_2$)$_2$—O—(CH$_2$)$_2$—O—(CH$_2$)$_2$—, —(CH$_2$)$_2$—O—(CH$_2$)$_4$—O—(CH$_2$)$_2$—, —(CH$_2$)$_2$—O—(CH$_2$)$_2$—O—(CH$_2$)$_6$—O—(CH$_2$)$_2$— or —(CH$_2$)$_2$—O—(CH$_2$)$_8$—O—(CH$_2$)$_2$—. Further, as the $C_{3-12}$ linear oxaalkylene groups, a $C_{4-6}$ linear oxaalkylene group can be mentioned, and a $C_{4-6}$ linear monooxaalkylene group can be particularly mentioned, and especially an monooxaalkylene group represented by the formula —(CH$_2$)$_m$—O—(CH$_2$)$_m$— (where each value m, being identical or different from each other, independently represents 2 or 3, such as 2) can be mentioned. More particularly, —(CH$_2$)$_2$—O—(CH$_2$)$_2$—, —(CH$_2$)$_2$—O—(CH$_2$)$_3$—, —(CH$_2$)$_3$—O—(CH$_2$)$_3$— or —(CH$_2$)$_2$—O—(CH$_2$)$_4$— can be mentioned.

According to an aspect of the present invention, in the formula (I), the plural groups R are identical or different from each other, each independently selected from the group consisting of $C_{1-4}$ linear or branched alkyl groups, preferably each independently selected from the group consisting of methyl and ethyl, more preferably all methyl.

According to an aspect of the present invention, in the formula (I), X is OH.

According to an aspect of the present invention, in the contacting step, the molar ratio of the organic template to the first oxide source (calculated on the basis of the first oxide) is generally in a range from 0.02 to 0.5, preferably from 0.05 to 0.5, from 0.15 to 0.5 or from 0.3 to 0.5.

According to an aspect of the present invention, in the contacting step, in addition to the compound represented by the formula (I), other organic templates conventionally used in the art for the preparation of molecular sieves may be further used as the organic template. Preferably, in the contacting step, only the compound represented by the formula (I) is used as the organic template. Here, the compound represented by the formula (I) can be used alone or in a combination of two or more thereof in any ratio.

According to an aspect of the present invention, in the contacting step, the first oxide source is generally a tetravalent oxide source, and for example, can be at least one selected from the group consisting of a silica source, a germanium dioxide source, a tin dioxide source, a titania source and a zirconium dioxide source, preferably a silica source ($SiO_2$) or a combination of a silica source and a germanium dioxide source. Said first oxide sources can be used alone or in a combination of two or more thereof in any ratio. When two or more are used in combination, the molar ratio between any two of the first oxide sources can be, for example, from 20:200 to 35:100. As an example of the combination, a combination of a silica source and a germanium dioxide source can be mentioned, in which case the molar ratio between the silica source and the germanium dioxide source can be, for example, from 20:200 to 35:100.

According to an aspect of the present invention, in the contacting step, as the first oxide source, any corresponding oxide source conventionally used for this purpose in the art can be used, including but not limited to, among others, oxides, hydroxides, alkoxides, metal oxyacid salts, acetates, oxalates, ammonium salts, sulfates, halogenated salts and nitrates of the corresponding metal in the first oxide. For example, when the first oxide is silica, examples of the first oxide source include silica sol, crude silica gel, tetraethyl orthosilicate, water glass, white carbon black, silicic acid, silica gel, potassium silicate, or the like. When the first oxide is germanium dioxide, examples of the first oxide source include germanium tetraalkoxide, germanium oxide, germanium nitrate, or the like. When the first oxide is tin dioxide, examples of the first oxide source include tin chloride, tin sulfate, tin nitrate, and the like. When the first oxide is titania, examples of the first oxide source include titanium tetraalkoxide, titanium dioxide, titanium nitrate, and the like. When the first oxide is zirconium dioxide, examples of the first oxide source include zirconium sulfate, zirconium chloride, zirconium nitrate, and the like. Said first oxide sources can be used alone or in a combination of two or more thereof in a desired ratio.

According to an aspect of the present invention, in the contacting step, the second oxide source is generally a trivalent oxide source, such as at least one selected from the group consisting of an alumina source, a boron oxide source, an iron oxide source, a gallium oxide source, a rare earth oxide source, an indium oxide source, and a vanadium oxide source, preferably an alumina ($Al_2O_3$) source. Said second oxide sources can be used alone or in a combination of two or more thereof in any ratio. When two or more are used in combination, the molar ratio between any two of the second oxide sources can be, for example, from 30:200 to 60:150.

According to an aspect of the present invention, in the contacting step, as the second oxide source, any corresponding oxide source conventionally used for this purpose in the art can be used, including but not limited to, among others, oxides, hydroxides, alkoxides, metal oxyacid salts, acetates, oxalates, ammonium salts, sulfates, halogenated salts and nitrates of the corresponding metal in the second oxide. For example, when the second oxide is alumina, examples of the second oxide source include aluminum chloride, aluminum sulfate, hydrated alumina, sodium metaaluminate, aluminum sol, aluminum hydroxide or the like. When the second oxide is boron oxide, examples of the second oxide source include boric acid, borate, borax, boron trioxide and the like. When the second oxide is iron oxide, examples of the second oxide source include iron nitrate, iron chloride, iron oxide, and the like. When the second oxide is gallium oxide, examples of the second oxide source include gallium nitrate, gallium sulfate, gallium oxide, and the like. When the second oxide is a rare earth oxide, examples of the second oxide source include lanthanum oxide, neodymium oxide, yttrium oxide, cerium oxide, lanthanum nitrate, neodymium nitrate, yttrium nitrate, ammonium cerium sulfate, and the like. When the second oxide is indium oxide, examples of the second oxide source include indium chloride, indium nitrate, indium oxide, and the like. When the second oxide is vanadium oxide, examples of the second oxide source include vanadium chloride, ammonium metavanadate, sodium vanadate, vanadium dioxide, vanadyl sulfate, and the like. Said second oxide sources can be used alone or in a combination of two or more thereof in a desired ratio.

According to an aspect of the present invention, in the contacting step, the molar ratio of the first oxide source (calculated on the basis of the first oxide, such as $SiO_2$) to the second oxide source (calculated on the basis of the second oxide, such as $Al_2O_3$) is generally in a range from 30 to 100, preferably from 55 to 100.

According to an aspect of the present invention, in the contacting step, the molar ratio of water to the first oxide source (calculated on the basis of the first oxide) is generally in a range from 5 to 50, preferably from 5 to 15.

According to an aspect of the present invention, in the contacting step, an alkali source may or may not be used. When the alkali source is not intentionally used, the group X contained in the compound represented by the formula (I) can be used to provide the $OH^-$ required herein. Here, as the alkali source, any alkali source conventionally used for this purpose in the art can be used, including but not limited to inorganic bases comprising an alkali metal or alkaline earth metal as the cation, particularly sodium hydroxide and potassium hydroxide. Said alkali sources can be used alone or in a combination of two or more thereof in any ratio.

According to an aspect of the present invention, in the contacting step, the molar ratio of the alkali source (calculated on the basis of $OH^-$) to the first oxide source (calculated on the basis of the first oxide) is generally in a range from 0 to 1, preferably from 0.04 to 1, from 0.1 to 1, from 0.2 to 1, from 0.3 to 0.7 or from 0.45 to 0.7.

According to an aspect of the present invention, in the contacting step, as the crystallization condition, the crystallization temperature is generally in a range from 80° C. to 120° C., preferably from 120° C. to 170° C. or from 120° C. to 200° C.

According to an aspect of the present invention, in the contacting step, as the crystallization condition, the crystallization period is generally at least 1 day, preferably at least 2 days, preferably from 3 days to 8 days, from 5 days to 8 days or from 4 days to 6 days.

According to an aspect of the present invention, in the method for the preparation of the molecular sieve, after the contacting step is completed, the molecular sieve can be separated as a product from the resultant reaction mixture by any separation method commonly known. Here, the molecular sieve product comprises the molecular sieve according to the present invention. Further, as the separation method, for example, a method comprising filtering, washing, and drying the resultant reaction mixture can be mentioned.

According to an aspect of the present invention, in the method for the preparation of the molecular sieve, the filtration, washing and drying can be carried out in any conventional manner known in the art. By way of example, as the filtration, for example, the resultant reaction mixture can be simply subjected to suction filtration. As the washing, for example, washing with deionized water can be performed until the pH of the filtrate reaches 7-9, preferably 8-9. The drying temperature is, for example, 40 to 250° C., preferably 60 to 150° C., and the drying time is, for example, 8 to 30 hours, preferably 10 to 20 hours. The drying can be carried out under normal pressure or under reduced pressure.

According to an aspect of the present invention, the method for the preparation of the molecular sieve may further comprise a step of calcining the resultant molecular sieve (hereinafter referred to as the calcination step) as needed to remove the organic template and possible moisture, and the like, so that a calcined molecular sieve can be obtained. In the context of the present specification, the molecular sieves before and after calcination are collectively referred to as the molecular sieve of the present invention or the molecular sieve according to the present invention.

According to an aspect of the present invention, in the method for the preparation of the molecular sieve, the calcination can be carried out in any conventional manner known in the art, for example, at a calcination temperature generally ranging from 300° C. to 750° C., preferably from 400° C. to 600° C. for a calcination period generally ranging from 1 hour to 10 hours, preferably from 3 hours to 6 hours. In addition, the calcination is generally carried out under an oxygen-containing atmosphere, such as an air or oxygen atmosphere.

According to an aspect of the present invention, if desired, the molecular sieve according to the present invention or any molecular sieve produced by the method for the preparation of a molecular sieve according to the present invention (in the context of the present specification, both are collectively referred to as the molecular sieve of the present invention or the molecular sieve according to the present invention) can further be subjected to ion exchange by any conventional means known in the art, for example by using an ion exchange or solution impregnation process (see, for example, U.S. Pat. Nos. 3,140,249 and 3,140,253, etc.), so that the metal cation (such as Na ion or K ion, depending on the preparation method) contained therein can be replaced in whole or in part by other cations. Examples of said other cation include hydrogen ion, other alkali metal ions (including K ion, Rb ion, etc.), ammonium ions (including $NH_4$ ion, quaternary ammonium ions such as tetramethylammonium ion and tetraethylammonium ion, etc.), alkaline earth metal ions (including Mg ion, Ca ion), Mn ion, Zn ion, Cd ion, noble metal ions (including Pt ion, Pd ion, Rh ion, etc.), Ni ion, Co ion, Ti ion, Sn ion, Fe ion and/or rare earth metal ions, and the like.

The molecular sieve according to the present invention can be further treated with a dilute acid solution or the like as needed to increase the silica-alumina ratio, or treated with water vapor to improve the resistance of the molecular sieve crystal to acid attack.

The molecular sieve according to the present invention has good thermal/hydrothermal stability and has a larger pore volume. Thus, the molecular sieve according to the present invention is capable of adsorbing more/larger molecules, thereby exhibiting excellent adsorptive/catalytic properties.

The molecular sieve according to the present invention has a relatively strong acidity, particularly a large number of L acid sites. This molecular sieve has not been produced in the prior art. As a result, the molecular sieve according to the present invention has better performance particularly in an acid-catalyzed reaction.

The molecular sieve according to the present invention can be in any physical form, such as powders, granules or molded articles (e.g., strips, clovers, etc.). These physical forms can be obtained in any conventional manner known in the art, and are not particularly limited.

Third Embodiment

According to an aspect of the present invention, there is provided a molecular sieve having an X-ray diffraction pattern substantially as shown in the following table.

| 2θ (°) | d-distance (Å) | Relative intensity ($I/I_0 \times 100$) |
|---|---|---|
| 5.2048 ± 0.05 | 16.96501 ± 0.05 | VS |
| 8.4762 ± 0.27 | 10.42335 ± 0.34 | W |
| 9.0095 ± 0.06 | 9.80755 ± 0.07 | M |
| 10.3943 ± 0.05 | 8.50381 ± 0.05 | W |
| 16.1228 ± 0.50 | 5.49296 ± 0.50 | W |
| 23.7405 ± 0.22 | 3.74484 ± 0.03 | W |

According to an aspect of the present invention, it is preferable that the X-ray diffraction pattern of the molecular sieve further includes an X-ray diffraction peak substantially as shown in the following table.

| 2θ (°) | d-distance (Å) | Relative intensity ($I/I_0 \times 100$) |
|---|---|---|
| 14.3448 ± 0.66 | 6.16955 ± 0.27 | W |
| 15.2971 ± 0.50 | 5.78752 ± 0.50 | W |
| 16.1979 ± 0.50 | 5.46765 ± 0.50 | W |
| 20.8653 ± 0.11 | 4.25393 ± 0.02 | W |
| 23.9532 ± 0.14 | 3.71207 ± 0.02 | W |

According to an aspect of the present invention, it is preferable that the X-ray diffraction pattern of the molecular sieve further includes an X-ray diffraction peak substantially as shown in the following table.

| 2θ (°) | d-distance (Å) | Relative intensity ($I/I_0 \times 100$) |
|---|---|---|
| 14.4217 ± 0.56 | 6.13681 ± 0.43 | W |
| 15.1988 ± 0.50 | 5.82474 ± 0.50 | W |
| 15.5903 ± 0.50 | 5.67936 ± 0.50 | W |
| 20.6353 ± 0.50 | 4.30082 ± 0.10 | W |
| 22.7406 ± 0.08 | 3.90718 ± 0.02 | W |
| 24.4468 ± 0.26 | 3.63823 ± 0.04 | W |

According to an aspect of the present invention, when observed using a scanning electron microscope (SEM), the molecular sieve (referring to its single crystal particle) has a crystal particle morphology from a flat prismatic shape to a flat cylindrical shape, particularly a native crystal particle morphology from a flat prismatic shape to a flat cylindrical shape. Here, the term "crystal particle morphology" refers to the (overall) outer shape exhibited by a single crystal particle of the molecular sieve in the observation field of the scanning electron microscope. The term "native" refers to the morphology of the molecular sieve objectively and directly presented after preparation, rather than the morphology of the molecular sieve presented after being artificially processed after preparation. The term "prism" refers to a convex prism and generally refers to a right prism and a regular polygonal prism (such as a regular hexagonal prism). It should be specially pointed out that since the growth process of the crystal of the molecular sieve may be disturbed by various factors, there may be a certain degree of deviation when its real crystal particle morphology is compared with a (truely) right prism or a (truely) regular polygonal prism in geometrical sense, such as a deviation of 30%, 20%, or 5%, resulting in the production of a beveled prism, or an irregular polygonal (or even a curved polygonal) prism, but the present invention is not intended to specify the degree of deviation. Moreover, any greater or smaller deviations do not depart from the scope of the present invention. The term "flat" means that the ratio of height to width (or diameter) (such as the aspect ratio as described below) is less than one. The expression "from a flat prismatic shape to a flat cylindrical shape" means that the crystal particle morphology of the molecular sieve can be a flat prismatic shape, a flat cylindrical shape, or any intermediate shape between the flat prismatic shape and the flat cylindrical shape. Examples of the intermediate shape include a shape obtained by rounding one or more edges of the flat prism. It is apparent that by rounding all the edges of the flat prism, it is possible to produce the flat cylinder.

Figure 81A:
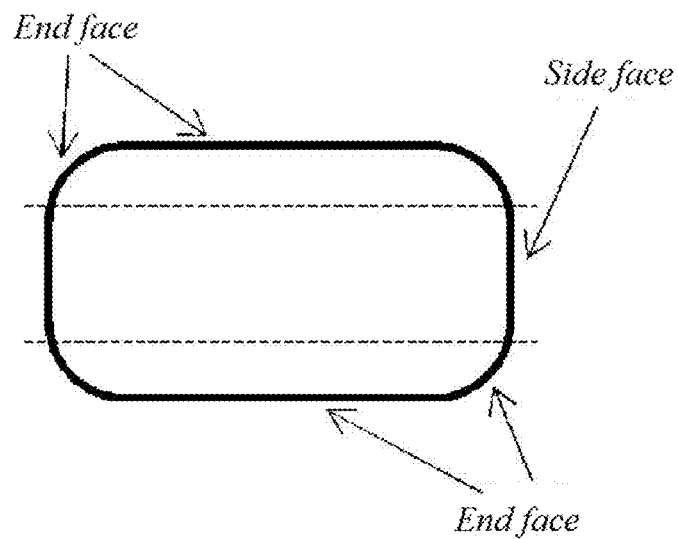
FIG. 81A is a schematic view showing the end face contour of the molecular sieve according to the present invention having a convex shape.
Figure 81B:
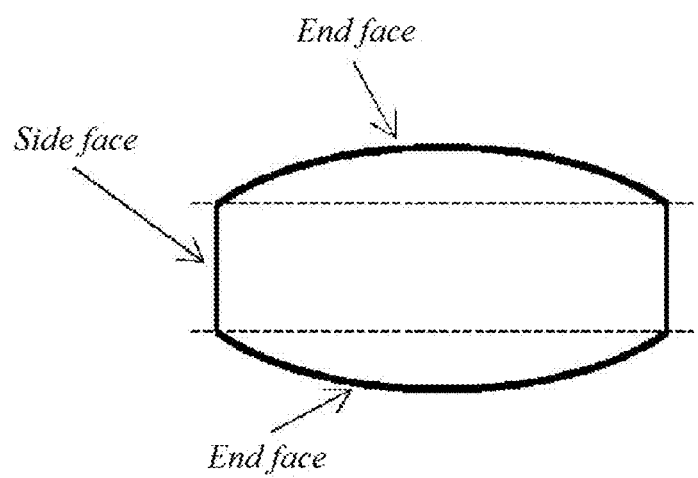
FIG. 81B is a schematic view showing the end face contour of the molecular sieve according to the present invention having another convex shape.
Figure 81C:
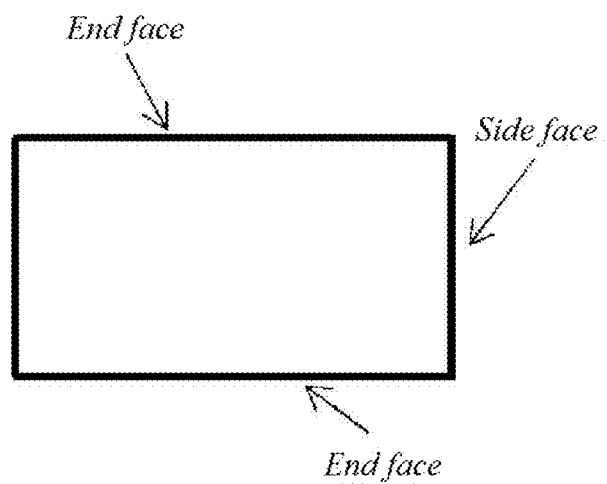
FIG. 81C is a schematic view showing the end face contour of the molecular sieve according to the present invention having a flat shape, instead of a convex shape.

According to a variant embodiment of the present invention, as previously described, the molecular sieve has a columnar crystal particle morphology when observed using a scanning electron microscope (SEM). A longitudinal section of the column can be obtained when it is longitudinally sectioned along the centerline thereof. The longitudinal section has end face contours on the upper and lower sides (a range out of the range surrounded by the two broken lines) and side contours on the left and right sides (a range within the range surrounded by the two broken lines). The molecular sieve of the present variant embodiment is unique in that one or both of the two end face contours have a convex shape, that is, the radius of curvature thereof has a positive value. The present invention is not intended to specify the value range of the radius of curvature as long as it has a positive value. Alternatively, it can be said that the molecular sieve of the variant embodiment generally has an outer shape obtained by rounding or chamfering the edge of one end face or both end faces of the column. This can be understood, for example, by referring to FIGS. 81A and 81B. Here, the FIGS. 81A and 81B are only provided for illustrating the present invention and are not intended to limit the present invention. In addition, FIG. 81C exemplifies a case where the end face contour does not have a convex shape but a flat shape.

The inventors of the present invention have found through careful investigation that the molecular sieve having both the aforementioned specific X-ray diffraction pattern and the aforementioned specific (native) crystal particle morphology has not been produced in the prior art.

According to an aspect of the present invention, the molecular sieve (a single crystal particle) has an effective diameter generally ranging from 100 nm to 1000 nm, preferably from 100 nm to 500 nm, when observed using a scanning electron microscope (SEM). Here, the term "effective diameter" means that two points are arbitrarily selected at the cross section of the molecular sieve (a single crystal particle) along the contour (edge) of the cross section, and the linear distance between the two points is measured, where the greatest linear distance is taken as the effective diameter. If the profile of the cross section of the molecular sieve is presented as a polygon such as a hexagon, the effective diameter generally refers to the linear distance between two vertices of the polygon that are farthest from each other, i.e. the diagonal distance. Briefly, the effective diameter substantially corresponds to the diameter of the circumcircle of the polygon representing the contour of the cross section. Alternatively, if the profile of the cross section of the molecular sieve is presented as a circle, the effective diameter refers to the diameter of the circle.

According to an aspect of the present invention, the molecular sieve (a single crystal particle) has a height generally ranging from 100 nm to 1000 nm, preferably from 150 nm to 300 nm, when observed using a scanning electron microscope (SEM). Here, the term "height" refers to a linear distance between the centers of the two end faces of a single crystal particle (columnar crystal particle) of the molecular sieve.

According to an aspect of the present invention, the molecular sieve (a single crystal particle) has an aspect ratio generally ranging from 0.1 to 0.9, preferably from 0.4 to 0.7, when observed using a scanning electron microscope (SEM). Here, the term "aspect ratio" refers to the ratio of the height to the effective diameter. The molecular sieve having both the aforementioned specific X-ray diffraction pattern and the aforementioned specific aspect ratio has not been produced in the prior art. For example, the crystal particle morphology of the molecular sieve in this case is similar to an oral tablet.

According to an aspect of the present invention, the molecular sieve has a total specific surface area generally ranging from 400 $m^2 \cdot g^{-1}$ to 600 $m^2 \cdot g^{-1}$, preferably from 450 $m^2 \cdot g^{-1}$ to 580 $m^2 \cdot g^{-1}$. Here, the total specific surface area is obtained using the liquid nitrogen adsorption method, calculated with the BET model.

According to an aspect of the present invention, the molecular sieve has a pore volume generally ranging from 0.3 ml/g to 0.5 ml/g, preferably from 0.30 ml/g to 0.40 ml/g. The molecular sieve according to the present invention has a very high pore volume, which indicates that it belongs to an ultra-macroporous molecular sieve. Here, the pore volume is obtained by low temperature nitrogen adsorption, calculated with the BET model.

According to an aspect of the present invention, the molecular sieve may have a schematic chemical composition represented by the formula "first oxide·second oxide". It is known that molecular sieves may sometimes contain a certain amount of moisture (especially just after synthesis), but it is considered not necessary in the present application to specify the amount of moisture because the presence or absence of the moisture has no substantial compact on the XRD spectrum of the molecular sieve. In view of this, the schematic chemical composition actually represents a water-free chemical composition of the molecular sieve. Moreover, it is apparent that the schematic chemical composition represents the chemical composition of the framework of the molecular sieve.

According to an aspect of the present invention, the molecular sieve may typically further comprise, in its composition, an organic template and water, etc., such as those filled in its pores, just after its synthesis. Therefore, the molecular sieve may sometimes have a schematic chemical composition represented by the formula "first oxide·second oxide·organic template·water".

Here, the molecular sieve having the schematic chemical composition represented by the formula "first oxide·second oxide·organic template·water" can be calcined to remove any organic template and water present in the pores thereof, so that the molecular sieve having the schematic chemical composition represented by the formula "first oxide·second oxide" can be obtained. Further, the calcination can be carried out in any conventional manner known in the art, for example at a calcination temperature generally ranging from 300° C. to 750° C., preferably from 400° C. to 600° C. for a calcination period generally ranging from 1 hour to 10 hours, preferably from 3 hours to 6 hours. In addition, the calcination is generally carried out under an oxygen-containing atmosphere, such as an air or oxygen atmosphere.

According to an aspect of the present invention, in the aforementioned schematic chemical composition, the first oxide is generally a tetravalent oxide, and can be, for example, at least one selected from the group consisting of silica, germanium dioxide, tin dioxide, titania, and zirconium dioxide, preferably silica ($SiO_2$) or a combination of silica and germanium dioxide. Said first oxides can be used alone or in a combination of two or more thereof in any ratio. When two or more are used in combination, the molar ratio between any two of the first oxides can be, for example, from 20:200 to 35:100. As an example of the combination, silica and germanium dioxide can be used in combination, in which case the molar ratio between the silica and the germanium dioxide can be, for example, from 20:200 to 35:100.

According to an aspect of the present invention, in the aforementioned schematic chemical composition, the second oxide is generally a trivalent oxide, and can be, for example, at least one selected from the group consisting of alumina, a boron oxide, an iron oxide, a gallium oxide, a rare earth oxide, an indium oxide and a vanadium oxide, preferably alumina ($Al_2O_3$). Said second oxides can be used alone or in a combination of two or more thereof in any ratio.

When two or more are used in combination, the molar ratio between any two of the second oxides can be, for example, from 30:200 to 60:150.

According to an aspect of the present invention, in the aforementioned schematic chemical composition, as an example of the organic template, any organic template useful in the preparation of molecular sieves can be mentioned, and especially, the organic template used in the preparation of the molecular sieve according to the present embodiment can be mentioned (see detailed description below). Said organic templates can be used alone or in a combination of two or more thereof in any ratio. In particular, examples of the organic template include compounds represented by the following formula (I).

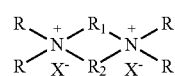
(I)

According to an aspect of the present invention, in the formula (I), the groups $R_1$ and $R_2$ are identical or different from each other, each independently selected from the group consisting of $C_{3-12}$ linear or branched alkylene groups, and the plural groups R are identical or different from each other, each independently selected from the group consisting of $C_{1-4}$ linear or branched alkyl groups, and X is OH.

According to an aspect of the present invention, in the aforementioned schematic chemical composition, the molar ratio of the first oxide to the second oxide (such as a molar ratio of $SiO_2$ to $Al_2O_3$) is generally in a range from 40 to 200, preferably from 40 to 150.

According to an aspect of the present invention, in the aforementioned schematic chemical composition, the molar ratio of water to the first oxide is generally in a range from 5 to 50, preferably from 5 to 15.

According to an aspect of the present invention, in the aforementioned schematic chemical composition, the molar ratio of the organic template to the first oxide is generally in a range from 0.02 to 0.5, preferably from 0.05 to 0.5, from 0.15 to 0.5 or from 0.3 to 0.5.

According to an aspect of the present invention, depending on the starting materials used in the preparation method, the molecular sieve may sometimes further comprise a metal cation such as an alkali metal and/or alkaline earth metal cation as a component in its composition (generally filled in its pores). In this case, the content of the metal cation, for example, the mass ratio of the metal cation to the first oxide is generally in a range from 0 to 0.02, preferably from 0.0002 to 0.006, but is not limited thereto.

According to an aspect of the present invention, the molecular sieve can be prepared by the following method. Here, the preparation method comprises a step of contacting a first oxide source, a second oxide source, an optional alkali source, an organic template, and water under crystallization conditions to produce a molecular sieve (hereinafter referred to as the contacting step).

According to an aspect of the present invention, in the method for the preparation of the molecular sieve, the contacting step can be carried out in any conventional manner known in the art, for example by using a method comprising mixing the first oxide source, the second oxide source, the optional alkali source, the organic template, and water, and subjecting the mixture to crystallization under the crystallization conditions.

According to an aspect of the present invention, in the contacting step, the organic template comprises at least a compound represented by the following formula (I). Here, the compound represented by the formula (I) can be used alone or in a combination of two or more thereof in any ratio.

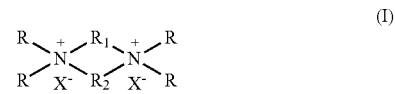
(I)

According to an aspect of the present invention, in the formula (I), the groups $R_1$ and $R_2$ are identical or different from each other, each independently selected from the group consisting of $C_{3-12}$ linear or branched alkylene groups.

According to a variant embodiment of the present invention, in the formula (I), the groups $R_1$ and $R_2$ are identical or different from each other, one of which is selected from the group consisting of $C_{3-12}$ linear alkylene groups and the other is selected from the group consisting of $C_{4-6}$ linear alkylene groups.

According to an aspect of the present invention, as an example of the $C_{3-12}$ linear or branched alkylene groups, a $C_{3-12}$ linear alkylene group can be mentioned, and specific examples thereof include n-propylene, isopropylidene, n-butylene, isobutylene, tert-butylene, n-pentylene, isopentylene, neopentylene, n-hexylene, isohexylene, n-octylene, isooctylene, neooctylene, nonylene (or an isomer thereof), decylene (or an isomer thereof), undecylene (or an isomer thereof) or dodecylene (or an isomer thereof), preferably n-propylene, n-butylene, n-pentylene, n-hexylene, n-heptylene, n-octylene, n-nonylene, n-decylene, n-undecylene or n-dodecylene.

According to an aspect of the present invention, as the $C_{4-6}$ linear alkylene groups, n-butylene, n-pentylene or n-hexylene can be particularly mentioned.

According to an aspect of the present invention, in the formula (I), the plural groups R are identical or different from each other, each independently selected from the group consisting of $C_{1-4}$ linear or branched alkyl groups, preferably each independently selected from the group consisting of methyl and ethyl, more preferably all methyl.

According to an aspect of the present invention, in the formula (I), X is OH.

According to an aspect of the present invention, in the contacting step, the molar ratio of the organic template to the first oxide source (calculated on the basis of the first oxide) is generally in a range from 0.02 to 0.5, preferably from 0.05 to 0.5, from 0.15 to 0.5 or from 0.3 to 0.5.

According to an aspect of the present invention, in the contacting step, in addition to the compound represented by the formula (I), other organic templates conventionally used in the art for the preparation of molecular sieves may be further used as the organic template. Preferably, in the contacting step, only the compound represented by the formula (I) is used as the organic template. Here, the compound represented by the formula (I) can be used alone or in a combination of two or more thereof in any ratio.

According to an aspect of the present invention, in the contacting step, the first oxide source is generally a tetravalent oxide source, and for example, can be at least one selected from the group consisting of a silica source, a germanium dioxide source, a tin dioxide source, a titania source and a zirconium dioxide source, preferably a silica source ($SiO_2$) or a combination of a silica source and a germanium dioxide source. Said first oxide sources can be used alone or in a combination of two or more thereof in any ratio. When two or more are used in combination, the molar ratio between any two of the first oxide sources can be, for example, from 30:200 to 60:150. As an example of the combination, a combination of a silica source and a germanium dioxide source can be mentioned, in which case the molar ratio between the silica source and the germanium dioxide source can be, for example, from 20:200 to 35:100.

According to an aspect of the present invention, in the contacting step, as the first oxide source, any corresponding oxide source conventionally used for this purpose in the art can be used, including but not limited to, among others, oxides, hydroxides, alkoxides, metal oxyacid salts, acetates, oxalates, ammonium salts, sulfates, halogenated salts and nitrates of the corresponding metal in the first oxide. For example, when the first oxide is silica, examples of the first oxide source include silica sol, crude silica gel, tetraethyl orthosilicate, water glass, white carbon black, silicic acid, silica gel, potassium silicate, or the like. When the first oxide is germanium dioxide, examples of the first oxide source include germanium tetraalkoxide, germanium oxide, germanium nitrate, or the like. When the first oxide is tin dioxide, examples of the first oxide source include tin chloride, tin sulfate, tin nitrate, and the like. When the first oxide is titania, examples of the first oxide source include titanium tetraalkoxide, titanium dioxide, titanium nitrate, and the like. When the first oxide is zirconium dioxide, examples of the first oxide source include zirconium chloride, zirconium sulfate, zirconium nitrate, and the like. Said first oxide sources can be used alone or in a combination of two or more thereof in a desired ratio.

According to an aspect of the present invention, in the contacting step, the second oxide source is generally a trivalent oxide source, such as at least one selected from the group consisting of an alumina source, a boron oxide source, an iron oxide source, a gallium oxide source, a rare earth oxide source, an indium oxide source, and a vanadium oxide source, preferably an alumina ($Al_2O_3$) source. Said second oxide sources can be used alone or in a combination of two or more thereof in any ratio. When two or more are used in combination, the molar ratio between any two of the second oxide sources can be, for example, from 20:200 to 35:100.

According to an aspect of the present invention, in the contacting step, as the second oxide source, any corresponding oxide source conventionally used for this purpose in the art can be used, including but not limited to, among others, oxides, hydroxides, alkoxides, metal oxyacid salts, acetates, oxalates, ammonium salts, sulfates, halogenated salts and nitrates of the corresponding metal in the second oxide. For example, when the second oxide is alumina, examples of the second oxide source include aluminum chloride, aluminum sulfate, hydrated alumina, sodium metaaluminate, aluminum sol, aluminum hydroxide or the like. When the second oxide is boron oxide, examples of the second oxide source include boric acid, borate, borax, boron trioxide and the like. When the second oxide is iron oxide, examples of the second oxide source include iron nitrate, iron chloride, iron oxide, and the like. When the second oxide is gallium oxide, examples of the second oxide source include gallium nitrate, gallium sulfate, gallium oxide, and the like. When the second oxide is a rare earth oxide, examples of the second oxide source include lanthanum oxide, neodymium oxide, yttrium oxide, cerium oxide, lanthanum nitrate, neodymium nitrate, yttrium nitrate, ammonium cerium sulfate, and the like. When the second oxide is indium oxide, examples of the second oxide source include indium chloride, indium nitrate, indium oxide, and the like. When the second oxide is vanadium oxide, examples of the second oxide source include vanadium chloride, ammonium metavanadate, sodium vanadate, vanadium dioxide, vanadyl sulfate, and the like. Said second oxide sources can be used alone or in a combination of two or more thereof in a desired ratio.

According to an aspect of the present invention, in the contacting step, the molar ratio of the first oxide source (calculated on the basis of the first oxide, such as $SiO_2$) to the second oxide source (calculated on the basis of the second oxide, such as $Al_2O_3$) is generally in a range from 40 to 200, preferably from 40 to 150.

According to an aspect of the present invention, in the contacting step, the molar ratio of water to the first oxide source (calculated on the basis of the first oxide) is generally in a range from 5 to 50, preferably from 5 to 15.

According to an aspect of the present invention, in the contacting step, an alkali source may or may not be used. When the alkali source is not intentionally used, the group X contained in the compound represented by the formula (I) can be used to provide the $OH^-$ required herein. Here, as the alkali source, any alkali source conventionally used for this purpose in the art can be used, including but not limited to inorganic bases comprising an alkali metal or alkaline earth metal as the cation, particularly sodium hydroxide and potassium hydroxide. Said alkali sources can be used alone or in a combination of two or more thereof in any ratio.

According to an aspect of the present invention, in the contacting step, the molar ratio of the alkali source (calculated on the basis of $OH^-$) to the first oxide source (calculated on the basis of the first oxide) is generally in a range from 0 to 1, preferably from 0.04 to 1, from 0.1 to 1, from 0.2 to 1, from 0.3 to 0.7 or from 0.45 to 0.7.

According to an aspect of the present invention, in the contacting step, as the crystallization condition, the crystallization temperature is generally in a range from 80° C. to 120° C., preferably from 120° C. to 170° C. or from 120° C. to 200° C.

According to an aspect of the present invention, in the contacting step, as the crystallization condition, the crystallization period is generally at least 1 day, preferably at least 2 days, preferably from 3 days to 8 days, from 5 days to 8 days or from 4 days to 6 days.

According to an aspect of the present invention, in the method for the preparation of the molecular sieve, after the contacting step is completed, the molecular sieve can be separated as a product from the resultant reaction mixture by any separation method commonly known. Here, the molecular sieve product comprises the molecular sieve according to the present invention. Further, as the separation method, for example, a method comprising filtering, washing, and drying the resultant reaction mixture can be mentioned.

According to an aspect of the present invention, in the method for the preparation of the molecular sieve, the filtration, washing and drying can be carried out in any conventional manner known in the art. By way of example, as the filtration, for example, the resultant reaction mixture can be simply subjected to suction filtration. As the washing, for example, washing with deionized water can be performed until the pH of the filtrate reaches 7-9, preferably 8-9. The drying temperature is, for example, 40 to 250° C., preferably 60 to 150° C., and the drying time is, for example, 8 to 30 hours, preferably 10 to 20 hours. The drying can be carried out under normal pressure or under reduced pressure.

According to an aspect of the present invention, the method for the preparation of the molecular sieve may further comprise a step of calcining the resultant molecular sieve (hereinafter referred to as the calcination step) as needed to remove the organic template and possible moisture, and the like, so that a calcined molecular sieve can be obtained. In the context of the present specification, the molecular sieves before and after calcination are collectively referred to as the molecular sieve of the present invention or the molecular sieve according to the present invention.

According to an aspect of the present invention, in the method for the preparation of the molecular sieve, the calcination can be carried out in any conventional manner known in the art, for example, at a calcination temperature generally ranging from 300° C. to 750° C., preferably from 400° C. to 600° C. for a calcination period generally ranging from 1 hour to 10 hours, preferably from 3 hours to 6 hours. In addition, the calcination is generally carried out under an oxygen-containing atmosphere, such as an air or oxygen atmosphere.

According to an aspect of the present invention, if desired, the molecular sieve according to the present invention or any molecular sieve produced by the method for the preparation of a molecular sieve according to the present invention (in the context of the present specification, both are collectively referred to as the molecular sieve of the present invention or the molecular sieve according to the present invention) can further be subjected to ion exchange by any conventional means known in the art, for example by using an ion exchange or solution impregnation process (see, for example, U.S. Pat. Nos. 3,140,249 and 3,140,253, etc.), so that the metal cation (such as Na ion or K ion, depending on the preparation method) contained therein can be replaced in whole or in part by other cations. Examples of said other cation include hydrogen ion, other alkali metal ions (including K ion, Rb ion, etc.), ammonium ions (including $NH_4$ ion, quaternary ammonium ions such as tetramethylammonium ion and tetraethylammonium ion, etc.), alkaline earth metal ions (including Mg ion, Ca ion), Mn ion, Zn ion, Cd ion, noble metal ions (including Pt ion, Pd ion, Rh ion, etc.), Ni ion, Co ion, Ti ion, Sn ion, Fe ion and/or rare earth metal ions, and the like.

The molecular sieve according to the present invention can be further treated with a dilute acid solution or the like as needed to increase the silica-alumina ratio, or treated with water vapor to improve the resistance of the molecular sieve crystal to acid attack.

The molecular sieve according to the present invention has good thermal/hydrothermal stability and has a larger pore volume. Thus, the molecular sieve according to the present invention is capable of adsorbing more/larger molecules, thereby exhibiting excellent adsorptive/catalytic properties.

The molecular sieve according to the present invention has a relatively strong acidity, particularly a large number of L acid sites. This molecular sieve has not been produced in the prior art. As a result, the molecular sieve according to the present invention has better performance particularly in an acid-catalyzed reaction.

The molecular sieve according to the present invention can be in any physical form, such as powders, granules or molded articles (e.g., strips, clovers, etc.). These physical forms can be obtained in any conventional manner known in the art, and are not particularly limited.

Fourth Embodiment

According to an aspect of the present invention, a method for the preparation of a molecular sieve is provided. Here, the preparation method comprises a step of contacting a first oxide source, a second oxide source, an optional alkali source, an organic template, and water under crystallization conditions to produce a molecular sieve (hereinafter referred to as the contacting step).

According to an aspect of the present invention, in the method for the preparation of the molecular sieve, the contacting step can be carried out in any conventional manner known in the art, for example by using a method comprising mixing the first oxide source, the second oxide source, the optional alkali source, the organic template, and water, and subjecting the mixture to crystallization under the crystallization conditions.

According to an aspect of the present invention, in the contacting step, the organic template comprises at least a compound represented by the following formula (I). Here, the compound represented by the formula (I) can be used alone or in a combination of two or more thereof in any ratio.

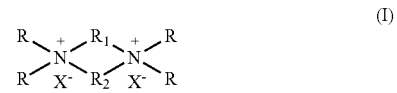

(I)

According to an aspect of the present invention, in the formula (I), the groups $R_1$ and $R_2$ are identical or different from each other, each independently selected from the group consisting of $C_{3-12}$ linear or branched alkylene groups.

According to a variant embodiment of the present invention, in the formula (I), the groups $R_1$ and $R_2$ are identical or different from each other, one of which is selected from the group consisting of $C_{3-12}$ linear alkylene groups and the other is selected from the group consisting of $C_{4-6}$ linear alkylene groups.

According to an aspect of the present invention, as an example of the $C_{3-12}$ linear or branched alkylene groups, a $C_{3-12}$ linear alkylene group can be mentioned, and specific examples thereof include n-propylene, isopropylidene, n-butylene, isobutylene, tert-butylene, n-pentylene, isopentylene, neopentylene, n-hexylene, isohexylene, n-octylene, isooctylene, neooctylene, nonylene (or an isomer thereof), decylene (or an isomer thereof), undecylene (or an isomer thereof) or dodecylene (or an isomer thereof), preferably n-propylene, n-butylene, n-pentylene, n-hexylene, n-heptylene, n-octylene, n-nonylene, n-decylene, n-undecylene or n-dodecylene.

According to an aspect of the present invention, as the $C_{4-6}$ linear alkylene groups, n-butylene, n-pentylene or n-hexylene can be particularly mentioned.

According to an aspect of the present invention, in the formula (I), the plural groups R are identical or different from each other, each independently selected from the group consisting of $C_{1-4}$ linear or branched alkyl groups, preferably each independently selected from the group consisting of methyl and ethyl, more preferably all methyl.

According to an aspect of the present invention, in the formula (I), X is OH.

According to an aspect of the present invention, in the contacting step, the molar ratio of the organic template to the first oxide source (calculated on the basis of the first oxide) is generally in a range from 0.02 to 0.5, preferably from 0.05 to 0.5, from 0.15 to 0.5 or from 0.3 to 0.5.

According to an aspect of the present invention, in the contacting step, in addition to the compound represented by the formula (I), other organic templates conventionally used in the art for the preparation of molecular sieves may be further used as the organic template. Preferably, in the contacting step, only the compound represented by the formula (I) is used as the organic template. Here, the compound represented by the formula (I) can be used alone or in a combination of two or more thereof in any ratio.

According to an aspect of the present invention, in the contacting step, the first oxide source is generally a tetravalent oxide source, and for example, can be at least one selected from the group consisting of a silica source, a germanium dioxide source, a tin dioxide source, a titania source and a zirconium dioxide source, preferably a silica source ($SiO_2$) or a combination of a silica source and a germanium dioxide source. Said first oxide sources can be used alone or in a combination of two or more thereof in any ratio. When two or more are used in combination, the molar ratio between any two of the first oxide sources can be, for example, from 20:200 to 35:100. As an example of the combination, a combination of a silica source and a germanium dioxide source can be mentioned, in which case the molar ratio between the silica source and the germanium dioxide source can be, for example, from 20:200 to 35:100.

According to an aspect of the present invention, in the contacting step, as the first oxide source, any corresponding oxide source conventionally used for this purpose in the art can be used, including but not limited to, among others, oxides, hydroxides, alkoxides, metal oxyacid salts, acetates, oxalates, ammonium salts, sulfates, halogenated salts and nitrates of the corresponding metal in the first oxide. For example, when the first oxide is silica, examples of the first oxide source include silica sol, crude silica gel, tetraethyl orthosilicate, water glass, white carbon black, silicic acid, silica gel, potassium silicate, or the like. When the first oxide is germanium dioxide, examples of the first oxide source include germanium tetraalkoxide, germanium oxide, germanium nitrate, or the like. When the first oxide is tin dioxide, examples of the first oxide source include tin chloride, tin sulfate, tin nitrate, and the like. When the first oxide is titania, examples of the first oxide source include titanium tetraalkoxide, titanium dioxide, titanium nitrate, and the like. When the first oxide is zirconium dioxide, examples of the first oxide source include zirconium chloride, zirconium sulfate, zirconium nitrate, and the like. Said first oxide sources can be used alone or in a combination of two or more thereof in a desired ratio.

According to an aspect of the present invention, in the contacting step, the second oxide source is generally a trivalent oxide source, such as at least one selected from the group consisting of an alumina source, a boron oxide source, an iron oxide source, a gallium oxide source, a rare earth oxide source, an indium oxide source, and a vanadium oxide source, preferably an alumina ($Al_2O_3$) source. Said second oxide sources can be used alone or in a combination of two or more thereof in any ratio. When two or more are used in combination, the molar ratio between any two of the second oxide sources can be, for example, from 30:200 to 60:150.

According to an aspect of the present invention, in the contacting step, as the second oxide source, any corresponding oxide source conventionally used for this purpose in the art can be used, including but not limited to, among others, oxides, hydroxides, alkoxides, metal oxyacid salts, acetates, oxalates, ammonium salts, sulfates, halogenated salts and nitrates of the corresponding metal in the second oxide. For example, when the second oxide is alumina, examples of the second oxide source include aluminum chloride, aluminum sulfate, hydrated alumina, sodium metaaluminate, aluminum sol, aluminum hydroxide or the like. When the second oxide is boron oxide, examples of the second oxide source include boric acid, borate, borax, boron trioxide and the like. When the second oxide is iron oxide, examples of the second oxide source include iron nitrate, iron chloride, iron oxide, and the like. When the second oxide is gallium oxide, examples of the second oxide source include gallium nitrate, gallium sulfate, gallium oxide, and the like. When the second oxide is a rare earth oxide, examples of the second oxide source include lanthanum oxide, neodymium oxide, yttrium oxide, cerium oxide, lanthanum nitrate, neodymium nitrate, yttrium nitrate, ammonium cerium sulfate, and the like. When the second oxide is indium oxide, examples of the second oxide source include indium chloride, indium nitrate, indium oxide, and the like. When the second oxide is vanadium oxide, examples of the second oxide source include vanadium chloride, ammonium metavanadate, sodium vanadate, vanadium dioxide, vanadyl sulfate, and the like. Said second oxide sources can be used alone or in a combination of two or more thereof in a desired ratio.

According to an aspect of the present invention, in the contacting step, the molar ratio of the first oxide source (calculated on the basis of the first oxide, such as $SiO_2$) to the second oxide source (calculated on the basis of the second oxide, such as $Al_2O_3$) is generally in a range from 5 to $\infty$, particularly from 5 to less than 40 (e.g. from 20 to less than 40), from 40 to 200 (e.g. from 40 to 150), and from greater than 200 to $\infty$ (e.g. from greater than 200 to 700). Here, when the molar ratio is $\infty$, it means that the second oxide source is not used or the second oxide source is not intentionally introduced in the contacting step.

According to an aspect of the present invention, in the contacting step, the molar ratio of water to the first oxide source (calculated on the basis of the first oxide) is generally in a range from 5 to 50, preferably from 5 to 15.

According to an aspect of the present invention, in the contacting step, an alkali source may or may not be used. When the alkali source is not intentionally used, the group X contained in the compound represented by the formula (I) can be used to provide the $OH^-$ required herein. Here, as the alkali source, any alkali source conventionally used for this purpose in the art can be used, including but not limited to inorganic bases comprising an alkali metal or alkaline earth metal as the cation, particularly sodium hydroxide and potassium hydroxide. Said alkali sources can be used alone or in a combination of two or more thereof in any ratio.

According to an aspect of the present invention, in the contacting step, the molar ratio of the alkali source (calculated on the basis of $OH^-$) to the first oxide source (calculated on the basis of the first oxide) is generally in a range from 0 to 1, preferably from 0.04 to 1, from 0.1 to 1, from 0.2 to 1, from 0.3 to 0.7 or from 0.45 to 0.7.

According to an aspect of the present invention, in the contacting step, as the crystallization condition, the crystallization temperature is generally in a range from 80° C. to 120° C., preferably from 120° C. to 170° C. or from 120° C. to 200° C.

According to an aspect of the present invention, in the contacting step, as the crystallization condition, the crystallization period is generally at least 1 day, preferably at least 2 days, preferably from 3 days to 8 days, from 5 days to 8 days or from 4 days to 6 days.

According to an aspect of the present invention, in the method for the preparation of the molecular sieve, after the contacting step is completed, the molecular sieve can be separated as a product from the resultant reaction mixture by any separation method commonly known. Here, the molecular sieve product comprises the molecular sieve according to the present invention. Further, as the separation method, for example, a method comprising filtering, washing, and drying the resultant reaction mixture can be mentioned.

According to an aspect of the present invention, in the method for the preparation of the molecular sieve, the filtration, washing and drying can be carried out in any conventional manner known in the art. By way of example, as the filtration, for example, the resultant reaction mixture can be simply subjected to suction filtration. As the washing, for example, washing with deionized water can be performed until the pH of the filtrate reaches 7-9, preferably 8-9. The drying temperature is, for example, 40 to 250° C., preferably 60 to 150° C., and the drying time is, for example, 8 to 30 hours, preferably 10 to 20 hours. The drying can be carried out under normal pressure or under reduced pressure.

According to an aspect of the present invention, the method for the preparation of the molecular sieve may further comprise a step of calcining the resultant molecular sieve (hereinafter referred to as the calcination step) as needed to remove the organic template and possible moisture, and the like, so that a calcined molecular sieve can be obtained. In the context of the present specification, the molecular sieves before and after calcination are collectively referred to as the molecular sieve of the present invention or the molecular sieve according to the present invention.

According to an aspect of the present invention, in the method for the preparation of the molecular sieve, the calcination can be carried out in any conventional manner known in the art, for example, at a calcination temperature generally ranging from 300° C. to 750° C., preferably from 400° C. to 600° C. for a calcination period generally ranging from 1 hour to 10 hours, preferably from 3 hours to 6 hours. In addition, the calcination is generally carried out under an oxygen-containing atmosphere, such as an air or oxygen atmosphere.

According to an aspect of the present invention, if desired, any molecular sieve produced as previously described (referred to as the molecular sieve according to the present invention or the molecular sieve according to the present invention) can be further subjected to ion exchanged by any conventional means known in the art, for example by using an ion exchange or solution impregnation process (see, for example, U.S. Pat. Nos. 3,140,249 and 3,140,253, etc.), so that the metal cation (such as Na ion or K ion, depending on the preparation method) contained therein can be replaced in whole or in part by other cation(s). Examples of said other cation include hydrogen ion, other alkali metal ions (including K ion, Rb ion, etc.), ammonium ions (including $NH_4$ ion, quaternary ammonium ions such as tetramethylammonium ion and tetraethylammonium ion, etc.), alkaline earth metal ions (including Mg ion, Ca ion), Mn ion, Zn ion, Cd ion, noble metal ions (including Pt ion, Pd ion, Rh ion, etc.), Ni ion, Co ion, Ti ion, Sn ion, Fe ion and/or rare earth metal ions, and the like.

The molecular sieve according to the present invention can be further treated with a dilute acid solution or the like as needed to increase the silica-alumina ratio, or treated with water vapor to improve the resistance of the molecular sieve crystal to acid attack.

The molecular sieve according to the present invention generally has an X-ray diffraction pattern substantially as shown in the following table.

| 2θ (°) | d-distance (Å) | Relative intensity ($I/I_0 \times 100$) |
|---|---|---|
| 5.2048 ± 0.05 | 16.96501 ± 0.05 | VS |
| 8.4762 ± 0.27 | 10.42335 ± 0.34 | W |
| 9.0095 ± 0.06 | 9.80755 ± 0.07 | M |
| 10.3943 ± 0.05 | 8.50381 ± 0.05 | W |

-continued

| 2θ (°) | d-distance (Å) | Relative intensity ($I/I_0 \times 100$) |
|---|---|---|
| 16.1228 ± 0.50 | 5.49296 ± 0.50 | W |
| 23.7405 ± 0.22 | 3.74484 ± 0.03 | W |

According to an aspect of the present invention, it is preferable that the X-ray diffraction pattern of the molecular sieve further includes an X-ray diffraction peak substantially as shown in the following table.

| 2θ (°) | d-distance (Å) | Relative intensity ($I/I_0 \times 100$) |
|---|---|---|
| 14.3448 ± 0.66 | 6.16955 ± 0.27 | W |
| 15.2971 ± 0.50 | 5.78752 ± 0.50 | W |
| 16.1979 ± 0.50 | 5.46765 ± 0.50 | W |
| 20.8653 ± 0.11 | 4.25393 ± 0.02 | W |
| 23.9532 ± 0.14 | 3.71207 ± 0.02 | W |

According to an aspect of the present invention, it is preferable that the X-ray diffraction pattern of the molecular sieve further includes an X-ray diffraction peak substantially as shown in the following table.

| 2θ (°) | d-distance (Å) | Relative intensity ($I/I_0 \times 100$) |
|---|---|---|
| 14.4217 ± 0.56 | 6.13681 ± 0.43 | W |
| 15.1988 ± 0.50 | 5.82474 ± 0.50 | W |
| 15.5903 ± 0.50 | 5.67936 ± 0.50 | W |
| 20.6353 ± 0.50 | 4.30082 ± 0.10 | W |
| 22.7406 ± 0.08 | 3.90718 ± 0.02 | W |
| 24.4468 ± 0.26 | 3.63823 ± 0.04 | W |

According to an aspect of the present invention, the molecular sieve generally has a columnar crystal particle morphology when observed using a scanning electron microscope (SEM). Here, the term "crystal particle morphology" refers to the (overall) outer shape exhibited by a single crystal particle of the molecular sieve in the observation field of the scanning electron microscope. Further, as the columnar shape, a prismatic shape, particularly a hexagonal prismatic shape, is preferred. Here, the prism refers to a convex prism and generally refers to a right prism and a regular polygonal prism (such as a regular hexagonal prism). It should be specially pointed out that since the growth process of the crystal of the molecular sieve may be disturbed by various factors, there may be a certain degree of deviation when its real crystal particle morphology is compared with a (truely) right prism or a (truely) regular polygonal prism in geometrical sense, such as a deviation of 30%, 20%, or 5%, resulting in the production of a beveled prism, or an irregular polygonal (or even a curved polygonal) prism, but the present invention is not intended to specify the degree of deviation. Moreover, any greater or smaller deviations do not depart from the scope of the present invention.

According to an aspect of the present invention, the molecular sieve (a single crystal particle) has an effective diameter generally ranging from 100 nm to 5000 nm when observed using a scanning electron microscope (SEM). Here, the term "effective diameter" means that two points are arbitrarily selected at the cross section of the molecular sieve (a single crystal particle) along the contour (edge) of the cross section, and the linear distance between the two points is measured, where the greatest linear distance is taken as the effective diameter. If the profile of the cross section of the molecular sieve is presented as a polygon such as a hexagon, the effective diameter generally refers to the linear distance between two vertices of the polygon that are farthest from each other, i.e. the diagonal distance. Briefly, the effective diameter substantially corresponds to the diameter of the circumcircle of the polygon representing the contour of the cross section.

According to an aspect of the present invention, the molecular sieve (a single crystal particle) has a height generally ranging from 100 nm to 3000 nm when observed using a scanning electron microscope (SEM). Here, the term "height" refers to a linear distance between the centers of the two end faces of a single crystal particle (columnar crystal particle) of the molecular sieve. In the usual case, the two end faces of the column of the molecular sieve are substantially parallel to each other, and the linear distance is the vertical distance between the two end faces, but the present invention is not limited thereto.

According to an aspect of the present invention, the molecular sieve (a single crystal particle) has an aspect ratio generally ranging from 0.1 to 8 when observed using a scanning electron microscope (SEM). Here, the term "aspect ratio" refers to the ratio of the height to the effective diameter.

According to an aspect of the present invention, the molecular sieve has a total specific surface area generally ranging from 400 m$^2$·g$^{-1}$ to 600 m$^2$·g$^{-1}$, preferably from 450 m$^2$·g$^{-1}$ to 580 m$^2$·g$^{-1}$. Here, the total specific surface area is obtained by low temperature nitrogen adsorption, calculated with the BET model.

According to an aspect of the present invention, the molecular sieve has a pore volume generally ranging from 0.3 ml/g to 0.5 ml/g, preferably from 0.30 ml/g to 0.40 ml/g. The molecular sieve according to the present invention has a very high pore volume, which indicates that it belongs to an ultra-macroporous molecular sieve. Here, the pore volume is obtained by low temperature nitrogen adsorption, calculated with the BET model.

The molecular sieve according to the present invention has good thermal/hydrothermal stability and has a larger pore volume. Thus, the molecular sieve according to the present invention is capable of adsorbing more/larger molecules, thereby exhibiting excellent adsorptive/catalytic properties.

The molecular sieve according to the present invention has a relatively strong acidity, particularly a large number of L acid sites. This molecular sieve has not been produced in the prior art. As a result, the molecular sieve according to the present invention has better performance particularly in an acid-catalyzed reaction.

The molecular sieve according to the present invention can be in any physical form, such as powders, granules or molded articles (e.g., strips, clovers, etc.). These physical forms can be obtained in any conventional manner known in the art, and are not particularly limited.

Fifth Embodiment

According to an aspect of the present invention, a method for the preparation of a molecular sieve is provided. Here, the preparation method comprises a step of contacting a first oxide source, a second oxide source, an optional alkali source, an organic template, and water under crystallization conditions to produce a molecular sieve (hereinafter referred to as the contacting step).

According to an aspect of the present invention, in the method for the preparation of the molecular sieve, the contacting step can be carried out in any conventional manner known in the art, for example by using a method comprising mixing the first oxide source, the second oxide source, the optional alkali source, the organic template, and water, and subjecting the mixture to crystallization under the crystallization conditions.

According to an aspect of the present invention, in the contacting step, the organic template comprises at least a compound represented by the following formula (I). Here, the compound represented by the formula (I) can be used alone or in a combination of two or more thereof in any ratio.

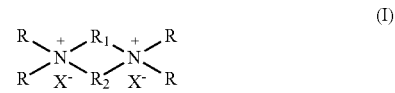

(I)

According to an aspect of the present invention, in the formula (I), the groups $R_1$ and $R_2$ are different from each other, one of which is selected from the group consisting of $C_{3-12}$ linear or branched alkylene groups, and the other is selected from the group consisting of $C_{3-12}$ linear or branched oxaalkylene groups.

According to an aspect of the present invention, as an example of the $C_{3-12}$ linear or branched alkylene groups, a $C_{3-12}$ linear alkylene group can be mentioned, and specific examples thereof include n-propylene, isopropylidene, n-butylene, isobutylene, tert-butylene, n-pentylene, isopentylene, neopentylene, n-hexylene, isohexylene, n-octylene, isooctylene, neooctylene, nonylene (or an isomer thereof), decylene (or an isomer thereof), undecylene (or an isomer thereof) or dodecylene (or an isomer thereof), preferably n-propylene, n-butylene, n-pentylene, n-hexylene, n-heptylene, n-octylene, n-nonylene, n-decylene, n-undecylene or n-dodecylene.

According to an aspect of the present invention, as the $C_{3-12}$ linear or branched oxaalkylene groups, for example, a $C_{3-12}$ linear oxaalkylene group can be mentioned, and specific examples thereof include —(CH$_2$)$_2$—O—(CH$_2$)—, —(CH$_2$)$_2$—O—(CH$_2$)$_2$—, —(CH$_2$)—O—(CH$_2$)$_3$—, —(CH$_2$)$_2$—O—(CH$_2$)$_3$—, —(CH$_2$)—O-propylene-, —(CH$_2$)—O—(CH$_2$)$_4$—, —(CH$_2$)—O—(CH$_2$)$_2$—O—(CH$_2$)—, —(CH$_2$)—O—(CH$_2$)$_2$—O—(CH$_2$)$_2$—, —(CH$_2$)—O-tertbutylene-, —(CH$_2$)$_2$—O—(CH$_2$)$_4$—, —(CH$_2$)$_3$—O—(CH$_2$)$_3$—, —(CH$_2$)—O-neopentylene-, —(CH$_2$)$_2$—O—(CH$_2$)$_6$—, —(CH$_2$)$_2$—O—(CH$_2$)$_7$—, —(CH$_2$)$_2$—O—(CH$_2$)$_8$—, —(CH$_2$)—O-isooctylene-, —(CH$_2$)$_2$—O—(CH$_2$)$_{10}$—, —(CH$_2$)$_2$—O-decylene or an isomer thereof-, —(CH$_2$)—O—(CH$_2$)$_6$—, —(CH$_2$)—O—(CH$_2$)$_7$—, —(CH$_2$)—O—(CH$_2$)$_8$—, —(CH$_2$)—O—(CH$_2$)$_{11}$—, —(CH$_2$)—O—(CH$_2$)$_2$—O—(CH$_2$)—, —(CH$_2$)$_2$—O—(CH$_2$)$_2$—O—(CH$_2$)$_2$—, —(CH$_2$)$_2$—O—(CH$_2$)$_4$—O—(CH$_2$)$_2$—, —(CH$_2$)$_2$—O—(CH$_2$)$_6$—O—(CH$_2$)$_2$— or —(CH$_2$)$_2$—O—(CH$_2$)$_8$—O—(CH$_2$)$_2$—. Further, as the $C_{3-12}$ linear oxaalkylene groups, a $C_{4-6}$ linear oxaalkylene group can be mentioned, and a $C_{4-6}$ linear monooxaalkylene group can be particularly mentioned, and especially an monoxaalkylene group represented by the formula —(CH$_2$)$_m$—O—(CH$_2$)$_m$— (where each value m, being identical or different from each other, independently represents 2 or 3, such as 2) can be mentioned. More particularly, —(CH$_2$)$_2$—O—(CH$_2$)$_2$—, —(CH$_2$)$_2$—O—(CH$_2$)$_3$—, —(CH$_2$)$_3$—O—(CH$_2$)$_3$— or —(CH$_2$)$_2$—O—(CH$_2$)$_4$— can be mentioned.

According to an aspect of the present invention, in the formula (I), the plural groups R are identical or different from each other, each independently selected from the group consisting of $C_{1-4}$ linear or branched alkyl groups, preferably each independently selected from the group consisting of methyl and ethyl, more preferably all methyl.

According to an aspect of the present invention, in the formula (I), X is OH.

According to an aspect of the present invention, in the contacting step, the molar ratio of the organic template to the first oxide source (calculated on the basis of the first oxide) is generally in a range from 0.02 to 0.5, preferably from 0.05 to 0.5, from 0.15 to 0.5 or from 0.3 to 0.5.

According to an aspect of the present invention, in the contacting step, in addition to the compound represented by the formula (I), other organic templates conventionally used in the art for the preparation of molecular sieves may be further used as the organic template. Preferably, in the contacting step, only the compound represented by the formula (I) is used as the organic template. Here, the compound represented by the formula (I) can be used alone or in a combination of two or more thereof in any ratio.

According to an aspect of the present invention, in the contacting step, the first oxide source is generally a tetravalent oxide source, and for example, can be at least one selected from the group consisting of a silica source, a germanium dioxide source, a tin dioxide source, a titania source and a zirconium dioxide source, preferably a silica source ($SiO_2$) or a combination of a silica source and a germanium dioxide source. Said first oxide sources can be used alone or in a combination of two or more thereof in any ratio. When two or more are used in combination, the molar ratio between any two of the first oxide sources can be, for example, from 20:200 to 35:100. As an example of the combination, a combination of a silica source and a germanium dioxide source can be mentioned, in which case the molar ratio between the silica source and the germanium dioxide source can be, for example, from 20:200 to 35:100.

According to an aspect of the present invention, in the contacting step, as the first oxide source, any corresponding oxide source conventionally used for this purpose in the art can be used, including but not limited to, among others, oxides, hydroxides, alkoxides, metal oxyacid salts, acetates, oxalates, ammonium salts, sulfates, halogenated salts and nitrates of the corresponding metal in the first oxide. For example, when the first oxide is silica, examples of the first oxide source include silica sol, crude silica gel, tetraethyl orthosilicate, water glass, white carbon black, silicic acid, silica gel, potassium silicate, or the like. When the first oxide is germanium dioxide, examples of the first oxide source include germanium tetraalkoxide, germanium oxide, germanium nitrate, or the like. When the first oxide is tin dioxide, examples of the first oxide source include tin chloride, tin sulfate, tin nitrate, and the like. When the first oxide is titania, examples of the first oxide source include titanium tetraalkoxide, titanium dioxide, titanium nitrate, and the like. When the first oxide is zirconium dioxide, examples of the first oxide source include zirconium chloride, zirconium sulfate, zirconium nitrate, and the like. Said first oxide sources can be used alone or in a combination of two or more thereof in a desired ratio.

According to an aspect of the present invention, in the contacting step, the second oxide source is generally a trivalent oxide source, such as at least one selected from the group consisting of an alumina source, a boron oxide source, an iron oxide source, a gallium oxide source, a rare earth oxide source, an indium oxide source, and a vanadium oxide source, preferably an alumina ($Al_2O_3$) source. Said second oxide sources can be used alone or in a combination of two or more thereof in any ratio. When two or more are used in combination, the molar ratio between any two of the second oxide sources can be, for example, from 30:200 to 60:150.

According to an aspect of the present invention, in the contacting step, as the second oxide source, any corresponding oxide source conventionally used for this purpose in the art can be used, including but not limited to, among others, oxides, hydroxides, alkoxides, metal oxyacid salts, acetates, oxalates, ammonium salts, sulfates, halogenated salts and nitrates of the corresponding metal in the second oxide. For example, when the second oxide is alumina, examples of the second oxide source include aluminum chloride, aluminum sulfate, hydrated alumina, sodium metaaluminate, aluminum sol, aluminum hydroxide or the like. When the second oxide is boron oxide, examples of the second oxide source include boric acid, borate, borax, boron trioxide and the like. When the second oxide is iron oxide, examples of the second oxide source include iron nitrate, iron chloride, iron oxide, and the like. When the second oxide is gallium oxide, examples of the second oxide source include gallium nitrate, gallium sulfate, gallium oxide, and the like. When the second oxide is a rare earth oxide, examples of the second oxide source include lanthanum oxide, neodymium oxide, yttrium oxide, cerium oxide, lanthanum nitrate, neodymium nitrate, yttrium nitrate, ammonium cerium sulfate, and the like. When the second oxide is indium oxide, examples of the second oxide source include indium chloride, indium nitrate, indium oxide, and the like. When the second oxide is vanadium oxide, examples of the second oxide source include vanadium chloride, ammonium metavanadate, sodium vanadate, vanadium dioxide, vanadyl sulfate, and the like. Said second oxide sources can be used alone or in a combination of two or more thereof in a desired ratio.

According to an aspect of the present invention, in the contacting step, the molar ratio of the first oxide source (calculated on the basis of the first oxide, such as $SiO_2$) to the second oxide source (calculated on the basis of the second oxide, such as $Al_2O_3$) is generally in a range from 5 to $\infty$, especially from 5 to less than 30 (e.g. from 10 to less than 30), from 30 to 100 (e.g. from 55 to 100), and from greater than 100 to $\infty$. (e.g. from 200 to $\infty$, or from 200 to 700). Here, when the molar ratio is $\infty$, it means that the second oxide source is not used or the second oxide source is not intentionally introduced in the contacting step.

According to an aspect of the present invention, in the contacting step, the molar ratio of water to the first oxide source (calculated on the basis of the first oxide) is generally in a range from 5 to 50, preferably from 5 to 15.

According to an aspect of the present invention, in the contacting step, an alkali source may or may not be used. When the alkali source is not intentionally used, the group X contained in the compound represented by the formula (I) can be used to provide the $OH^-$ required herein. Here, as the alkali source, any alkali source conventionally used for this purpose in the art can be used, including but not limited to inorganic bases comprising an alkali metal or alkaline earth metal as the cation, particularly sodium hydroxide and potassium hydroxide. Said alkali sources can be used alone or in a combination of two or more thereof in any ratio.

According to an aspect of the present invention, in the contacting step, the molar ratio of the alkali source (calculated on the basis of $OH^-$) to the first oxide source (calculated on the basis of the first oxide) is generally in a range from 0 to 1, preferably from 0.04 to 1, from 0.1 to 1, from 0.2 to 1, from 0.3 to 0.7 or from 0.45 to 0.7.

According to an aspect of the present invention, in the contacting step, as the crystallization condition, the crystallization temperature is generally in a range from 80° C. to 120° C., preferably from 120° C. to 170° C. or from 120° C. to 200° C.

According to an aspect of the present invention, in the contacting step, as the crystallization condition, the crystallization period is generally at least 1 day, preferably at least 2 days, preferably from 3 days to 8 days, from 5 days to 8 days or from 4 days to 6 days.

According to an aspect of the present invention, in the method for the preparation of the molecular sieve, after the contacting step is completed, the molecular sieve can be separated as a product from the resultant reaction mixture by any separation method commonly known. Here, the molecular sieve product comprises the molecular sieve according to the present invention. Further, as the separation method, for example, a method comprising filtering, washing, and drying the resultant reaction mixture can be mentioned.

According to an aspect of the present invention, in the method for the preparation of the molecular sieve, the filtration, washing and drying can be carried out in any conventional manner known in the art. By way of example, as the filtration, for example, the resultant reaction mixture can be simply subjected to suction filtration. As the washing, for example, washing with deionized water can be performed until the pH of the filtrate reaches 7-9, preferably 8-9. The drying temperature is, for example, 40 to 250° C., preferably 60 to 150° C., and the drying time is, for example, 8 to 30 hours, preferably 10 to 20 hours. The drying can be carried out under normal pressure or under reduced pressure.

According to an aspect of the present invention, the method for the preparation of the molecular sieve may further comprise a step of calcining the resultant molecular sieve (hereinafter referred to as the calcination step) as needed to remove the organic template and possible moisture, and the like, so that a calcined molecular sieve can be obtained. In the context of the present specification, the molecular sieves before and after calcination are collectively referred to as the molecular sieve of the present invention or the molecular sieve according to the present invention.

According to an aspect of the present invention, in the method for the preparation of the molecular sieve, the calcination can be carried out in any conventional manner known in the art, for example, at a calcination temperature generally ranging from 300° C. to 750° C., preferably from 400° C. to 600° C. for a calcination period generally ranging from 1 hour to 10 hours, preferably from 3 hours to 6 hours. In addition, the calcination is generally carried out under an oxygen-containing atmosphere, such as an air or oxygen atmosphere.

According to an aspect of the present invention, if desired, any molecular sieve produced as previously described (referred to as the molecular sieve according to the present invention or the molecular sieve according to the present invention) can be further subjected to ion exchanged by any conventional means known in the art, for example by using an ion exchange or solution impregnation process (see, for example, U.S. Pat. Nos. 3,140,249 and 3,140,253, etc.), so that the metal cation (such as Na ion or K ion, depending on the preparation method) contained therein can be replaced in whole or in part by other cation(s). Examples of said other cation include hydrogen ion, other alkali metal ions (including K ion, Rb ion, etc.), ammonium ions (including $NH_4$ ion, quaternary ammonium ions such as tetramethylammonium ion and tetraethylammonium ion, etc.), alkaline earth metal ions (including Mg ion, Ca ion), Mn ion, Zn ion, Cd ion, noble metal ions (including Pt ion, Pd ion, Rh ion, etc.), Ni ion, Co ion, Ti ion, Sn ion, Fe ion and/or rare earth metal ions, and the like.

The molecular sieve according to the present invention can be further treated with a dilute acid solution or the like as needed to increase the silica-alumina ratio, or treated with water vapor to improve the resistance of the molecular sieve crystal to acid attack.

The molecular sieve according to the present invention generally has an X-ray diffraction pattern substantially as shown in the following table.

| $2\theta$ (°) | d-distance (Å) | Relative intensity ($I/I_0 \times 100$) |
|---|---|---|
| 5.2048 ± 0.05 | 16.96501 ± 0.05 | VS |
| 8.4762 ± 0.27 | 10.42335 ± 0.34 | W |
| 9.0095 ± 0.06 | 9.80755 ± 0.07 | M |
| 10.3943 ± 0.05 | 8.50381 ± 0.05 | W |
| 16.1228 ± 0.50 | 5.49296 ± 0.50 | W |
| 23.7405 ± 0.22 | 3.74484 ± 0.03 | W |

According to an aspect of the present invention, it is preferable that the X-ray diffraction pattern of the molecular sieve further includes an X-ray diffraction peak substantially as shown in the following table.

| $2\theta$ (°) | d-distance (Å) | Relative intensity ($I/I_0 \times 100$) |
|---|---|---|
| 14.3448 ± 0.66 | 6.16955 ± 0.27 | W |
| 15.2971 ± 0.50 | 5.78752 ± 0.50 | W |
| 16.1979 ± 0.50 | 5.46765 ± 0.50 | W |
| 20.8653 ± 0.11 | 4.25393 ± 0.02 | W |
| 23.9532 ± 0.14 | 3.71207 ± 0.02 | W |

According to an aspect of the present invention, it is preferable that the X-ray diffraction pattern of the molecular sieve further includes an X-ray diffraction peak substantially as shown in the following table.

| $2\theta$ (°) | d-distance (Å) | Relative intensity ($I/I_0 \times 100$) |
|---|---|---|
| 14.4217 ± 0.56 | 6.136810 ± 0.43 | W |
| 15.1988 ± 0.50 | 5.82474 ± 0.50 | W |
| 15.5903 ± 0.50 | 5.67936 ± 0.50 | W |
| 20.6353 ± 0.50 | 4.30082 ± 0.10 | W |
| 22.7406 ± 0.08 | 3.90718 ± 0.02 | W |
| 24.4468 ± 0.26 | 3.63823 ± 0.04 | W |

According to an aspect of the present invention, the molecular sieve generally has a columnar crystal particle morphology when observed using a scanning electron microscope (SEM). Here, the term "crystal particle morphology" refers to the (overall) outer shape exhibited by a single crystal particle of the molecular sieve in the observation field of the scanning electron microscope. Further, as the columnar shape, a prismatic shape, particularly a hexagonal prismatic shape, is preferred. Here, the prism refers to a convex prism and generally refers to a right prism and a regular polygonal prism (such as a regular hexagonal prism). It should be specially pointed out that since the growth process of the crystal of the molecular sieve may be disturbed by various factors, there may be a certain degree of deviation when its real crystal particle morphology is compared with a (truely) right prism or a (truely) regular polygonal prism in geometrical sense, such as a deviation of 30%, 20%, or 5%, resulting in the production of a beveled prism, or an irregular polygonal (or even a curved polygonal) prism, but the present invention is not intended to specify the degree of deviation. Moreover, any greater or smaller deviations do not depart from the scope of the present invention.

According to an aspect of the present invention, the molecular sieve (a single crystal particle) has an effective diameter generally ranging from 100 nm to 5000 nm when observed using a scanning electron microscope (SEM). Here, the term "effective diameter" means that two points are arbitrarily selected at the cross section of the molecular sieve (a single crystal particle) along the contour (edge) of the cross section, and the linear distance between the two points is measured, where the greatest linear distance is taken as the effective diameter. If the profile of the cross section of the molecular sieve is presented as a polygon such as a hexagon, the effective diameter generally refers to the linear distance between two vertices of the polygon that are farthest from each other, i.e. the diagonal distance. Briefly, the effective diameter substantially corresponds to the diameter of the circumcircle of the polygon representing the contour of the cross section.

According to an aspect of the present invention, the molecular sieve (a single crystal particle) has a height generally ranging from 100 nm to 3000 nm when observed using a scanning electron microscope (SEM). Here, the term "height" refers to a linear distance between the centers of the two end faces of a single crystal particle (columnar crystal particle) of the molecular sieve. In the usual case, the two end faces of the column of the molecular sieve are substantially parallel to each other, and the linear distance is the vertical distance between the two end faces, but the present invention is not limited thereto.

According to an aspect of the present invention, the molecular sieve (a single crystal particle) has an aspect ratio generally ranging from 0.1 to 8 when observed using a scanning electron microscope (SEM). Here, the term "aspect ratio" refers to the ratio of the height to the effective diameter.

According to an aspect of the present invention, the molecular sieve has a total specific surface area generally ranging from 400 $m^2 \cdot g^{-1}$ to 600 $m^2 \cdot g^{-1}$, preferably from 450 $m^2 \cdot g^{-1}$ to 580 $m^2 \cdot g^{-1}$. Here, the total specific surface area is obtained using the liquid nitrogen adsorption method, calculated with the BET model.

According to an aspect of the present invention, the molecular sieve has a pore volume generally ranging from 0.3 ml/g to 0.5 ml/g, preferably from 0.30 ml/g to 0.40 ml/g. The molecular sieve according to the present invention has a very high micropore volume, which indicates that it belongs to an ultra-macroporous molecular sieve. Here, the pore volume is obtained using the liquid nitrogen adsorption method, calculated with the BET model.

The molecular sieve according to the present invention has good thermal/hydrothermal stability and has a larger pore volume. Thus, the molecular sieve according to the present invention is capable of adsorbing more/larger molecules, thereby exhibiting excellent adsorptive/catalytic properties.

The molecular sieve according to the present invention has a relatively strong acidity, particularly a large number of L acid sites. This molecular sieve has not been produced in the prior art. As a result, the molecular sieve according to the present invention has better performance particularly in an acid-catalyzed reaction.

The molecular sieve according to the present invention can be in any physical form, such as powders, granules or molded articles (e.g., strips, clovers, etc.). These physical forms can be obtained in any conventional manner known in the art, and are not particularly limited.

Sixth Embodiment

The molecular sieve according to the present invention can be used in combination with other materials, thereby obtaining a molecular sieve composition. As such other materials, for example, active materials and inactive materials can be mentioned. Examples of the active materials include, among others, synthetic zeolite and natural zeolite. Examples of the inactive materials (generally referred to as a binder) include, among other, clay, carclazyte, silica gel, and alumina. Said other materials can be used alone or in a combination of two or more thereof in any ratio. As to the amount of said other materials, there is no particular limitation, and any amount conventional used in the art can be directly adopted.

The molecular sieve or molecular sieve composition according to the present invention is particularly suitable for use as an adsorbent, for example, for separating at least one component from a mixture of components in a gas phase or a liquid phase.

The molecular sieve or molecular sieve composition according to the present invention is particularly suitable for use as a catalyst in the conversion reaction of hydrocarbons. Examples of the conversion reaction of hydrocarbons include, among others, catalytic cracking, hydrocracking, disproportionation, alkylation, oligomerization, and isomerization reactions.

The molecular sieve or molecular sieve composition according to the present invention is particularly suitable for use as a carrier or a carrier component of catalysts, and active component(s) can be supported onto it in any conventional manner known in the art, such as by solution impregnation. Said active component includes, but are not limited to, active metal components (including Ni, Co, Mo, W or Cu, etc.), reactive inorganic auxiliaries (such as F, P, etc.) and organic compounds (such as organic acids, organic amines, etc.). Said active components can be used alone or in a combination of two or more thereof in any ratio. As to the amount of the active component, there is no particular limitation, and any amount conventional used in the art can be directly adopted.

EXAMPLES

The present invention is further illustrated with reference to the following examples, but the present invention is not limited thereto.

In the context of the present specification, including the following examples and comparative examples, an Autochem 112920 temperature programmed desorber, Microtek, the United States, was used. Test conditions were as follows: 0.2 g molecular sieve of 20-40 mesh was weighed into a sample tube, placed in a heating furnace using He gas (25 mL/min) as the carrier gas, raised to a temperature of 600° C. at 20° C./min, and purged for 60 min to remove impurities adsorbed on the surface of the molecular sieve; then, the temperature was lowered to 100° C., the temperature was kept for 10 min, and the gas was switched to $NH_3$—He mixture (10% $NH_{3+90}$% He) to conduct adsorption for 30 min; and then, the resultant was purged with He gas for 90 min until the baseline was stable to desorb the physically adsorbed $NH_3$; the temperature was increased to 600° C. at a heating rate of 10° C./min for desorption, and the desorption was conducted for 30 min and then completed; a TCD detector was used to detect changes in the gas composition, and an integration was automatically performed by the instrument to provide an acid amount distribution.

In the context of the present specification, including the following examples and comparative examples, XRD testing was performed using the Netherland, PANalytical Corporation equipment. Test conditions: Cu target, Kα radiation, Ni filter, tube voltage 40 kV, tube current 40 mA, and scanning range 2-50°.

In the context of the present specification, including the following examples and comparative examples, a TECNAIG$^2$F20 (200 kV) scanning electron microscope, FEI Corporation, the United States, was used. Test conditions were as follows: a sample was prepared using the suspension method, and in particular 0.01 g of a molecular sieve sample was placed in a 2 mL glass bottle, dispersed with absolute ethanol, and shaked evenly; one drop of the resultant was taken with a dropper, dropped on a sample net having a diameter of 3 mm, dried, placed in the injector, and then inserted into the electron microscope for observation. The observation may be conducted using a magnification of 10,000 times or a magnification of 50,000 times. Further, the molecular sieve was observed at a magnification of 50,000 times, an observation field was randomly selected, and the average of the sum of the effective diameters and the average of the sum of the heights of all molecular sieve crystals in the observation field were calculated. The operation was repeated for a total of 10 times. The average of the sum of the average values obtained in the 10 times of operations was taken as the effective diameter and the height, respectively.

In the context of the present specification, including the following examples and comparative examples, a Varian $^{UNITY}$ INOVA 500 MHz nuclear magnetic resonance spectrometer, Varian, the United States, was used. Test conditions: solid double resonance probe, Φ4 mm ZrO$_2$ rotor. Experimental parameters: test temperature being room temperature, scan times nt=5000, pulse width pw=3.9 μs, spectral width sw=31300 Hz, resonance frequency of the observation nuclear Sfrq=125.64 MHz, sampling time at=0.5 s, chemical displacement calibration $δ_{TMS}$=0, delay time d1=4.0 s, decoupled mode dm=nny (reverse gated decoupling), deuterated chloroform lock field.

In the context of the present specification, including the following examples and comparative examples, a Model 3013 X-ray fluorescence spectrometer, Japanese Science and Technology Co., Ltd., was used. Test conditions: tungsten target, excitation voltage 40 kV, excitation current 50 mA. Experimental procedure was as follows: the sample was tabletted, then mounted on an X-ray fluorescence spectrometer, and excited under the irradiation of X-rays to emit fluorescence; the relationship between the fluorescence wavelength λ and the atomic number Z of the element was as follows: $λ=K(Z-S)^{-2}$, with K being a constant, so that whenever the wavelength λ of the fluorescence was measured, the element can be determined. The intensity of the characteristic lines of each element was measured by a scintillation counter and a proportional counter, and elemental or semi-quantitative analysis was performed.

In the context of the present specification, including the following examples and comparative examples, a FTS3000 type FT-IR spectrometer, BIO-RAD Company, the United States, was used. Test conditions were as follows: evacuated to $10^{-3}$ Pa at 350° C., and the wave number range was 1300-3900 cm$^{-1}$. The sample was tabletted, then placed in an in-situ cell of the infrared spectrometer and sealed, evacuated to $10^{-3}$ Pa at 350° C. for 1 h to desorb the gas molecules on the surface of the sample, and cooled to room temperature. Pyridine/2,4,6-trimethylpyridine with a pressure of 2.67 Pa was introduced into the in-situ cell, and after equilibrium adsorption for 30 min, the temperature was raised to 200° C., and again evacuated to $10^{-3}$ Pa for 30 min, and then cooled to room temperature. The infrared absorption spectrum of the adsorption of pyridine/2,4,6-trimethylpyridine at 200° C. was recorded by scanning in the wave number range of 1300-3900 cm$^{-1}$. The sample in the infrared absorption cell was moved to the heat treatment zone, heated to 350° C., evacuated to $10^{-3}$ Pa, held for 30 min, cooled to room temperature, and the infrared spectrum of the pyridine adsorption at 350° C. was recorded.

In the context of the present specification, including the following examples and comparative examples, all of the pharmaceuticals and raw materials are either commercially available or can be prepared based on existing knowledge.

First Embodiment, Fourth Embodiment, and Sixth Embodiment

In the context of the present embodiment, including the following examples and comparative examples, the total specific surface area, pore volume and pore diameter of the molecular sieve were measured by the following analytical methods.

Equipment: Micromeritic ASAP2010 Static Nitrogen Adsorber

Measurement conditions: the sample was placed in a sample processing system, evacuated to $1.35×10^{-2}$ Pa at 350° C., and kept at this temperature and pressure for 15 h to purify the sample; at a liquid nitrogen temperature of −196° C., the adsorption amount and desorption amount of nitrogen of the purified sample under different specific pressure P/P0 conditions were measured, and an adsorption-desorption isotherm curve was obtained; and then, the total specific surface area was calculated with the two-parameter BET equation, and the adsorption capacity at the specific pressure P/P0≈0.98 was taken as the pore volume of the sample, and the pore diameter distribution was calculated with the BJH model.

Example I Series

Example I-1

Preparation of Template A:

15 g (0.087 mol) of tetramethylhexamethylenediamine was added to a 500 ml three-necked flask, 250 ml of isopropanol was added, and 18.8 g (0.087 mol) of 1,4-dibromobutane was added dropwise at room temperature. The addition was completed after 15 minutes, and the temperature was raised till refluxing. The solution gradually changed from colorless and transparent to white and turbid. The reaction was followed by high performance liquid chromatography (HPLC). After the reaction was completed, 200 ml of ethyl acetate was added to the reaction mixture, and the mixture was refluxed for 1 hour, cooled and filtered with suction. The resulted solid was washed with ethyl acetate and then with diethyl ether to give 30 g of a white solid product as 1,1,6,6-tetramethyl-1,6-diaza-12-membered ring-1,6-dibromide (a compound where n is 4, m is 6, R is methyl, X is Br), having a relative molecular weight of 388.2, a melting point of 273.7° C. $^1$H NMR spectrum shows chemical shift (300 MHz, CDCl$_3$) δ 1.50 (t, 4H), 1.90 (t, 8H), 3.14 (s, 12H), 3.40 (t, 8H).

Preparation of Template B: Br in Template A was replaced with OH⁻ by ion exchange; ion exchange resin was a strong basic styrene type anion exchange resin, working solution was 15 m % aqueous solution of Template A, operating temperature was 25° C., the mass ratio of the working fluid to the ion exchange resin was 1:3; the flow rate was 3 drops/second; the exchanged solution was dehydrated by a rotary evaporator to give a product that is a compound of formula (I) where n is 4, m is 6, R is methyl, and X is OH, having a relative molecular weight of 262.2, and a purity of 99.21%. Its bromine content was 0.79 m %.

Example I-2

Preparation of Template C 10 g (0.058 mol) of tetramethylhexamethylenediamine was added to a 500 ml three-necked flask, 250 ml of isopropanol was added, and 16.6 g (0.058 mol) of 1,9-dibromodecane was added dropwise at room temperature. The addition was completed after 15 minutes, and the temperature was raised till refluxing. The solution gradually changed from colorless and transparent to white and turbid. The reaction was followed by high performance liquid chromatography (HPLC). After the reaction was completed, 200 ml of ethyl acetate was added to the reaction mixture, and the mixture was refluxed for 1 hour, cooled and filtered with suction. The resulted solid was washed with ethyl acetate and then with diethyl ether to give 25 g of a white solid product, as 1,1,8,8-tetramethyl-1,8-diaza-17-membered ring-1,8-dibromide (a compound where n is 9, m is 6, R is methyl, X is Br), having a relative molecular weight of 458.4. $^1$H NMR spectrum shows chemical shift (300 MHz, CDCl$_3$) δ 1.51 (t, 14H), 1.92 (t, 8H), 3.16 (s, 12H), 3.40 (t, 8H).

Preparation of Template D: Br in Template C was replaced with OH⁻ by ion exchange; ion exchange resin was strong basic styrene type anion exchange resin, working solution was 15 m % aqueous solution of Template C, operating temperature was 25° C., the mass ratio of the working fluid to the ion exchange resin was 1:3; the flow rate was 3 drops/second; the exchanged solution was dehydrated by a rotary evaporator to give a product that is a compound of the formula (I), where n is 9, m is 6, R is methyl, X is OH, having a relative molecular weight of 332.4, and a purity of 99.8%. Its bromine content was 0.2 m %.

Example I-3

5.35 g of Template D was added to a 45 mL Teflon container, 0.157 g of sodium hydroxide was added, stirred for 30 minutes until homogeneous, and then 3 g of crude silica gel (Qingdao Haiyang Chemical Co., Ltd., industrial product, SiO$_2$ content of 98%, Al$_2$O$_3$ content of 0.253%) and 0.033 g of solid NaAlO$_2$ was added, and the resultant was allowed to stand and aged for 1 hour to achieve a thorough mixing. The molar ratios of the components were as follows: H$_2$O/SiO$_2$=6, Template D/SiO$_2$=0.10, NaOH/SiO$_2$=0.08.

The above mixture was placed in a 45 mL steel autoclave with a Teflon liner, capped and sealed. The autoclave was placed in a rotating convection oven at a rotational speed of 20 rpm, and reacted at 120° C. for 1 day and then raised to 180° C. to react for 5 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 2:
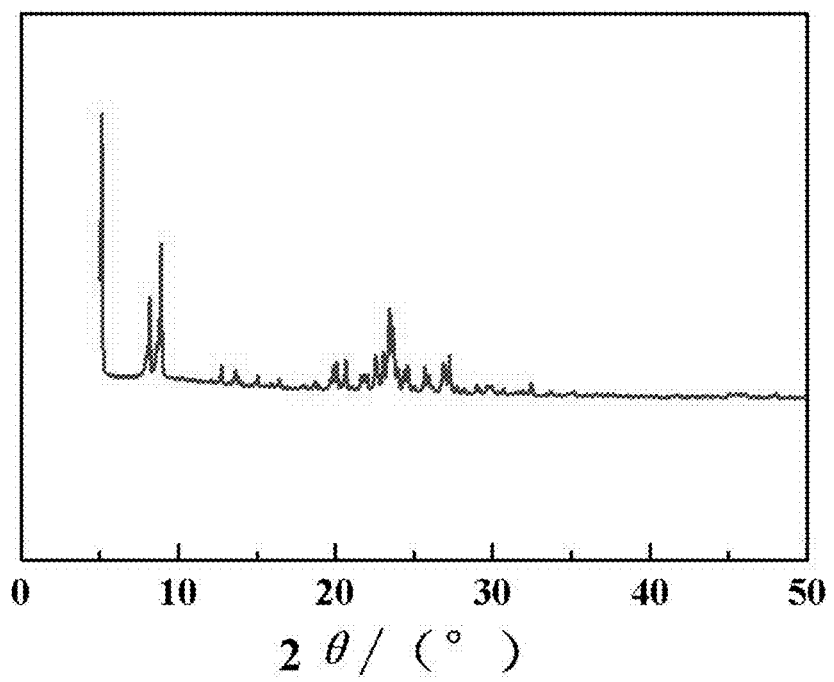
FIG. 2 is an XRD pattern of the molecular sieve produced in Example I-3.

The scanning electron micrograph of the product was shown in FIG. 1. It can be easily seen in the figure that the molecular sieve has the hexagonal prismatic crystal particle morphology, with an effective diameter of 600 nm, a height of 800 nm, and an aspect ratio of 1.33. In accordance with the measurement, the molecular sieve had a total specific surface area of 560 m$^2$·g$^{-1}$ and a pore volume of 0.360 ml/g. The XRD pattern of the product was shown in FIG. 2. The XRF analysis showed that the molecular sieve had a Si/Al$_2$=210.

Example I-4

8.024 g of Template D was added to a 45 mL Teflon container, 0.157 g of sodium hydroxide was added, stirred for 30 minutes until homogeneous, and then 3 g of white carbon black (Qingdao Haiyang Chemical Co., Ltd., industrial product, SiO$_2$ content of 98%) was added, and the resultant was allowed to stand and aged for 1 hour to achieve a thorough mixing. The molar ratios of the components were as follows: H$_2$O/SiO$_2$=10, Template D/SiO$_2$=0.15, NaOH/SiO$_2$=0.08.

The above mixture was placed in a 45 mL steel autoclave with a Teflon liner, capped and sealed. The autoclave was placed in a rotating convection oven at a rotational speed of 20 rpm, and reacted at 110° C. for 1 day and then heated to 160° C. to react for 5 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 3:
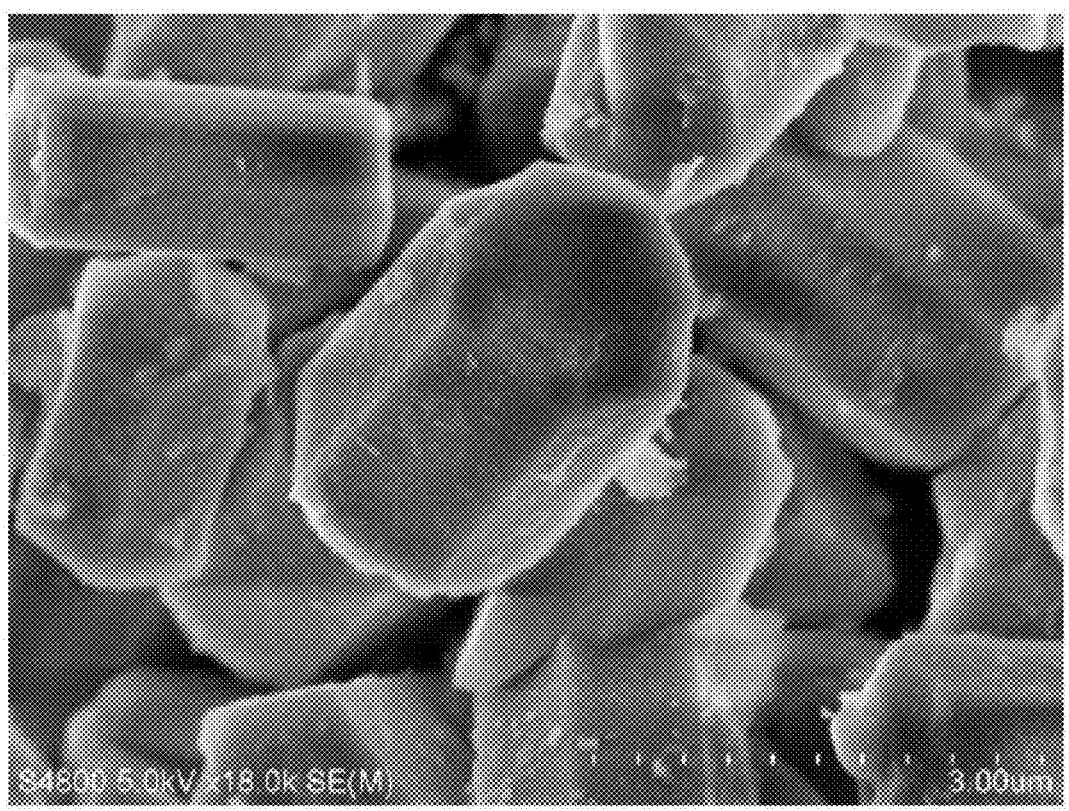
FIG. 3 is a scanning electron micrograph of the molecular sieve produced in Example I-4.
Figure 4:
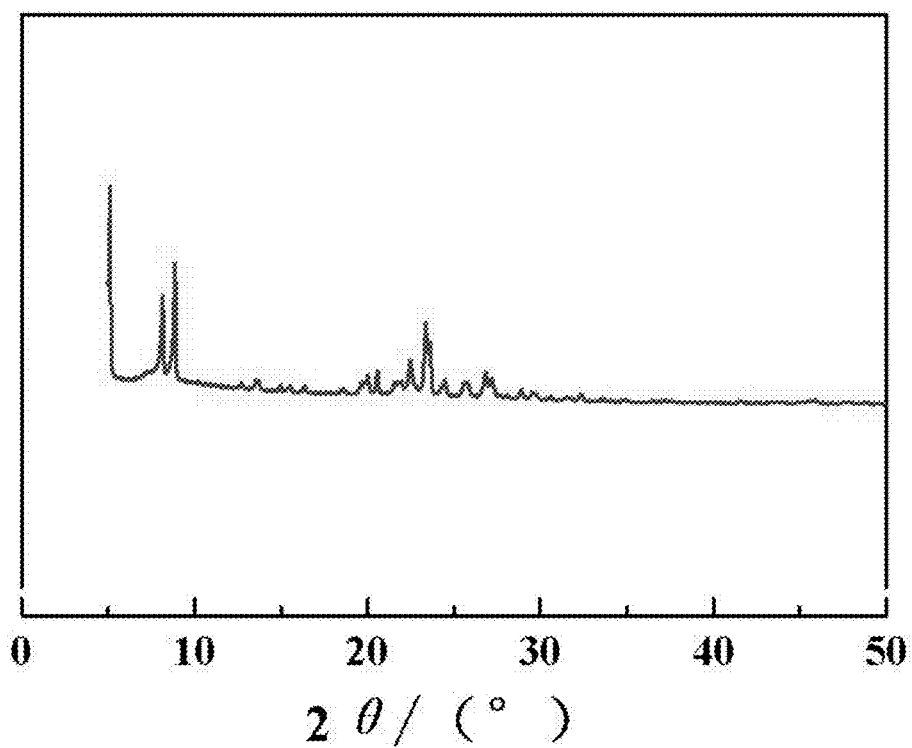
FIG. 4 is an XRD pattern of the molecular sieve produced in Example I-4.

The scanning electron micrograph of the product was shown in FIG. 3. It can be easily seen in the figure that the molecular sieve has the hexagonal prismatic crystal particle morphology, with an effective diameter of 1800 nm, a height of 2400 nm, and an aspect ratio of 1.33. In accordance with the measurement, the molecular sieve had a total specific surface area of 560 m$^2$·g$^{-1}$ and a pore volume of 0.496 ml/g. The XRD pattern of the product was shown in FIG. 4. The XRF analysis showed that the molecular sieve had a Si/Al$_2$=∞.

Example I-5

7.157 g of Template B was added to a 45 mL Teflon container, 0.157 g of sodium hydroxide was added, stirred for 30 minutes until homogeneous, and then 3 g of crude silica gel (Qingdao Haiyang Chemical Co., Ltd., industrial product, SiO$_2$ content of 98%, Al$_2$O$_3$ content of 0.253%) was added, and the resultant was allowed to stand and aged for 1 hour to achieve a thorough mixing. The molar ratios of the components were as follows: H$_2$O/SiO$_2$=7.3, Template D/SiO$_2$=0.15, NaOH/SiO$_2$=0.08. The XRF analysis showed that the molecular sieve had a Si/Al$_2$=625.

The above mixture was placed in a 45 mL steel autoclave with a Teflon liner, capped and sealed. The autoclave was placed in a rotating convection oven at a rotation speed of 20 rpm, and reacted at 130° C. for 2 days and then heated to 160° C. to react for 4 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 5:
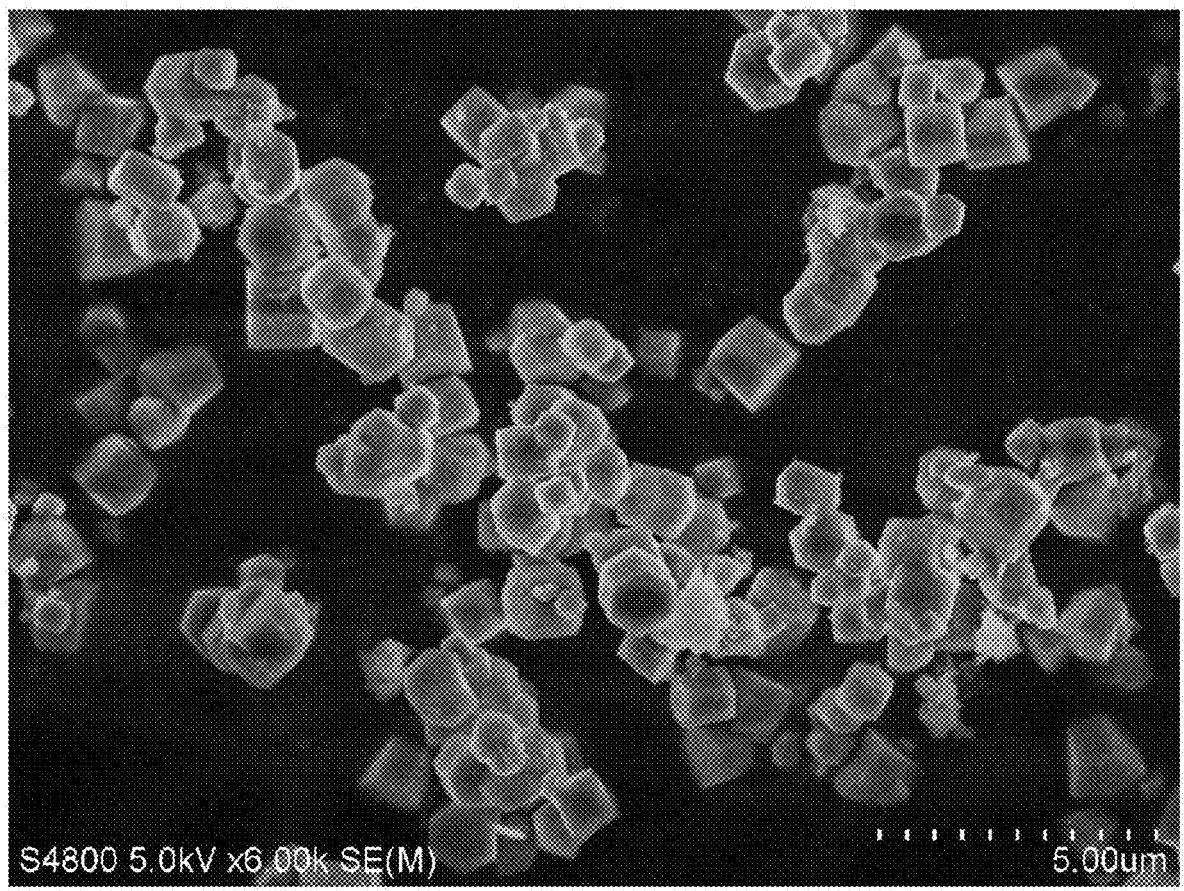
FIG. 5 is a scanning electron micrograph of the molecular sieve produced in Example I-5.
Figure 6:
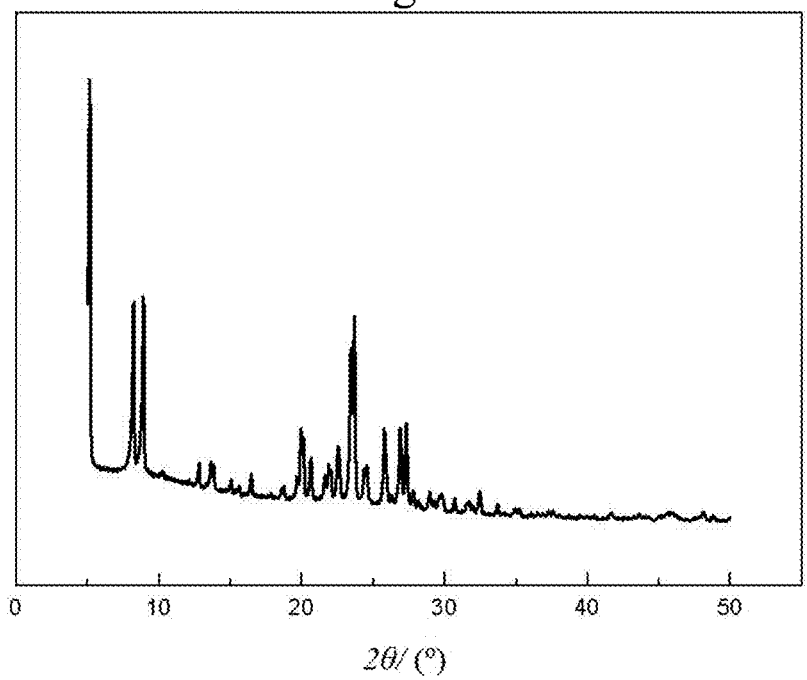
FIG. 6 is an XRD pattern of the molecular sieve produced in Example I-5.

The scanning electron micrograph of the product was shown in FIG. 5. It can be easily seen in the figure that the molecular sieve has the hexagonal prismatic crystal particle morphology, with an effective diameter of 700 nm, a height of 950 nm, and an aspect ratio of 1.36. In accordance with the measurement, the molecular sieve had a total specific surface area of 558 m²·g⁻¹ and a pore volume of 0.443 ml/g. The XRD pattern of the product was shown in FIG. 6.

Example I-6

8.024 g of Template D was added to a 45 mL Teflon container, 0.157 g of sodium hydroxide was added, stirred for 30 minutes until homogeneous, and then 3 g of crude silica gel (Qingdao Haiyang Chemical Co., Ltd., industrial product, SiO$_2$ content of 98%, Al$_2$O$_3$ content of 0.253%) was added, and the resultant was allowed to stand and aged for 1 hour to achieve a thorough mixing. The molar ratios of the components were as follows: H$_2$O/SiO$_2$=7.3, Template D/SiO$_2$=0.15, NaOH/SiO$_2$=0.08.

The above mixture was placed in a 45 mL steel autoclave with a Teflon liner, capped and sealed. The autoclave was placed in a rotating convection oven at a rotation speed of 20 rpm, and reacted at 120° C. for 1 day and then heated to 150° C. to react for 5 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 7:
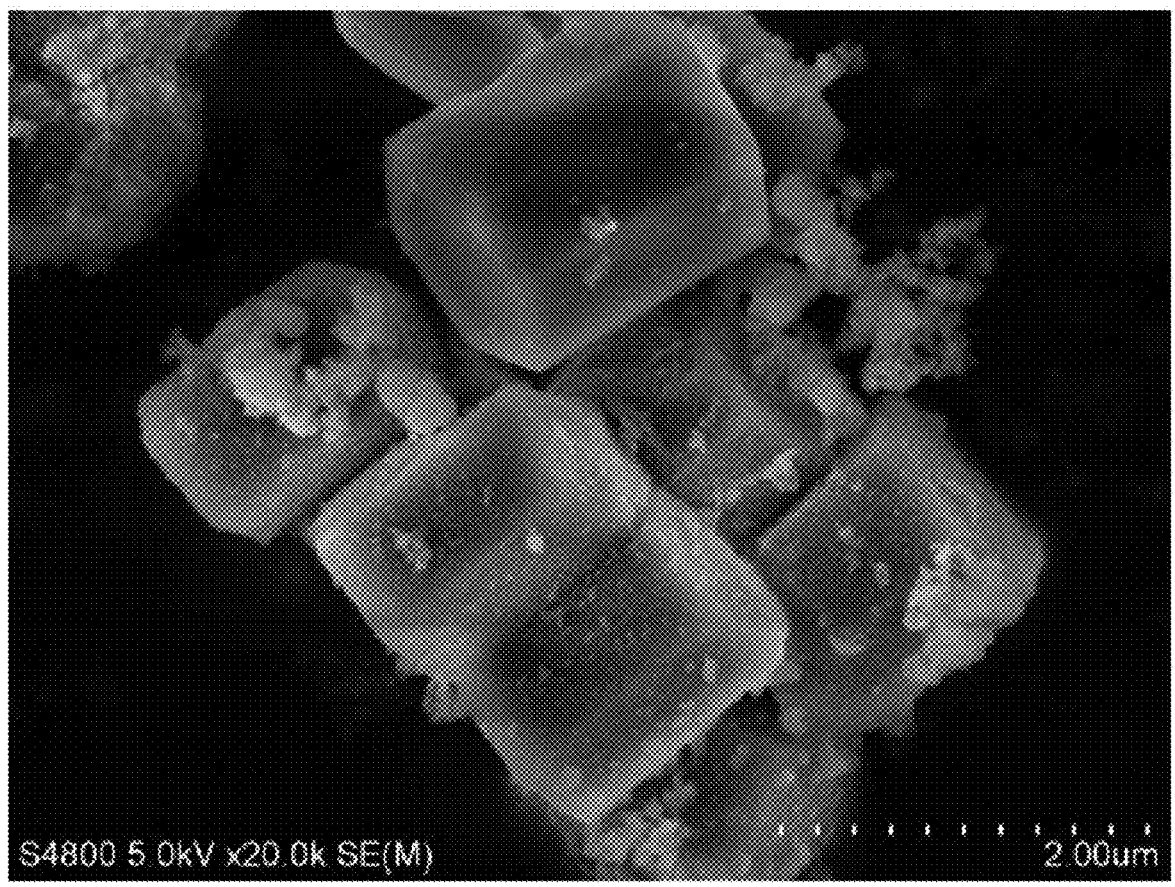
FIG. 7 is a scanning electron micrograph of the molecular sieve produced in Example I-6.
Figure 8:
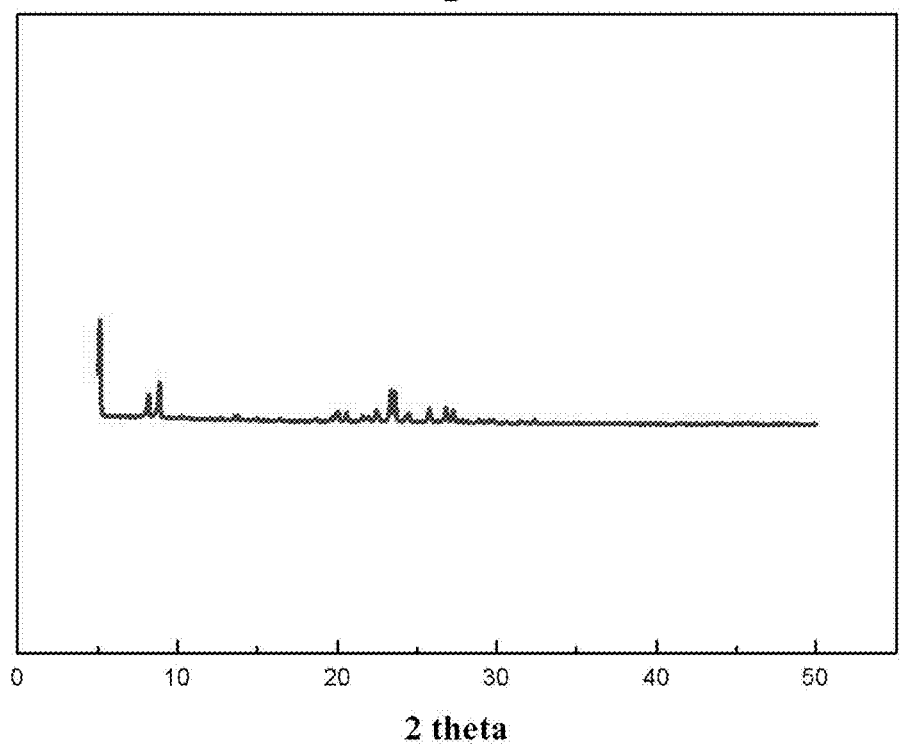
FIG. 8 is an XRD pattern of the molecular sieve produced in Example I-6.
Figure 12:
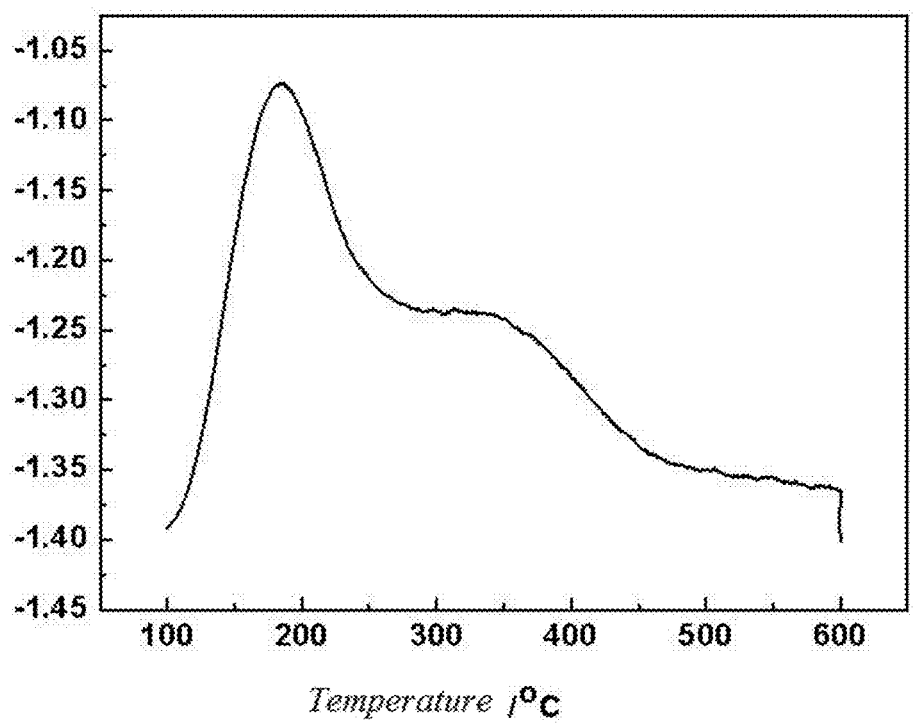
FIG. 12 is a NH3-TPD pattern of the molecular sieve produced in Example I-6.
Figure 13:
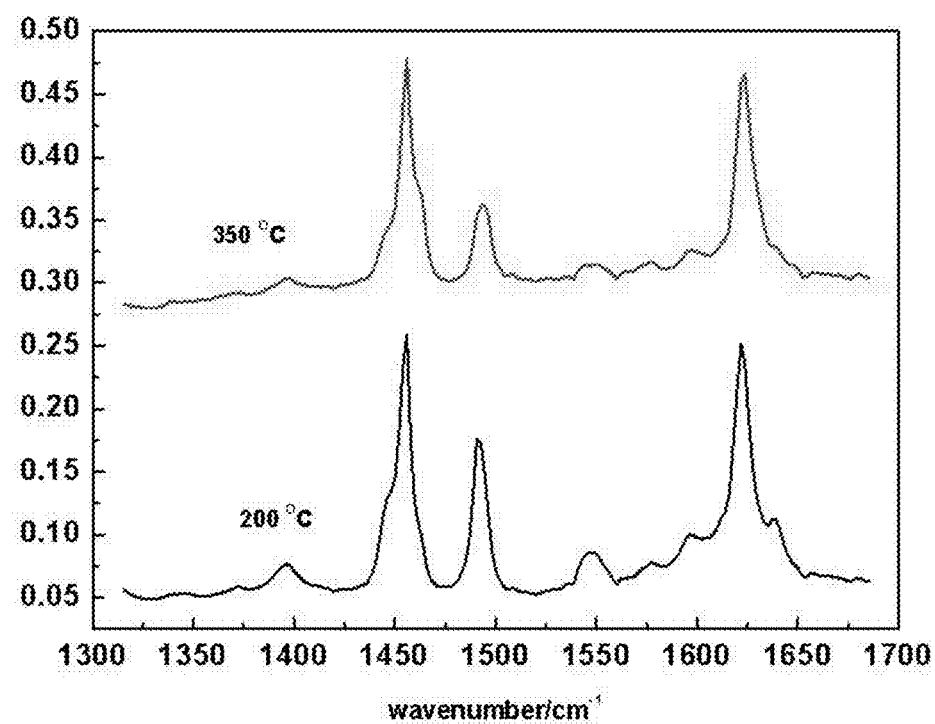
FIG. 13 is an IR spectra of the molecular sieve produced in Example I-6.

The scanning electron micrograph of the product was shown in FIG. 7. It can be easily seen in the figure that the molecular sieve has the hexagonal prismatic crystal particle morphology, with an effective diameter of 1200 nm, a height of 1400 nm, and an aspect ratio of 1.17. In accordance with the measurement, the molecular sieve had a total specific surface area of 533 m²·g⁻¹ and a pore volume of 0.295 ml/g. The XRD pattern of the product was shown in FIG. 8. The results of NH$_3$-TPD indicate (FIG. 12) that the molecular sieves had a significant acidity. The results of the infrared spectrum show (FIG. 13) that the molecular sieve has a low content of B acid and a high content of L acid.

Example I-7

7.157 g of Template B was added to a 45 mL Teflon container, 0.314 g of sodium hydroxide was added, and stirred for 30 minutes until homogeneous, and then 3 g of crude silica gel (Qingdao Haiyang Chemical Co., Ltd., industrial product, SiO$_2$ content of 98%, Al$_2$O$_3$ content of 0.253%) was added, and the resultant was allowed to stand and aged for 1 hour to achieve a thorough mixing. The molar ratios of the components were as follows: H$_2$O/SiO$_2$=7.3, Template B/SiO$_2$=0.15, NaOH/SiO$_2$=0.16.

The above mixture was placed in a 45 mL steel autoclave with a Teflon liner, capped and sealed, and the autoclave was placed in a rotating convection oven at a rotational speed of 20 rpm and reacted at 160° C. for 6 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 9:
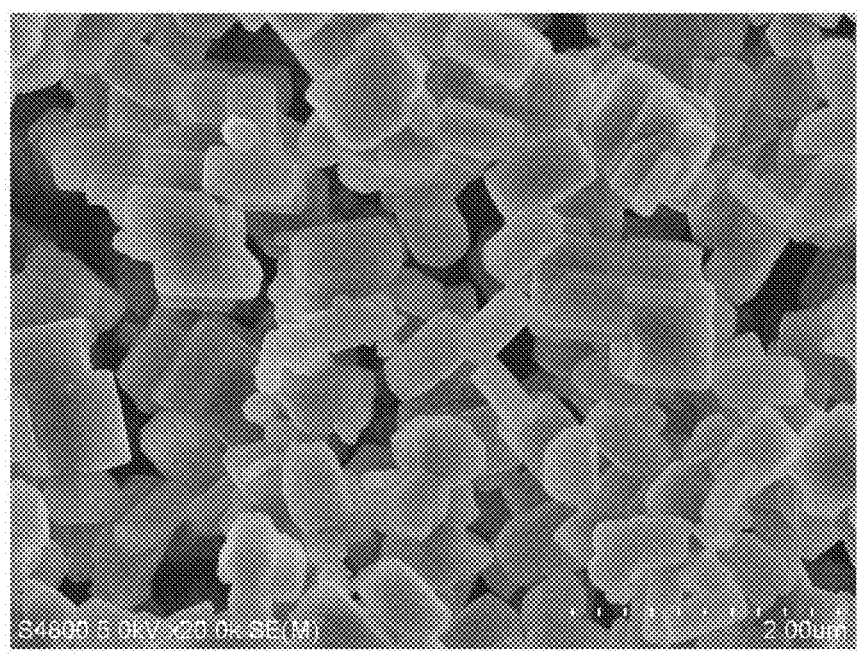
FIG. 9 is a scanning electron micrograph of the molecular sieve produced in Example I-7.
Figure 10:
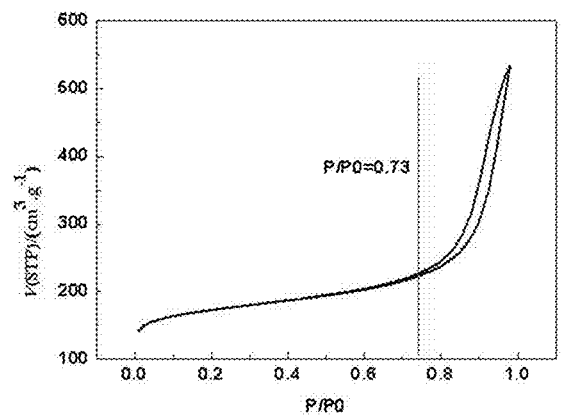
FIG. 10 is an isotherm adsorption-desorption curve of the molecular sieve produced in Example I-7.
Figure 11:
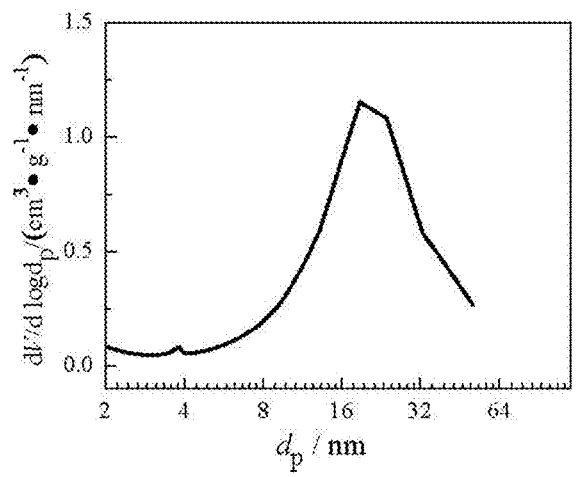
FIG. 11 is a pore diameter distribution curve of the molecular sieve produced in Example I-7.

The scanning electron micrograph of the product was shown in FIG. 9. It can be easily seen in the figure that the molecular sieve has the hexagonal prismatic crystal particle morphology, with an effective diameter of 400 nm, a height of 600 nm, and an aspect ratio of 1.50. In accordance with the measurement, the molecular sieve had a total specific surface area of 568 m²·g⁻¹ and a pore volume of 0.309 ml/g. The XRF analysis showed a Si/Al$_2$=521. The BET isotherm adsorption curve and the pore diameter distribution curve are shown in FIG. 10 and FIG. 11, respectively.

Example II Series

Example II-1

Preparation of Template A:

15 g (0.087 mol) of tetramethylhexamethylenediamine was added to a 500 ml three-necked flask, 250 ml of isopropanol was added, and 18.8 g (0.087 mol) of 1,4-dibromobutane was added dropwise at room temperature. The addition was completed after 15 minutes, and the temperature was raised till refluxing. The solution gradually changed from colorless and transparent to white and turbid. The reaction was followed by high performance liquid chromatography (HPLC). After the reaction was completed, 200 ml of ethyl acetate was added to the reaction mixture, and the mixture was refluxed for 1 hour, cooled and filtered with suction. The resulted solid was washed with ethyl acetate and then with diethyl ether to give 30 g of a white solid product as 1,1,6,6-tetramethyl-1,6-diaza-12-membered ring-1,6-dibromide (a compound where n is 4, m is 6, R is methyl, X is Br), having a relative molecular weight of 388.2, a melting point of 273.7° C. ¹H NMR spectrum shows chemical shift (300 MHz, CDCl$_3$) δ 1.50 (t, 4H), 1.90 (t, 8H), 3.14 (s, 12H), 3.40 (t, 8H).

Preparation of Template B: Br in Template A was replaced with OH⁻ by ion exchange; ion exchange resin was a strong basic styrene type anion exchange resin, working solution was 15 m % aqueous solution of Template A, operating temperature was 25° C., the mass ratio of the working fluid to the ion exchange resin was 1:3; the flow rate was 3 drops/second; the exchanged solution was dehydrated by a rotary evaporator to give a product that is a compound of formula (I) where n is 4, m is 6, R is methyl, and X is OH, having a relative molecular weight of 262.2, and a purity of 99.21%. its bromine content was 0.79 m %.

Example II-2

Preparation of Template C 10 g (0.058 mol) of tetramethylhexamethylenediamine was added to a 500 ml three-necked flask, 250 ml of isopropanol was added, and 16.6 g (0.058 mol) of 1,9-dibromodecane was added dropwise at room temperature. The addition was completed after 15 minutes, and the temperature was raised till refluxing. The solution gradually changed from colorless and transparent to white and turbid. The reaction was followed by high performance liquid chromatography (HPLC). After the reaction was completed, 200 ml of ethyl acetate was added to the reaction mixture, and the mixture was refluxed for 1 hour, cooled and filtered with suction. The resulted solid was washed with ethyl acetate and then with diethyl ether to give 25 g of a white solid product, as 1,1,8,8-tetramethyl-1,8-diaza-17-membered ring-1,8-dibromide (a compound where n is 9, m is 6, R is methyl, X is Br), having a relative molecular weight of 458.4. ¹H NMR spectrum shows chemical shift (300 MHz, CDCl$_3$) δ 1.51 (t, 14H), 1.92 (t, 8H), 3.16 (s, 12H), 3.40 (t, 8H).

Preparation of Template D: Br in Template C was replaced with OH⁻ by ion exchange; ion exchange resin was strong basic styrene type anion exchange resin, working solution was 15 m % aqueous solution of Template C, operating temperature was 25° C., the mass ratio of the working fluid to the ion exchange resin was 1:3; the flow rate was 3 drops/second; the exchanged solution was dehydrated by a rotary evaporator to give a product that is a compound of the formula (I), where n is 9, m is 6, R is methyl, X is OH, having a relative molecular weight of 332.4, and a purity of 99.8%. Its bromine content was 0.2 m %.

Example II-3

1.467 g of sodium metaaluminate was added to a 45 mL Teflon container, 1.925 g of Template B was added, and then 3 g of silica gel (Qingdao Haiyang Chemical Co., Ltd., industrial product, $SiO_2$ content of 98.05%) was added, and the resultant was allowed to stand and aged for 1 hour to achieve a thorough mixing. The molar ratios of the components were as follows: $SiO_2/Al_2O_3$=35, $H_2O/SiO_2$=6.5, Template B/$SiO_2$=0.15, NaOH/$SiO_2$=0.08.

The above mixture was placed in a 45 mL steel autoclave with a Teflon liner, capped and sealed. The autoclave was placed in a rotating convection oven at a rotation speed of 20 rpm, and reacted at 120° C. for 1 day and then heated to 150° C. to react for 5 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 14:
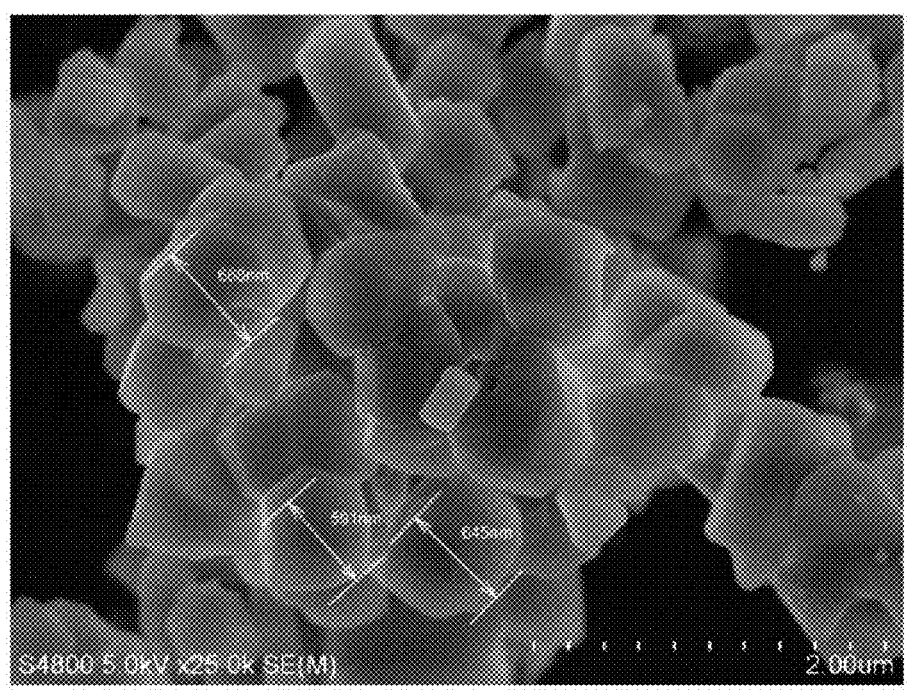
FIG. 14 is a scanning electron micrograph of the molecular sieve produced in Example II-3.
Figure 15:
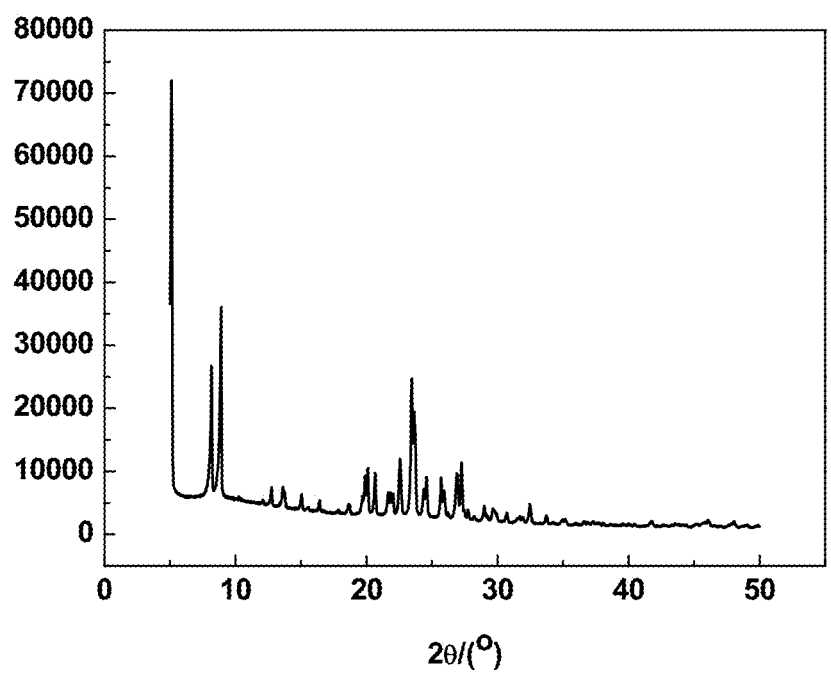
FIG. 15 is an XRD pattern of the molecular sieve produced in Example II-3.

The scanning electron micrograph of the product was shown in FIG. 14. It can be easily seen in the figure that the molecular sieve has the hexagonal prismatic crystal particle morphology, with an effective diameter of 650 nm, a height of 600 nm, and an aspect ratio of 1. In accordance with the measurement, the molecular sieve had a total specific surface area of 553 $m^2 \cdot g^{-1}$ and a pore volume of 0.295 ml/g. The XRD pattern of the product was shown in FIG. 15. The product has a silica-alumina ratio of 35.20.

Example II-4

1.23 g of sodium metaaluminate was added to a 45 mL Teflon container, 1.925 g of Template B was added, and then 9 g of silica sol (Qingdao Haiyang Chemical Co., Ltd., industrial product, $SiO_2$ content of 30%) was added, and the resultant was allowed to stand and aged for 1 hour to achieve a thorough mixing. The molar ratios of the components were as follows: $SiO_2/Al_2O_3$=35, $H_2O/SiO_2$=7.1, Template B/$SiO_2$=0.15, NaOH/$SiO_2$=0.12. The above mixture was placed in a 45 mL steel autoclave with a Teflon liner, capped and sealed. The autoclave was placed in a rotating convection oven at a rotational speed of 20 rpm, and reacted at 120° C. for 1 day and then heated to 150° C. to react for 5 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 16:
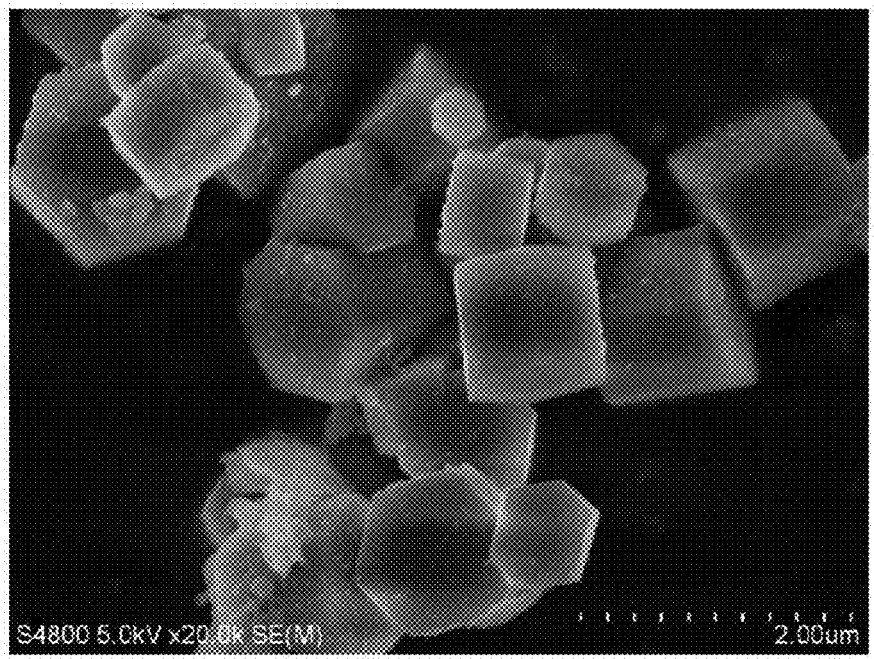
FIG. 16 is a scanning electron micrograph of the molecular sieve produced in Example II-4.
Figure 17:
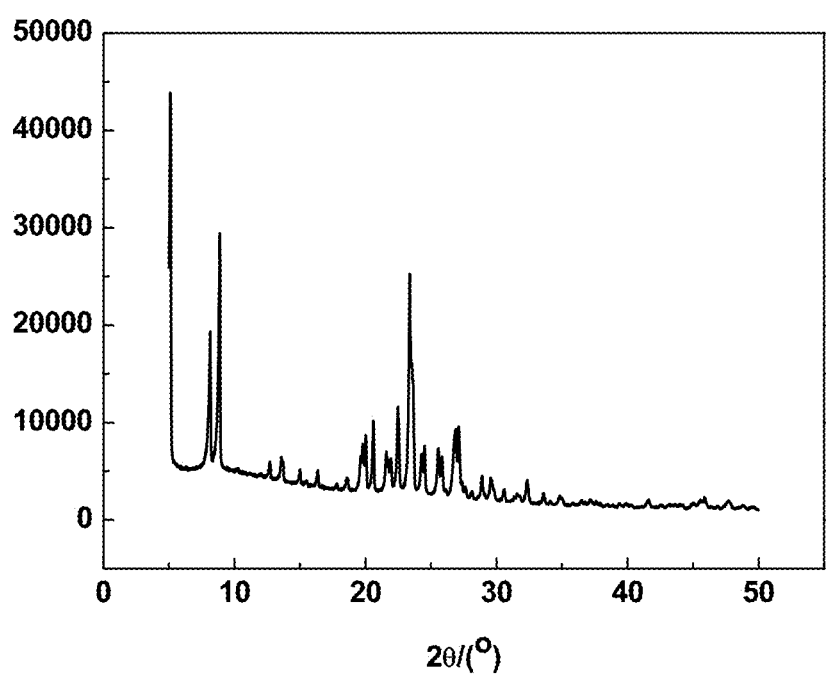
FIG. 17 is an XRD pattern of the molecular sieve produced in Example II-4.

The scanning electron micrograph of the product was shown in FIG. 16. It can be easily seen in the figure that the molecular sieve has the hexagonal prismatic crystal particle morphology, with an effective diameter of 1200 nm, a height of 1000 nm, and an aspect ratio of 0.833. In accordance with the measurement, the molecular sieve had a total specific surface area of 558 $m^2 \cdot g^{-1}$ and a pore volume of 0.51 ml/g. The XRD pattern of the product was shown in FIG. 17. The product has a silica-alumina ratio of 36.38.

Example II-5

1.957 g of sodium metaaluminate was added to a 45 mL Teflon container, 2.44 g of Template D, 0.157 g of sodium hydroxide was added, stirred for 30 minutes until homogeneous, and then 9 g of silica sol (Qingdao Haiyang Chemical Co., Ltd., industrial product, $SiO_2$ content of 30%) was added, and the resultant was allowed to stand and aged for 1 hour to achieve a thorough mixing. The molar ratios of the components were as follows: $SiO_2/Al_2O_3$=30, $H_2O/SiO_2$=7.1, Template D/$SiO_2$=0.15, NaOH/$SiO_2$=0.2.

The above mixture was placed in a 45 mL steel autoclave with a Teflon liner, capped and sealed. The autoclave was placed in a rotating convection oven at a rotation speed of 20 rpm, and reacted at 120° C. for 1 day and then heated to 150° C. to react for 5 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 18:
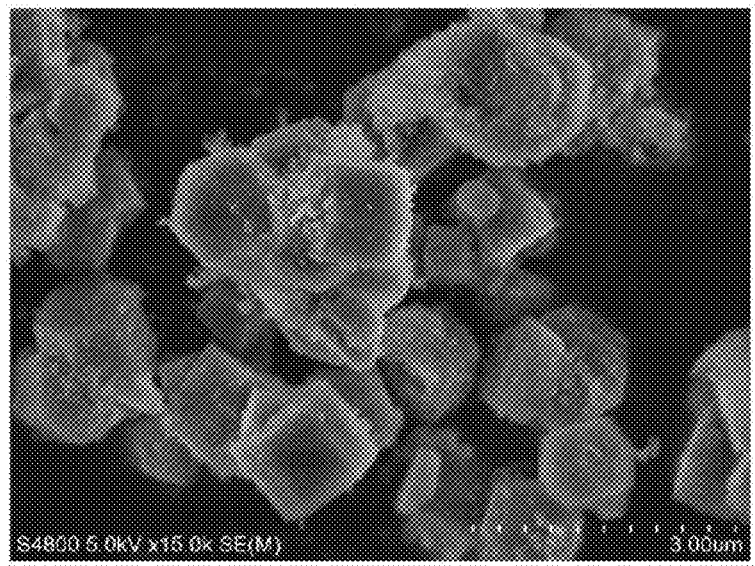
FIG. 18 is a scanning electron micrograph of the molecular sieve produced in Example II-5.
Figure 19:
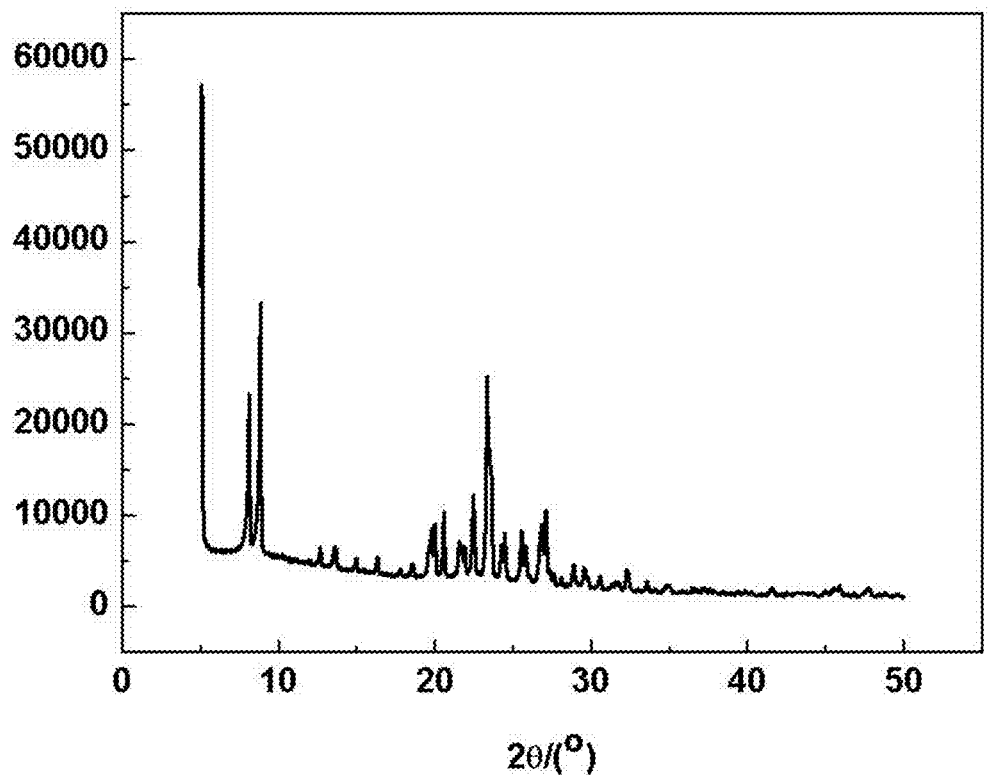
FIG. 19 is an XRD pattern of the molecular sieve produced in Example II-5.

The scanning electron micrograph of the product was shown in FIG. 18. It can be easily seen in the figure that the molecular sieve has the hexagonal prismatic crystal particle morphology, with an effective diameter of 900 nm, a height of 1000 nm, and an aspect ratio of 1.11. In accordance with the measurement, the molecular sieve had a total specific surface area of 543 $m^2 \cdot g^{-1}$ and a pore volume of 0.304 ml/g. The XRD pattern of the product was shown in FIG. 19. The product has a silica-alumina ratio of 33.68.

Example II-6

1.23 g of sodium metaaluminate was added to a 45 mL Teflon container, 2.44 g of Template D, 0.353 g of sodium hydroxide, and then 3 g of white carbon black (Qingdao Haiyang Chemical Co., Ltd., industrial product, $SiO_2$ content of 98%) were added, and the resultant was allowed to stand and aged for 1 hour to achieve a thorough mixing. The molar ratios of the components were as follows: $SiO_2/Al_2O_3$=35, $H_2O/SiO_2$=6.5, Template D/$SiO_2$=0.15, NaOH/$SiO_2$=0.30. The above mixture was placed in a 45 mL steel autoclave with a Teflon liner, capped and sealed. The autoclave was placed in a rotating convection oven at a rotation speed of 20 rpm, and reacted at 120° C. for 1 day and then heated to 150° C. to react for 4 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 20:
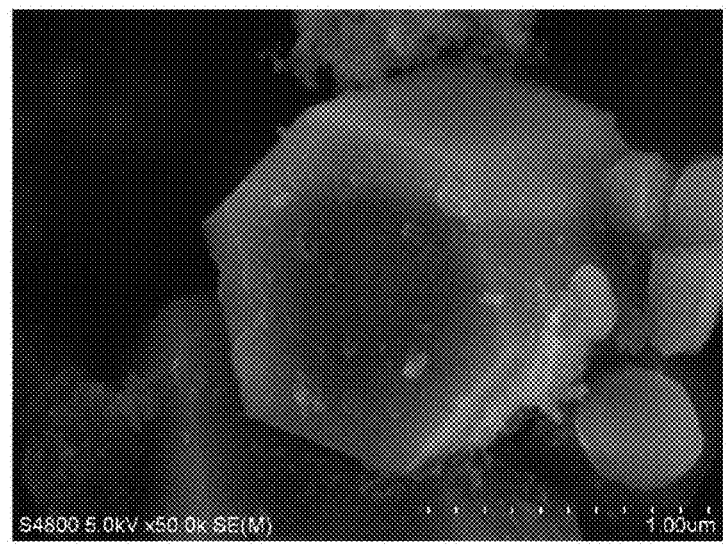
FIG. 20 is a scanning electron micrograph of the molecular sieve produced in Example II-6.
Figure 21:
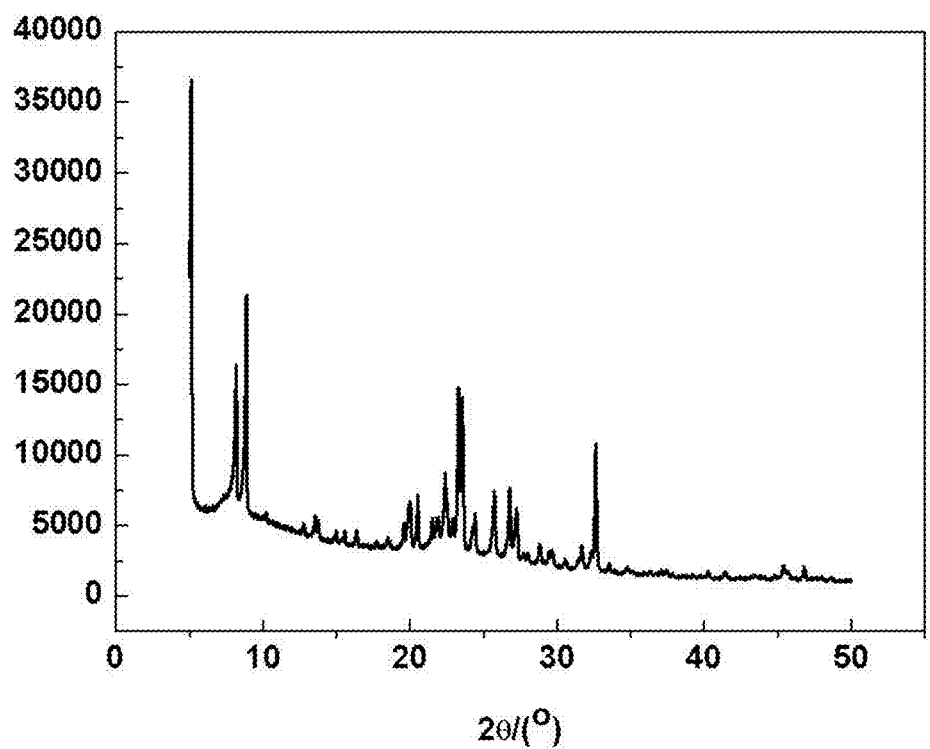
FIG. 21 is an XRD pattern of the molecular sieve produced in Example II-6.

The scanning electron micrograph of the product was shown in FIG. 20. It can be easily seen in the figure that the molecular sieve has the hexagonal prismatic crystal particle morphology, with an effective diameter of 1200 nm, a height of 1300 nm, and an aspect ratio of 1.08. In accordance with the measurement, the molecular sieve had a total specific surface area of 534 $m^2 \cdot g^{-1}$ and a pore volume of 0.304 ml/g. The XRD pattern of the product was shown in FIG. 21. The product has a silica-alumina ratio of 30.21.

Example II-7

0.75 g SB powder (imported from Germany, 76.5% $Al_2O_3$ content) was added to a 45 mL Teflon container, 2.85 g of Template A was added, and then 3 g of silica gel (Qingdao Haiyang Chemical Co., Ltd., industrial product, $SiO_2$ content of 98.05%) was added, and the resultant was allowed to stand and aged for 1 hour to achieve a thorough mixing. The molar ratios of the components were as follows: $SiO_2/Al_2O_3$=30, $H_2O/SiO_2$=6.5, Template B/$SiO_2$=0.15, NaOH/$SiO_2$=0.08. The above mixture was placed in a 45 mL steel autoclave with a Teflon liner, capped and sealed. The autoclave was placed in a rotating convection oven at a rotation speed of 20 rpm, and reacted at 120° C. for 1 day and then heated to 150° C. to react for 5 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 22:
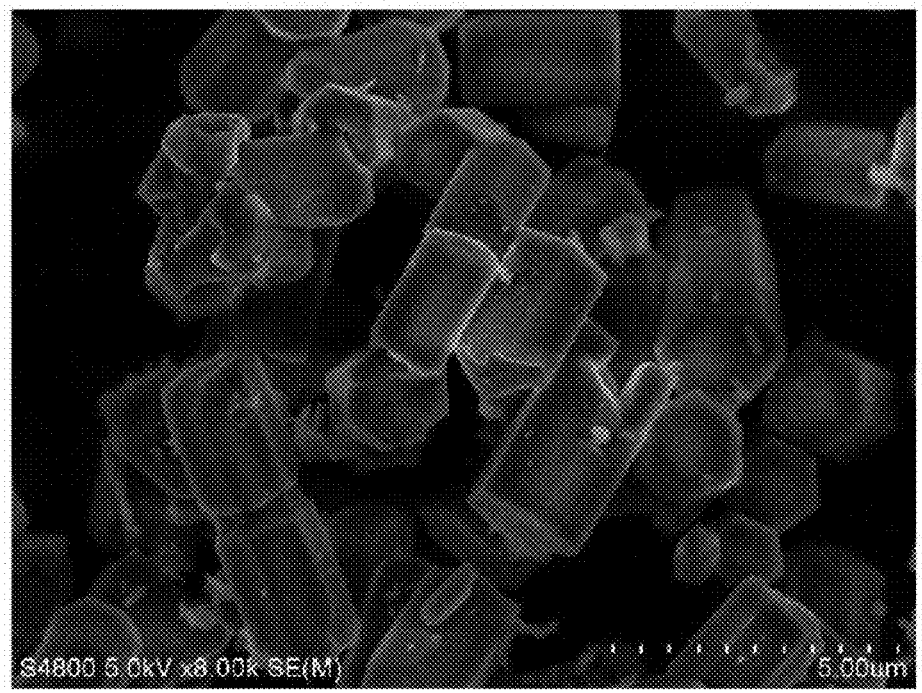
FIG. 22 is a scanning electron micrograph of the molecular sieve produced in Example II-7.
Figure 23:
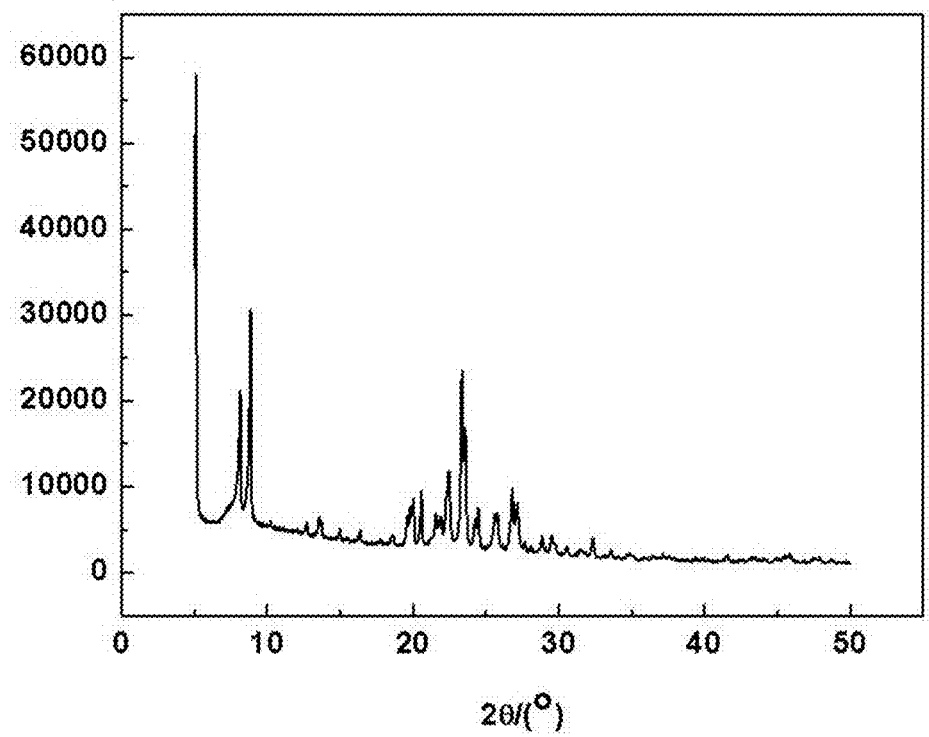
FIG. 23 is an XRD pattern of the molecular sieve produced in Example II-7.

The scanning electron micrograph of the product was shown in FIG. 22. It can be easily seen in the figure that the molecular sieve has the hexagonal prismatic crystal particle morphology, with an effective diameter of 1500 nm, a height of 2000 nm, and an aspect ratio of 1.33. In accordance with the measurement, the molecular sieve had a total specific surface area of 560 $m^2 \cdot g^{-1}$ and a pore volume of 0.342 ml/g. The XRD pattern of the product was shown in FIG. 23. The product has a silica-alumina ratio of 35.29.

Example II-8

1.957 g sodium metaaluminate was added to a 45 mL Teflon container, 3.37 g Template C, 0.274 g of sodium hydroxide, and then 3 g silica gel (Qingdao Haiyang Chemical Co., Ltd., industrial product, $SiO_2$ content of 98.05%) were added, and the resultant was allowed to stand and aged for 1 hour to achieve a thorough mixing. The molar ratios of the components were as follows: $SiO_2/Al_2O_3$=30, $H_2O/SiO_2$=6.5, Template B/$SiO_2$=0.15, NaOH/$SiO_2$=0.30. The above mixture was placed in a 45 mL steel autoclave with a Teflon liner, capped and sealed. The autoclave was placed in a rotating convection oven at a rotation speed of 20 rpm, and reacted at 120° C. for 1 day and then heated to 150° C. to react for 5 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 24:
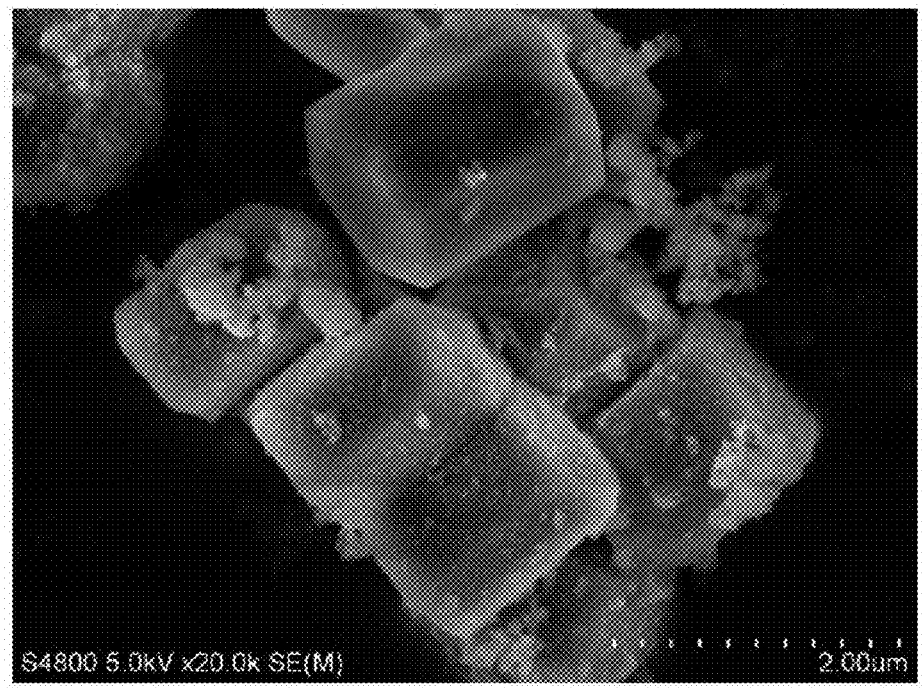
FIG. 24 is a scanning electron micrograph of the molecular sieve produced in Example II-8.
Figure 25:
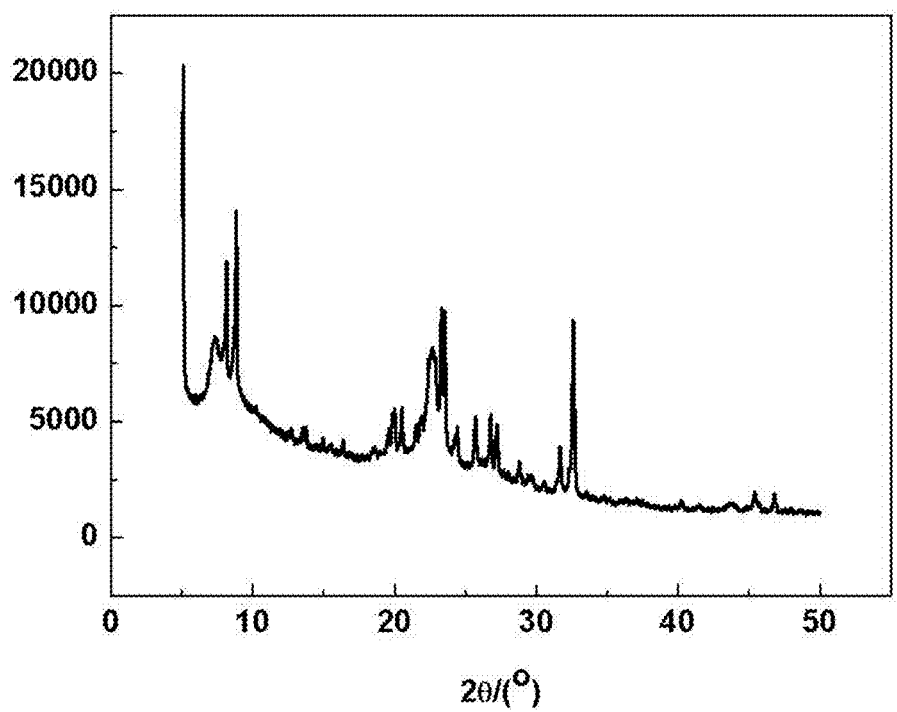
FIG. 25 is an XRD pattern of the molecular sieve produced in Example II-8.

The scanning electron micrograph of the product was shown in FIG. 24. It can be easily seen in the figure that the molecular sieve has the hexagonal prismatic crystal particle morphology, with an effective diameter of 1000 nm, a height of 1400 nm, and an aspect ratio of 1.4. In accordance with the measurement, the molecular sieve had a total specific surface area of 498 $m^2 \cdot g^{-1}$ and a pore volume of 0.403 ml/g. The XRD pattern of the product was shown in FIG. 25. The product has a silica-alumina ratio of 34.20.

Example II-9

1.957 g of sodium metaaluminate was added to a 45 mL Teflon container, 3.365 g of Template C, 0.0784 g of sodium hydroxide, and then 9 g of silica sol (Qingdao Haiyang Chemical Co., Ltd., industrial product, $SiO_2$ content of 30%) were added, and the resultant was allowed to stand and aged for 1 hour to achieve a thorough mixing. The molar ratios of the components were as follows: $SiO_2/Al_2O_3$=30, $H_2O/SiO_2$=6.5, Template C/$SiO_2$=0.15, NaOH/$SiO_2$=0.20. The above mixture was placed in a 45 mL steel autoclave with a Teflon liner, capped and sealed. The autoclave was placed in a rotating convection oven at a rotation speed of 20 rpm, and reacted at 120° C. for 1 day and then heated to 150° C. to react for 5 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 26:
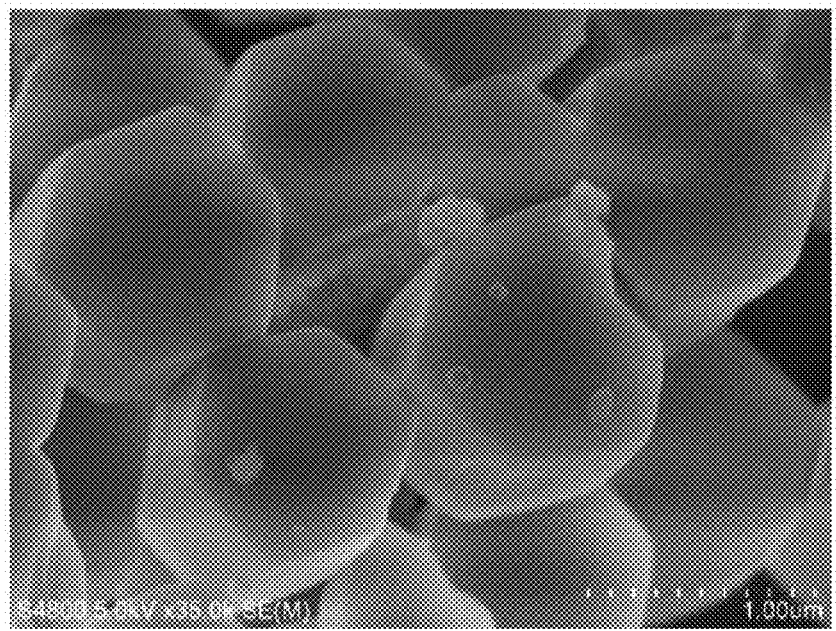
FIG. 26 is a scanning electron micrograph of the molecular sieve produced in Example II-9.
Figure 27:
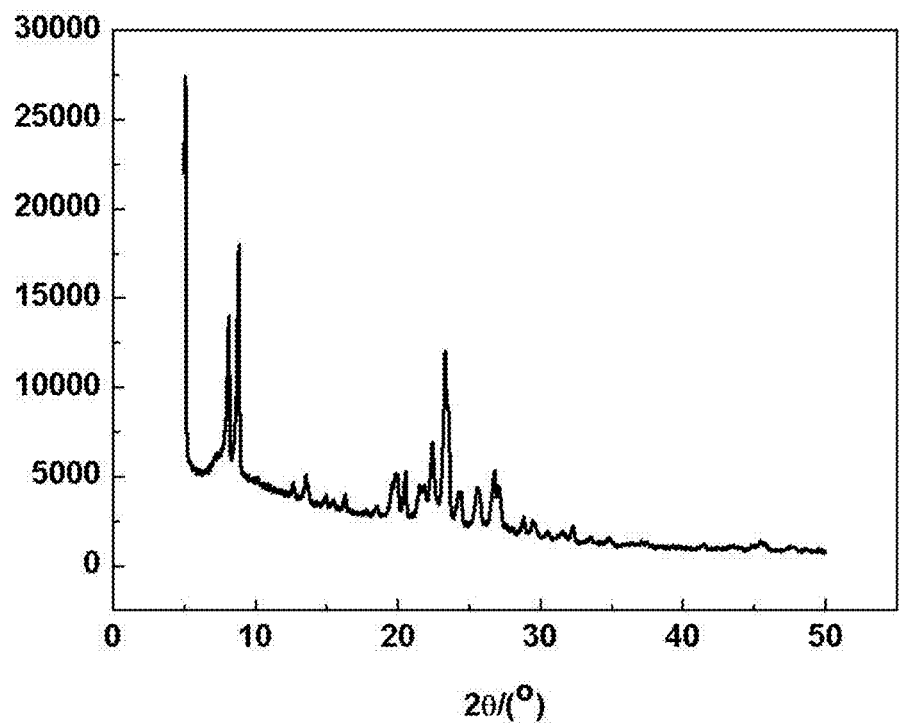
FIG. 27 is an XRD pattern of the molecular sieve produced in Example II-9.

The scanning electron micrograph of the product was shown in FIG. 26. It can be easily seen in the figure that the molecular sieve has the hexagonal columnar crystal particle morphology, with an effective diameter of 800 nm, a height of 900 nm, and an aspect ratio of 1.125. In accordance with the measurement, the molecular sieve had a total specific surface area of 564 $m^2 \cdot g^{-1}$ and a pore volume of 0.350 ml/g. The XRD pattern of the product was shown in FIG. 27. The product has a silica-alumina ratio of 35.28.

Example II-10

0.187 g SB powder (imported from Germany, 76.5% $Al_2O_3$ content) was added to a 45 mL Teflon container, 1.925 g of Template B was added, and then 3 g of silica gel (Qingdao Haiyang Chemical Co., Ltd., industrial product, $SiO_2$ content of 98.05%) was added, and the resultant was allowed to stand and aged for 1 hour to achieve a thorough mixing. The molar ratios of the components were as follows: $SiO_2/Al_2O_3$=20, $H_2O/SiO_2$=6.5, Template B/$SiO_2$=0.15, NaOH/$SiO_2$=0.08. The above mixture was placed in a 45 mL steel autoclave with a Teflon liner, capped and sealed. The autoclave was placed in a rotating convection oven at a rotational speed of 20 rpm, and reacted at 110° C. for 1 day and then heated to 150° C. to react for 5 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 28:
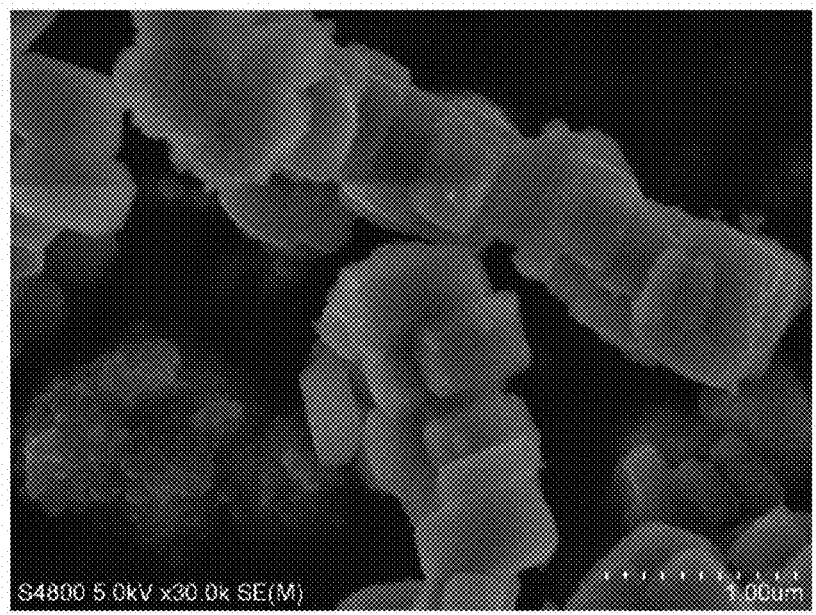
FIG. 28 is a scanning electron micrograph of the molecular sieve produced in Example II-10.
Figure 29:
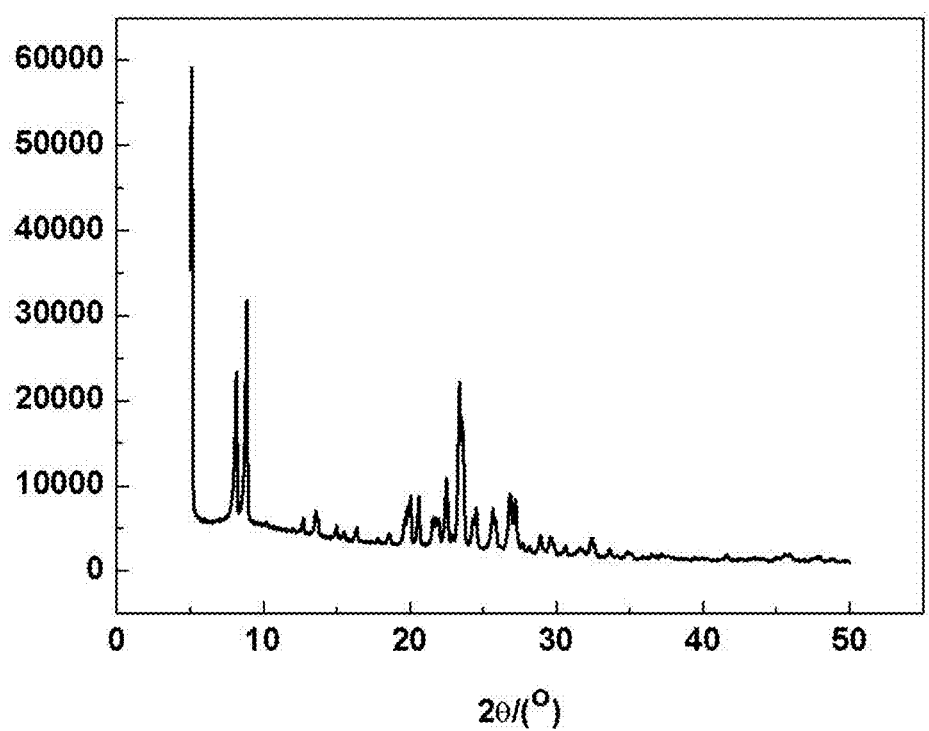
FIG. 29 is an XRD pattern of the molecular sieve produced in Example II-10.

The scanning electron micrograph of the product was shown in FIG. 28. It can be easily seen in the figure that the molecular sieve has the hexagonal prismatic crystal particle morphology, with an effective diameter of 300 nm, a height of 900 nm, and an aspect ratio of 3.0. In accordance with the measurement, the molecular sieve had a total specific surface area of 473 $m^2 \cdot g^{-1}$ and a pore volume of 0.356 ml/g. The XRD pattern of the product was shown in FIG. 29. The product has a silica-alumina ratio of 35.38.

Example II-11

5.87 g of sodium metaaluminate was added to a 45 mL Teflon container, 1.925 g of Template B was added, and then 3 g of silica gel (Qingdao Haiyang Chemical Co., Ltd., industrial product, $SiO_2$ content of 98.05%) was added, and the resultant was allowed to stand and aged for 1 hour to achieve a thorough mixing. The molar ratios of the components were as follows: $SiO_2/Al_2O_3$=10, $H_2O/SiO_2$=6.5, Template B/$SiO_2$=0.15, NaOH/$SiO_2$=0.487.

The above mixture was placed in a 45 mL steel autoclave with a Teflon liner, capped and sealed. The autoclave was placed in a rotating convection oven at a rotation speed of 20 rpm, and reacted at 120° C. for 1 day and then heated to 150° C. to react for 5 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 30:
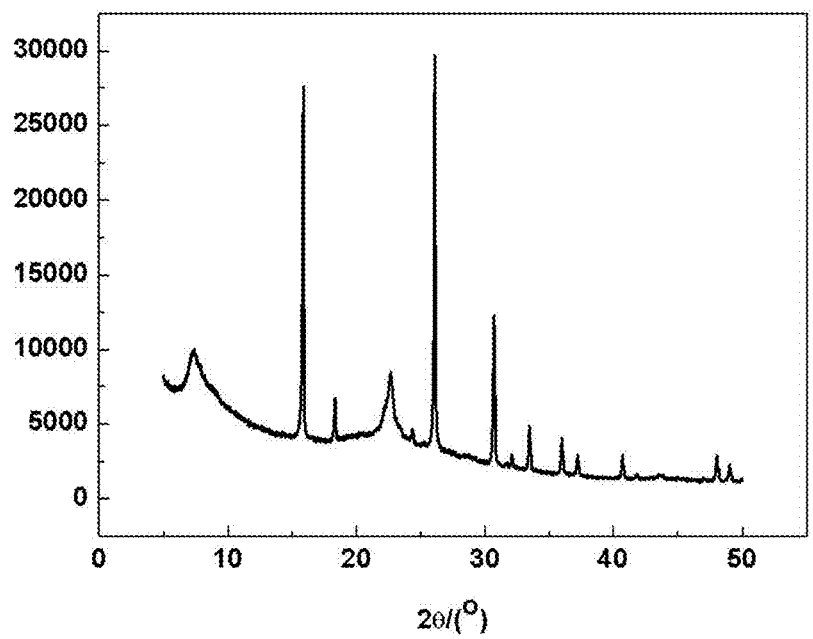
FIG. 30 is an XRD pattern of the molecular sieve produced in Example II-11.

The XRD pattern of this product was shown in FIG. 30, which is an ANA molecular sieve.

Example II-12

Figure 31:
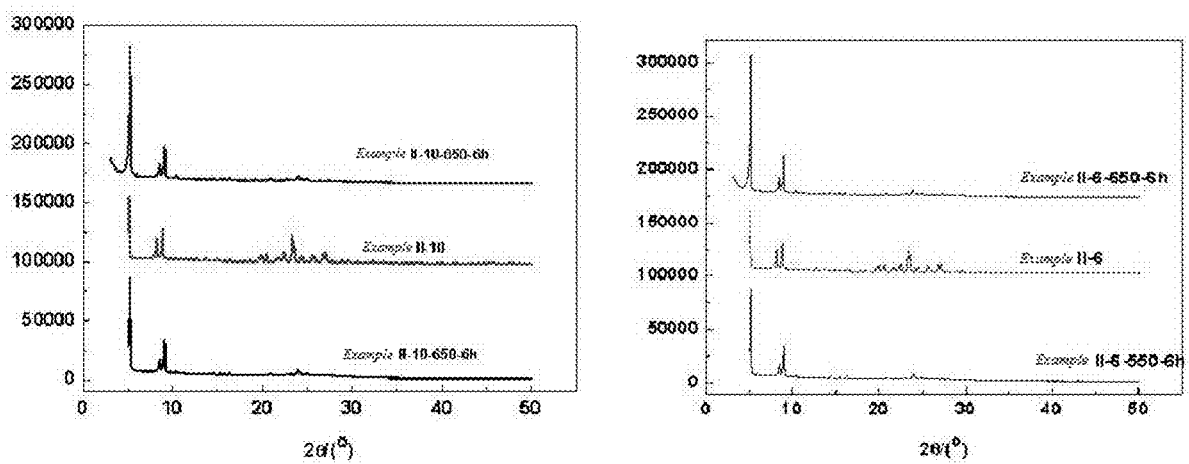
FIG. 31 is an XRD pattern of the molecular sieves produced in Examples II-3 to II-8 after calcination.

This example was provided to exemplify the thermal stability (XRD) of the molecular sieves produced in Examples II-3 to II-8. FIG. 31 shows that the silica-alumina ratio was 30 or 40, and the molecular sieve with a sodium-to-silicon ratio of 0.08-0.30 has good thermal stability after calcination at 550° C., 650° C. or 750° C. for 6 h.

Example II-13

This example was provided to exemplify the acidity of the molecular sieves produced in Examples II-6 and II-8. Table II-1 shows that the molecular sieves with a silica-alumina ratio of 30 or 40 exhibit a higher B/L ratio, and they are expected to be used in acidic catalytic reactions.

TABLE II-1

| | 200° C. | | | 350° C. | | |
|---|---|---|---|---|---|---|
| | B (µmol/g) | L (µmol/g) | B/L | B (µmol/g) | L (µmol/g) | B/L |
| Ex. 11-6 | 103.4 | 115.9 | 0.892 | 53.4 | 107.8 | 0.496 |
| Ex. 11-8 | 36.1 | 58.6 | 0.616 | 13 | 53.9 | 0.242 |

First Embodiment, Fifth Embodiment, and Sixth Embodiment

In the context of the present embodiment, including the following examples and comparative examples, the total specific surface area, pore volume and pore diameter of the molecular sieve were measured by the following analytical methods.

Equipment: Micromeritic ASAP2010 Static Nitrogen Adsorber

Measurement conditions: The sample was placed in a sample processing system, evacuated to $1.35 \times 10^{-2}$ Pa at 350° C., and kept at this temperature and pressure for 15 h to purify the sample. At the liquid nitrogen temperature of −196° C., the adsorption amount and desorption amount of nitrogen of the purified sample under different specific pressure P/P0 conditions were measured, and an adsorption-desorption isotherm curve was obtained. Then, the total specific surface area was calculated with the two-parameter BET equation, and the adsorption capacity at the specific pressure P/P0≈0.98 was taken as the pore volume of the sample, and the pore diameter was calculated according to the BJH model.

Example III Series

Example III-1

Preparation of Template A: 15 g (0.094 mol) of bis[2-(N,N-dimethylaminoethyl)]ether was added to a two-necked flask, 100 mL of isopropanol was added, and 9.5 g (0.047 mol) of 1,3-dibromopropane was added dropwise with stirring at 25° C. After the addition was completed, the temperature was raised to reflux temperature, and the resultant was refluxed for 30 min. The solution changed from colorless to white and turbid, and then was reacted at reflux temperature for 12 h, cooled to 25° C., and 50 mL of ethyl acetate was added. The resultant was stirred for 15 min to form a white turbid liquid, and filtered, and the resulted solid was washed with ethyl acetate to give 13.2 g of a product as a compound of the formula (I), where n is 1, m is 2, R is methyl, and X is Br, having a melting point of 250.3° C., a purity of 99.9 m %, a relative molecular weight of 362.2. $^1$H-NMR spectrum shows chemical shift (300 MHZ, internal standard TMS, solvent CDCl$_2$) δ (ppm): 1.49 (2H, m), 2.27 (4H, m), 2.36 (4H, t), 2.53 (4H, t), 3.47 (4H, t).

Preparation of Template B: Br in Template A was replaced with OH$^-$ by ion exchange; ion exchange resin was a strong basic styrene type anion exchange resin, working solution was 15 m % aqueous solution of Template A, operating temperature was 25° C., the mass ratio of the working fluid to the ion exchange resin was 1:3; the flow rate was 3 drops/second; the exchanged solution was dehydrated by a rotary evaporator to give a product that is a compound of the formula (I), where n is 1, m is 2, R is methyl and X is OH, having a relative molecular weight of 236.2 and a purity of 98.2%. Its bromine content was 0.79 m %.

Example III-2

Preparation of Template C: a compound of the formula (I), where n is 6, m is 2, R is methyl, and X is Br, was produced according to the method as described in Example III-1 for Template A, except that 12.78 g (0.047 mol) of 1,8-dibromooctane was used in place of 1,3-dibromopropane. The test provided 17.6 g of a product having a melting point of 288.2° C., a relative molecular weight of 432.2, a purity of 99.9 m %. $^1$H-NMR spectrum shows chemical shift (300 MHZ, internal standard TMS, solvent CDCl$_2$) δ (ppm): 1.29 (2H, s), 1.39 (2H, m), 1.43 (2H, s), 2.27 (2H, m), 2.36 (2H, m), 2.55 (2H, m), 3.63 (4H, m).

Preparation of Template D: Br in Template C was replaced with OH$^-$ by ion exchange; ion exchange resin was strong basic styrene type anion exchange resin, working solution was 15 m % aqueous solution of Template C, operating temperature was 25° C., the mass ratio of the working fluid to the ion exchange resin was 1:3; the flow rate was 3 drops/second; the exchanged solution was dehydrated by a rotary evaporator to give a product that is a compound of the formula (I), where n is 6, m is 2, R is methyl, X is OH, having a relative molecular weight of 306.2, and a purity of 99.5 m %. Its bromine content was 0.2 m %.

Example III-3

0.134 g of sodium metaaluminate was added to a 45 mL Teflon container, 1.81 g of Template B was added, stirred for 30 minutes until homogeneous, and then 3 g of crude silica gel (Qingdao Haiyang Chemical Co., Ltd., industrial product, SiO$_2$ content of 98.05%) and 6.3 g of deionized water were added, and well mixed for 5 minutes. The molar ratios of the components were as follows: SiO$_2$/Al$_2$O$_3$=25, H$_2$O/SiO$_2$=7, Template B/SiO$_2$=0.16, OH$^-$/SiO$_2$=0.31.

The above mixture was placed in a 45 mL steel autoclave with a Teflon liner, capped and sealed, and the autoclave was placed in a rotating convection oven at a rotational speed of 20 rpm and reacted at 150° C. for 5 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 32:
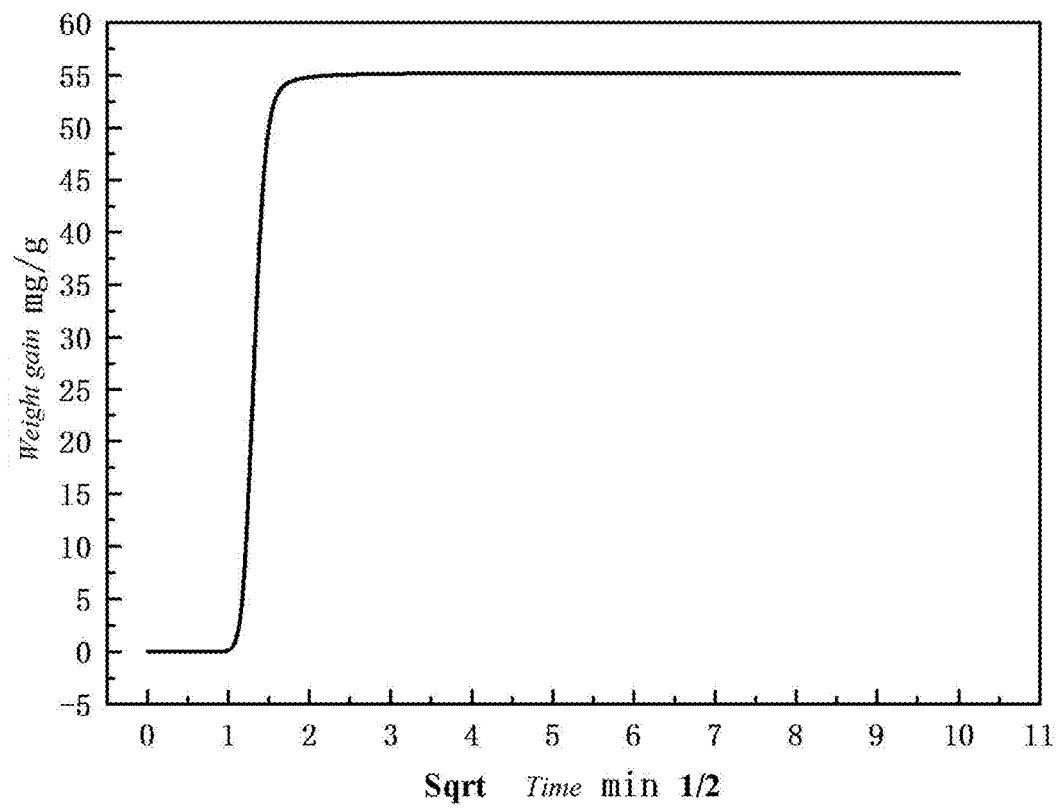
FIG. 32 is an adsorption curve of 2,2-diethylbutane on the molecular sieve produced in Example III-3 after calcination.
Figure 34:
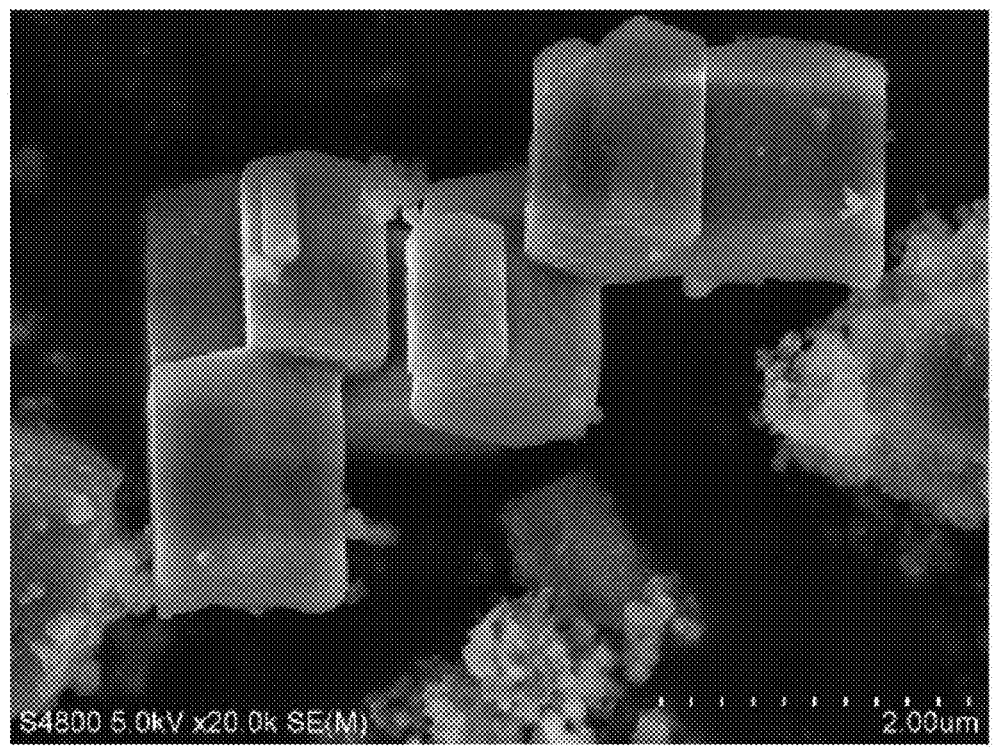
FIG. 34 is a scanning electron micrograph of the molecular sieve produced in Example III-3.
Figure 35:
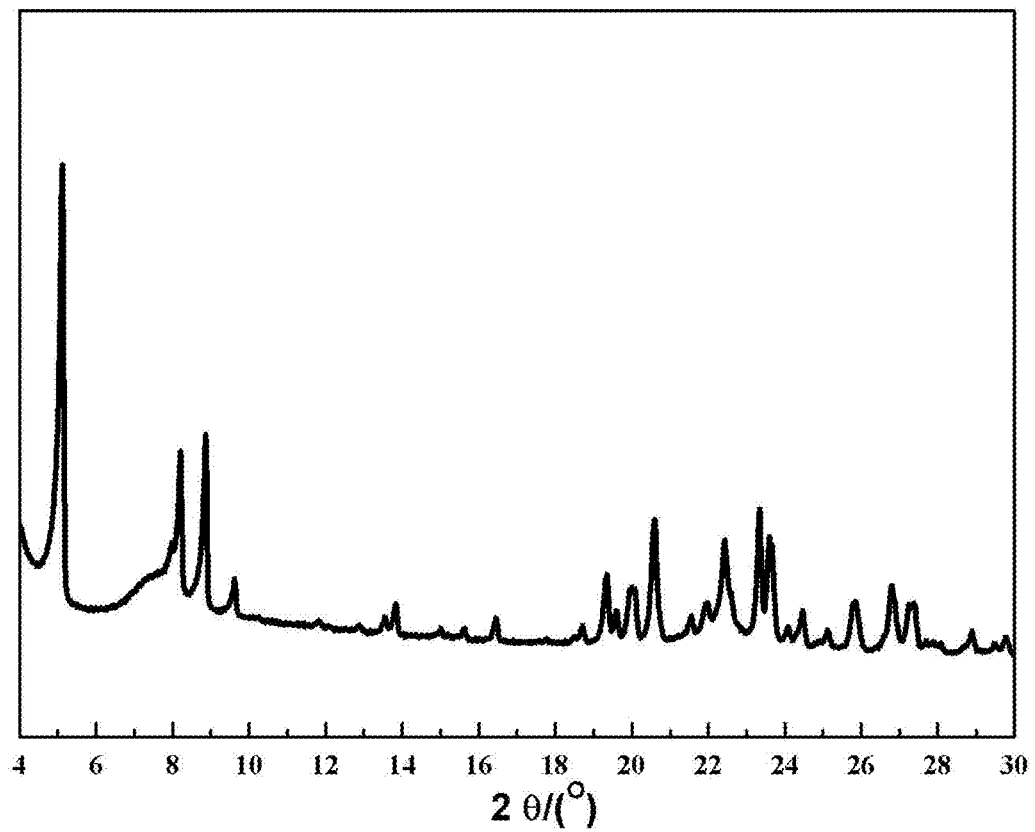
FIG. 35 is an XRD pattern of the molecular sieve produced in Example III-3.

The scanning electron micrograph of the product was shown in FIG. 34. It can be easily seen in the figure that the molecular sieve has the hexagonal prismatic crystal particle morphology, with an effective diameter of 1000 nm, a height of 1200 nm, and an aspect ratio of 1.2. In accordance with the measurement, the molecular sieve had a total specific surface area of 523 m$^2 \cdot$g$^{-1}$ and a pore volume of 0.356 ml/g. The XRF analysis showed a Si/Al$_2$=23. The XRD pattern of this product was shown in FIG. 35. FIG. 32 shows the adsorption curve of 2,2-diethylbutane on the product after calcination at 550° C. for 3 h. It can be seen from the curve that the adsorption capacity of the product for 2,2-diethylbutane is about 55 mg/g.

Example III-4

0.134 g of sodium metaaluminate was added to a 45 mL Teflon container, 3.0 g of Template D, and 9.31 g of deionized water were added, stirred for 30 minutes until homogeneous, and then 4 g of crude silica gel (Qingdao Haiyang Chemical Co., Ltd., industrial product, $SiO_2$ content of 98.05%) was added, and well mixed for 5 minutes. The molar ratios of the components were as follows: $SiO_2/Al_2O_3$=21, $H_2O/SiO_2$=8, Template $D/SiO_2$=0.15, $OH^-/SiO_2$=0.30. The above mixture was placed in a 45 mL steel autoclave with a Teflon liner, capped and sealed, and the autoclave was placed in a rotating convection oven at a rotational speed of 20 rpm and reacted at 150° C. for 5 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 37:
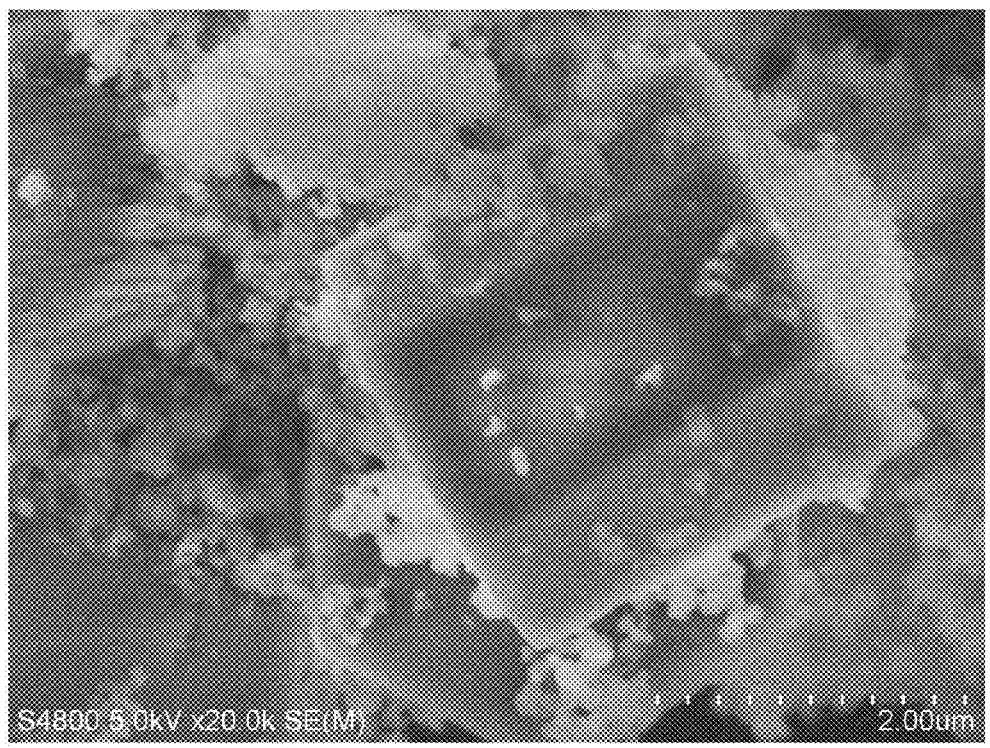
FIG. 37 is a scanning electron micrograph of the molecular sieve produced in Example III-4.

The scanning electron micrograph of the product was shown in FIG. 37. It can be easily seen in the figure that the molecular sieve has the hexagonal columnar crystal particle morphology, with an effective diameter of 2200 nm, a height of 3000 nm, and an aspect ratio of 1.36. In accordance with the measurement, the molecular sieve had a total specific surface area of 573 m$^2 \cdot$g$^{-1}$ and a pore volume of 0.387 ml/g. The XRF analysis showed a $Si/Al_2$=25.

Example III-5

0.134 g of sodium metaaluminate was added to a 45 mL Teflon container, 1.78 g of Template A was added, stirred for 30 minutes until homogeneous, and then 3 g of crude silica gel (Qingdao Haiyang Chemical Co., Ltd., industrial product, $SiO_2$ content of 98.05%), 6.98 g of deionized water, and 0.4 g of NaOH were added, and well mixed for 5 minutes. The molar ratios of the components were as follows: $SiO_2/Al_2O_3$=23, $H_2O/SiO_2$=8, Template $A/SiO_2$=0.10, $OH^-/SiO_2$=0.20. The above mixture was placed in a 45 mL steel autoclave with a Teflon liner, capped and sealed, and the autoclave was placed in a rotating convection oven at a rotational speed of 20 rpm and reacted at 150° C. for 4 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 38:
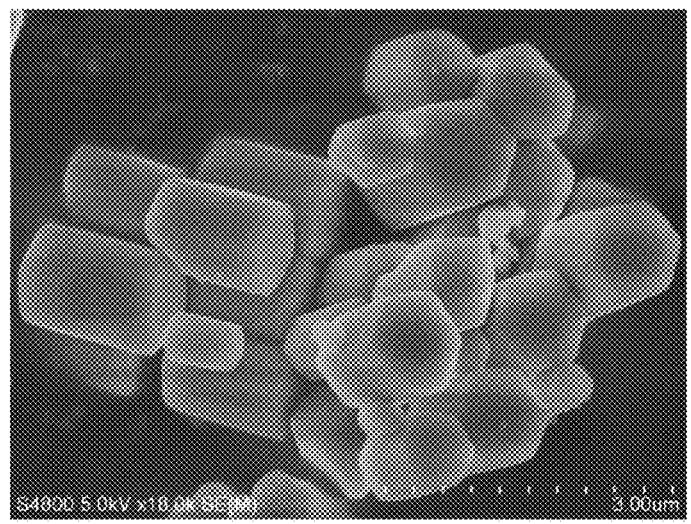
FIG. 38 is a scanning electron micrograph of the molecular sieve produced in Example III-5.

The scanning electron micrograph of the product was shown in FIG. 38. It can be easily seen in the figure that the molecular sieve has the hexagonal prismatic crystal particle morphology, with an effective diameter of 900 nm, a height of 1200 nm, and an aspect ratio of 1.33. In accordance with the measurement, the molecular sieve had a total specific surface area of 520 m$^2 \cdot$g$^{-1}$ and a pore volume of 0.367 ml/g. The XRF analysis showed a $Si/Al_2$=24.

Example III-6

0.134 g of sodium metaaluminate was added to a 45 mL Teflon container, 3.70 g of Template B was added, stirred for 30 minutes until homogeneous, and then 3 g of crude silica gel (Qingdao Haiyang Chemical Co., Ltd., industrial product, $SiO_2$ content of 98.05%) and 6.11 g of deionized water were added, well mixed for 5 minutes. The molar ratios of the components were as follows: $SiO_2/Al_2O_3$=26, $H_2O/SiO_2$=7, Template $B/SiO_2$=0.32, $OH^-/SiO_2$=0.64.

The above mixture was placed in a 45 mL steel autoclave with a Teflon liner, capped and sealed, and the autoclave was placed in a rotating convection oven at a rotational speed of 20 rpm and reacted at 150° C. for 5 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 39:
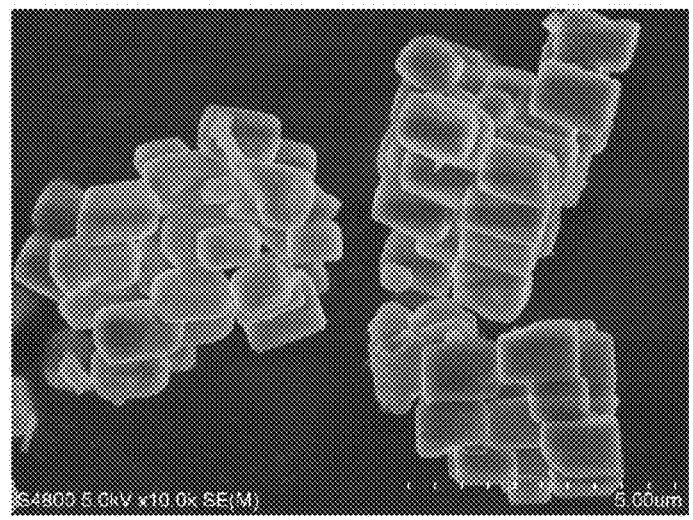
FIG. 39 is a scanning electron micrograph of the molecular sieve produced in Example III-6.

The scanning electron micrograph of the product was shown in FIG. 39. It can be easily seen in the figure that the molecular sieve has the hexagonal columnar crystal particle morphology, with an effective diameter of 1000 nm, a height of 1500 nm, and an aspect ratio of 1.5. In accordance with the measurement, the molecular sieve had a total specific surface area of 537 m$^2 \cdot$g$^{-1}$ and a pore volume of 0.389 ml/g. The XRF analysis showed a $Si/Al_2$=24.

Figure 33:
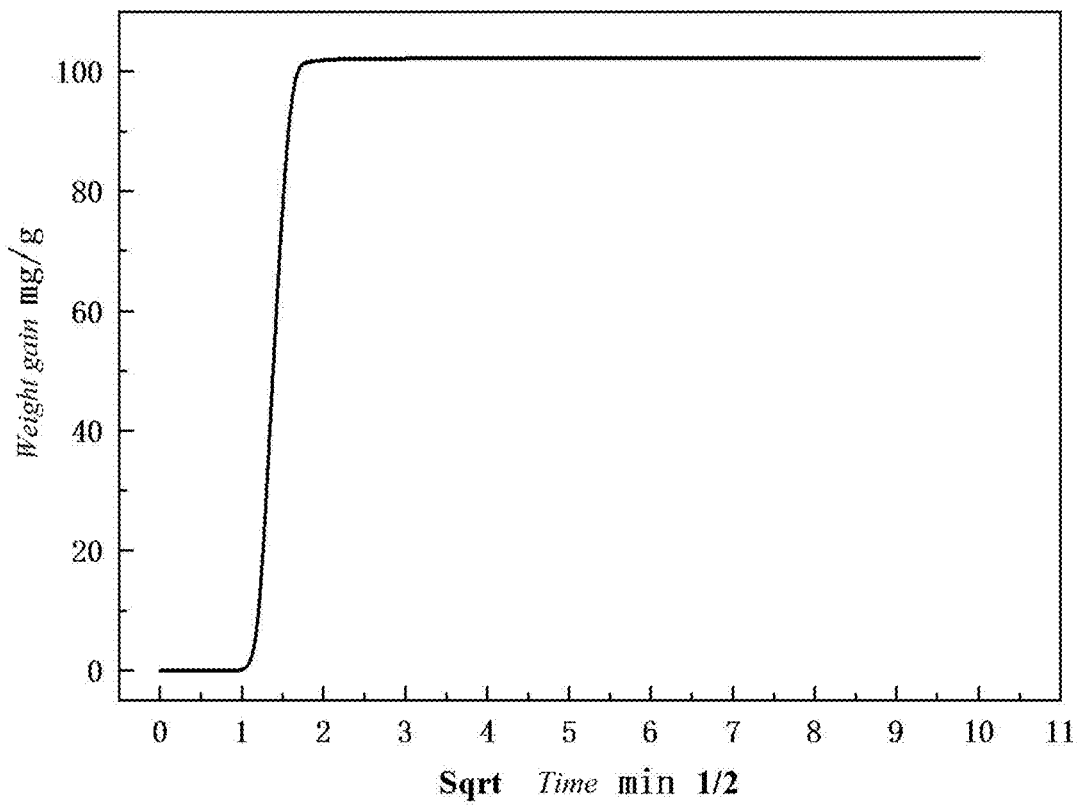
FIG. 33 is an adsorption curve of 3-propyl-4-butyloctane on the molecular sieve produced in Example III-6 after calcination.
Figure 36:
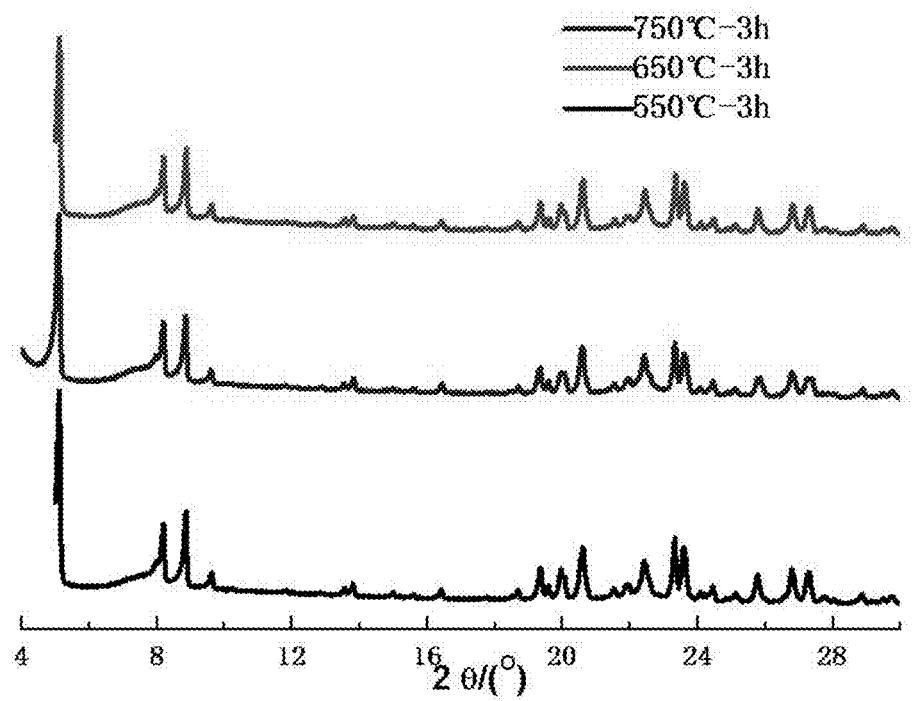
FIG. 36 is an XRD pattern of the molecular sieve produced in Example III-6 after calcination.

The product was calcined, separately, at 550° C., 650° C., and 750° C. for 3 h, and the XRD pattern of the product after calcination was shown in FIG. 36, with each characteristic peak still existing. FIG. 33 shows the adsorption curve of 3-propyl-4-butyloctane on the product after calcination at 550° C. for 3 h. As can be seen from the figure, the adsorption capacity of the product for 3-propyl-4-butyloctyl is as high as about 102 mg/g.

Example III-7

0.134 g of sodium metaaluminate was added to a 45 mL Teflon container, and 7.0 g of Template D and 9.31 g of deionized water were added, stirred for 30 minutes until homogeneous, and then 4 g of crude silica gel (Qingdao Haiyang Chemical Co., Ltd., industrial product, $SiO_2$ content of 98.05%) was added, and well mixed for 5 minutes. The molar ratios of the components were as follows: $SiO_2/Al_2O_3$=22, $H_2O/SiO_2$=8, Template $D/SiO_2$=0.35, $OH^-/SiO_2$=0.70. The above mixture was placed in a 45 mL steel autoclave with a Teflon liner, capped and sealed, and the autoclave was placed in a rotating convection oven at a rotational speed of 20 rpm and reacted at 150° C. for 5 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 40:
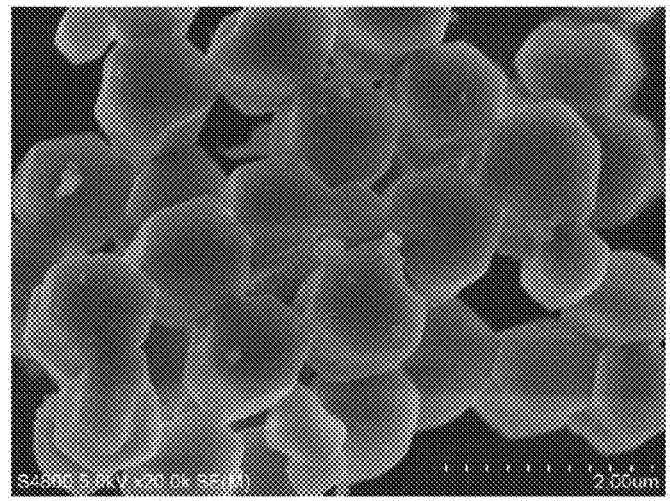
FIG. 40 is a scanning electron micrograph of the molecular sieve produced in Example III-7.
Figure 42:
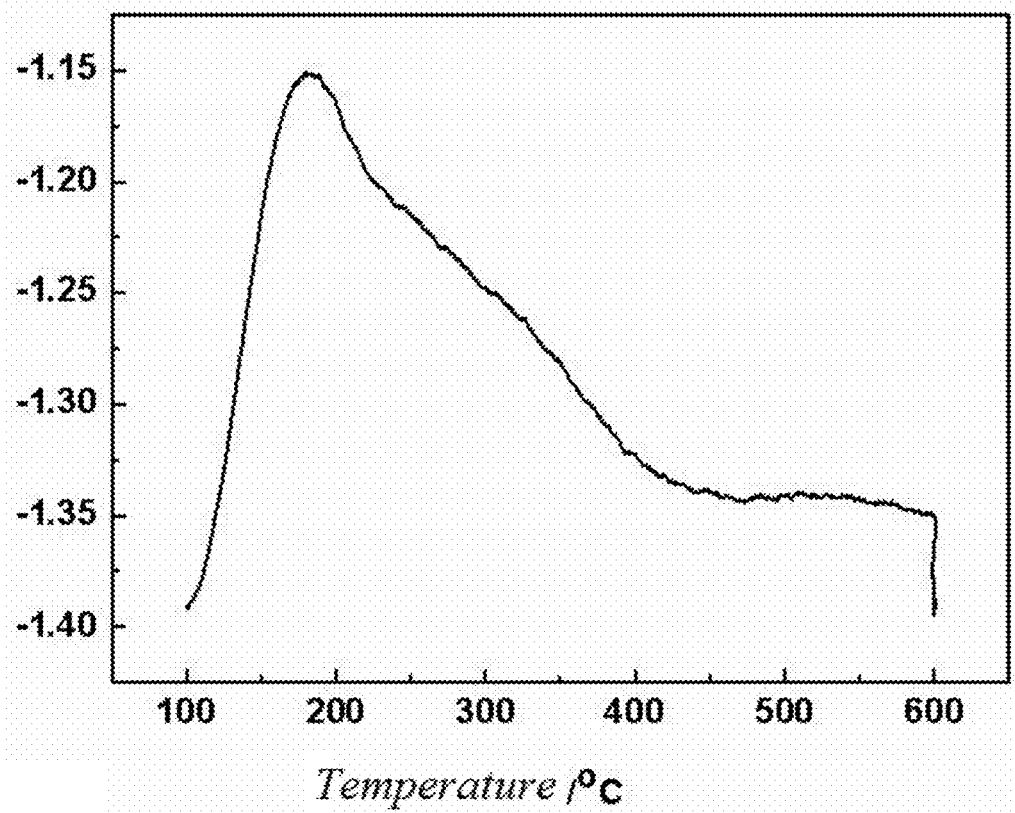
FIG. 42 is a NH3-TPD pattern of the molecular sieve produced in Example III-7.
Figure 43:
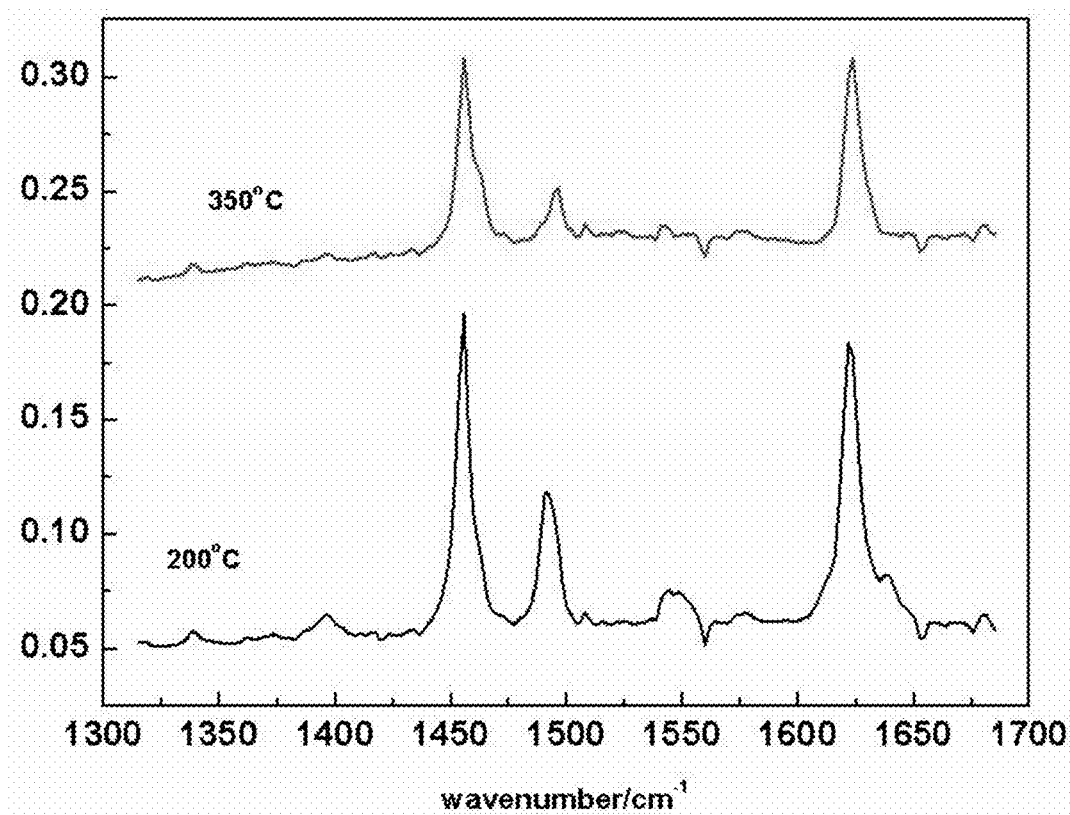
FIG. 43 is an IR spectra of the molecular sieve produced in Example III-7.

The scanning electron micrograph of the product was shown in FIG. 40. It can be easily seen in the figure that the molecular sieve has the hexagonal prismatic crystal particle morphology, with an effective diameter of 1200 nm, a height of 1400 nm, and an aspect ratio of 1.17. In accordance with the measurement, the molecular sieve had a total specific surface area of 538 m$^2 \cdot$g$^{-1}$ and a pore volume of 0.408 ml/g. The XRF analysis showed a $Si/Al_2$=23. The results of NH3-TPD indicate (FIG. 42) that the molecular sieve has a significant acidity. The results of the infrared spectrum show (FIG. 43) that the molecular sieve has a low content of B acid and a high content of L acid.

Example III-8

0.134 g of sodium metaaluminate was added to a 45 mL Teflon container, 7.41 g of Template C was added, stirred for 30 minutes until homogeneous, and then 3 g of crude silica gel (Qingdao Haiyang Chemical Co., Ltd., industrial product, $SiO_2$ content of 98.05%), 6.98 g of deionized water, and 0.4 g of NaOH were added, and well mixed for 5 minutes. The molar ratios of the components were as follows: $SiO_2/Al_2O_3=21$, $H_2O/SiO_2=8$, Template $C/SiO_2=0.35$, $OH^-/SiO_2=0.20$. The above mixture was placed in a 45 mL steel autoclave with a Teflon liner, capped and sealed, and the autoclave was placed in a rotating convection oven at a rotational speed of 20 rpm and reacted at 150° C. for 4 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 41:
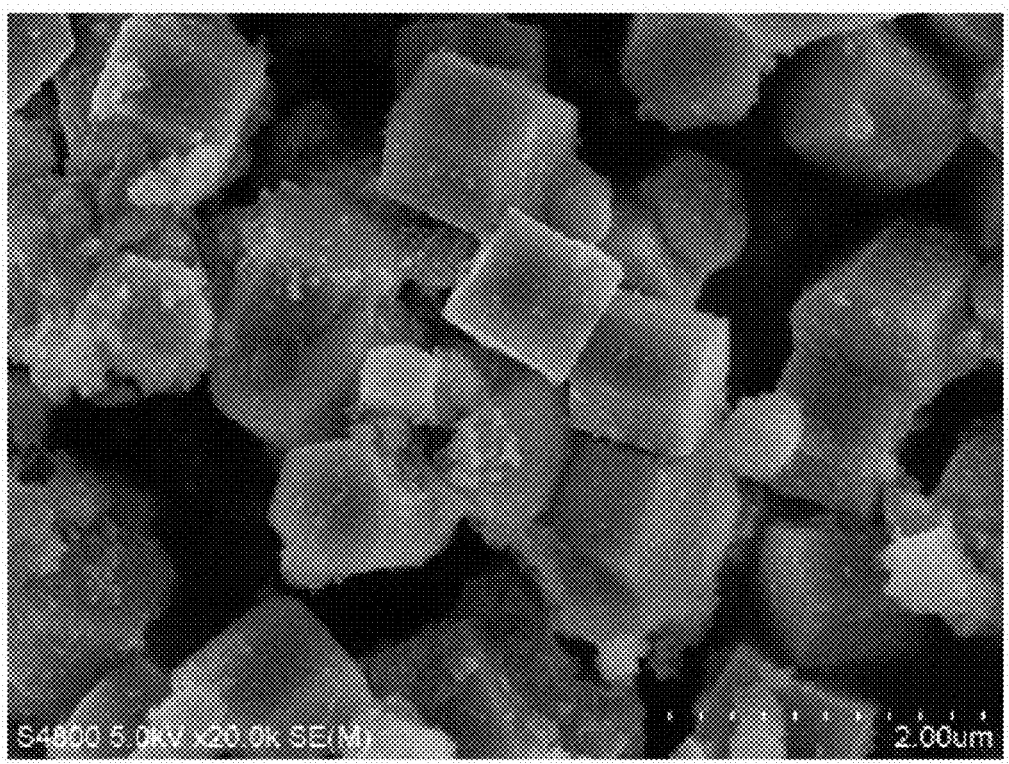
FIG. 41 is a scanning electron micrograph of the molecular sieve produced in Example III-8.

The scanning electron micrograph of the product was shown in FIG. 41. It can be easily seen in the figure that the molecular sieve has the hexagonal prismatic crystal particle morphology, with an effective diameter of 1200 nm, a height of 1600 nm, and an aspect ratio of 1.33. In accordance with the measurement, the molecular sieve had a total specific surface area of 546 $m^2 \cdot g^{-1}$ and a pore volume of 0.397 ml/g. The XRF analysis showed a $Si/Al_2=28$.

Example IV Series

Example IV-1

Preparation of Template A: 15 g (0.094 mol) of bis[2-(N, N-dimethylaminoethyl)]ether was added to a two-necked flask, 100 mL of isopropanol was added, and 9.5 (0.047 mol) of 1,3-dibromopropane was added dropwise with stirring at 25° C. After the addition was completed, the temperature was raised to reflux temperature, and the resultant was refluxed for 30 min. The solution changed from colorless to white and turbid, and then was reacted at reflux temperature for 12 h, cooled to 25° C., and 50 mL of ethyl acetate was added. The resultant was stirred for 15 min to form a white turbid liquid, and filtered, and the resulted solid was washed with ethyl acetate to give 13.2 g of a product as a compound of the formula (I), where n is 1, m is 2, R is methyl, and X is Br, having a melting point of 250.3° C., a purity of 99.9%, a relative molecular weight of 362.2. $^1$H-NMR spectrum shows chemical shift (300 MHZ, internal standard TMS, solvent $CDCl_2$) δ (ppm): 1.49 (2H, m), 2.27 (4H, m), 2.36 (4H, t), 2.53 (4H, t), 3.47 (4H, t).

Preparation of Template B: Br in Template A was replaced with $OH^-$ by ion exchange; ion exchange resin was a strong basic styrene type anion exchange resin, working solution was 15 m % aqueous solution of Template A, operating temperature was 25° C., the mass ratio of the working fluid to the ion exchange resin was 1:3; the flow rate was 3 drops/second; the exchanged solution was dehydrated by a rotary evaporator to give a product that is a compound of the formula (I), where n is 1, m is 2, R is methyl and X is OH, having a relative molecular weight of 236.2 and a purity of 99.21%. Its bromine content was 0.79 m %.

Example IV-2

Preparation of Template C: A compound of the formula (I), wherein n is 6, m is 2, R is methyl, and X is Br, was produced according to the method as described in Example IV-1 for Template A, except that 12.78 g (0.047 mol) of 1,8-dibromooctane was used in place of 1,3-dibromopropane. The test provided 17.6 g of a product having a melting point of 288.2° C., a relative molecular weight of 432.2, a purity of 99.9%. $^1$H-NMR spectrum shows chemical shift (300 MHZ, internal standard TMS, solvent $CDCl_2$) δ (ppm): 1.29 (2H, s), 1.39 (2H, m), 1.43 (2H, s), 2.27 (2H, m), 2.36 (2H, m), 2.55 (2H, m), 3.63 (4H, m).

Preparation of Template D: Br in Template C was replaced with $OH^-$ by ion exchange; ion exchange resin was strong basic styrene type anion exchange resin, working solution was 15 m % aqueous solution of Template C, operating temperature was 25° C., the mass ratio of the working fluid to the ion exchange resin was 1:3; the flow rate was 3 drops/second; the exchanged solution was dehydrated by a rotary evaporator to give a product that is a compound of the formula (I), where n is 6, m is 2, R is methyl, X is OH, having a relative molecular weight of 306.2, and a purity of 99.8%. Its bromine content was 0.2 m %.

Example IV-3

6.975 g of Template D was added to a 45 mL Teflon container, 0.259 g of sodium metaaluminate was added, stirred for 30 minutes until homogeneous, and then 3 g of crude silica gel (Qingdao Haiyang Chemical Co., Ltd., industrial product, $SiO_2$ content of 98%, $Al_2O_3$ content of 0.253%) was added, and the resultant was allowed to stand and aged for 1 hour to achieve a thorough mixing. The molar ratios of the components were as follows: $SiO_2/Al_2O_3=201$, $H_2O/SiO_2=5.8$, Template $D/SiO_2=0.15$, $NaOH/SiO_2=0.05$.

The above mixture was placed in a 45 mL steel autoclave with a Teflon liner, capped and sealed. The autoclave was placed in a rotating convection oven at a rotational speed of 20 rpm, and reacted at 120° C. for 1 day and then heated to 160° C. to react for 5 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 44:
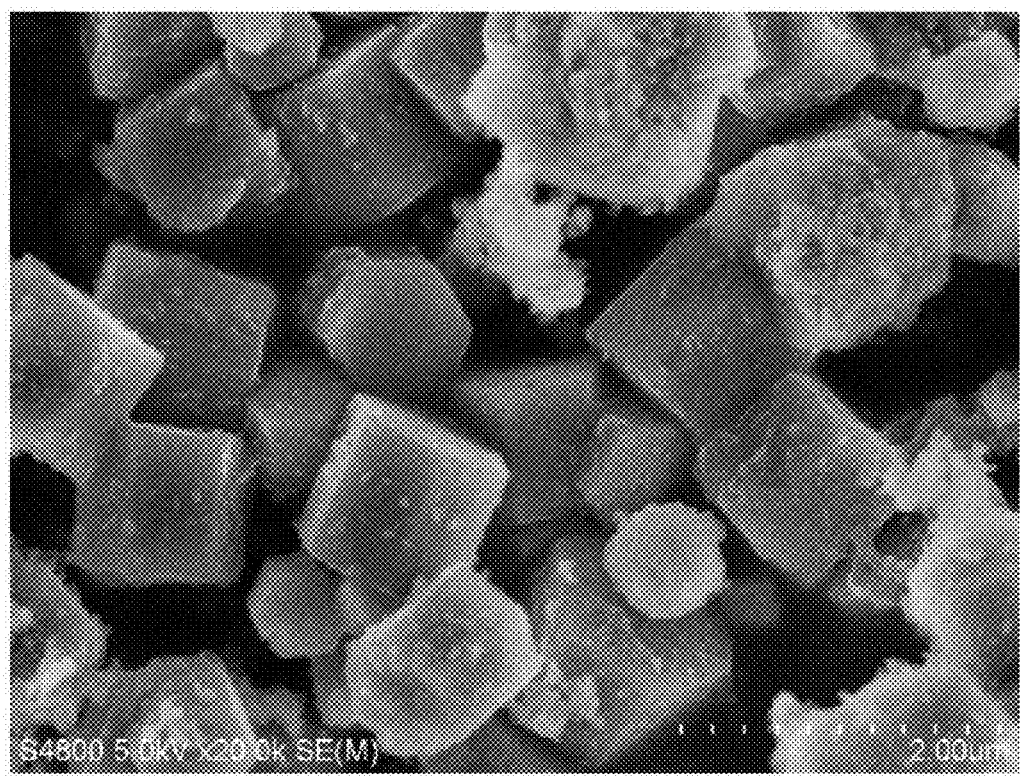
FIG. 44 is a scanning electron micrograph of the molecular sieve produced in Example IV-3.
Figure 45:
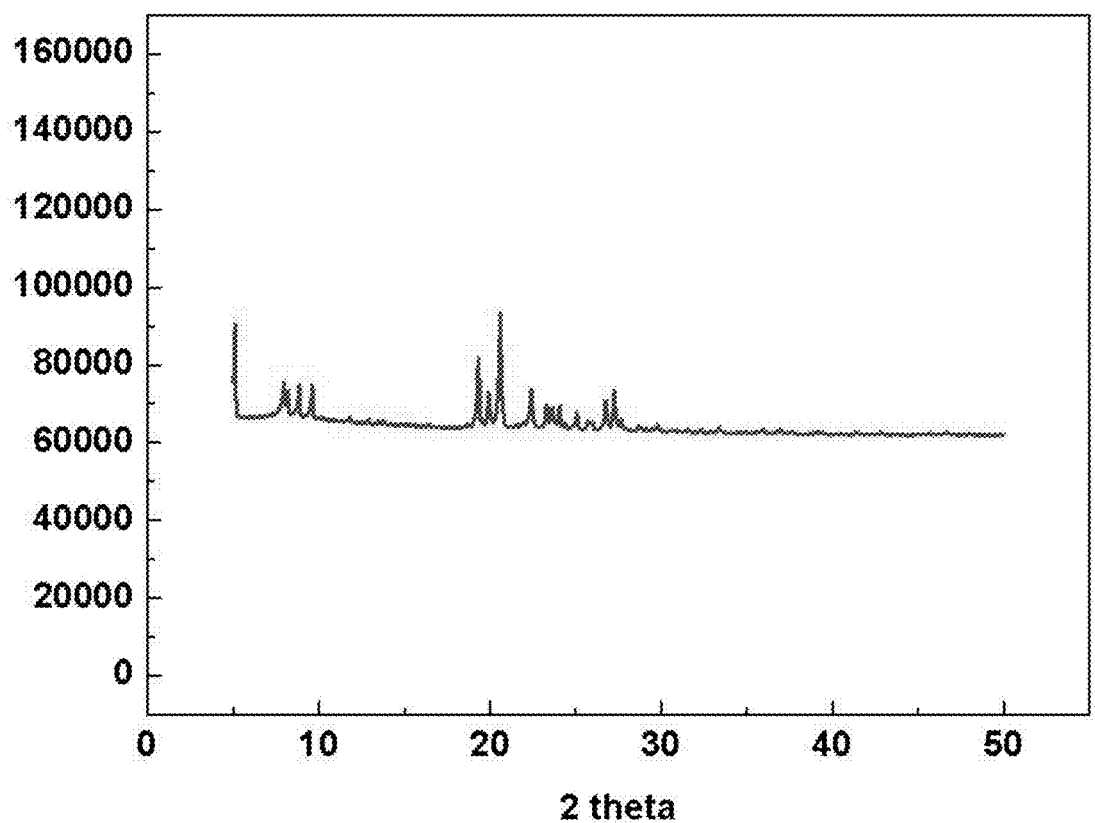
FIG. 45 is an XRD pattern of the molecular sieve produced in Example IV-3.

The scanning electron micrograph of the product was shown in FIG. 44. It can be easily seen in the figure that the molecular sieve has the hexagonal prismatic crystal particle morphology, with an effective diameter of 800 nm, a height of 1000 nm, and an aspect ratio of 1.25. In accordance with the measurement, the molecular sieve had a total specific surface area of 564 $m^2 \cdot g^{-1}$ and a pore volume of 0.394 ml/g. The XRD pattern of the product was shown in FIG. 45. The XRF analysis showed that the molecular sieve had a $Si/Al_2=203$.

Example IV-4

3.71 g of Template B was added to a 45 mL Teflon container, 0.246 g of sodium metaaluminate was added, stirred for 30 minutes until homogeneous, and then 3 g of white carbon black (Qingdao Haiyang Chemical Co., Ltd., industrial product, $SiO_2$ content of 98%) and 6.02 g of deionized water were added, and the resultant was allowed to stand and aged for 1 hour to achieve a thorough mixing. The molar ratios of the components were as follows: $SiO_2/Al_2O_3=240$, $H_2O/SiO_2=7.1$, Template $B/SiO_2=0.15$, $NaOH/SiO_2=0.04$.

The above mixture was placed in a 45 mL steel autoclave with a Teflon liner, capped and sealed. The autoclave was placed in a rotating convection oven at a rotation speed of 20 rpm, and reacted at 110° C. for 1 day and then heated to 170° C. to react for 5 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 46:
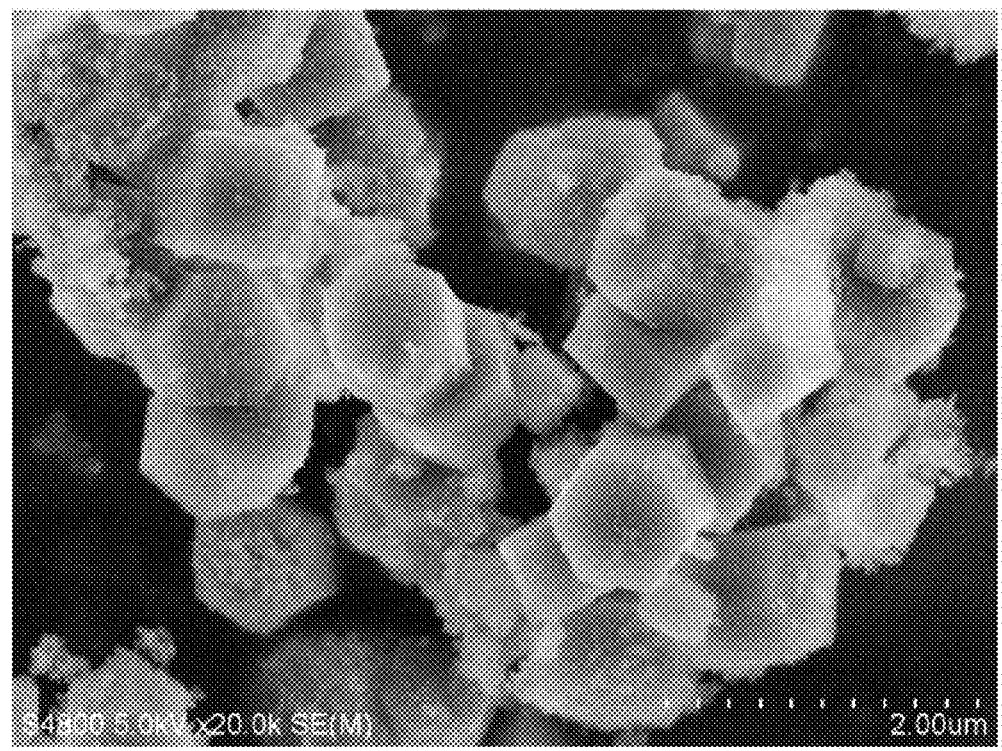
FIG. 46 is a scanning electron micrograph of the molecular sieve produced in Example IV-4.
Figure 47:
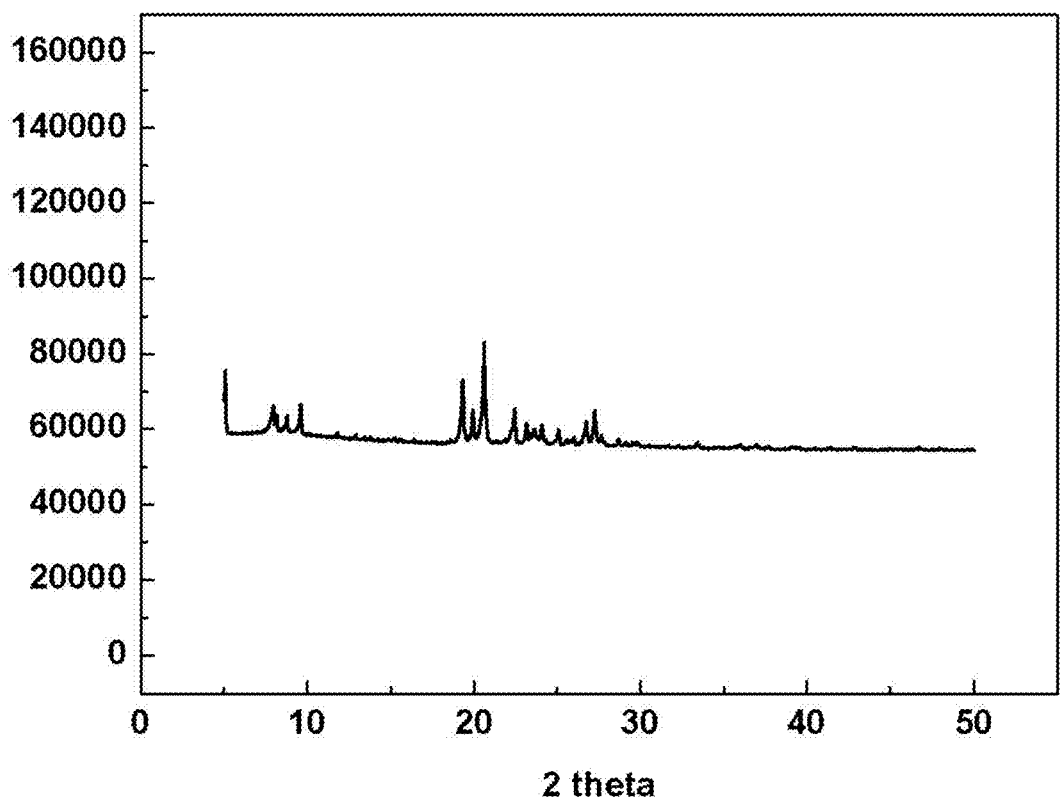
FIG. 47 is an XRD pattern of the molecular sieve produced in Example IV-4.

The scanning electron micrograph of the product was shown in FIG. 46. It can be easily seen in the figure that the molecular sieve has the hexagonal prismatic crystal particle morphology, with an effective diameter of 800 nm, a height of 1000 nm, and an aspect ratio of 1.25. In accordance with the measurement, the molecular sieve had a total specific surface area of 483 $m^2 \cdot g^{-1}$ and a pore volume of 0.285 ml/g. The XRD pattern of the product was shown in FIG. 47. The XRF analysis showed that the molecular sieve had a $Si/Al_2$=226.

Example IV-5

4.65 g of Template D was added to a 45 mL Teflon container, sodium metaaluminate was added to 0.245 g, stirred for 30 minutes to homogeneity, and then 3 g of crude silica gel (Qingdao Haiyang Chemical Co., Ltd., industrial product, $SiO_2$ content of 98%, was added. The $Al_2O_3$ content was 0.253%) and 6 g of deionized water, and the resultant was allowed to stand and aged for 1 hour to achieve a thorough mixing. The molar ratios of the components were as follows: $SiO_2/Al_2O_3$=242, $H_2O/SiO_2$=9.5, Template $D/SiO_2$=0.10, $NaOH/SiO_2$=0.03.

The above mixture was placed in a 45 mL steel autoclave with a Teflon liner, capped and sealed. The autoclave was placed in a rotating convection oven at a rotational speed of 20 rpm, and reacted at 120° C. for 1 day and then heated to 160° C. to react for 5 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 48:
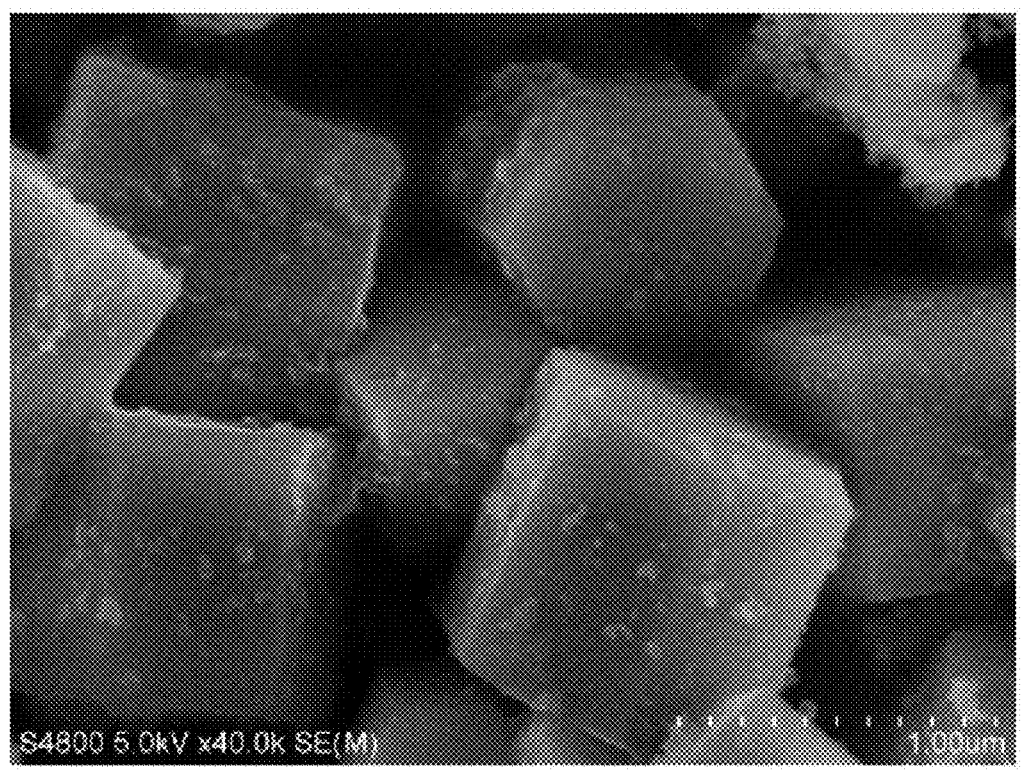
FIG. 48 is a scanning electron micrograph of the molecular sieve produced in Example IV-5.
Figure 49:
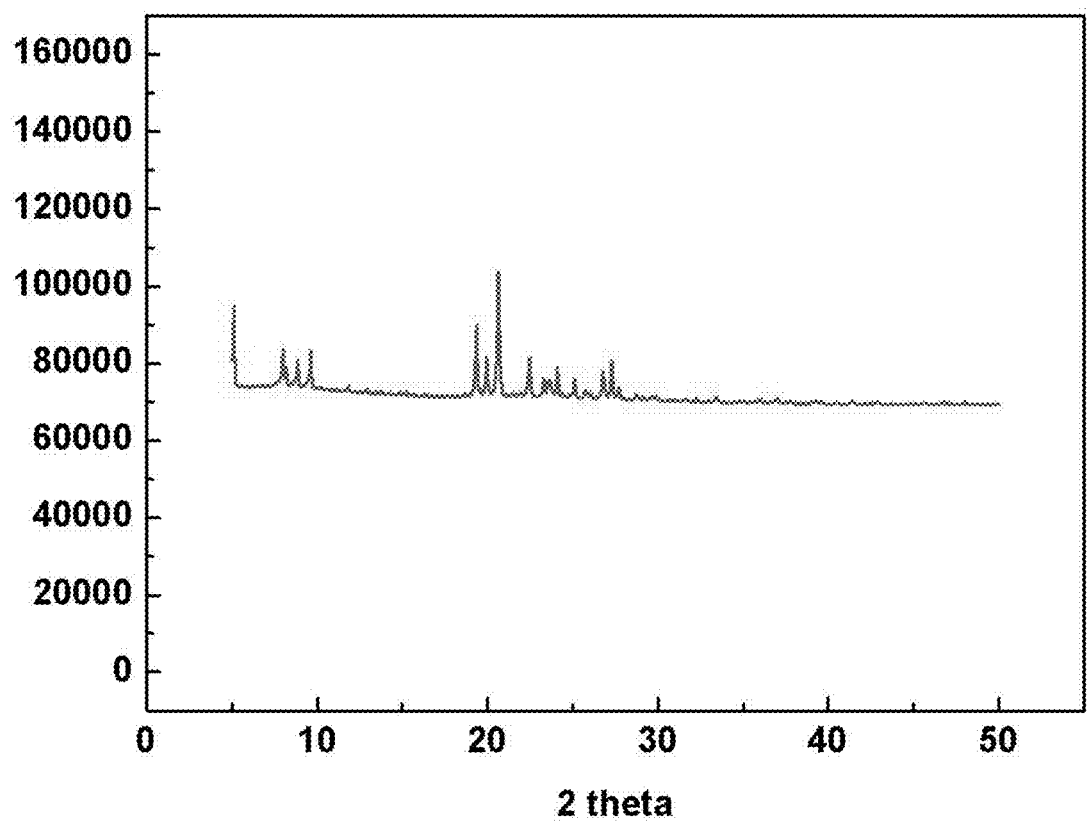
FIG. 49 is an XRD pattern of the molecular sieve produced in Example IV-5.

The scanning electron micrograph of the product was shown in FIG. 48. It can be easily seen in the figure that the molecular sieve has the hexagonal prismatic crystal particle morphology, with an effective diameter of 700 nm, a height of 900 nm, and an aspect ratio of 1.285. In accordance with the measurement, the molecular sieve had a total specific surface area of 464 $m^2 \cdot g^{-1}$ and a pore volume of 0.384 ml/g. The XRD pattern of the product was shown in FIG. 49. The XRF analysis showed that the molecular sieve had a $Si/Al_2$=253.

Example IV-6

5 g of Template B was added to a 45 mL Teflon container, 0.159 g of sodium metaaluminate was added, stirred for 30 minutes until homogeneous, and then 3 g of crude silica gel (Qingdao Haiyang Chemical Co., Ltd., industrial product, $SiO_2$ content of 98%, $Al_2O_3$ content of 0.253%) was added, and the resultant was allowed to stand and aged for 1 hour to achieve a thorough mixing. The molar ratios of the components were as follows: $SiO_2/Al_2O_3$=300, $H_2O/SiO_2$=7.3, Template $B/SiO_2$=0.15, $NaOH/SiO_2$=0.03.

The above mixture was placed in a 45 mL steel autoclave with a Teflon liner, capped and sealed. The autoclave was placed in a rotating convection oven at a rotation speed of 20 rpm, and reacted at 120° C. for 1 day and then heated to 150° C. to react for 5 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 50:
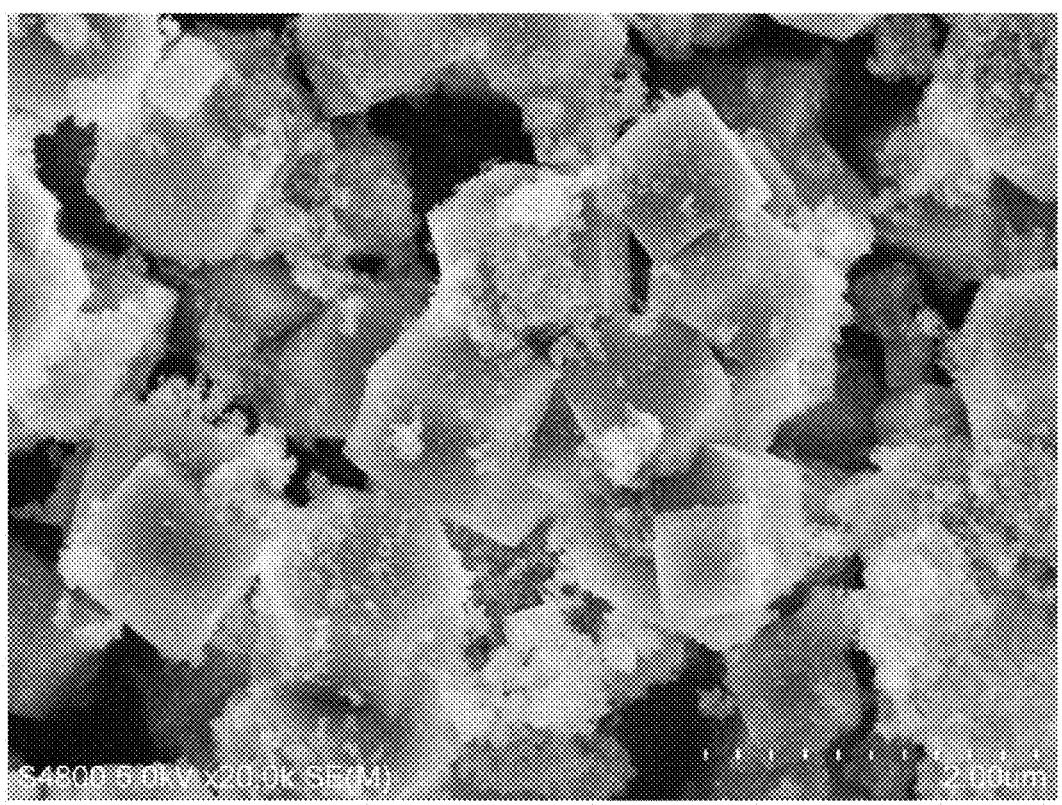
FIG. 50 is a scanning electron micrograph of the molecular sieve produced in Example IV-6.
Figure 51:
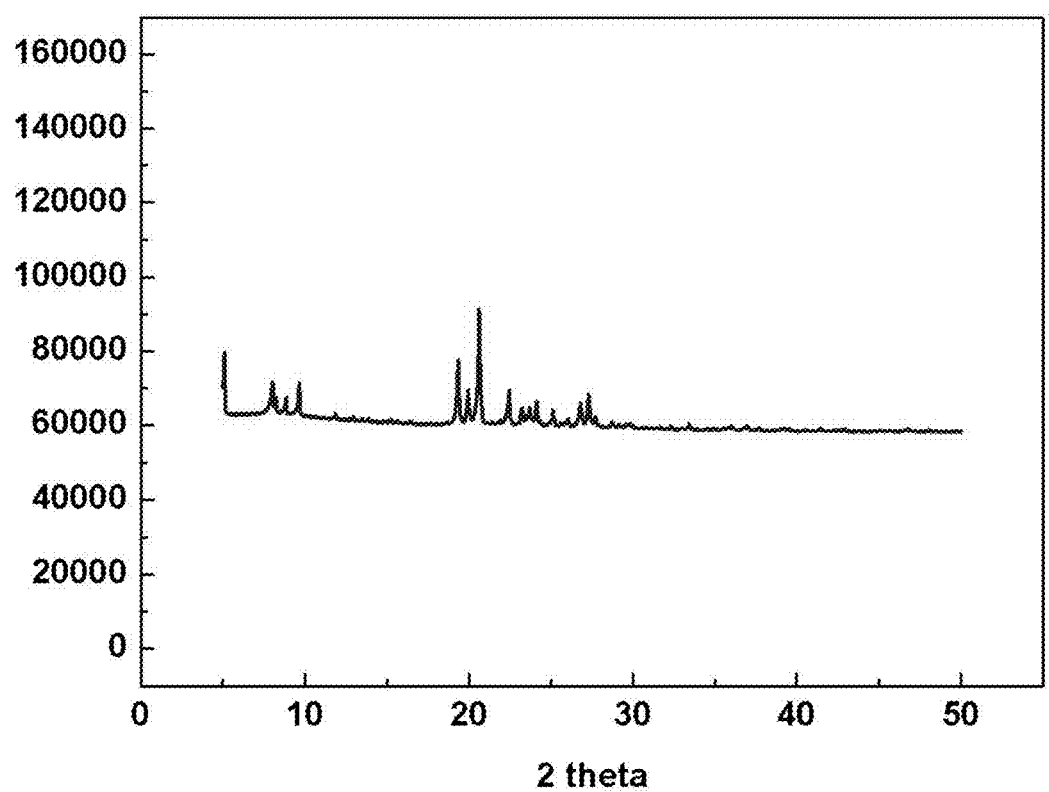
FIG. 51 is an XRD pattern of the molecular sieve produced in Example IV-6.

The scanning electron micrograph of the product was shown in FIG. 50. It can be easily seen in the figure that the molecular sieve has the hexagonal prismatic crystal particle morphology, with an effective diameter of 1000 nm, a height of 1000 nm, and an aspect ratio of 1.0. In accordance with the measurement, the molecular sieve had a total specific surface area of 538 $m^2 \cdot g^{-1}$ and a pore volume of 0.376 ml/g. The XRD pattern of the product was shown in FIG. 51. The XRF analysis showed that the molecular sieve had a $Si/Al_2$=304.

Example IV-7

6.975 g of Template D was added to a 45 mL Teflon container, 0.295 g of sodium metaaluminate was added, stirred for 30 minutes until homogeneous, and then 3 g of crude silica gel (Qingdao Haiyang Chemical Co., Ltd., industrial product, $SiO_2$ content of 98%, $Al_2O_3$ content of 0.253%) and 3.5 g of deionized water were added, and the resultant was allowed to stand and aged for 1 hour to achieve a thorough mixing. The molar ratios of the components were as follows: $SiO_2/Al_2O_3$=201, $H_2O/SiO_2$=9.8, Template $D/SiO_2$=0.15, $NaOH/SiO_2$=0.025.

The above mixture was placed in a 45 mL steel autoclave with a Teflon liner, capped and sealed. The autoclave was placed in a rotating convection oven at a rotational speed of 20 rpm, and reacted at 120° C. for 2 days and then heated to 150° C. to react for 3 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product. The XRF analysis showed a $Si/Al_2$=207.

Example IV-8

3.70 g of Template B was added to a 45 mL Teflon container, 0.288 g of sodium metaaluminate was added, stirred for 30 minutes until homogeneous, and then 3 g of crude silica gel (Qingdao Haiyang Chemical Co., Ltd., industrial product, $SiO_2$ content of 98%, $Al_2O_3$ content of 0.253%) and 3.2 g of deionized water were added, and the resultant was allowed to stand and aged for 1 hour to achieve a thorough mixing. The molar ratios of the components were as follows: $SiO_2/Al_2O_3$=205, $H_2O/SiO_2$=8.2, Template $D/SiO_2$=0.15, $NaOH/SiO_2$=0.025.

Figure 52:
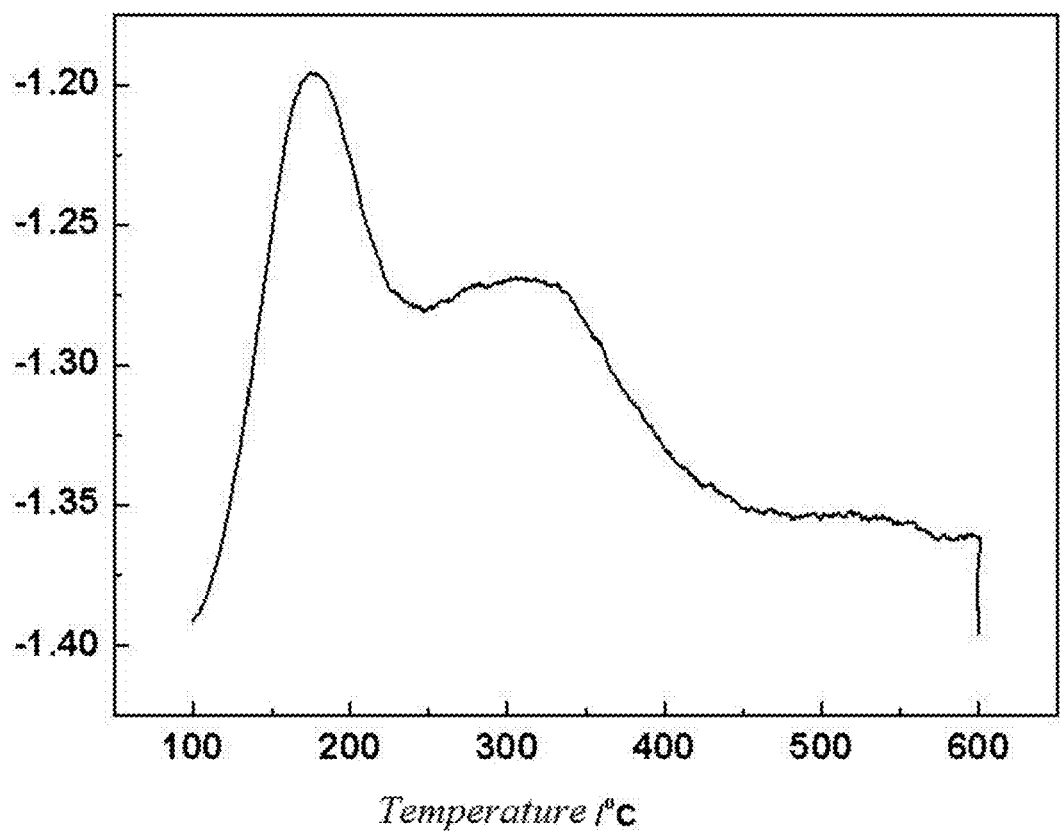
FIG. 52 is a NH3-TPD pattern of the molecular sieve produced in Example IV-8.
Figure 53:
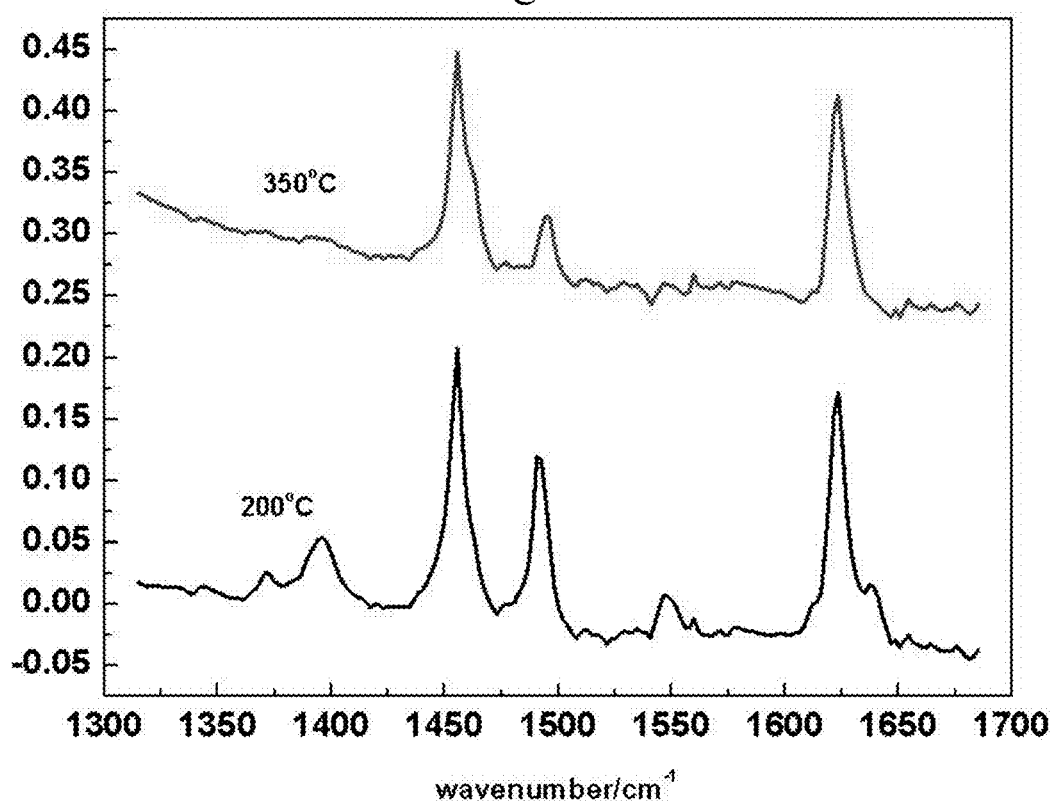
FIG. 53 is an IR spectra of the molecular sieve produced in Example IV-8.

The above mixture was placed in a 45 mL steel autoclave with a Teflon liner, capped and sealed. The autoclave was placed in a rotating convection oven at a rotation speed of 20 rpm, and reacted at 120° C. for 1 day and then heated to 150° C. to react for 6 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product. The XRF analysis showed a $Si/Al_2$=211. The results of NH3-TPD indicate (FIG. 52) that the molecular sieve has a significant acidity. The results of the infrared spectrum show (FIG. 53) that the molecular sieve has a low content of B acid and a high content of L acid.

Example IV-9

4.65 g of Template D was added to a 45 mL Teflon container, 0.297 g of sodium metaaluminate was added, stirred for 30 minutes until homogeneous, and then 3 g of white carbon black (Qingdao Haiyang Chemical Co., Ltd., industrial product, $SiO_2$ content of 98%) and 4 g deionized water were added, and the resultant was allowed to stand and aged for 1 hour to achieve a thorough mixing. The molar ratios of the components were as follows: $SiO_2/Al_2O_3=204$, $H_2O/SiO_2=8.4$, Template $D/SiO_2=0.10$, $NaOH/SiO_2=0.05$.

The above mixture was placed in a 45 mL steel autoclave with a Teflon liner, capped and sealed. The autoclave was placed in a rotating convection oven at a rotational speed of 20 rpm, and reacted at 120° C. for 1 day and then heated to 160° C. to react for 4 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product. The XRF analysis showed a $Si/Al_2=207$.

Second Embodiment and Sixth Embodiment

In the context of the present embodiment, including the following examples and comparative examples, the total specific surface area, pore volume and pore diameter of the micropores of the molecular sieve were measured by the following analytical methods.

Equipment: Micromeritic ASAP2010 Static Nitrogen Adsorber

Measurement conditions: The sample was placed in a sample processing system, and evacuated to $1.33 \times 10^{-2}$ Pa at 300° C., and kept at this temperature and pressure for 8 h to purify the sample. At the liquid nitrogen temperature of −196° C., the adsorption amount and desorption amount of nitrogen of the purified sample under different specific pressure P/P0 conditions were measured, and an adsorption-desorption isotherm curve was obtained. Then, the specific surface area was calculated with the two-parameter Horvath-Kawaioe formula. The adsorption capacity at the specific pressure P/P0≈0.983 was taken as the pore volume of the sample, and the pore diameter was calculated according to the DFT density functional theory model.

In these embodiments, including the following examples and comparative examples, the total specific surface area, pore volume and pore diameter of the mesopores of the molecular sieve were measured by the following analytical methods.

Equipment: Micromeritic ASAP2010 Static Nitrogen Adsorber

Measurement conditions: The sample was placed in a sample processing system, evacuated to $1.35 \times 10^{-2}$ Pa at 350° C., and kept at this temperature and pressure for 15 h to purify the sample. At the liquid nitrogen temperature of −196° C., the adsorption amount and desorption amount of nitrogen of the purified sample under different specific pressure P/P0 conditions were measured, and an adsorption-desorption isotherm curve was obtained. Then, the specific surface area was calculated with the two-parameter BET equation, and the adsorption capacity at the specific pressure P/P0≈0.98 was taken as the pore volume of the sample, and the pore diameter was calculated according to the Horvath-Kawaioe model.

In these embodiments, including the following examples and comparative examples, the total specific surface area, pore volume and pore diameter of the coarse pores of the molecular sieve were measured by the following analytical methods.

Equipment: Micromeritic AutoPore IV 9510 Mercury Injector

Measurement conditions: an appropriate amount of dry sample was placed into the sample tube, put into the instrument, evacuated to 50 umg for low pressure operation, and the weighing was completed under the low pressure. The sample tube filled with mercury was put into the high pressure chamber and further pressurized to 60,000 pisa to force mercury to enter the pores. Based on the applied pressure P, the corresponding pore diameter r (nm) can be calculated. The pore volume of pores having the corresponding size can be calculated based on the amount of intruded mercury, and the curve of the pore volume as a function of the pore diameter can be obtained, thereby providing a pore diameter distribution curve. The length of the pore was calculated from the pore volume and the pore diameter, assuming that the pore was a columnar through hole, and the surface area was obtained by multiplying the circumference of the pore by the length thereof.

Example V-1

Preparation of Template A: 15 g (0.094 mol) of bis[2-(N, N-dimethylaminoethyl)]ether was added to a two-necked flask, 100 mL of isopropanol was added, and 9.5 (0.047 mol) of 1,3-dibromopropane was added dropwise with stirring at 25° C. After the addition was completed, the temperature was raised to reflux temperature, and the resultant was refluxed for 30 min. The solution changed from colorless to white and turbid, and then was reacted at reflux temperature for 12 h, cooled to 25° C., and 50 mL of ethyl acetate was added. The resultant was stirred for 15 min to form a white turbid liquid, and filtered, and the resulted solid was washed with ethyl acetate to give 13.2 g of a product as a compound of the formula (I), where n is 1, m is 2, R is methyl, and X is Br, having a melting point of 250.3° C., a purity of 99.9 m %, a relative molecular weight of 362.2. $^1$H-NMR spectrum shows chemical shift (300 MHZ, internal standard TMS, solvent $CDCl_2$) δ (ppm): 1.49 (2H, m), 2.27 (4H, m), 2.36 (4H, t), 2.53 (4H, t), 3.47 (4H, t).

Preparation of Template B: Br in Template A was replaced with OH⁻ by ion exchange; ion exchange resin was a strong basic styrene type anion exchange resin, working solution was 15 m % aqueous solution of Template A, operating temperature was 25° C., the mass ratio of the working fluid to the ion exchange resin was 1:3; the flow rate was 3 drops/second; the exchanged solution was dehydrated by a rotary evaporator to give a product that is a compound of the formula (I), where n is 1, m is 2, R is methyl and X is OH, having a relative molecular weight of 236.2 and a purity of 98.2%. Its bromine content was 0.79 m %.

Example V-2

Preparation of Template C: a compound of the formula (I), wherein n is 6, m is 2, R is methyl, and X is Br, was produced according to the method as described in Example V-1 for Template A, except that 12.78 g (0.047 mol) of 1,8-dibromooctane was used in place of 1,3-dibromopropane. The test provided 17.6 g of a product having a melting point of 288.2° C., a relative molecular weight of 432.2, a purity of 99.9 m %. $^1$H-NMR spectrum shows chemical shift (300 MHZ, internal standard TMS, solvent $CDCl_2$) δ (ppm): 1.29 (2H, s), 1.39 (2H, m), 1.43 (2H, s), 2.27 (2H, m), 2.36 (2H, m), 2.55 (2H, m), 3.63 (4H, m).

Preparation of Template D: Br in Template C was replaced with OH⁻ by ion exchange; ion exchange resin was strong basic styrene type anion exchange resin, working solution was 15 m % aqueous solution of Template C, operating temperature was 25° C., the mass ratio of the working fluid to the ion exchange resin was 1:3; the flow rate was 3 drops/second; the exchanged solution was dehydrated by a rotary evaporator to give a product that is a compound of the formula (I), where n is 6, m is 2, R is methyl, X is OH, having a relative molecular weight of 306.2, and a purity of 99.5 m %. Its bromine content was 0.2 m %.

Example V-3

0.134 g of sodium metaaluminate was added to a 45 mL Teflon container, 1.81 g of Template B was added, stirred for 30 minutes until homogeneous, and then 3 g of crude silica gel (Qingdao Haiyang Chemical Co., Ltd., industrial product, $SiO_2$ content of 98.05%) and 6.3 g of deionized water were added, and well mixed for 5 minutes. The molar ratios of the components were as follows: $SiO_2/Al_2O_3=61$, $H_2O/SiO_2=7$, Template $B/SiO_2=0.16$, $OH^-/SiO_2=0.31$.

The above mixture was placed in a 45 mL steel autoclave with a Teflon liner, capped and sealed, and the autoclave was placed in a rotating convection oven at a rotational speed of 20 rpm and reacted at 160° C. for 5 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 56:
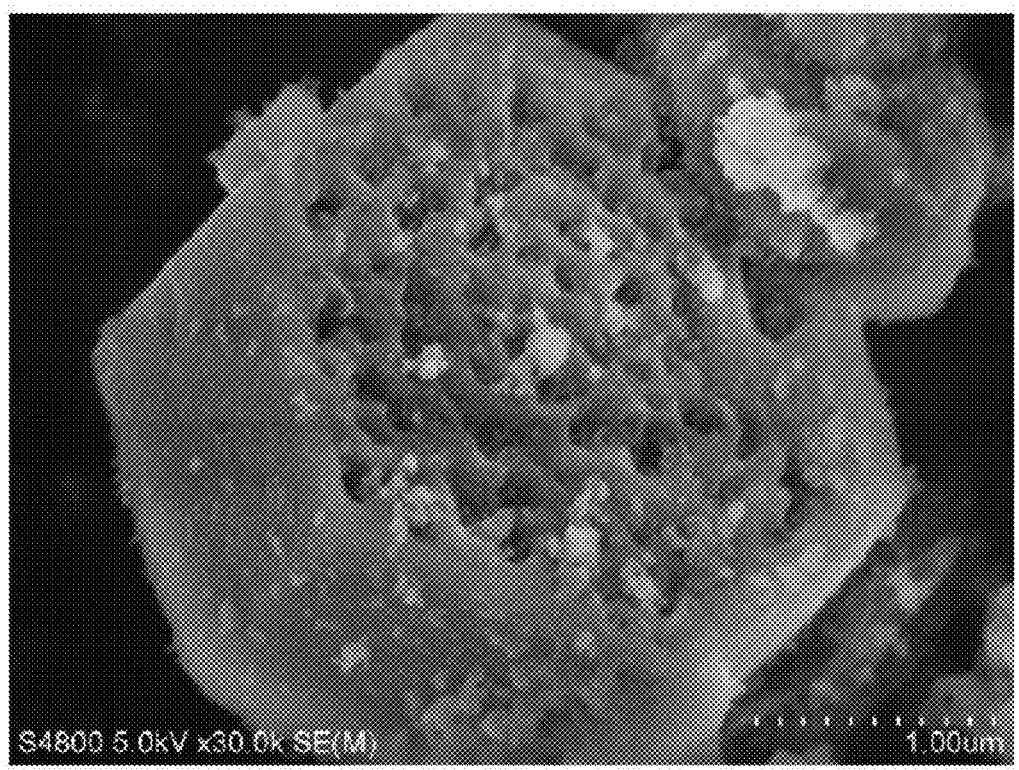
FIG. 56 is a scanning electron micrograph of the molecular sieve produced in Example V-1.

The scanning electron micrograph of the product was shown in FIG. 56. It can be easily seen in the figure that the molecular sieve has a crystal particle morphology of hexagonal prismatic shape and sponge structure, and has an effective diameter of 2500 nm, a height of 1000 nm, and an aspect ratio of 0.4. In accordance with the measurement, the molecular sieve comprises coarse pores, mesopores and micropores, wherein the coarse pores have a diameter of 150 nm, a total specific surface area of 89 $m^2 \cdot g^{-1}$, and a pore volume of 1.36 ml/g; the mesopores have a diameter of 4 nm, a total specific surface area of 126 $m^2 \cdot g^{-1}$, and a pore volume of 0.29 ml/g; and the micropores have a diameter of 0.5 nm and 1.2 nm, a total specific surface area of 163 $m^2 \cdot g^{-1}$, and a pore volume of 0.07 ml/g. The XRF analysis showed a $Si/Al_2=48$.

Figure 54:
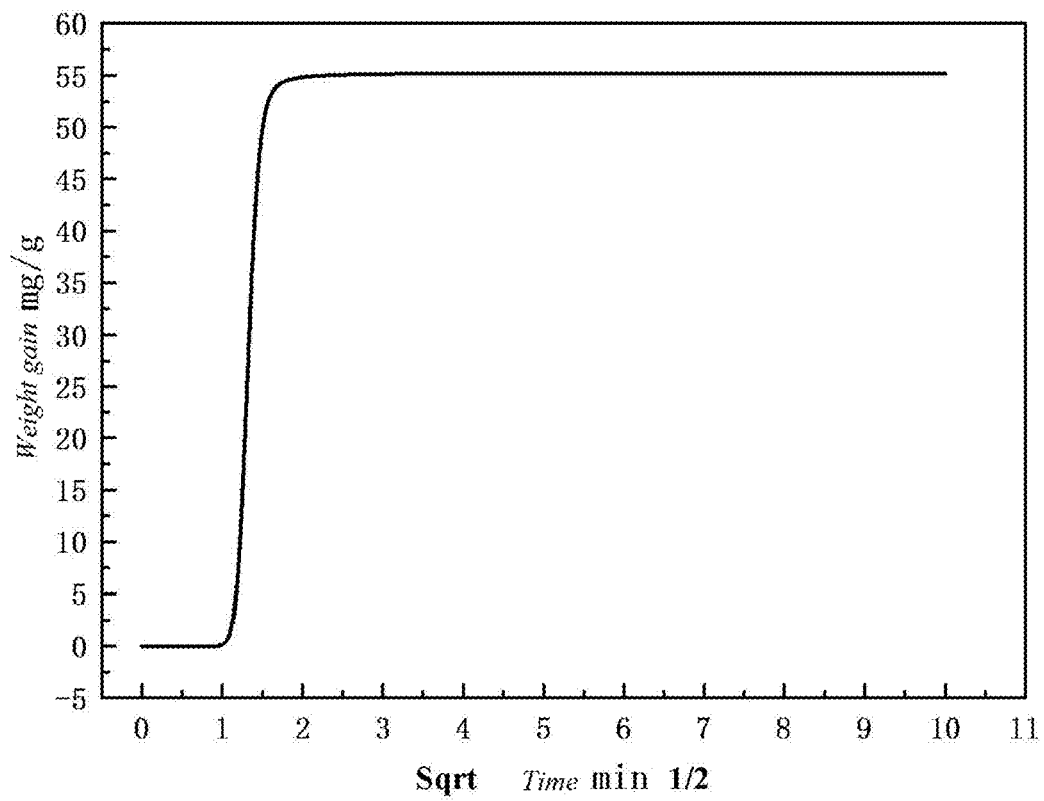
FIG. 54 is an adsorption curve of 2,2-diethylbutane on the molecular sieve produced in Example V-3 after calcination.
Figure 57:
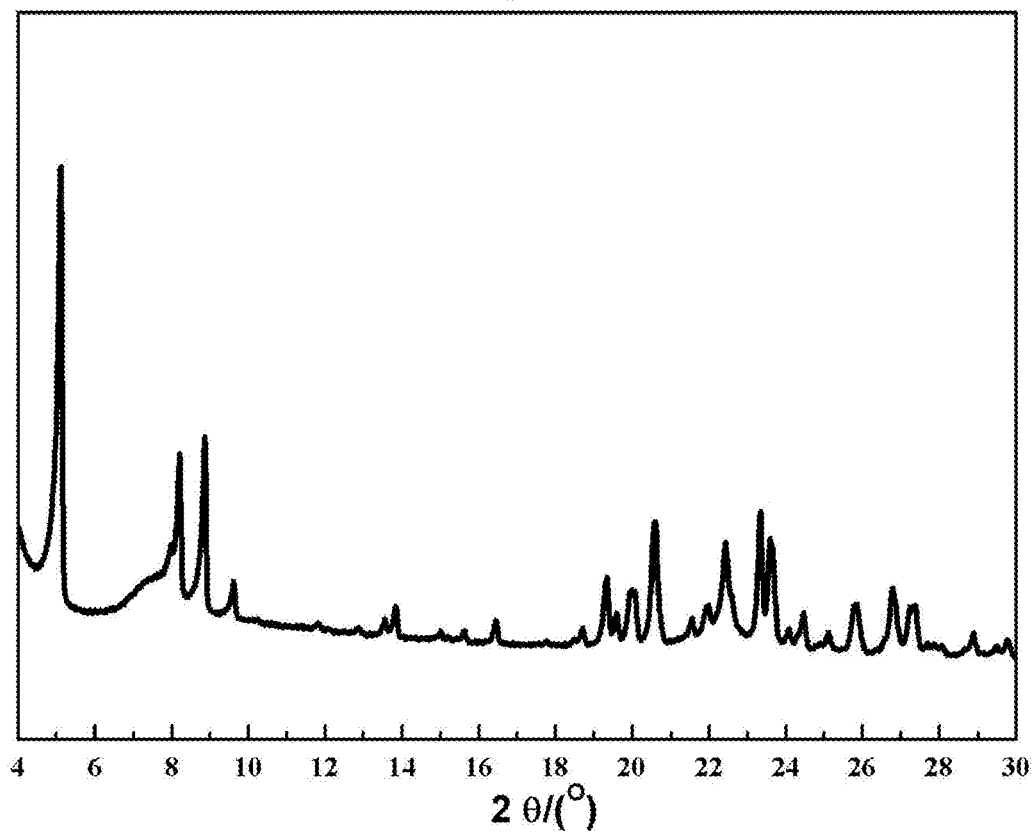
FIG. 57 is an XRD pattern of the molecular sieve produced in Example V-3.

The XRD pattern of this product was shown in FIG. 57. FIG. 54 shows the adsorption curve of 2,2-diethylbutane on the product after calcination at 550° C. for 3 h. It can be seen from the curve that the adsorption capacity of the product for 2,2-diethylbutane is about 55 mg/g.

Example V-4

0.134 g of sodium metaaluminate was added to a 45 mL Teflon container, 3.0 g of Template D, 9.31 g of deionized water was added, stirred for 30 minutes until homogeneous, and then 4 g of crude silica gel (Qingdao Haiyang Chemical Co., Ltd., industrial product, $SiO_2$ content of 98.05%) was added, and well mixed for 5 minutes. The molar ratios of the components were as follows: $SiO_2/Al_2O_3=81$, $H_2O/SiO_2=8$, Template $D/SiO_2=0.15$, $OH^-/SiO_2=0.30$.

The above mixture was placed in a 45 mL steel autoclave with a Teflon liner, capped and sealed, and the autoclave was placed in a rotating convection oven at a rotational speed of 20 rpm and reacted at 160° C. for 5 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 59:
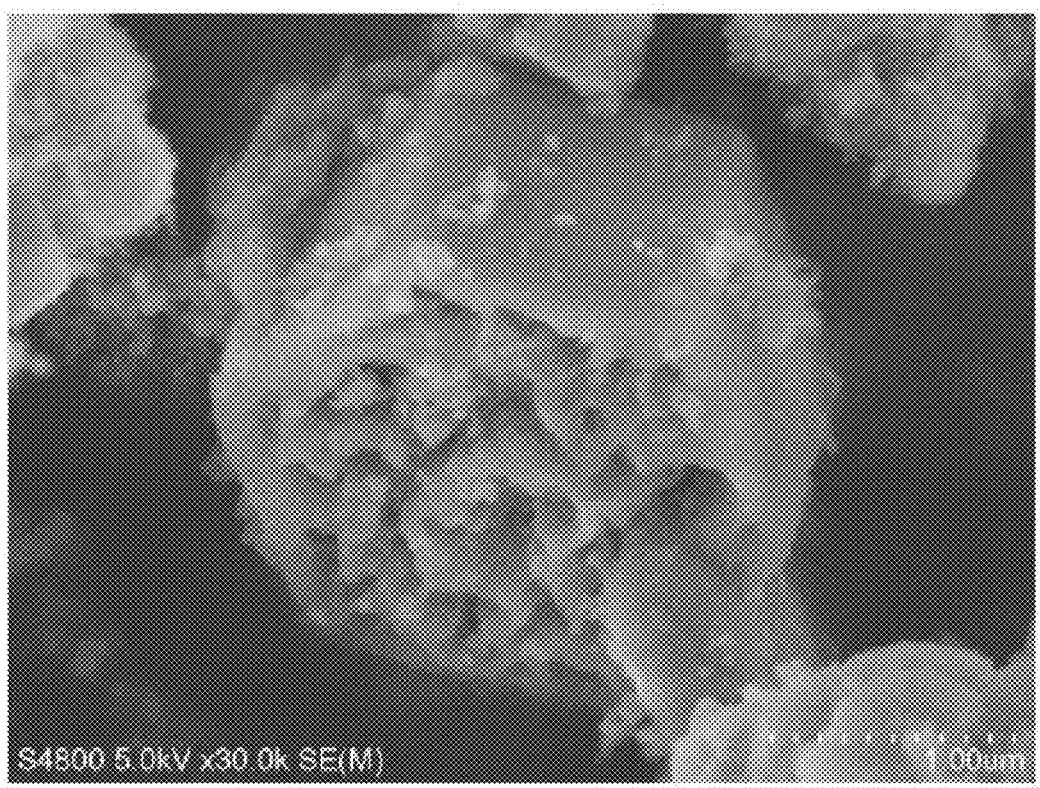
FIG. 59 is a scanning electron micrograph of the molecular sieve produced in Example V-4.

The scanning electron micrograph of the product was shown in FIG. 59. It can be easily seen in the figure that the molecular sieve has a crystal particle morphology of hexagonal prismatic shape and sponge structure, with an effective diameter of 2500 nm, a height of 850 nm, and an aspect ratio of 0.34. In accordance with the measurement, the molecular sieve comprises coarse pores, mesopores and micropores, wherein the coarse pores have a diameter of 400 nm, a total specific surface area of 65 $m^2 \cdot g^{-1}$, and a pore volume of 0.387 ml/g; the mesopores have a diameter of 5 nm, a total specific surface area of 116 $m^2 \cdot g^{-1}$, and a pore volume of 0.28 ml/g; and the micropores have a diameter of 0.5 nm and 1.2 nm, a total specific surface area of 149 $m^2 \cdot g^{-1}$, and a pore volume of 0.107 ml/g. The XRF analysis showed a $Si/Al_2=75$.

Example V-5

0.134 g of sodium metaaluminate was added to a 45 mL Teflon container, 1.78 g of Template A was added, stirred for 30 minutes until homogeneous, and then 3 g of crude silica gel (Qingdao Haiyang Chemical Co., Ltd., industrial product, $SiO_2$ content of 98.05%), 6.98 g of deionized water, and 0.4 g of NaOH were added, and well mixed for 5 minutes. The molar ratios of the components were as follows: $SiO_2/Al_2O_3=61$, $H_2O/SiO_2=8$, Template $A/SiO_2=0.10$, $OH^-/SiO_2=0.20$.

The above mixture was placed in a 45 mL steel autoclave with a Teflon liner, capped and sealed, and the autoclave was placed in a rotating convection oven at a rotational speed of 20 rpm and reacted at 160° C. for 4 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 60:
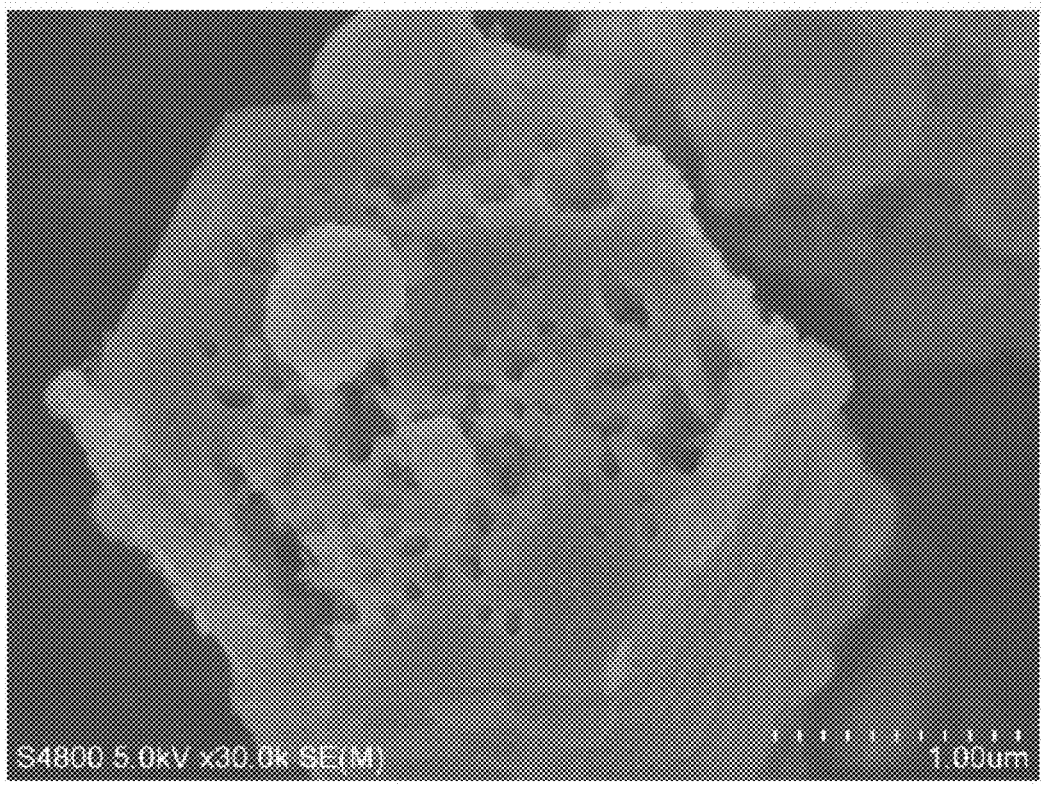
FIG. 60 is a scanning electron micrograph of the molecular sieve produced in Example V-5.

The scanning electron micrograph of the product was shown in FIG. 60. It can be easily seen in the figure that the molecular sieve has a crystal particle morphology of hexagonal prismatic shape and sponge structure, with an effective diameter of 2200 nm, a height of 3500 nm, and an aspect ratio of 1.59. In accordance with the measurement, the molecular sieve comprises coarse pores, mesopores and micropores, wherein the coarse pores have a diameter of 100 nm, a total specific surface area of 365 $m^2 \cdot g^{-1}$, and a pore volume of 0.365 ml/g; the mesopores have a diameter of 8 nm, a total specific surface area of 115 $m^2 \cdot g^{-1}$, and a pore volume of 0.22 ml/g; and the micropores have a diameter of 4 nm and 1.2 nm, a total specific surface area of 280 $m^2 \cdot g^{-1}$, and a pore volume of 0.145 ml/g. The XRF analysis showed a $Si/Al_2=56$.

Example V-6

0.134 g of sodium metaaluminate was added to a 45 mL Teflon container, 3.70 g of Template B was added, stirred for 30 minutes until homogeneous, and then 3 g of crude silica gel (Qingdao Haiyang Chemical Co., Ltd., industrial product, $SiO_2$ content of 98.05%) and 6.11 g of deionized water were added, well mixed for 5 minutes. The molar ratios of the components were as follows: $SiO_2/Al_2O_3=61$, $H_2O/SiO_2=7$, Template $B/SiO_2=0.32$, $OH^-/SiO_2=0.64$.

The above mixture was placed in a 45 mL steel autoclave with a Teflon liner, capped and sealed, and the autoclave was placed in a rotating convection oven at a rotational speed of 20 rpm and reacted at 160° C. for 5 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 61:
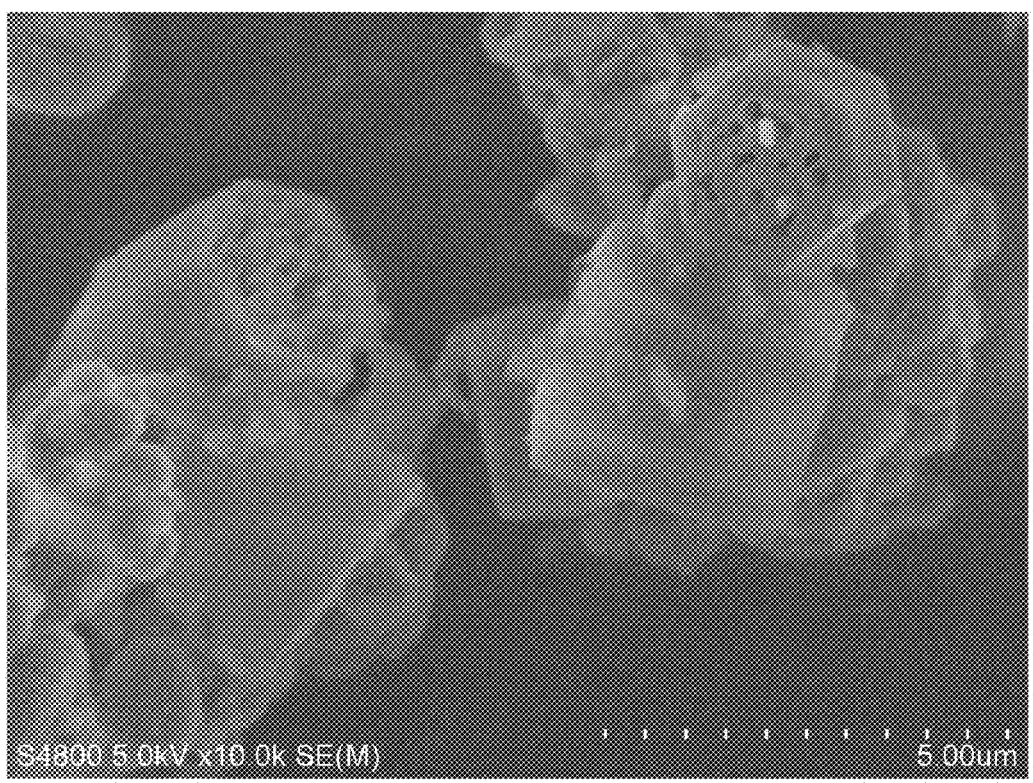
FIG. 61 is a scanning electron micrograph of the molecular sieve produced in Example V-6.

The scanning electron micrograph of the product was shown in FIG. 61. It can be easily seen in the figure that the molecular sieve has a crystal particle morphology of hexagonal prismatic shape and sponge structure, with an effective diameter of 1750 nm, a height of 4000 nm, and an aspect ratio of 2.29. In accordance with the measurement, the molecular sieve comprises coarse pores, mesopores and micropores, wherein the coarse pores have a diameter of 200 nm, a total specific surface area of 65 $m^2 \cdot g^{-1}$, and a pore volume of 0.390 ml/g; the mesopores have a diameter of 9 nm, a total specific surface area of 145 $m^2 \cdot g^{-1}$, and a pore volume of 0.16 ml/g; and the micropores have a diameter of 4 nm and 1.2 nm, a total specific surface area of 220 $m^2 \cdot g^{-1}$, and a pore volume of 0.130 ml/g. The XRF analysis showed a $Si/Al_2=54$.

Figure 55:
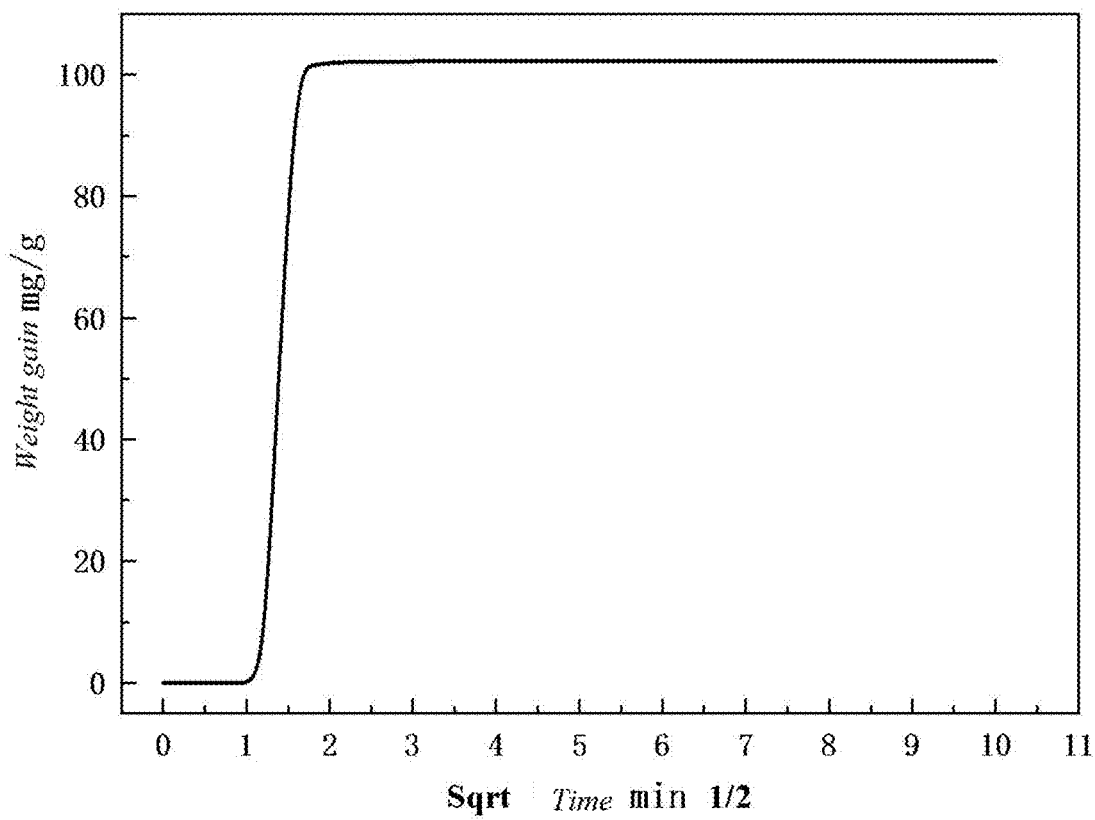
FIG. 55 is an adsorption curve of 3-propyl-4-butyloctane on the molecular sieve produced in Example V-6 after calcination.
Figure 58:
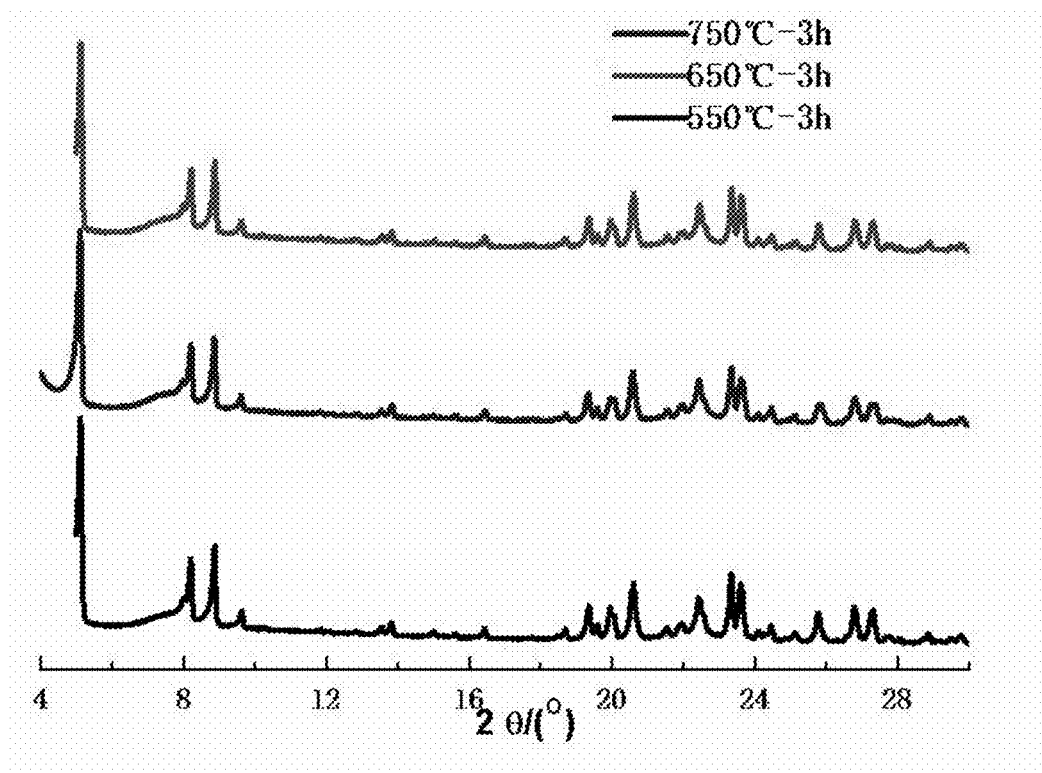
FIG. 58 is an XRD pattern of the molecular sieve produced in Example V-6 after calcination.

The product was calcined, separately, at 550° C., 650° C. and 750° C. for 3 h, and the XRD pattern of the product after calcination is shown in FIG. 58, with each characteristic peak still existing. FIG. 55 is an adsorption curve of 3-propyl-4-butyloctane on the product after calcination at 550° C. for 3 h. As can be seen from the figure, the adsorption capacity of the product for 3-propyl-4-butyloctyl is as high as about 102 mg/g.

Example V-7

0.134 g of sodium metaaluminate was added to a 45 mL Teflon container, and 7.0 g of Template D and 9.31 g of deionized water were added, stirred for 30 minutes until homogeneous, and then 4 g of crude silica gel (Qingdao Haiyang Chemical Co., Ltd., industrial product, $SiO_2$ content of 98.05%) was added, and well mixed for 5 minutes. The molar ratios of the components were as follows: $SiO_2/Al_2O_3=82$, $H_2O/SiO_2=8$, Template $D/SiO_2=0.35$, $OH^-/SiO_2=0.70$.

The above mixture was placed in a 45 mL steel autoclave with a Teflon liner, capped and sealed, and the autoclave was placed in a rotating convection oven at a rotational speed of 20 rpm and reacted at 160° C. for 5 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 62:
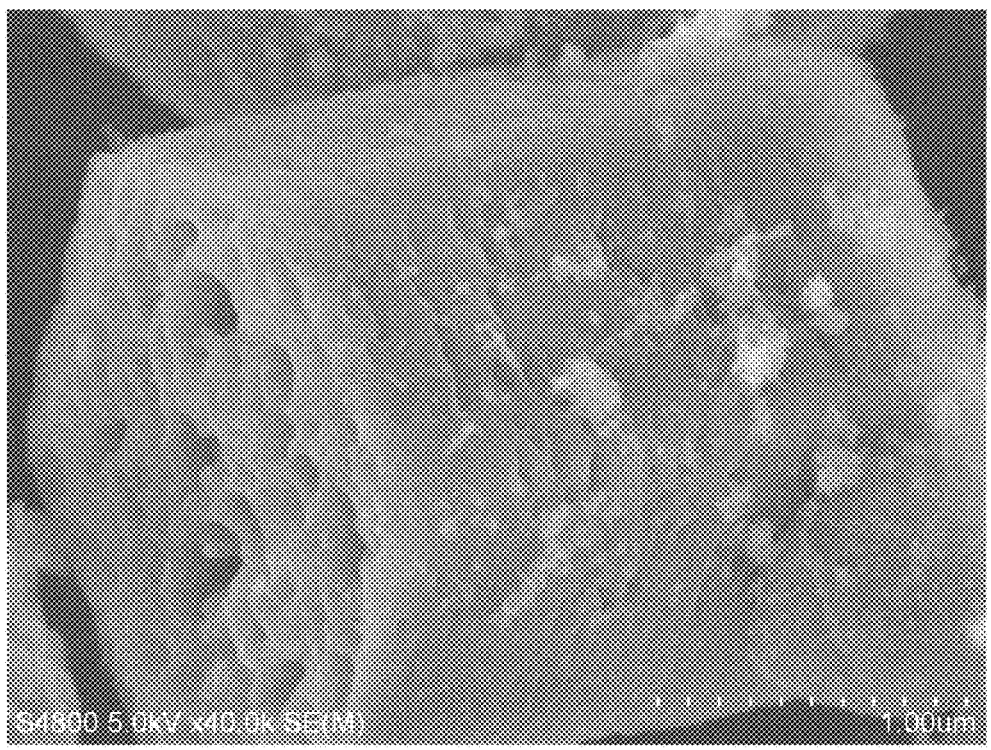
FIG. 62 is a scanning electron micrograph of the molecular sieve produced in Example V-7.
Figure 67:
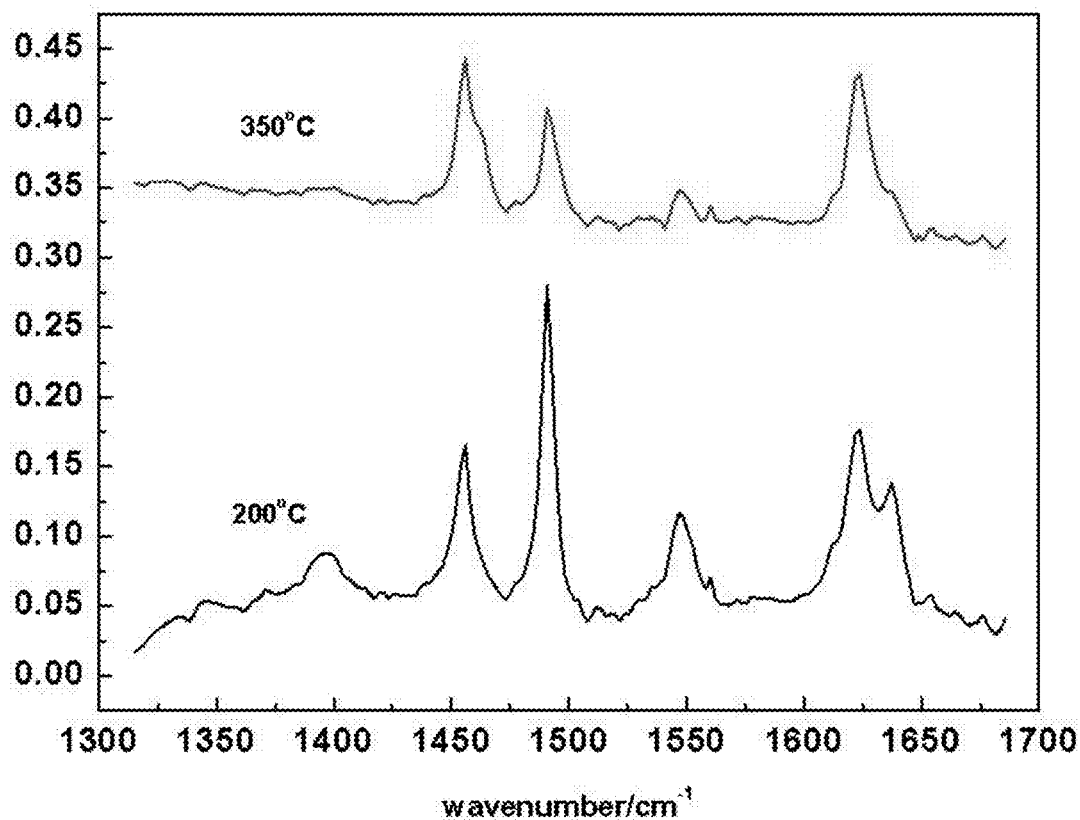
FIG. 67 is an IR spectra of the molecular sieve produced in Example V-7.

The scanning electron micrograph of the product was shown in FIG. 62) that the molecular sieve has a significant acidity. The results of the infrared spectrum show (FIG. 67) that the molecular sieve has a low content of B acid and a high content of L acid.

Example V-8

0.134 g of sodium metaaluminate was added to a 45 mL Teflon container, 7.41 g of Template C was added, stirred for 30 minutes until homogeneous, and then 3 g of crude silica gel (Qingdao Haiyang Chemical Co., Ltd., industrial product, $SiO_2$ content of 98.05%), 6.98 g of deionized water, and 0.4 g of NaOH were added, and well mixed for 5 minutes. The molar ratios of the components were as follows: $SiO_2/Al_2O_3=61$, $H_2O/SiO_2=8$, Template $C/SiO_2=0.35$, $OH^-/SiO_2=0.20$.

The above mixture was placed in a 45 mL steel autoclave with a Teflon liner, capped and sealed, and the autoclave was placed in a rotating convection oven at a rotational speed of 20 rpm and reacted at 160° C. for 4 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 63:
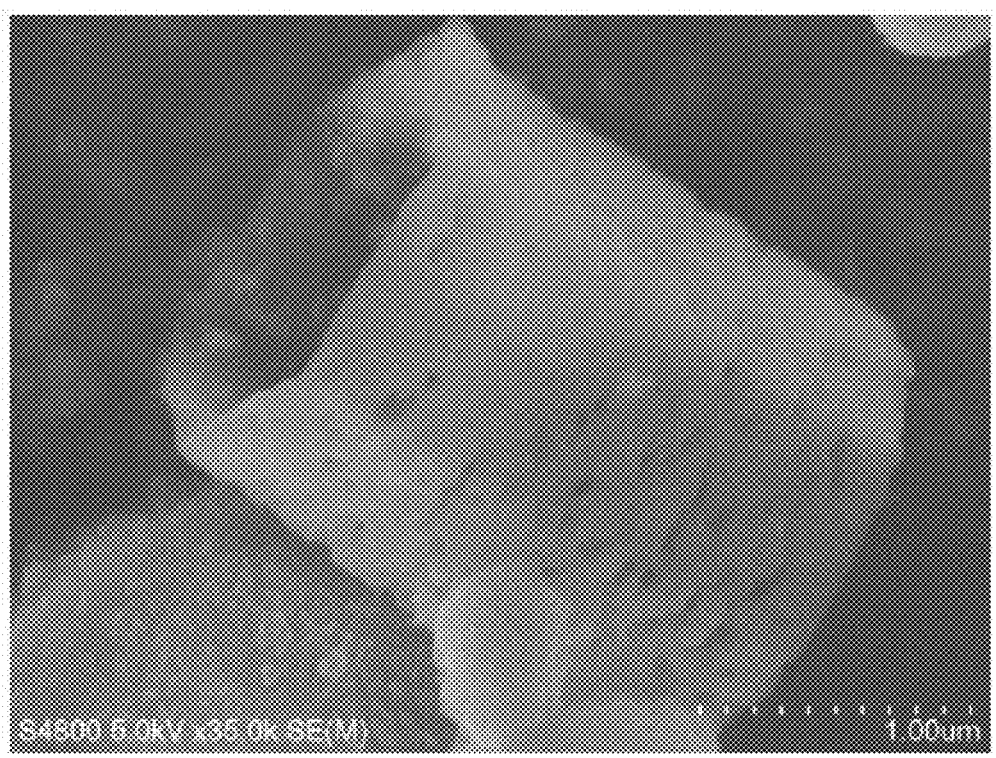
FIG. 63 is a scanning electron micrograph of the molecular sieve produced in Example V-8.

The scanning electron micrograph of the product was shown in FIG. 63. It can be easily seen in the figure that the molecular sieve has a crystal particle morphology of hexagonal prismatic shape and sponge structure, with an effective diameter of 1200 nm, a height of 1700 nm, and an aspect ratio of 1.42. In accordance with the measurement, the molecular sieve comprises coarse pores, mesopores and micropores, wherein the coarse pores have a diameter of 1000 nm, a total specific surface area of 26 $m^2 \cdot g^{-1}$, and a pore volume of 0.253 ml/g; the mesopores have a diameter of 8 nm, a total specific surface area of 142 $m^2 \cdot g^{-1}$, and a pore volume of 0.216 ml/g; and the micropores have a diameter of 4 nm and 1.2 nm, a total specific surface area of 194 m 2/g, and a pore volume of 0.037 ml/g. The XRF analysis showed a $Si/Al_2=54$.

Third Embodiment and Sixth Embodiment

In the context of the present embodiment, including the following examples and comparative examples, the total specific surface area, pore volume and pore diameter of the molecular sieve were measured by the following analytical methods.

Equipment: Micromeritic ASAP2010 Static Nitrogen Adsorber

Measurement conditions: The sample was placed in a sample processing system, evacuated to $1.35 \times 10^{-2}$ Pa at 350° C., and kept at this temperature and pressure for 15 h to purify the sample. At the liquid nitrogen temperature of −196° C., the adsorption amount and desorption amount of nitrogen of the purified sample under different specific pressure P/P0 conditions were measured, and an adsorption-desorption isotherm curve was obtained. Then, the total specific surface area was calculated with the two-parameter BET equation. The adsorption capacity at the specific pressure $P/P0 \approx 0.98$ was taken as the pore volume of the sample, and the pore diameter distribution was calculated according to the BJH model.

Example VI-1

Preparation of Template A:

15 g (0.087 mol) of tetramethylhexamethylenediamine was added to a 500 ml three-necked flask, 250 ml of isopropanol was added, and 18.8 g (0.087 mol) of 1,4-dibromobutane was added dropwise at room temperature. The addition was completed after 15 minutes, and the temperature was raised till refluxing. The solution gradually changed from colorless and transparent to white and turbid. The reaction was followed by high performance liquid chromatography (HPLC). After the reaction was completed, 200 ml of ethyl acetate was added to the reaction mixture, and the mixture was refluxed for 1 hour, cooled and filtered with suction. The resulted solid was washed with ethyl acetate and then with diethyl ether to give 30 g of a white solid product as 1,1,6,6-tetramethyl-1,6-diaza-12-membered ring-1,6-dibromide (a compound where n is 4, m is 6, R is methyl, X is Br), having a relative molecular weight of 388.2, a melting point of 273.7° C. $^1H$ NMR spectrum shows chemical shift (300 MHz, $CDCl_3$) δ 1.50 (t, 4H), 1.90 (t, 8H), 3.14 (s, 12H), 3.40 (t, 8H).

Preparation of Template B: Br in Template A was replaced with $OH^-$ by ion exchange; ion exchange resin was a strong basic styrene type anion exchange resin, working solution was 15 m % aqueous solution of Template A, operating temperature was 25° C., the mass ratio of the working fluid to the ion exchange resin was 1:3; the flow rate was 3 drops/second; the exchanged solution was dehydrated by a rotary evaporator to give a product that is a compound of formula (I) where n is 4, m is 6, R is methyl, and X is OH, having a relative molecular weight of 262.2, and a purity of 99.21%. Its bromine content was 0.79 m %.

Example VI-2

Preparation of Template C 10 g (0.058 mol) of tetramethylhexamethylenediamine was added to a 500 ml three-necked flask, 250 ml of isopropanol was added, and 16.6 g (0.058 mol) of 1,9-dibromodecane was added dropwise at room temperature. The addition was completed after 15 minutes, and the temperature was raised till refluxing. The solution gradually changed from colorless and transparent to white and turbid. The reaction was followed by high performance liquid chromatography (HPLC). After the reaction was completed, 200 ml of ethyl acetate was added to the reaction mixture, and the mixture was refluxed for 1 hour, cooled and filtered with suction. The resulted solid was washed with ethyl acetate and then with diethyl ether to give 25 g of a white solid product, as 1,1,8,8-tetramethyl-1,8-diaza-17-membered ring-1,8-dibromide (a compound where n is 9, m is 6, R is methyl, X is Br), having a relative molecular weight of 458.4. $^1$H NMR spectrum shows chemical shift (300 MHz, CDCl$_3$) δ 1.51 (t, 14H), 1.92 (t, 8H), 3.16 (s, 12H), 3.40 (t, 8H).

Preparation of Template D: Br in Template C was replaced with OH$^-$ by ion exchange; ion exchange resin was strong basic styrene type anion exchange resin, working solution was 15 m % aqueous solution of Template C, operating temperature was 25° C., the mass ratio of the working fluid to the ion exchange resin was 1:3; the flow rate was 3 drops/second; the exchanged solution was dehydrated by a rotary evaporator to give a product that is a compound of the formula (I), where n is 9, m is 6, R is methyl, X is OH, having a relative molecular weight of 332.4, and a purity of 99.8%. Its bromine content was 0.2 m %.

Example VI-3

0.132 g of sodium metaaluminate was added to a 45 mL Teflon container, 8.024 g of Template B was added, and then 3 g of crude silica gel (Qingdao Haiyang Chemical Co., Ltd., industrial product, SiO$_2$ content of 98.05%) was added, and the resultant was allowed to stand and aged for 1 hour to achieve a thorough mixing. The molar ratios of the components were as follows: SiO$_2$/Al$_2$O$_3$=60, H$_2$O/SiO$_2$=7.8, and Template B/SiO$_2$=0.15.

The above mixture was placed in a 45 mL steel autoclave with a Teflon liner, capped and sealed. The autoclave was placed in a rotating convection oven at a rotation speed of 20 rpm, and reacted at 120° C. for 1 day and then heated to 150° C. to react for 5 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 68:
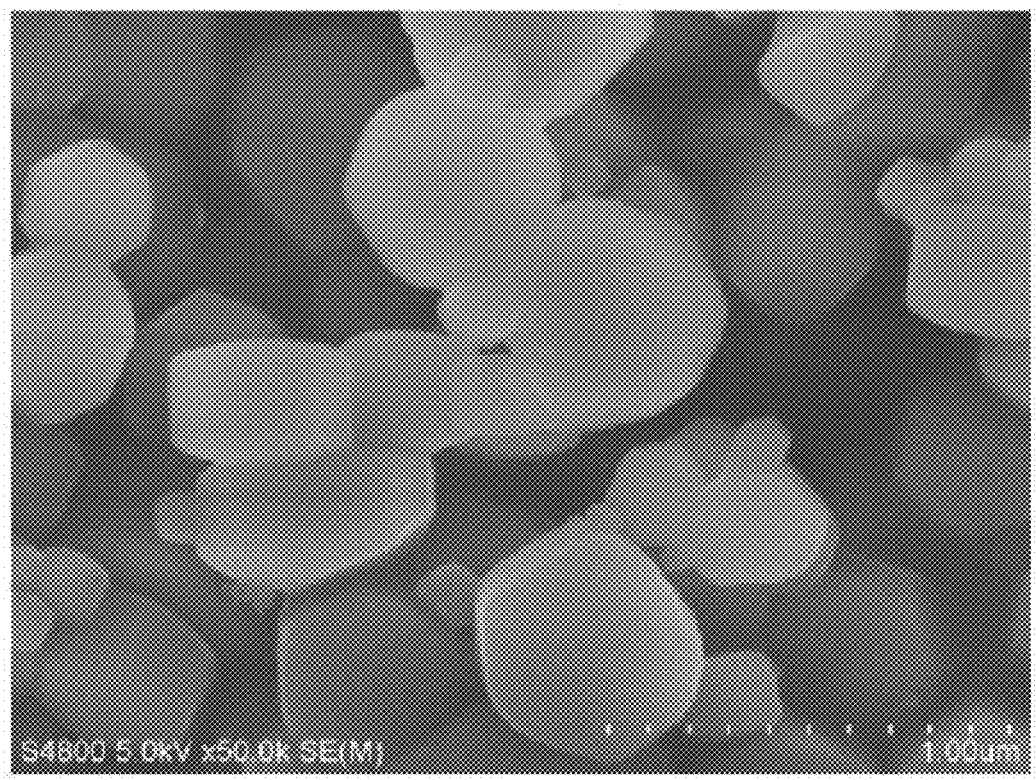
FIG. 68 is a scanning electron micrograph of the molecular sieve produced in Example VI-3.
Figure 69:
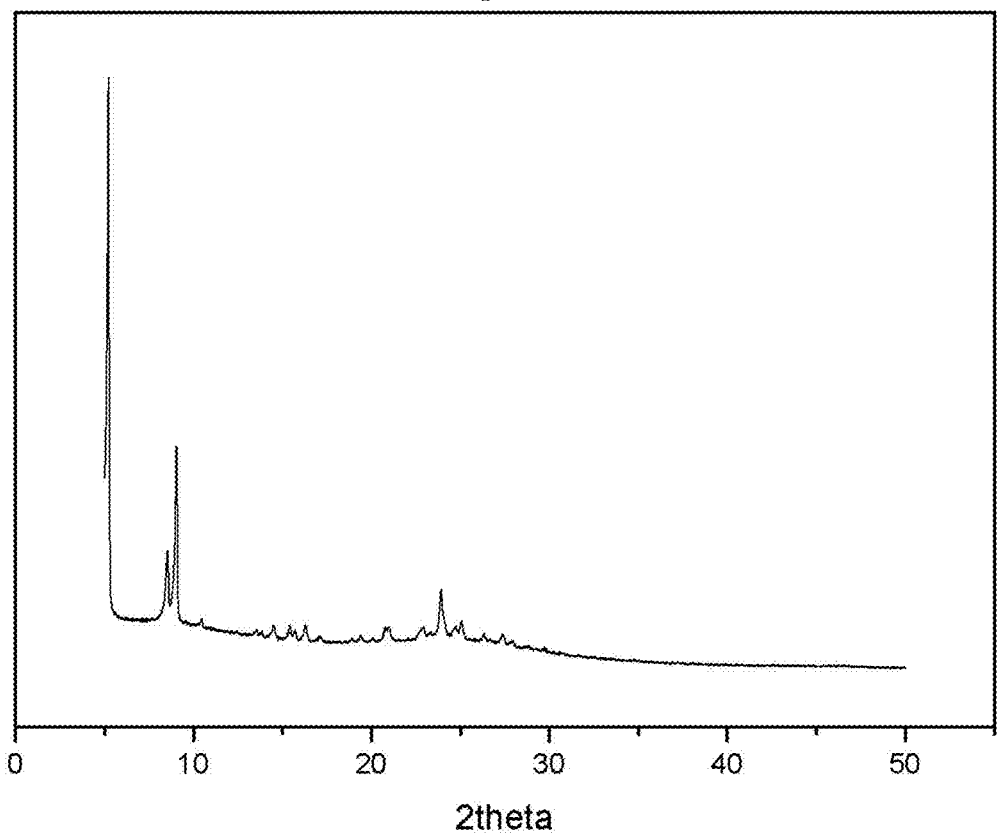
FIG. 69 is an XRD pattern of the molecular sieve produced in Example VI-3.
Figure 70:
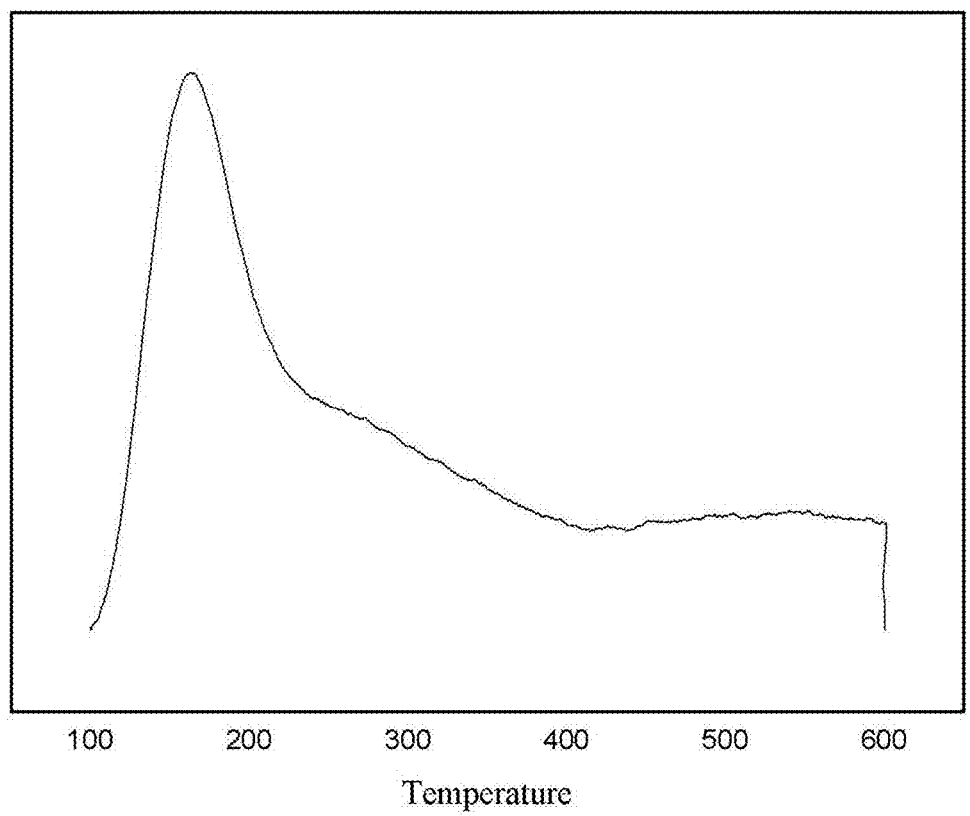
FIG. 70 is a NH3-TPD diagram of the molecular sieve produced in Example VI-3.
Figure 71:
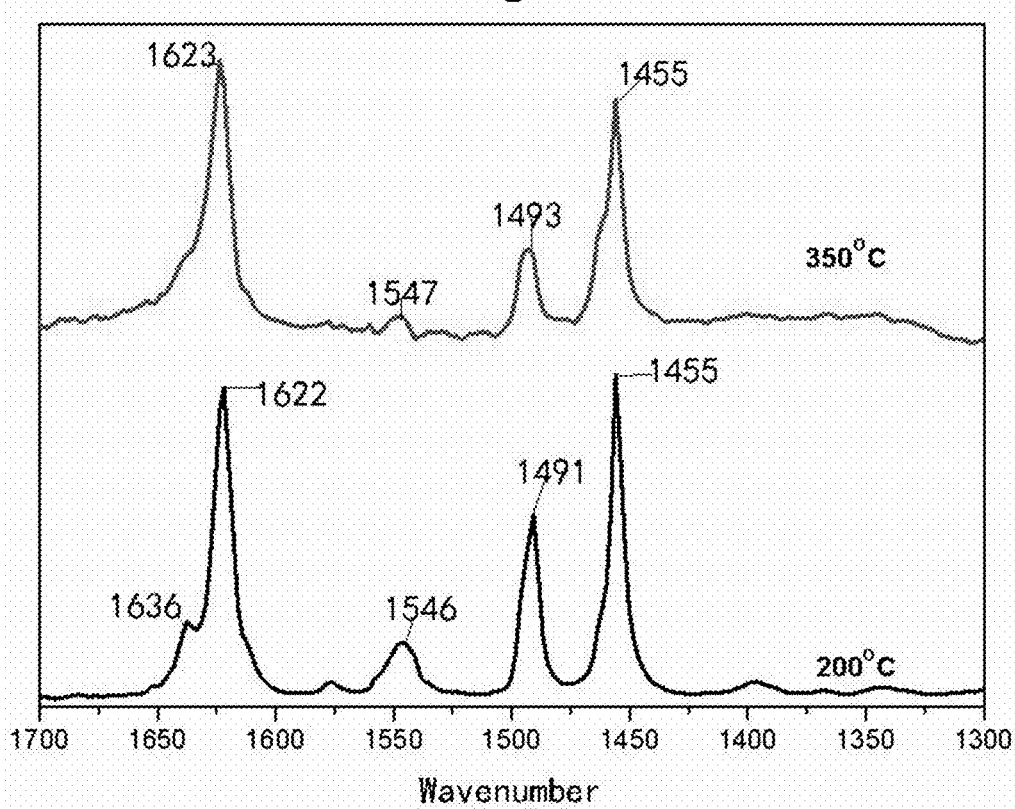
FIG. 71 is an infrared spectrum of the molecular sieve produced in Example VI-3.

The scanning electron micrograph of the product was shown in FIG. 68. It can be easily seen in the figure that the molecular sieve has the flat prismatic or flat cylindrical crystal particle morphology, with an effective diameter of 600 nm, a height of 300 nm, and an aspect ratio of 0.5. In accordance with the measurement, the molecular sieve had a total specific surface area of 518 m$^2$·g$^{-1}$ and a pore volume of 0.351 ml/g. The XRF analysis showed a Si/Al$_2$=63. The XRD pattern of the product was shown in FIG. 69. The results of NH3-TPD indicate (FIG. 70) that the molecular sieve has a significant acidity. The results of the infrared spectrum show (FIG. 71) that the molecular sieve has a low content of B acid and a high content of L acid.

Example VI-4

0.735 g of sodium metaaluminate was added to a 45 mL Teflon container, 8.024 g of Template B was added, and then 3 g of crude silica gel (Qingdao Haiyang Chemical Co., Ltd., industrial product, SiO$_2$ content of 98.05%) was added, and the resultant was allowed to stand and aged for 1 hour to achieve a thorough mixing. The molar ratios of the components were as follows: SiO$_2$/Al$_2$O$_3$=80, H$_2$O/SiO$_2$=7.5, and Template B/SiO$_2$=0.15. The above mixture was placed in a 45 mL steel autoclave with a Teflon liner, capped and sealed. The autoclave was placed in a rotating convection oven at a rotational speed of 20 rpm, and reacted at 120° C. for 1 day and then heated to 150° C. to react for 5 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 72:
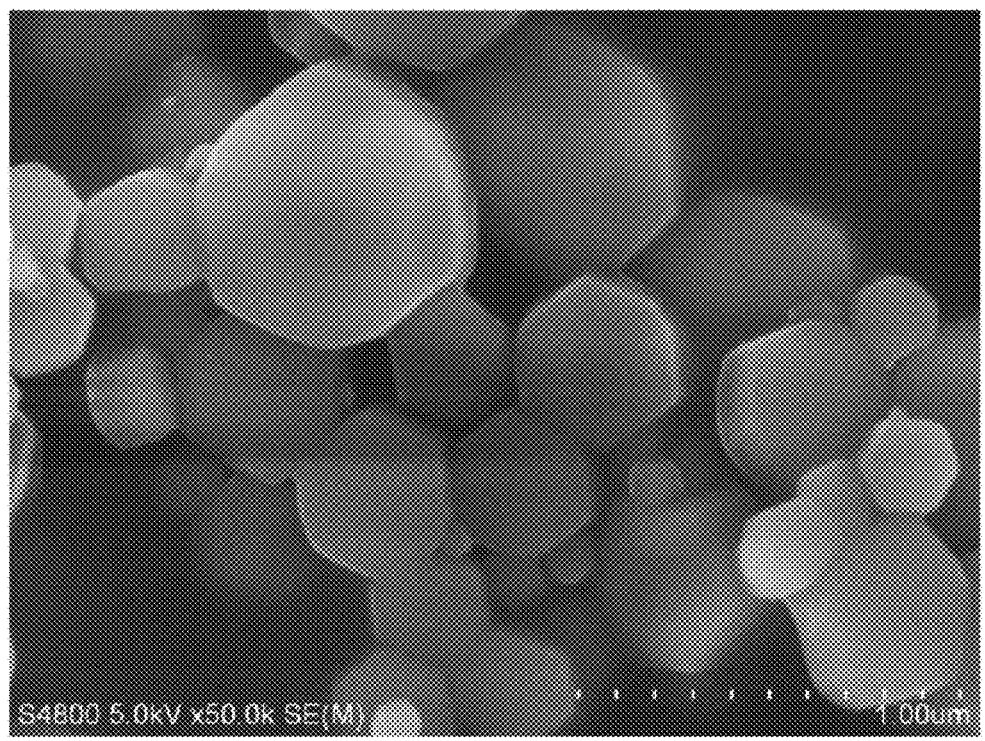
FIG. 72 is a scanning electron micrograph of the molecular sieve produced in Example VI-4.
Figure 73:
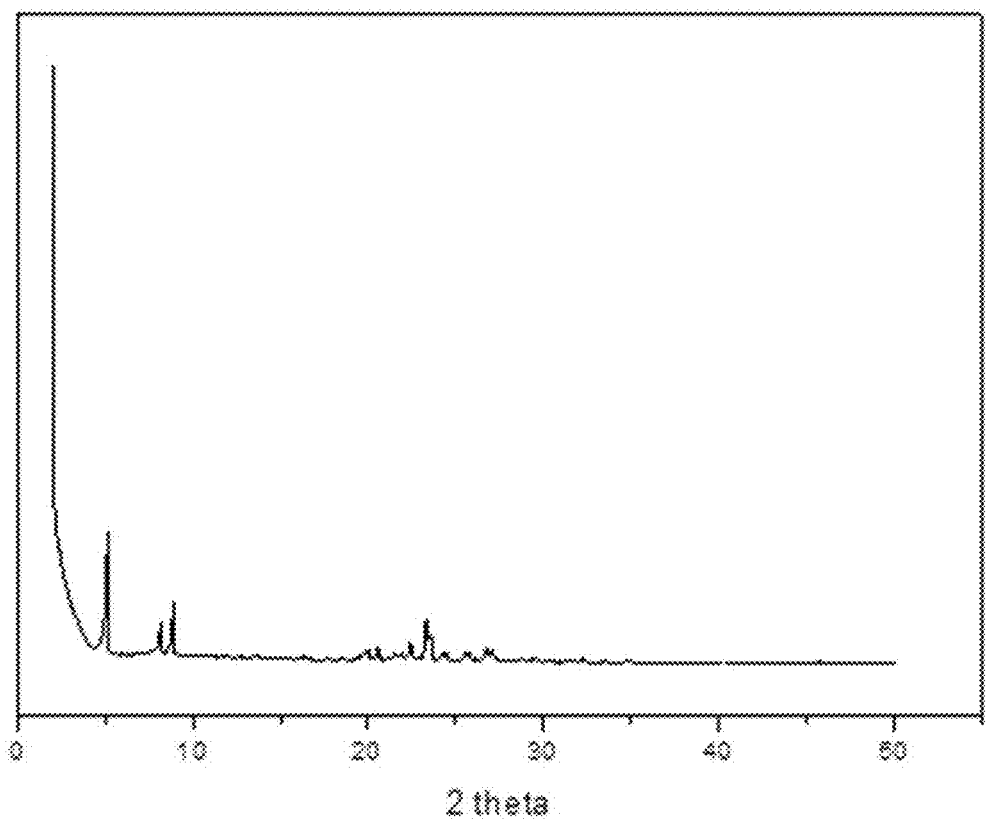
FIG. 73 is an XRD pattern of the molecular sieve produced in Example VI-4.

The scanning electron micrograph of the product was shown in FIG. 72. It can be easily seen in the figure that the molecular sieve has the flat prismatic or flat cylindrical crystal particle morphology, with an effective diameter of 300 nm, a height of 200 nm, and an aspect ratio of 0.67. In accordance with the measurement, the molecular sieve had a total specific surface area of 482 m$^2$·g$^{-1}$ and a pore volume of 0.346 ml/g. The XRF analysis showed a Si/Al$_2$=84. The XRD pattern of the product was shown in FIG. 73.

Example VI-5

0.132 g of sodium metaaluminate was added to a 45 mL Teflon container, 8.731 g of Template D was added, and then 3 g of crude silica gel (Qingdao Haiyang Chemical Co., Ltd., industrial product, SiO$_2$ content of 98.05%) was added, and the resultant was allowed to stand and aged for 1 hour to achieve a thorough mixing. The molar ratios of the components were as follows: SiO$_2$/Al$_2$O$_3$=60, H$_2$O/SiO$_2$=8, and Template D/SiO$_2$=0.15. The above mixture was placed in a 45 mL steel autoclave with a Teflon liner, capped and sealed. The autoclave was placed in a rotating convection oven at a rotation speed of 20 rpm, and reacted at 120° C. for 1 day and then heated to 150° C. to react for 4 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 74:
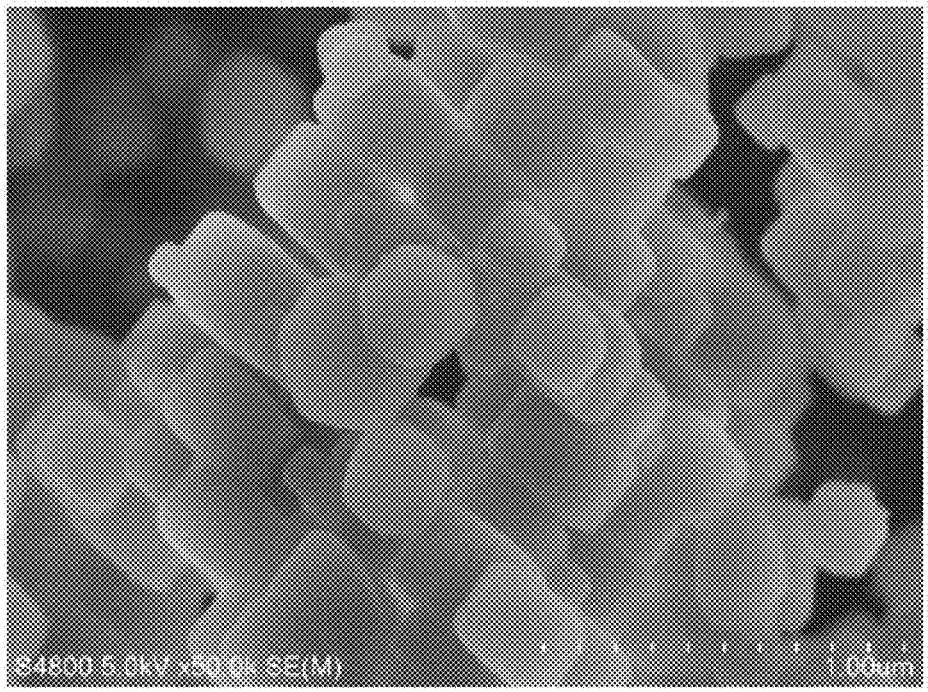
FIG. 74 is a scanning electron micrograph of the molecular sieve produced in Example VI-5.

The scanning electron micrograph of the product was shown in FIG. 74. It can be easily seen in the figure that the molecular sieve has the flat prismatic or flat cylindrical crystal particle morphology, with an effective diameter of 300 nm, a height of 200 nm, and an aspect ratio of 0.67. In accordance with the measurement, the molecular sieve had a total specific surface area of 452 m$^2$·g$^{-1}$ and a pore volume of 0.385 ml/g. The XRF analysis showed a Si/Al$_2$=62.

Example VI-6

0.132 g of sodium metaaluminate was added to a 45 mL Teflon container, 4.1 g of Template D was added, stirred for 30 minutes until homogeneous, and then 3 g of crude silica gel (Qingdao Haiyang Chemical Co., Ltd., industrial product, $SiO_2$ content of 98.05%) was added, and the resultant was allowed to stand and aged for 1 hour to achieve a thorough mixing. The molar ratios of the components were as follows: $SiO_2/Al_2O_3$=60, $H_2O/SiO_2$=7, and Template D/$SiO_2$=0.32.

The above mixture was placed in a 45 mL steel autoclave with a Teflon liner, capped and sealed. The autoclave was placed in a rotating convection oven at a rotation speed of 20 rpm, and reacted at 120° C. for 1 day and then heated to 150° C. to react for 5 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 75:
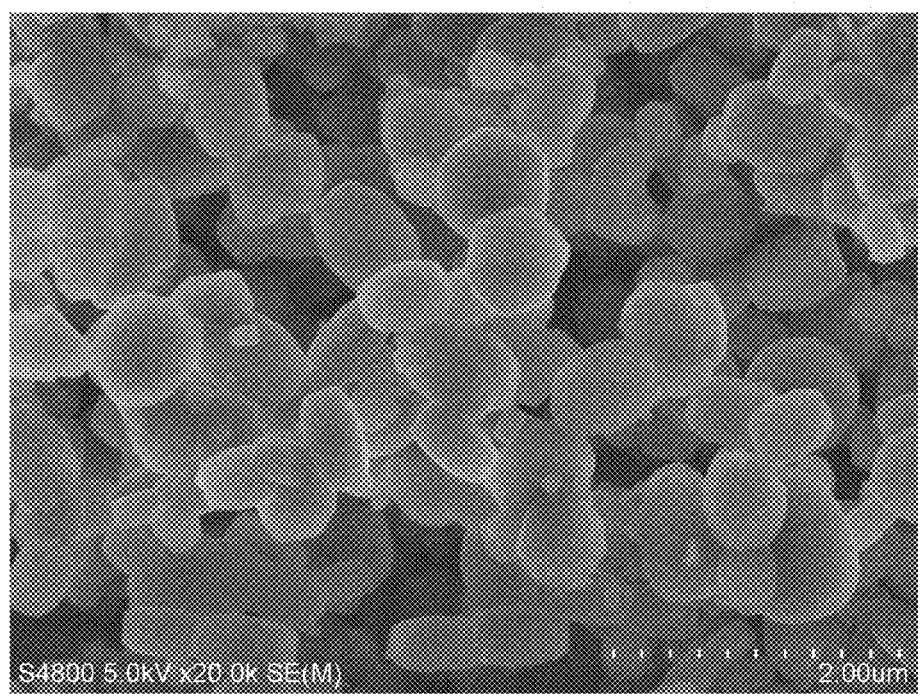
FIG. 75 is a scanning electron micrograph of the molecular sieve produced in Example VI-6.

The scanning electron micrograph of the product was shown in FIG. 75. It can be easily seen in the figure that the molecular sieve has the flat prismatic or flat cylindrical crystal particle morphology, with an effective diameter of 600 nm, a height of 400 nm and an aspect ratio of 0.67. In accordance with the measurement, the molecular sieve had a total specific surface area of 487 $m^2 \cdot g^{-1}$ and a pore volume of 0.387 ml/g. The XRF analysis showed a $Si/Al_2$=63.

Example VI-7

0.132 g of sodium metaaluminate was added to a 45 mL Teflon container, 6.0 g of Template C was added, and then 4 g of crude silica gel (Qingdao Haiyang Chemical Co., Ltd., industrial product, $SiO_2$ content of 98.05%) was added, and the resultant was allowed to stand and aged for 1 hour to achieve a thorough mixing. The molar ratios of the components were as follows: $SiO_2/Al_2O_3$=80, $H_2O/SiO_2$=5, and Template C/$SiO_2$=0.2. The above mixture was placed in a 45 mL steel autoclave with a Teflon liner, capped and sealed. The autoclave was placed in a rotating convection oven at a rotational speed of 20 rpm, and reacted at 110° C. for 1 day and then heated to 150° C. to react for 5 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 76:
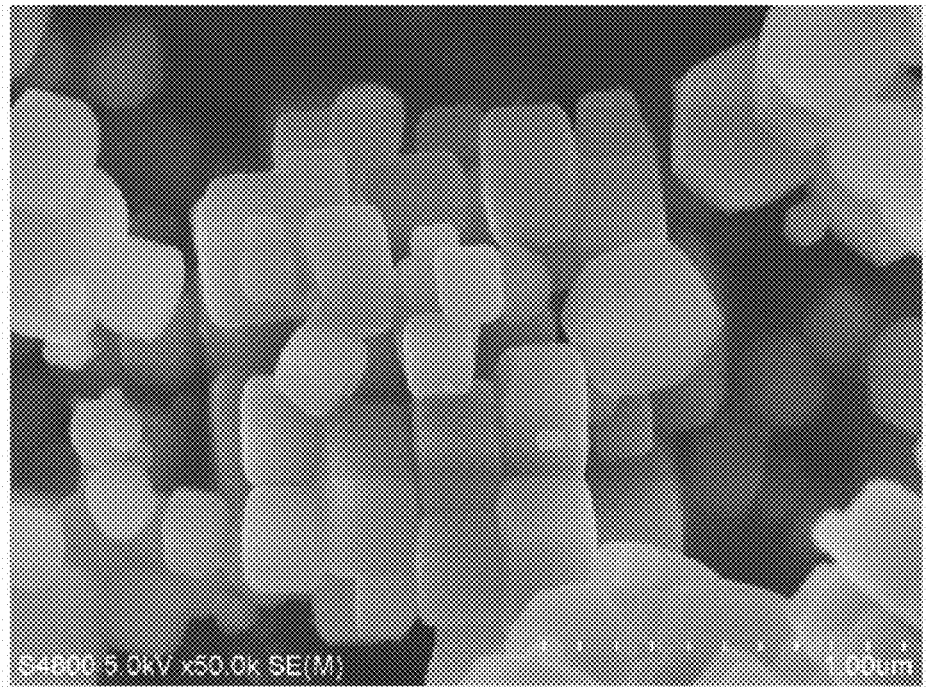
FIG. 76 is a scanning electron micrograph of the molecular sieve produced in Example VI-7.

The scanning electron micrograph of the product was shown in FIG. 76. It can be easily seen in the figure that the molecular sieve has the flat prismatic or flat cylindrical crystal particle morphology, with an effective diameter of 400 nm, a height of 200 nm, and an aspect ratio of 0.5. In accordance with the measurement, the molecular sieve had a total specific surface area of 412 $m^2 \cdot g^{-1}$ and a pore volume of 0.372 ml/g. The XRF analysis showed a $Si/Al_2$=83.

Example VI-8

0.132 g of sodium metaaluminate was added to a 45 mL Teflon container, 4 g of Template A was added, and then 3 g of crude silica gel (Qingdao Haiyang Chemical Co., Ltd., industrial product, $SiO_2$ content of 98.05%) was added, and the resultant was allowed to stand and aged for 1 hour to achieve a thorough mixing. The molar ratios of the components were as follows: $SiO_2/Al_2O_3$=60, $H_2O/SiO_2$=5, and Template C/$SiO_2$=0.2. The above mixture was placed in a 45 mL steel autoclave with a Teflon liner, capped and sealed. The autoclave was placed in a rotating convection oven at a rotation speed of 20 rpm, and reacted at 120° C. for 1 day and then heated to 150° C. to react for 5 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 77:
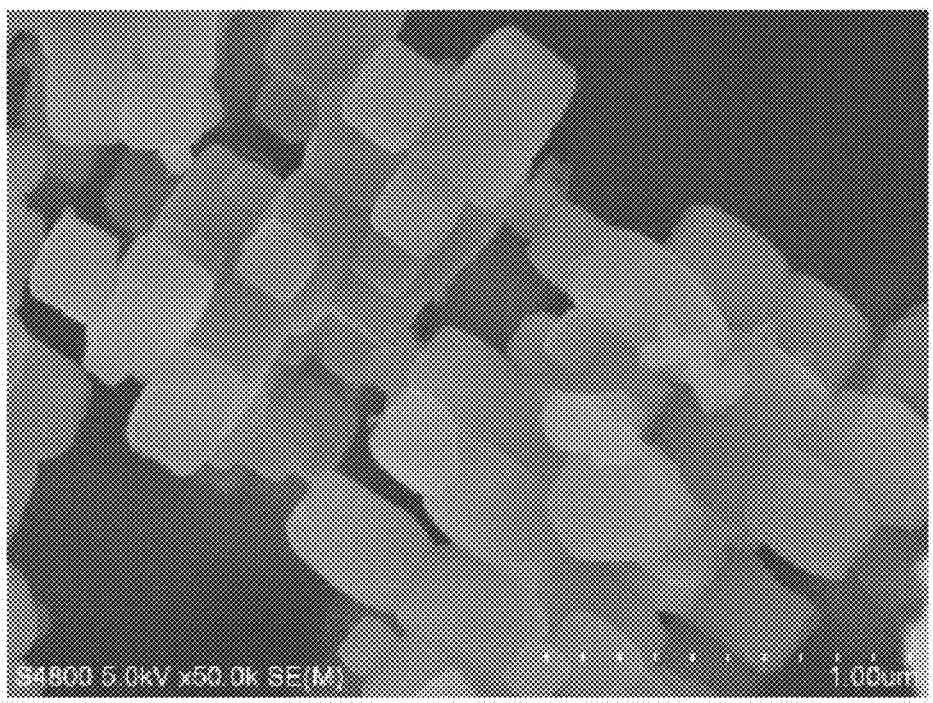
FIG. 77 is a scanning electron micrograph of the molecular sieve produced in Example VI-8.

The scanning electron micrograph of the product was shown in FIG. 77. It can be easily seen in the figure that the molecular sieve has the flat prismatic or flat cylindrical crystal particle morphology, with an effective diameter of 400 nm, a height of 250 nm and an aspect ratio of 0.625. In accordance with the measurement, the molecular sieve had a total specific surface area of 427 $m^2 \cdot g^{-1}$ and a pore volume of 0.418 ml/g. The XRF analysis showed a $Si/Al_2$=58.

Example VI-9

0.588 g of sodium metaaluminate was added to a 45 mL Teflon container, 8.024 g of Template B was added, and then 3 g of crude silica gel (Qingdao Haiyang Chemical Co., Ltd., industrial product, $SiO_2$ content of 98.05%) was added, and the resultant was allowed to stand and aged for 1 hour to achieve a thorough mixing. The molar ratios of the components were as follows: $SiO_2/Al_2O_3$=100, $H_2O/SiO_2$=7.6, and Template B/$SiO_2$=0.15.

The above mixture was placed in a 45 mL steel autoclave with a Teflon liner, capped and sealed. The autoclave was placed in a rotating convection oven at a rotation speed of 20 rpm, and reacted at 120° C. for 1 day and then heated to 150° C. to react for 5 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product.

Figure 78:
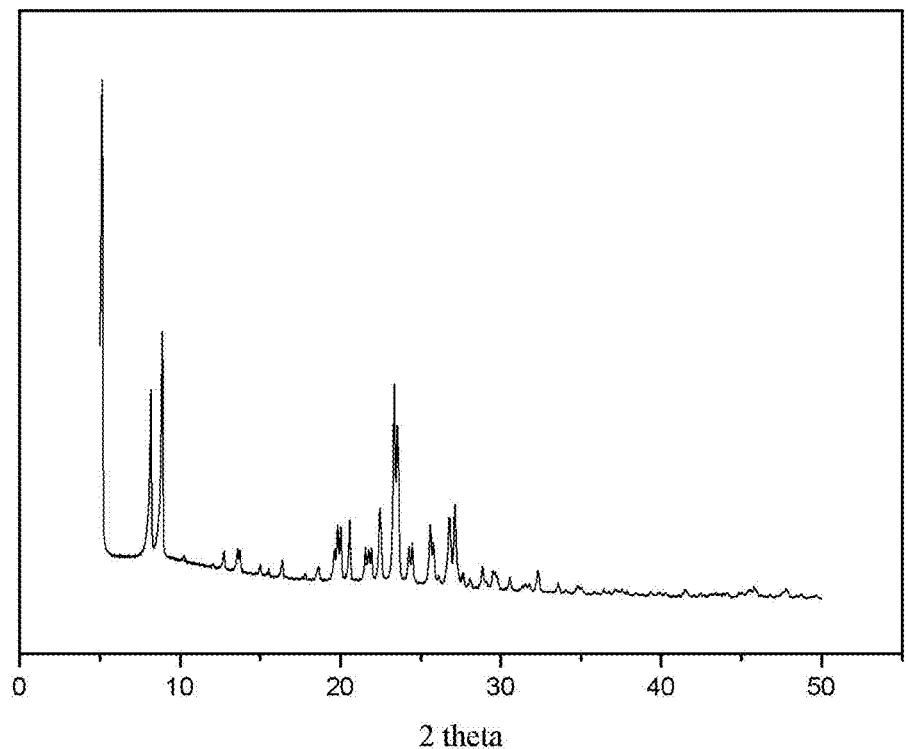
FIG. 78 is an XRD pattern of the molecular sieve produced in Example VI-9.

The XRD pattern of this product was shown in FIG. 78.

Example VI-10

0.49 g of sodium metaaluminate was added to a 45 mL Teflon container, 8.024 g of Template B was added, and then 3 g crude silica gel (Qingdao Haiyang Chemical Co., Ltd., industrial product, $SiO_2$ content was 98.05%) was added, and the resultant was allowed to stand and aged for 1 hour to achieve a thorough mixing. The molar ratios of the components were as follows: $SiO_2/Al_2O_3$=120, $H_2O/SiO_2$=7.5, and Template B/$SiO_2$=0.15.

Figure 79:
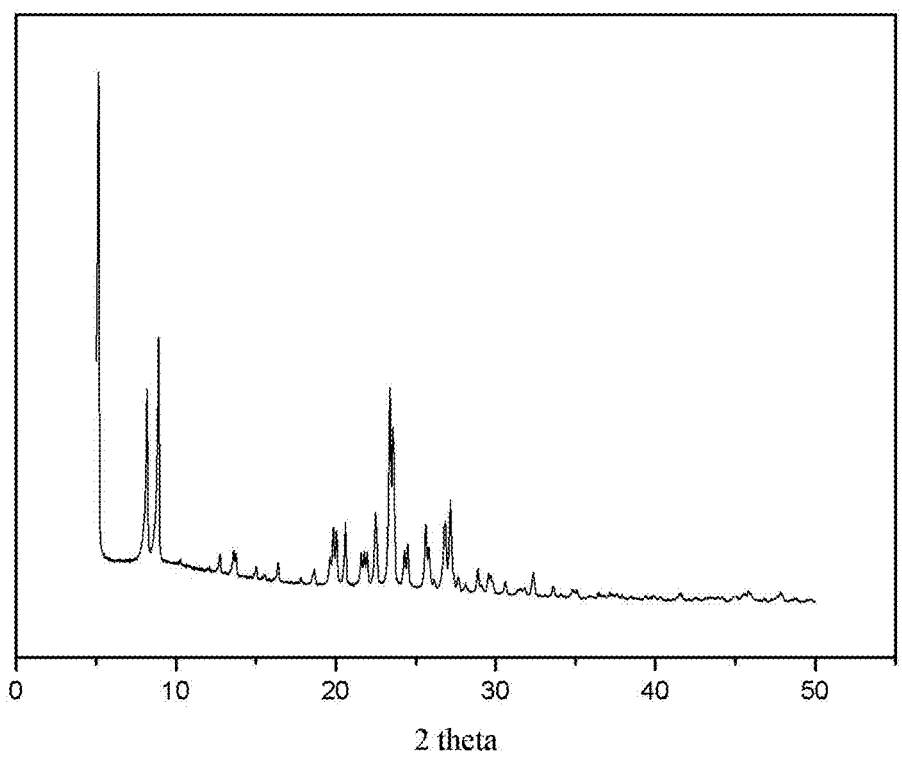
FIG. 79 is an XRD pattern of the molecular sieve produced in Example VI-10.

The above mixture was placed in a 45 mL steel autoclave with a Teflon liner, capped and sealed. The autoclave was placed in a rotating convection oven at a rotation speed of 20 rpm, and reacted at 120° C. for 1 day and then heated to 150° C. to react for 5 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product. The XRD pattern of this product was shown in FIG. 79.

Example VI-11

0.392 g of sodium metaaluminate was added to a 45 mL Teflon container, 8.024 g of Template B was added, and then 3 g of crude silica gel (Qingdao Haiyang Chemical Co., Ltd., industrial product, $SiO_2$ content was 98.05%) was added, and the resultant was allowed to stand and aged for 1 hour to achieve a thorough mixing. The molar ratios of the components were as follows: $SiO_2/Al_2O_3$=150, $H_2O/SiO_2$=7.3, Template B/$SiO_2$=0.15.

Figure 80:
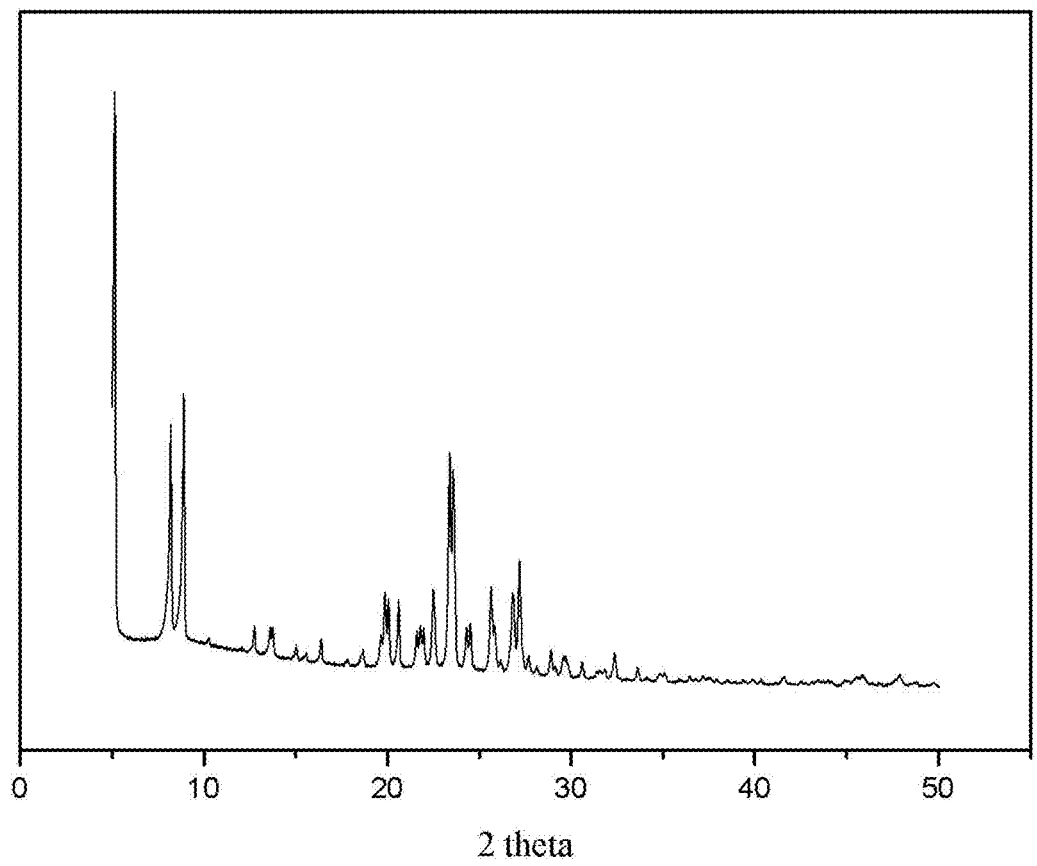
FIG. 80 is an XRD pattern of the molecular sieve produced in Example VI-11.

The above mixture was placed in a 45 mL steel autoclave with a Teflon liner, capped and sealed. The autoclave was placed in a rotating convection oven at a rotation speed of 20 rpm, and reacted at 120° C. for 1 day and then heated to 150° C. to react for 5 days. The autoclave was taken out and rapidly cooled to room temperature, and the mixture was separated on a high-speed centrifuge at 5000 rpm, and the solid was collected, washed thoroughly with deionized water, and dried at 100° C. for 5 hours to give a product. The XRD pattern of this product was shown in FIG. 80.

Numerous details are described in the description of the present application, but it can be understood that the embodiments disclosed herein can be practiced without those details. In some instances, well-known methods, structures, and techniques are not shown in detail, so as not to obscure the understanding of the description.

Similarly, in the description of the exemplary embodiments of the present disclosure, the various features are sometimes grouped together into a single embodiment, a single figure, or the description thereof, so as to make the disclosure concise and to help the understanding of ore or more of the aspects as disclosed herein. However, the disclosure should not be interpreted as reflecting the intention that the claimed invention requires more features than those explicitly recited in each claim. Rather, as reflected in the claims, the claimed technical solution may contain fewer features as compared to a single embodiment described in the specification. Therefore, claims following specific embodiments are hereby explicitly incorporated into the specific embodiments, and each of the claims can be considered as a single embodiment of the present invention.

It should also be noted that, in this context, relational terms such as first and second, etc. are used merely to distinguish one entity or operation from another entity or operation, without necessarily requiring or implying that there is really such a relationship or order between said entities or operations. Furthermore, the term "comprise", "comprising", or any other variants thereof are intended to encompass a non-exclusive inclusion, such that a process, method, article, or device comprising a plurality of elements may comprise not only those elements but also other elements, or elements that are inherent to such a process, method, article, or device. In the absence of a further limitation, an element defined by the phrase "comprising one . . . " does not exclude the presence of an additional number of the same element in the process, method, article, or device.

The above examples are provided merely to illustrate the technical solutions of the embodiments of the present disclosure, and are not intended to be limiting; although the present invention has been described in detail with reference to the aforementioned embodiments, those skilled in the art will understand that the technical solutions described in the embodiments can be modified, or some technical features contained therein can be replaced by equivalents thereof; and such modification or replacement would not depart the corresponding technical solution from the spirit or scope of the embodiments of the present disclosure.

We claim:

1. A method for the preparation of a molecular sieve, comprising:
    contacting a first oxide source, a second oxide source, an organic template, and water under crystallization conditions to produce a molecular sieve,
    wherein the first oxide is at least one selected from silica, germanium dioxide, tin dioxide, titania, and zirconium dioxide,
    the second oxide is at least one selected from alumina, a boron oxide, an iron oxide, a gallium oxide, a rare earth oxide, an indium oxide, and a vanadium oxide, and
    wherein the organic template comprises a compound represented by the following formula (I),

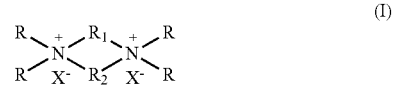

wherein the groups $R_1$ and $R_2$ are different from each other, each independently selected from $C_{3-12}$ linear alkylene groups, $C_{3-12}$ branched alkylene groups, $C_{3-12}$ linear oxaalkylene groups, and $C_{3-12}$ branched oxaalkylene groups;
    the plural groups R are identical or different from each other, each independently selected from $C_{1-4}$ linear alkyl groups and $C_{1-4}$ branched alkyl groups; and
    X is OH.

2. The method according to claim 1, wherein the first oxide is silica or a combination of silica and germanium dioxide.

3. The method according to claim 1, wherein the second oxide is alumina.

4. The method according to claim 1, wherein the groups $R_1$ and $R_2$ are different from each other, with one of them being selected from $C_{3-12}$ linear alkylene groups, and the other being selected from $C_{3-12}$ linear alkylene groups and $C_{3-12}$ linear oxaalkylene groups.

5. The method according to claim 1, wherein the groups $R_1$ and $R_2$ are different from each other, with one of them being selected from $C_{3-12}$ linear alkylene groups and the other being selected from $C_{4-6}$ linear alkylene groups and $C_{4-6}$ linear oxaalkylene groups.

6. The method according to claim 5, wherein one of the groups $R_1$ and $R_2$ is selected from $C_{3-12}$ linear alkylene groups and the other of the groups $R_1$ and $R_2$ is selected from $C_{4-6}$ linear oxaalkylene groups, wherein the $C_{4-6}$ linear oxaalkylene group is represented by the formula —$(CH_2)_m$—O—$(CH_2)_m$—, wherein each value m, being identical or different from each other, independently represents 2 or 3.

7. The method according to claim 1, wherein the plural groups R are identical or different from each other, each independently selected from methyl and ethyl.

8. The method according to claim 1, wherein:
    a molar ratio of the first oxide source, calculated on the basis of the first oxide, to the second oxide source, calculated on the basis of the second oxide, is in a range from 5 to ∞;
    a molar ratio of water to the first oxide source, calculated on the basis of the first oxide, is in a range from 5 to 50; and
    a molar ratio of the organic template to the first oxide source, calculated on the basis of the first oxide, is in a range from 0.02 to 0.5.

9. The method according to claim 1, wherein:
    a molar ratio of the first oxide source, calculated on the basis of the first oxide, to the second oxide source, calculated on the basis of the second oxide, is in a range from 25 to 95;

a molar ratio of water to the first oxide source, calculated on the basis of the first oxide, is in a range from 5 to 15; and a molar ratio of the organic template to the first oxide source, calculated on the basis of the first oxide, is in a range from 0.15 to 0.5.

10. The method according to claim 1, wherein the contacting step is carried out in the presence of an alkali source that is an inorganic base comprising an alkali metal or alkaline earth metal as the cation.

11. The method according to claim 10, wherein the molar ratio of the alkali source, calculated on the basis of $OH^-$, to the first oxide source, calculated on the basis of the first oxide, is in a range from 0.04 to 1.

12. The method according to claim 1, wherein the crystallization conditions include: a crystallization temperature ranging from 80° C. to 120° C., and a crystallization period of at least 1 day.

13. The method according to claim 1, wherein the method further comprises calcining the molecular sieve under the following conditions: a calcination temperature ranging from 300° C. to 750° C., and a calcination period ranging from 1 hour to 10 hours.

14. A molecular sieve obtained by the method according to claim 1, having an X-ray diffraction pattern substantially as shown in the following table,

| 2θ (°) | d-distance (Å) | Relative intensity ($I/I_0 \times 100$) |
|---|---|---|
| 5.2048 ± 0.05 | 16.96501 ± 0.05 | >70 |
| 8.4762 ± 0.27 | 10.42335 ± 0.34 | <20 |
| 9.0095 ± 0.06 | 9.80755 ± 0.07 | 20-40 |
| 10.3943 ± 0.05 | 8.50381 ± 0.05 | <20 |
| 16.1228 ± 0.50 | 5.49296 ± 0.50 | <20 |
| 23.7405 ± 0.22 | 3.74484 ± 0.03 | <20. |

15. The molecular sieve according to claim 14, wherein the X-ray diffraction pattern further comprises X-ray diffraction peaks substantially as shown in the following table,

| 2θ (°) | d-distance (Å) | Relative intensity ($I/I_0 \times 100$) |
|---|---|---|
| 14.3448 ± 0.66 | 6.16955 ± 0.27 | <20 |
| 15.2971 ± 0.50 | 5.78752 ± 0.50 | <20 |
| 16.1979 ± 0.50 | 5.46765 ± 0.50 | <20 |
| 20.8653 ± 0.11 | 4.25393 ± 0.02 | <20 |
| 23.9532 ± 0.14 | 3.71207 ± 0.02 | <20. |

16. The molecular sieve according to claim 14, wherein the X-ray diffraction pattern further comprises X-ray diffraction peaks substantially as shown in the following table,

| 2θ (°) | d-distance (Å) | Relative intensity ($I/I_0 \times 100$) |
|---|---|---|
| 14.4217 ± 0.56 | 6.13681 ± 0.43 | <20 |
| 15.1988 ± 0.50 | 5.82474 ± 0.50 | <20 |
| 15.5903 ± 0.50 | 5.67936 ± 0.50 | <20 |
| 20.6353 ± 0.50 | 4.30082 ± 0.10 | <20 |
| 22.7406 ± 0.08 | 3.90718 ± 0.02 | <20 |
| 24.4468 ± 0.26 | 3.63823 ± 0.04 | <20. |

17. A molecular sieve composition, comprising a molecular sieve according to claim 14, and a binder.

18. A process for the conversion of a hydrocarbon, comprising a step of subjecting the hydrocarbon to a conversion reaction in the presence of a catalyst, wherein the catalyst comprises or is produced from a molecular sieve according to claim 14.

19. The process according to claim 18, wherein the conversion reaction is selected from catalytic cracking, hydrocracking, disproportionation, alkylation, oligomerization, and isomerization reactions.

20. The method according to claim 1, wherein the molecular sieve has an X-ray diffraction pattern substantially as shown in the following table,

| 2θ (°) | d-distance (Å) | Relative intensity ($I/I_0 \times 100$) |
|---|---|---|
| 5.2048 ± 0.05 | 16.96501 ± 0.05 | >70 |
| 8.4762 ± 0.27 | 10.42335 ± 0.34 | <20 |
| 9.0095 ± 0.06 | 9.80755 ± 0.07 | 20-40 |
| 10.3943 ± 0.05 | 8.50381 ± 0.05 | <20 |
| 16.1228 ± 0.50 | 5.49296 ± 0.50 | <20 |
| 23.7405 ± 0.22 | 3.74484 ± 0.03 | <20. |

* * * * *